US010500264B2

(12) United States Patent
Whitehead et al.

(10) Patent No.: US 10,500,264 B2
(45) Date of Patent: Dec. 10, 2019

(54) DEVELOPMENT OF MUTATIONS USEFUL FOR ATTENUATING DENGUE VIRUSES AND CHIMERIC DENGUE VIRUSES

(71) Applicant: The United States of America, as represented by the Secretary, Dept. of Health and Human Services, Rockville, MD (US)

(72) Inventors: Stephen S. Whitehead, Bethesda, MD (US); Brian R. Murphy, Bethesda, MD (US); Kathryn A. Hanley, Las Cruces, NM (US); Joseph E. Blaney, Gettysburg, PA (US); Ching-Juh Lai, Bethesda, MD (US)

(73) Assignee: The United States of America, as represented by the Secretary, Department of Health and Human Services, Rockville, MD (US)

(*) Notice: Subject to any disclaimer, the term of this patent is extended or adjusted under 35 U.S.C. 154(b) by 0 days.

(21) Appl. No.: 15/650,482

(22) Filed: Jul. 14, 2017

(65) Prior Publication Data

US 2018/0008693 A1 Jan. 11, 2018

Related U.S. Application Data

(60) Division of application No. 14/096,424, filed on Dec. 4, 2013, now Pat. No. 9,707,287, which is a division of application No. 13/240,849, filed on Sep. 22, 2011, now Pat. No. 8,632,782, which is a division of application No. 12/396,376, filed on Mar. 2, 2009, now Pat. No. 8,039,003, which is a continuation of application No. 11/446,050, filed on Jun. 2, 2006, now Pat. No. 7,560,118, which is a division of application No. 10/719,547, filed on Nov. 21, 2003, now Pat. No. 7,226,602, which is a continuation of application No. PCT/US02/16308, filed on May 22, 2002.

(60) Provisional application No. 60/293,049, filed on May 22, 2001.

(51) Int. Cl.

| | |
|---|---|
| ***A61K 39/12*** | (2006.01) |
| ***C12N 7/00*** | (2006.01) |
| ***A61K 39/295*** | (2006.01) |
| ***C12Q 1/70*** | (2006.01) |
| *A61K 39/00* | (2006.01) |

(52) U.S. Cl.

CPC ............ *A61K 39/12* (2013.01); *A61K 39/295* (2013.01); *C12N 7/00* (2013.01); *C12Q 1/701* (2013.01); *A61K 2039/5252* (2013.01); *A61K 2039/5254* (2013.01); *A61K 2039/5256* (2013.01); *A61K 2039/54* (2013.01); *A61K 2039/575* (2013.01); *A61K 2039/70* (2013.01); *C12N 2770/24121* (2013.01); *C12N 2770/24134* (2013.01); *C12N 2770/24161* (2013.01); *C12N 2770/24162* (2013.01); *C12N 2770/24171* (2013.01); *C12Q 2600/156* (2013.01); *G01N 2333/18* (2013.01); *G01N 2500/10* (2013.01); *Y02A 50/386* (2018.01)

(58) Field of Classification Search

CPC ...................... A61K 39/12; C12N 2770/24121

See application file for complete search history.

(56) References Cited

U.S. PATENT DOCUMENTS

| | | | |
|---|---|---|---|
| 5,494,671 | A | 2/1996 | Lai et al. |
| 6,074,865 | A | 6/2000 | Kelly et al. |
| 6,455,509 | B1 | 9/2002 | Kochel et al. |

FOREIGN PATENT DOCUMENTS

| | | | |
|---|---|---|---|
| WO | WO 1990/014837 | A1 | 12/1990 |
| WO | WO 1993/013202 | A1 | 7/1993 |
| WO | WO 1995/017211 | A1 | 6/1995 |
| WO | WO 1997/002348 | A1 | 1/1997 |
| WO | WO 00/57910 | | 10/2000 |
| WO | WO 2000/057907 | A2 | 10/2000 |

OTHER PUBLICATIONS

Shurtleff, A. C., et al., 2001, Genetic Variation in the 3' Non-Coding Region of Dengue Viruses, Virol. 281:75-87.*

Concalves de Castro, M., et al., 2013, Genetic Variation in the 3' Untranslated Region of Dengue Virus Serotype 3 Strains Isolated from Mosquitoes and Humans in Brazil, Virol. J. 10(3):1-11.*

Alstead et al., "Dengue and chikungunya virus infection in man in Thailand, 1962-1964. IV. Epidemiologic studies in the Bangkok metropolitan area," *Am. J. Trop. Med. Hyg*., vol. 18, pp. 997-1021, 1969.

Angsubhakorn et al., "Dengue-3 (16562) PGMK 33 vaccine: neurovirulence, viremia and immune responses in Macaca fascicularis," *Southeast Asian J. Trop. Med. Public Health*, vol. 25, pp. 554-559, 1994.

Bancroft et al., "Dengue virus type 2 vaccine: reactogenicity and immunogenicity in soldiers," *J. Infect. Dis*., vol. 149, pp. 1005-1010, 1984.

Bancroft et al., "Dengue-2 vaccine: virological, immunological, and clinical responses of six yellow fever-immune recipients," *Infect. Immun*., vol. 31, pp. 698-703, 1981.

Bhamarapravati et al., "Live attenuated tetravalent dengue vaccine," *Vaccine*, vol. 18(Suppl. 2), pp. 44-47, 2000.

Bhamarapravati et al., "Live attenuated tetravalent dengue vaccine," In *D. J. Gubler, and G. Kuna (ed.), Dengue and Dengue Hemorrhagic Fever. CAB International*, New York, N.Y, pp. 367-377, 1997.

(Continued)

*Primary Examiner* — Jeffrey S Parkin

(74) *Attorney, Agent, or Firm* — Klarquist Sparkman, LLP

(57) ABSTRACT

A menu of mutations was developed that is useful in fine-tuning the attenuation and growth characteristics of dengue virus vaccines.

13 Claims, 12 Drawing Sheets

Specification includes a Sequence Listing.

(56) References Cited

OTHER PUBLICATIONS

Bhamarpravati et al., "Immunization with a live attenuated dengue-2-virus candidate vaccine (16681-PDK 53): clinical, immunological and biological responses in adult volunteers," *Bull World Health Organ.*, vol. 65, pp. 189-195, 1987.
Blaney et al., "Chemical mutagenesis of dengue virus type 4 yields mutant viruses which are temperature sensitive in vero cells or human liver cells and attenuated in mice," *J. Virol.*, vol. 75, pp. 9731-9740, 2001.
Blaney et al., "Genetic basis of attenuation of dengue virus type 4 small plaque mutants with restricted replication in suckling mice and SCID mice transplanted with human liver cells," *Virology*, vol. 300, pp. 125-139, 2002.
Blaney et al., "Genetically modified, live attenuated dengue virus type 3 vaccine candidates," *Am. J. Trop. Med. Hyg.*, vol. 71, pp. 811-821, 2004.
Blaney et al., "Mutations which enhance the replication of dengue virus type 4 and an antigenic chimeric Dengue virus type 2/4 vaccine candidate in Vero cells," *Vaccine*, vol. 21, pp. 4317-4327, 2003.
Blaney et al., "Recombinant, live-attenuated tetravalent dengue virus vaccine formulations induce a balanced, broad, and protective neutralizing antibody response against each of the four serotypes in Rhesus monkeys," *J. Virol*, vol. 79, pp. 5516-5528, 2005.
Blaney et al., "Temperature sensitive mutations in the genes encoding the ns1, ns2a, and ns5 nonstructural proteins of dengue virus type 4 restrict replication in the brains of mice," *Arch Virol.*, vol. 148, pp. 999-1006, 2003.
Blok et al., "Comparison of a dengue-2 virus and its candidate vaccine derivative: sequence relationships with the flaviviruses and other viruses," *Virology*, vol. 187, pp. 573-590, 1992.
Bray et al., "Construction of intertypic chimeric dengue viruses by substitution of structural protein genes," *PNAS USA*, vol. 88, pp. 10342-10346, 1991.
Bray et al., "Monkeys immunized with intertypic chimeric dengue viruses are protected against wild-type virus challenge," *J. Virol.*, vol. 70, pp. 4162-4166, 1996.
Burke et al., "A prospective study of dengue infections in Bangkok," *Am. J. Trop. Med. Hyg.*, vol. 38, pp. 172-180, 1988.
Butrapet et al., "Attenuation markers of a candidate dengue type 2 vaccine virus, strain 16681 (PDK-53), are defined by mutations in the 5' noncoding region and nonstructural proteins 1 and 3," *J. Viral.*, vol. 74, pp. 3011-3019, 2000.
CDC, "Public Health Dispatch: Outbreak of poliomyelitis—Dominican Republic and Haiti, 2000," *MMWR Morb. Mortal Wkly. Rep.*, vol. 49, pp. 1094-1104, 2000.
Chambers et al., "Yellow fever/Japanese encephalitis chimeric viruses: construction and biological properties," *J. Virol.*, vol. 73, pp. 3095-3101, 1999.
Chang, "Molecular biology of dengue viruses," in *D. J. Gubler, and G. Kuno (ed.), Dengue and Dengue Hemmorrhagic Fever. CAB International*, New York, N.Y., p. 175-198, 1997.
Chen et al., "Construction of intertypic chimeric dengue viruses exhibiting type 3 antigenicity and neurovirulence for mice," *J. Virol.*, vol. 69, pp. 5186-5190, 1995.
Cole et al., "Pathogenesis of type 1 dengue virus infection in suckling, weanling and adult mice. I. The relation of virus replication to interferon and antibody formation," *Am. J. Epidemiol.*, vol. 89, pp. 669-680, 1969.
Cole et al., "Pathogenesis of type 1 dengue virus infection in suckling, weaning and adult mice. II. lmmunofluorescent and histological studies," *J. Comp. Pathol.*, vol. 83, pp. 243-252, 1973.
Couvelard et al., "Report of a fatal case of dengue infection with hepatitis: demonstration of dengue antigens in hepatocytes and liver apoptosis," *Hum. Pathol.*, vol. 30, pp. 1106-1110, 1999.
Database NCBI, XP0021317338 retrieved from NCBI accession No. GI:12018173; Database accession No. AF 326827, Jan. 3, 2001.
Database NCBI XP002317339, retrieved from NCBI accession No. GI1:2018169; Database accession No. AF326825, Jan. 3, 2001.
Dunster et al., "Molecular and biological changes associated with HeLa cell attenuation of wild-type yellow fever virus," *Virology*, vol. 261, pp. 309-318, 1999.
Durbin et al., "A recombinant live attenuated dengue virus type 4 vaccine candidate is highly attenuated and immunogenic in humans," *Clinical Infectious Diseases*, vol. 31, No. 1, pp. 223, 2000.
Durbin et al., "Attenuation and immunogenicity in humans of a live dengue virus type-4 vaccine candidate with a 30 nucleotide deletion and its 3'-untranslated region," *Am. J. Trop. Med. Hyg.*, vol. 65, pp. 405-413, 2001.
Eckels et al., "Dengue-2 vaccine: preparation from a small-plaque virus clone," *Infect. lmmun.*, vol. 27, pp. 175-180, 1980.
Eckels et al., "Selection of attenuated dengue 4 viruses by serial passage in primary kidney cells. V. Human response to immunization with a candidate vaccine prepared in fetal rhesus lung cells," *A. J. Trop. Med. Hyg.*, vol. 33, pp. 684-689, 1984.
Edelman et al., "A live attenuated dengue-1 vaccine candidate (45AZ5) passaged in primary dog kidney cell culture is attenuated and immunogenic for humans," *J. Infect. Dis.*, vol. 170, pp. 1448-1455, 1994.
European Patent Office Communication for European Application 02739358.6 dated Sep. 11, 2006.
European Search Report from European Patent Application No. 10181776, search completed on Jan. 28, 2011.
European Search Report from European Patent application No. 10181786, search completed on Feb. 3, 2011.
European Search Report, from European Patent Application No. 10181804, search completed on Feb. 11, 2011.
Grard et al., "Genetic characterization of tick-borne flaviviruses: new insights into evolution, pathogenic determinants and taxonomy," *Virol*, vol. 361, pp. 80-92, 2007.
Guble et al., "Dengue and dengue hemorrhagic fever," *Clin. Microbial. Rev.*, vol. 11, pp. 480-496, 1998.
Gubler, "Impact of dengue/dengue hemorrhagic fever on the developing world," *Adv. Virus Res.*, vol. 53, pp. 35-70, 1999.
Guirakhoo et al., "Recombinant chimeric yellow fever-dengue type 2 virus is immunogenic and protective in nonhuman primates," *J. Virol.*, vol. 74, pp. 5477-5485, 2000.
Hahn et al, "Nucleotide sequence of dengue 2 RNA and comparison of the encoded proteins with those of other flaviviruses," *Virol*, vol. 162, No. 1, pp. 167-180, 1988 (abstract only).
Halstead et al., "Dengue and chikungunya virus infection in man in Thailand, 1962-1964. IV. Epidemiologic studies in the Bangkok metropolitan area," *Am. J. Trop. Med. Hyg.*, vol. 18, pp. 997-1021, 1969.
Halstead et al., "Dengue viruses and mononuclear phagocytes. II. Identity of blood and tissue leukocytes supporting in vitro infection," *J. Exp. Med.*, vol. 146, pp. 218-229, 1977.
Hanley et al., "A trade-off in replication in mosquito versus mammalian systems conferred by a point mutation in the ns4b protein of dengue virus type 4," *Virology*, vol. 312, pp. 222-232, 2003.
Hanley et al., "Introduction of mutations into the non-structural genes or 3' untranslated region of an attenuated dengue 44 virus type 4 vaccine candidate further decreases replication in rhesus monkeys while retaining protective immunity," *Vaccine*, vol. 22, pp. 3440-3448, 2004.
Hanley et al., "Paired charge-to-alanine mutagenesis of dengue virus type 4 NS5 generates mutants with temperature-sensitive, host range, and mouse attenuation phenotypes," *J. Virol.*, vol. 76, pp. 525-531, 2002.
Hoke et al., "Preparation of an attenuated dengue 4 (341750 Carib) virus vaccine. 11. Safety and immunogenicity in humans," *Am. J. Trop. Med. Hyg.*, vol. 43, pp. 219-226, 1990.
Holbrook et al., "The French neurotropic vaccine strain of yellow fever virus accumulates mutations slowly during passage in cell culture," *Virus Res.*, No. 69, pp. 31-39, 2000.
Huang et al., "Chimeric dengue type 2 (vaccine strain PDK-53)/dengue type 1 virus as a potential candidate dengue type 1 virus vaccine," *J. Virol.*, vol. 74, pp. 3020-3028, 2000.

(56) References Cited

OTHER PUBLICATIONS

Huerre et al., "Liver histopathology and biological correlates in five cases of fatal dengue fever in Vietnamese children," *Virchows Arch.*, vol. 438, pp. 107-115, 2001.
Igarashi, "Impact of dengue virus infection and its control," *FEMS Immunol. Med. Microbiol.*, vol. 18, pp. 291-300, 1997.
India Patent Office Communication pursuant to India Patent Application No. 204/delnp/2005, dated Jan. 4, 2007.
Innis et al., "Virulence of a live dengue virus vaccine candidate: a possible new marker of dengue virus attenuation," *J. Infect. Dis.*, vol. 158, pp. 876-880, 1988.
Innis, "Dengue and dengue hemorrhagic fever," in *J. S. Porterfield (ed.), Exotic Viral Infections. Chapman and Hall, London, United Kingdom* pp. 103-146, 1995.
Jennings et al., "Analysis of a yellow fever virus isolated from a fatal case of vaccine-associated human encephalitis," *J. Infect. Dis.*, vol. 169, pp. 512-518, 1994.
Kalayanarooj et al., "Early clinical and laboratory indicators of acute dengue illness," *J. Infect. Dis.*, vol. 176, pp. 313-321, 1997.
Kanesa-Thasan et al. "Safety and immunogenicity of attenuated dengue virus vaccines (Aventis Pasteur) in human volunteers," *Vaccine*, vol. 19, pp. 3179-3188, 2001.
Kraiselburd et al., "Quantity of dengue virus required to infect rhesus monkeys," *Trans. R. Soc. Trop. Med. Hyg.*, vol. 79, pp. 248-251, 1985.
Kuno et al., "Full-length sequencing and genomic characterization of Bagaza, Kedougou, and Zika viruses," *Arch Virol*, vol. 152, pp. 687-696, 2007.
Kuo et al., "Liver biochemical tests and dengue fever," *Am. J. Trop. Med. Hyg.*, vol. 47, pp. 265-270, 1992.
Kurane et al., "Dengue-2 virus infection of human mononuclear cell lines and establishment of persistent infections," *Arch. Virol.*, vol. 110, pp. 91-101, 1990.
Lai et al., "Evaluation of molecular strategies to develop a live dengue vaccine," *Clinical and Diagnostic Virology*, vol. 10 (2/3), pp. 173-179, 1998.
Lai et al., "Infectious RNA transcribed from stably cloned full-length cDNA of dengue type 4 virus," *Proc. Natl. Acad. Sci. USA*, vol. 88, pp. 5139-5143, 1991.
Lee et al., "Changes in the dengue virus major envelope protein on passaging and their localization on the three dimensional structure of the protein," *Virology*, vol. 232, pp. 281-290, 1997.
Libraty et al., "Human dendritic cells are activated by dengue virus infection: enhancement by gamma interferon and implications for disease pathogenesis," *J. Virol.*, vol. 75, No. 3501-3508, 2001.
Lin et al., "Analysis of the complete genome of the tick-borne flavivirus Omsk hemorrhagic fever virus," *Virol*, vol. 313, pp. 81-90, 2003.
Lin et al., "Infection of five human liver cell lines by dengue-2 virus," *J. Med. Virol.*, vol. 60, pp. 425-431, 2000.
Lin et al., "Study of dengue virus infection in SCID mice engrafted with human K562 cells," *J. Virol.*, vol. 72, pp. 9729-9737, 1998.
Marchette et al., "Preparation of an attenuated dengue 4 (341750 carib) virus vaccine, pre-clinical studies," *American Journal of Tropical medicine & Hygiene*, vol. 43, No. 2, pp. 212-218, 1990.
Marianneau et al., "Dengue 1 virus binding to human hepatoma HepG2 and simian Vero cell surfaces differs," *J. Gen. Virol.*, vol. 77, pp. 2547-2554, 1996.
Martin et al., "The vaccine origin of the 1968 epidemic of type 3 poliomyelitis in Poland," *Virology*, vol. 278, pp. 42-49, 2000.
McKee et al., "Lack of attenuation of a candidate dengue 1 vaccine (45AZ5) in human volunteers," *Am. J. Trop. Med. Hyg.*, vol. 36, pp. 435-442, 1987.
Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," *Journal of Virology*, vol. 70, No. 6, pp. 3930-3937, 1996.
Mohan et al., "Hepatic dysfunction in childhood dengue infection," *J. Trop. Pediatr.*, vol. 46, pp. 40-43, 2000.
Monath et al., "Recombinant, chimeric live, attenuated vaccine (ChimerfiVax.TM.) incorporating the envelope genes of Japanese encephalitis (SA14-14-2) virus and the capsid and nonstructural genes of yellow fever (17D) virus is safe, immunogenic and protective in non-human primates," *Vaccine*, vol. 17, pp. 1869-1882, 1999.
Murgue et al., "Prospective study of the duration and magnitude of viraemia in children hospitalized during the 1996-1997 dengue-2 outbreak in French Polynesia," *J. Med. Virol.*, vol. 60, pp. 432-438, 2000.
Nakabayashi et al., "Growth of human hepatoma cell lines with differentiated functions in chemically defined medium," *Cancer Res.*, vol. 42, pp. 3858-3863, 1982.
Ni et al., "Molecular basis of attenuation of neurovirulence of wild-type Japanese encephalitis virus strain SA14," *J. Gen. Virol.*, vol. 76, pp. 409-413, 1995.
Pletnev et al., "Attenuation of the Langat tick-borne flavivirus by chimerization with mosquito-borne flavivirus dengue type 4," *PNAS USA*, vol. 95, pp. 1746-1751, 1998.
Puri et al., "Molecular analysis of dengue virus attenuation after serial passage in primary dog kidney cells," *J. Gen. Virol.*, vol. 78, pp. 2287-2291, 1997.
Rosen et al., "Detection of dengue virus RNA by reverse transcription-polymerase chain reaction in the liver and lymphoid organs but not in the brain in fatal human infection," *Am. J. Trop. Med. Hyg.*, vol. 61, pp. 720-724, 1999.
Rothman, "Dengue: defining protective versus pathologic immunity," *J. Clin. Invest.*, vol. 113, No. 7, pp. 946-951, 2004.
Ruiz et al., "Phylogenetic comparison of the DEN-2 Mexican isolate with other flaviviruses," *Intervirol*, vol. 43, pp. 48-54, 2000.
Sabin et al., "Production of immunity to dengue with virus modified by propagation in mice," *Science*, vol. 101, pp. 640-642, 1945.
Sabin, "Recent advances in our knowledge of dengue and sandfly fever," Am. J. Trop. Med. Hyg., vol. 4, pp. 198-207, 1955.
Sabin, "Research on dengue during World War II," *Am. J. Trop. Med. Hyg.*, vol. 1, pp. 30-50, 1952.
Scott et al., "Isolation of dengue viruses from peripheral blood leukocytes of patients with hemorrhagic fever," *J. Infect. Dis.*, vol. 141, pp. 1-6, 1980.
Stephenson, "Understanding dengue pathogenesis: implications for vaccine design," *Bull, WHO*, vol. 83, pp. 308-314, 2005.
Thein et al., "Risk factors in dengue shock syndrome," *Am. J. Trop. Med. Hyg.*, vol. 56, pp. 566-572, 1997.
Theofilopoulos et al., "Replication of dengue-2 virus in cultured human lymphoblastoid cells and subpopulations of human peripheral leukocytes," *J. Immunol.*, vol. 117, pp. 953-961, 1976.
Thomas et al., "The necessity and quandaries of dengue vaccine development," *J. Infect. Dis.*, vol. 203, pp. 299-303, 2011.
Troye et al., "A live attenuated recombinant dengue-4 virus vaccine candidate with restricted capacity for dissemination in mosquitoes and lack of transmission from vaccines to mosquitoes," *Am. J. Trop. Med. Hyg.*, vol. 65, pp. 414-419, 2001.
Valle et al., "Mutagenesis of the NS3 protease of dengue virus type 2," *J. Virol.*, vol. 72, pp. 624-632, 1998.
Vaughn et al., "Dengue viremia titer, antibody response pattern, and virus serotype correlate with disease severity," *J. Infect. Dis.*, vol. 181, pp. 2-9, 2000.
Vaughn et al., "Testing of a dengue 2 live-attenuated vaccine (strain 16681 PDK 53) in ten American volunteers," *Vaccine*, vol. 14, pp. 329-336, 1996.
Wahid et al., "A comparison of the pattern of liver involvement in dengue hemorrhagic fever with classic dengue fever," *Southeast Asian J. Trop. Med. Public Health*, vol. 31, pp. 259-263, 2000.
Wang et al., "Comparison of the genomes of the wild-type French viscerotropic strain of yellow fever virus with its vaccine derivative French neurotropic vaccine," *J. Gen. Virol.*, vol. 76, pp. 2749-2755, 1995.
Watts et al., "Evaluation of Toxorhynchites splendens (Diptera:Culicidae) as a bioassay host for dengue viruses," *J. Med. Entomol.*, vol. 19, pp. 54-59, 1982.

(56) References Cited

OTHER PUBLICATIONS

Whitehead et al., "A live attenuated dengue virus type 1 vaccine candidate with a 30-nucleotide deletion in the 3' untranslated region is highly attenuated and immunogenic in monkeys," *J. Virol.*, vol. 77, pp. 1653-1657, 2003.
Whitehead et al., "Substitution of the structural genes of dengue virus type 4 with those of type 2 results in chimeric vaccine candidates which are attenuated for mosquitoes, mice, and rhesus monkeys," *Vaccine*, vol. 21, pp. 4307-4316, 2003.
Wisseman et al., "Attenuated living type 1 dengue vaccines," *Am J. Trop. Med. Hyg.*, vol. 12, pp. 620-623, 1963.
Wu et al., "Human skin Langerhans cells are targets of dengue virus infection," *Nat. Med.*, vol. 6, pp. 816-820, 2000.
Yauch et al., "Mouse models of dengue virus infection and disease," *Antivir. Res.* vol. 80, pp. 87-93, 2008.
Yoshii et al., "Construction of an infectious cDNA clone for Omsk hemorrhagic fever virus, and characterization of mutations in NS2A and NS5," *Vir. Res.*, vol. 155, pp. 61-68, 2011.

* cited by examiner

FIG. 4A
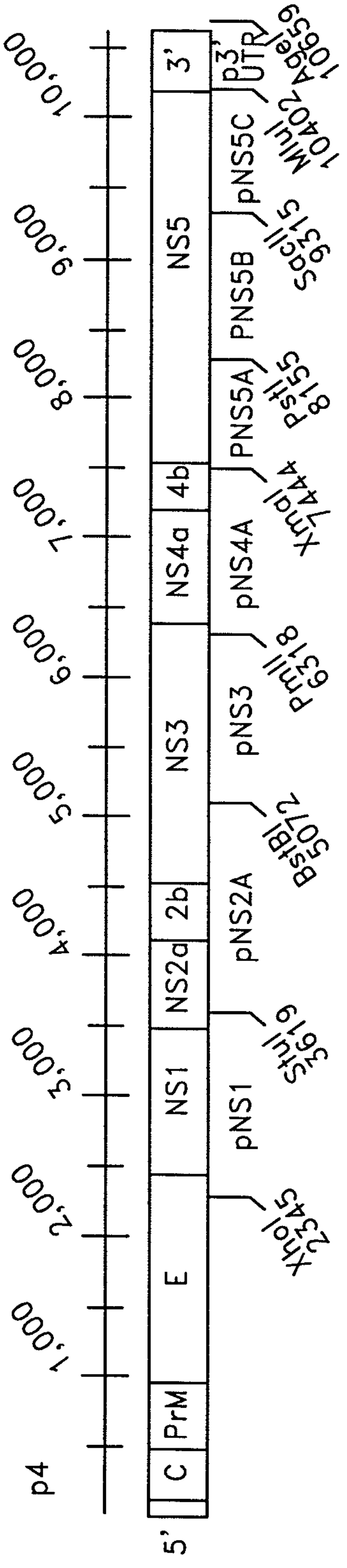
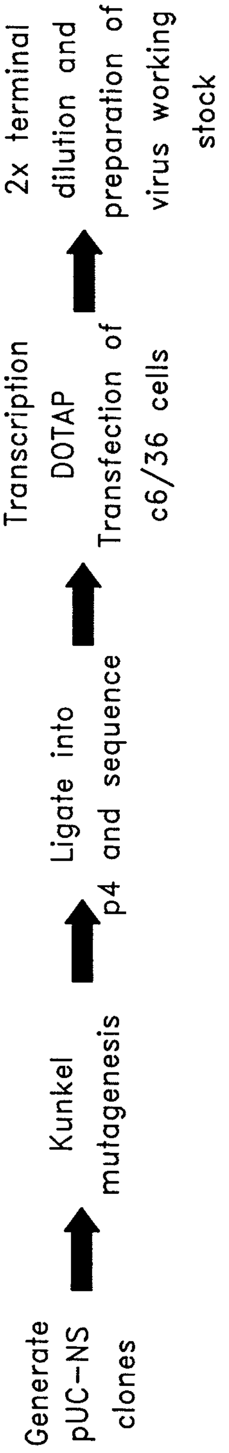
FIG. 4B

```
1   GTGTTGETLG EKWKRQLNSL DRKEFEEYKR SGILEVDRTE AKSALKDGSK    SAM
51  IKHAVSRGSS KIRWIVERGM VKPKGKVVDL GCGRGGWSYY MATLKNVTEV
101 KGYTKGGPGH EEPIPMATYG WNLVKLHSGV DVFYKPTEQV DTLLCDIGES
151 SSNPTIEEGR TLRVLKMVEP WLSSKPEFCI KVLNPYMPTV IEELEKLQRK
201 HGGNLVRCPL SRNSTHEMYW VSGASGNIVS SVNTTSKMLL NRFTTRHRKP
251 TYEKDVDLGA GTRSVSTETE KPDMTIIGRR LQRLQEEHKE TWHYDQENPY
301 RTWAYHGSYE APSTGSASSM VNGVVKLLTK PWDVIPMVTQ LAMTDTTPFG    Importin -
351 QQRVFKEKVD TRTPQPKPGT RMVMTTTANW LWALLGKKKN PRLCTREEFI    binding +
401 SKVRSNAAIG AVFQEEQGWT SASEAVNDSR FWELVDKERA LHQEGKCESC    NLS
451 VYNMMGKREK KLGEFGRAKG SRAIWYMWLG ARFLEFEALG FLNEDHWFGR
501 ENSWSGVEGE GLHRLGYILE EIDKKDGDLM YADDTAGWDT RITEDDLQNE
551 ELITEQMAPH HKILAKAIFK LTYQNKVVKV LRPTPRGAVM DIISRKDQRG
601 SGQVGTYGLN TFTNMEVQLI RQMEAEGVIT QDDMQNPKGL KERVEKWLKE
651 CGVDRLKRMA ISGDDCVVKP LDERFGTSLL FLNDMGKVRK DIPQWEPSKG    Polymerase
701 WKNWQEVPFC SHHFHKIFMK DGRSLVVPCR NQDELIGRAR ISQGAGWSLR
751 ETACLGKAYA QMWSLMYFHR RDLRLASMAI CSAVPTEWFP TSRTTWSIHA
801 HHQWMTTEDM LKVWNRVWIE DNPNMTDKTP VHSWEDIPYL GKREDLWCGS
851 LIGLSSRATW AKNIHTAITQ VRNLIGKEEY VDYMPVMKRY SAPSESEGVL
```

*FIG. 5*

SEQUENCE LISTING

```
<160> NUMBER OF SEQ ID NOS: 70

<210> SEQ ID NO 1
<211> LENGTH: 900
<212> TYPE: PRT
<213> ORGANISM: Dengue 4 virus

<400> SEQUENCE: 1

Gly Thr Gly Thr Thr Gly Glu Thr Leu Gly Glu Lys Trp Lys Arg Gln
1               5                   10                  15

Leu Asn Ser Leu Asp Arg Lys Glu Phe Glu Glu Tyr Lys Arg Ser Gly
            20                  25                  30

Ile Leu Glu Val Asp Arg Thr Glu Ala Lys Ser Ala Leu Lys Asp Gly
        35                  40                  45

Ser Lys Ile Lys His Ala Val Ser Arg Gly Ser Ser Lys Ile Arg Trp
    50                  55                  60

Ile Val Glu Arg Gly Met Val Lys Pro Lys Gly Lys Val Val Asp Leu
65                  70                  75                  80

Gly Cys Gly Arg Gly Gly Trp Ser Tyr Tyr Met Ala Thr Leu Lys Asn
                85                  90                  95

Val Thr Glu Val Lys Gly Tyr Thr Lys Gly Gly Pro Gly His Glu Glu
            100                 105                 110

Pro Ile Pro Met Ala Thr Tyr Gly Trp Asn Leu Val Lys Leu His Ser
        115                 120                 125

Gly Val Asp Val Phe Tyr Lys Pro Thr Glu Gln Val Asp Thr Leu Leu
    130                 135                 140

Cys Asp Ile Gly Glu Ser Ser Ser Asn Pro Thr Ile Glu Glu Gly Arg
145                 150                 155                 160

Thr Leu Arg Val Leu Lys Met Val Glu Pro Trp Leu Ser Ser Lys Pro
                165                 170                 175

Glu Phe Cys Ile Lys Val Leu Asn Pro Tyr Met Pro Thr Val Ile Glu
            180                 185                 190

Glu Leu Glu Lys Leu Gln Arg Lys His Gly Gly Asn Leu Val Arg Cys
        195                 200                 205

Pro Leu Ser Arg Asn Ser Thr His Glu Met Tyr Trp Val Ser Gly Ala
    210                 215                 220

Ser Gly Asn Ile Val Ser Ser Val Asn Thr Thr Ser Lys Met Leu Leu
225                 230                 235                 240

Asn Arg Phe Thr Thr Arg His Arg Lys Pro Thr Tyr Glu Lys Asp Val
                245                 250                 255

Asp Leu Gly Ala Gly Thr Arg Ser Val Ser Thr Glu Thr Glu Lys Pro
            260                 265                 270

Asp Met Thr Ile Ile Gly Arg Arg Leu Gln Arg Leu Gln Glu Glu His
        275                 280                 285

Lys Glu Thr Trp His Tyr Asp Gln Glu Asn Pro Tyr Arg Thr Trp Ala
    290                 295                 300

Tyr His Gly Ser Tyr Glu Ala Pro Ser Thr Gly Ser Ala Ser Ser Met
305                 310                 315                 320
```

```
Val Asn Gly Val Val Lys Leu Leu Thr Lys Pro Trp Asp Val Ile Pro
                325                 330                 335

Met Val Thr Gln Leu Ala Met Thr Asp Thr Thr Pro Phe Gly Gln Gln
            340                 345                 350

Arg Val Phe Lys Glu Lys Val Asp Thr Arg Thr Pro Gln Pro Lys Pro
        355                 360                 365

Gly Thr Arg Met Val Met Thr Thr Thr Ala Asn Trp Leu Trp Ala Leu
    370                 375                 380

Leu Gly Lys Lys Lys Asn Pro Arg Leu Cys Thr Arg Glu Glu Phe Ile
385                 390                 395                 400

Ser Lys Val Arg Ser Asn Ala Ala Ile Gly Ala Val Phe Gln Glu Glu
                405                 410                 415

Gln Gly Trp Thr Ser Ala Ser Glu Ala Val Asn Asp Ser Arg Phe Trp
            420                 425                 430

Glu Leu Val Asp Lys Glu Arg Ala Leu His Gln Glu Gly Lys Cys Glu
        435                 440                 445

Ser Cys Val Tyr Asn Met Met Gly Lys Arg Glu Lys Lys Leu Gly Glu
    450                 455                 460

Phe Gly Arg Ala Lys Gly Ser Arg Ala Ile Trp Tyr Met Trp Leu Gly
465                 470                 475                 480

Ala Arg Phe Leu Glu Phe Glu Ala Leu Gly Phe Leu Asn Glu Asp His
                485                 490                 495

Trp Phe Gly Arg Glu Asn Ser Trp Ser Gly Val Glu Gly Glu Gly Leu
            500                 505                 510

His Arg Leu Gly Tyr Ile Leu Glu Glu Ile Asp Lys Lys Asp Gly Asp
        515                 520                 525

Leu Met Tyr Ala Asp Asp Thr Ala Gly Trp Asp Thr Arg Ile Thr Glu
    530                 535                 540

Asp Asp Leu Gln Asn Glu Glu Leu Ile Thr Glu Gln Met Ala Pro His
545                 550                 555                 560

His Lys Ile Leu Ala Lys Ala Ile Phe Lys Leu Thr Tyr Gln Asn Lys
                565                 570                 575

Val Val Lys Val Leu Arg Pro Thr Pro Arg Gly Ala Val Met Asp Ile
            580                 585                 590

Ile Ser Arg Lys Asp Gln Arg Gly Ser Gly Gln Val Gly Thr Tyr Gly
        595                 600                 605

Leu Asn Thr Phe Thr Asn Met Glu Val Gln Leu Ile Arg Gln Met Glu
    610                 615                 620

Ala Glu Gly Val Ile Thr Gln Asp Asp Met Gln Asn Pro Lys Gly Leu
625                 630                 635                 640

Lys Glu Arg Val Glu Lys Trp Leu Lys Glu Cys Gly Val Asp Arg Leu
                645                 650                 655

Lys Arg Met Ala Ile Ser Gly Asp Asp Cys Val Val Lys Pro Leu Asp
            660                 665                 670

Glu Arg Phe Gly Thr Ser Leu Leu Phe Leu Asn Asp Met Gly Lys Val
        675                 680                 685

Arg Lys Asp Ile Pro Gln Trp Glu Pro Ser Lys Gly Trp Lys Asn Trp
    690                 695                 700

Gln Glu Val Pro Phe Cys Ser His His Phe His Lys Ile Phe Met Lys
705                 710                 715                 720

Asp Gly Arg Ser Leu Val Val Pro Cys Arg Asn Gln Asp Glu Leu Ile
                725                 730                 735

Gly Arg Ala Arg Ile Ser Gln Gly Ala Gly Trp Ser Leu Arg Glu Thr
```

```
            740                 745                 750

Ala Cys Leu Gly Lys Ala Tyr Ala Gln Met Trp Ser Leu Met Tyr Phe
        755                 760                 765

His Arg Arg Asp Leu Arg Leu Ala Ser Met Ala Ile Cys Ser Ala Val
    770                 775                 780

Pro Thr Glu Trp Phe Pro Thr Ser Arg Thr Thr Trp Ser Ile His Ala
785                 790                 795                 800

His His Gln Trp Met Thr Thr Glu Asp Met Leu Lys Val Trp Asn Arg
                805                 810                 815

Val Trp Ile Glu Asp Asn Pro Asn Met Thr Asp Lys Thr Pro Val His
            820                 825                 830

Ser Trp Glu Asp Ile Pro Tyr Leu Gly Lys Arg Glu Asp Leu Trp Cys
        835                 840                 845

Gly Ser Leu Ile Gly Leu Ser Ser Arg Ala Thr Trp Ala Lys Asn Ile
    850                 855                 860

His Thr Ala Ile Thr Gln Val Arg Asn Leu Ile Gly Lys Glu Glu Tyr
865                 870                 875                 880

Val Asp Tyr Met Pro Val Met Lys Arg Tyr Ser Ala Pro Ser Glu Ser
                885                 890                 895

Glu Gly Val Leu
            900


<210> SEQ ID NO 2
<211> LENGTH: 233
<212> TYPE: DNA
<213> ORGANISM: Dengue 4 virus

<400> SEQUENCE: 2

gactagcggt tagaggagac ccctcccatc actgataaaa cgcagcaaaa gggggcccga      60

agccaggagg aagctgtact cctggtggaa ggactagagg ttagaggaga cccccccaac     120

acaaaaacag catattgacg ctgggaaaga ccagagatcc tgctgtctct gcaacatcaa     180

tccaggcaca gagcgccgca agatggattg gtgttgttga tccaacaggt tct            233


<210> SEQ ID NO 3
<211> LENGTH: 228
<212> TYPE: DNA
<213> ORGANISM: Dengue 1 virus

<400> SEQUENCE: 3

gactagtggt tagaggagac ccctcccaag acacaacgca gcagcggggc ccaacaccag      60

gggaagctgt accctggtgg taaggactag aggttagagg agacccccccg cacaacaaca     120

aacagcatat tgacgctggg agagaccaga gatcctgctg tctctacagc atcattccag     180

gcacagaacg ccaaaaaatg gaatggtgct gttgaatcaa caggttct                  228


<210> SEQ ID NO 4
<211> LENGTH: 230
<212> TYPE: DNA
<213> ORGANISM: Dengue 2 virus

<400> SEQUENCE: 4

gactagcggt tagaggagac ccctccctta caaatcgcag caacaatggg ggcccaaggt      60

gagatgaagc tgtagtctca ctggaaggac tagaggttag aggagacccc cccaaaacaa     120

aaaacagcat attgacgctg ggaaagacca gagatcctgc tgtctcctca gcatcattcc     180

aggcacagaa cgccagaaaa tggaatggtg ctgttgaatc aacaggttct                230
```

<210> SEQ ID NO 5
<211> LENGTH: 227
<212> TYPE: DNA
<213> ORGANISM: Dengue 3 virus

<400> SEQUENCE: 5
gactagtggt tagaggagac ccctcccatg acacaacgca gcagcggggc ccgagcactg 60
agggaagctg tacctccttg caaaggacta gaggttatag gagacccccc gcaaacaaaa 120
acagcatatt gacgctggga gagaccagag atcctgctgt ctcctcagca tcattccagg 180
cacagaacgc cagaaaatgg aatggtgctg ttgaatcaac aggttct 227

<210> SEQ ID NO 6
<211> LENGTH: 227
<212> TYPE: DNA
<213> ORGANISM: West Nile virus

<400> SEQUENCE: 6
gactagaggt tagaggagac cccgcgtaaa aaagtgcacg gcccaacttg gctgaagctg 60
taagccaagg gaaggactag aggttagagg agaccccgtg ccaaaaacac caaaagaaac 120
agcatattga cacctgggat agactagggg atcttctgct ctgcacaacc agccacacgg 180
cacagtgcgc cgacataggt ggctggtggt gctagaacac aggatct 227

<210> SEQ ID NO 7
<211> LENGTH: 229
<212> TYPE: DNA
<213> ORGANISM: Japanese encephalitis virus

<400> SEQUENCE: 7
gactagaggt tagaggagac cccgtggaaa caacaacatg cggcccaagc cccctcgaag 60
ctgtagagga ggtggaagga ctagaggtta gaggagaccc cgcatttgca tcaaacagca 120
tattgacacc tgggaataga ctgggagatc ttctgctcta tctcaacatc agctactagg 180
cacagagcgc cgaagtatgt acgtggtggt gaggaagaac acaggatct 229

<210> SEQ ID NO 8
<211> LENGTH: 241
<212> TYPE: DNA
<213> ORGANISM: Yellow fever virus

<400> SEQUENCE: 8
aacctggttt ctgggacctc ccaccccaga gtaaaaagaa cggagcctcc gctaccaccc 60
tcccacgtgg tggtagaaag acggggtcta gaggttagag gagaccctcc agggaacaaa 120
tagtgggacc atattgacgc cagggaaaga ccggagtggt tctctgcttt tcctccagag 180
gtctgtgagc acagtttgct caagaataag cagacctttg gatgacaaac acaaaaccac 240
t 241

<210> SEQ ID NO 9
<211> LENGTH: 249
<212> TYPE: DNA
<213> ORGANISM: Powassan virus

<400> SEQUENCE: 9
aaacgaactt tgtgagacca aaaggcctcc tggaaggctc accaggagtt aggccgttta 60
ggagcccccg agcataactc gggaggaggg aggaagaaaa ttggcaatct tcctcgggat 120

-continued

```
ttttccgcct cctatactaa atttccccca ggaaactggg ggggcggttc ttgttctccc    180

tgagccacca ccatccaggc acagatagcc tgacaaggag atggtgtgtg actcggaaaa    240

acacccgct                                                            249


<210> SEQ ID NO 10
<211> LENGTH: 250
<212> TYPE: DNA
<213> ORGANISM: Louping ill virus

<400> SEQUENCE: 10

tgcaagattt tgcgagaccc cccgccccat gacaaggccg aacatggagc attaaaggga     60

ggcccccgga agcatgcttc cgggaggagg gaagagagaa attggcagct ctcttcaggg    120

tttttcctcc tcctatacca aatttccccc tcgacagagg gggggcggtt cttgttctcc    180

ctgagccacc atcacccaga cacagatagt ctgacaagga ggtgatgtgt gactcggaaa    240

aacacccgct                                                           250


<210> SEQ ID NO 11
<211> LENGTH: 250
<212> TYPE: DNA
<213> ORGANISM: Tick-borne encephalitis virus

<400> SEQUENCE: 11

tgaaaaattt tgtgagaccc cctgcatcat gataaggccg aacatggtgc atgaaagggg     60

aggcccccgg aagcacgctt ccgggaggag ggaagagaga aattggcagc tctcttcagg    120

atttttcctc ctcctataca aaattccccc tcggtagagg gggggcggtt cttgttctcc    180

ctgagccacc atcacccaga cacaggtagt ctgacaagga ggtgatgtgt gactcggaaa    240

aacacccgct                                                           250


<210> SEQ ID NO 12
<211> LENGTH: 247
<212> TYPE: DNA
<213> ORGANISM: Langat virus

<400> SEQUENCE: 12

tgtgaaactt tgtgagaccc cttgcgtcca gagaaggccg aactgggcgt tataaggagg     60

cccccagggg gaaacccctg ggaggaggga agagagaaat tggcaactct cttcaggata    120

tttcctcctc ctataccaaa ttccccctcg tcagaggggg ggcggttctt gttctccctg    180

agccaccatc acctagacac agatagtctg aaaaggaggt gatgcgtgtc tcggaaaaac    240

acccgct                                                              247


<210> SEQ ID NO 13
<211> LENGTH: 3387
<212> TYPE: PRT
<213> ORGANISM: Dengue 4 virus strain 2A

<400> SEQUENCE: 13

Met Asn Gln Arg Lys Lys Val Val Arg Pro Pro Phe Asn Met Leu Lys
1               5                   10                  15

Arg Glu Arg Asn Arg Val Ser Thr Pro Gln Gly Leu Val Lys Arg Phe
            20                  25                  30

Ser Thr Gly Leu Phe Ser Gly Lys Gly Pro Leu Arg Met Val Leu Ala
        35                  40                  45

Phe Ile Thr Phe Leu Arg Val Leu Ser Ile Pro Pro Thr Ala Gly Ile
    50                  55                  60
```

```
Leu Lys Arg Trp Gly Gln Leu Lys Lys Asn Lys Ala Ile Lys Ile Leu
65                  70                  75                  80

Ile Gly Phe Arg Lys Glu Ile Gly Arg Met Leu Asn Ile Leu Asn Gly
                85                  90                  95

Arg Lys Arg Ser Thr Ile Thr Leu Leu Cys Leu Ile Pro Thr Val Met
            100                 105                 110

Ala Phe Ser Leu Ser Thr Arg Asp Gly Glu Pro Leu Met Ile Val Ala
        115                 120                 125

Lys His Glu Arg Gly Arg Pro Leu Leu Phe Lys Thr Thr Glu Gly Ile
    130                 135                 140

Asn Lys Cys Thr Leu Ile Ala Met Asp Leu Gly Glu Met Cys Glu Asp
145                 150                 155                 160

Thr Val Thr Tyr Lys Cys Pro Leu Leu Val Asn Thr Glu Pro Glu Asp
                165                 170                 175

Ile Asp Cys Trp Cys Asn Leu Thr Ser Thr Trp Val Met Tyr Gly Thr
            180                 185                 190

Cys Thr Gln Ser Gly Glu Arg Arg Arg Glu Lys Arg Ser Val Ala Leu
        195                 200                 205

Thr Pro His Ser Gly Met Gly Leu Glu Thr Arg Ala Glu Thr Trp Met
    210                 215                 220

Ser Ser Glu Gly Ala Trp Lys His Ala Gln Arg Val Glu Ser Trp Ile
225                 230                 235                 240

Leu Arg Asn Pro Gly Phe Ala Leu Leu Ala Gly Phe Met Ala Tyr Met
                245                 250                 255

Ile Gly Gln Thr Gly Ile Gln Arg Thr Val Phe Phe Val Leu Met Met
            260                 265                 270

Leu Val Ala Pro Ser Tyr Gly Met Arg Cys Val Gly Val Gly Asn Arg
        275                 280                 285

Asp Phe Val Glu Gly Val Ser Gly Gly Ala Trp Val Asp Leu Val Leu
    290                 295                 300

Glu His Gly Gly Cys Val Thr Thr Met Ala Gln Gly Lys Pro Thr Leu
305                 310                 315                 320

Asp Phe Glu Leu Thr Lys Thr Thr Ala Lys Glu Val Ala Leu Leu Arg
                325                 330                 335

Thr Tyr Cys Ile Glu Ala Ser Ile Ser Asn Ile Thr Thr Ala Thr Arg
            340                 345                 350

Cys Pro Thr Gln Gly Glu Pro Tyr Leu Lys Glu Glu Gln Asp Gln Gln
        355                 360                 365

Tyr Ile Cys Arg Arg Asp Val Val Asp Arg Gly Trp Gly Asn Gly Cys
    370                 375                 380

Gly Leu Phe Gly Lys Gly Gly Val Val Thr Cys Ala Lys Phe Ser Cys
385                 390                 395                 400

Ser Gly Lys Ile Thr Gly Asn Leu Val Gln Ile Glu Asn Leu Glu Tyr
                405                 410                 415

Thr Val Val Val Thr Val His Asn Gly Asp Thr His Ala Val Gly Asn
            420                 425                 430

Asp Thr Ser Asn His Gly Val Thr Ala Met Ile Thr Pro Arg Ser Pro
        435                 440                 445

Ser Val Glu Val Lys Leu Pro Asp Tyr Gly Glu Leu Thr Leu Asp Cys
    450                 455                 460

Glu Pro Arg Ser Gly Ile Asp Phe Asn Glu Met Ile Leu Met Lys Met
465                 470                 475                 480
```

-continued

```
Lys Lys Lys Thr Trp Leu Val His Lys Gln Trp Phe Leu Asp Leu Pro
                485                 490                 495

Leu Pro Trp Thr Ala Gly Ala Asp Thr Ser Glu Val His Trp Asn Tyr
            500                 505                 510

Lys Glu Arg Met Val Thr Phe Lys Val Pro His Ala Lys Arg Gln Asp
        515                 520                 525

Val Thr Val Leu Gly Ser Gln Glu Gly Ala Met His Ser Ala Leu Ala
    530                 535                 540

Gly Ala Thr Glu Val Asp Ser Gly Asp Gly Asn His Met Phe Ala Gly
545                 550                 555                 560

His Leu Lys Cys Lys Val Arg Met Glu Lys Leu Arg Ile Lys Gly Met
                565                 570                 575

Ser Tyr Thr Met Cys Ser Gly Lys Phe Ser Ile Asp Lys Glu Met Ala
            580                 585                 590

Glu Thr Gln His Gly Thr Thr Val Val Lys Val Lys Tyr Glu Gly Ala
        595                 600                 605

Gly Ala Pro Cys Lys Val Pro Ile Glu Ile Arg Asp Val Asn Lys Glu
    610                 615                 620

Lys Val Val Gly Arg Ile Ile Ser Ser Thr Pro Leu Ala Glu Asn Thr
625                 630                 635                 640

Asn Ser Val Thr Asn Ile Glu Leu Glu Pro Pro Phe Gly Asp Ser Tyr
                645                 650                 655

Ile Val Ile Gly Val Gly Asn Ser Ala Leu Thr Leu His Trp Phe Arg
            660                 665                 670

Lys Gly Ser Ser Ile Gly Lys Met Phe Glu Ser Thr Tyr Arg Gly Ala
        675                 680                 685

Lys Arg Met Ala Ile Leu Gly Glu Thr Ala Trp Asp Phe Gly Ser Val
    690                 695                 700

Gly Gly Leu Phe Thr Ser Leu Gly Lys Ala Val His Gln Val Phe Gly
705                 710                 715                 720

Ser Val Tyr Thr Thr Met Phe Gly Gly Val Ser Trp Met Ile Arg Ile
                725                 730                 735

Leu Ile Gly Phe Leu Val Leu Trp Ile Gly Thr Asn Ser Arg Asn Thr
            740                 745                 750

Ser Met Ala Met Thr Cys Ile Ala Val Gly Gly Ile Thr Leu Phe Leu
        755                 760                 765

Gly Phe Thr Val Gln Ala Asp Met Gly Cys Val Val Ser Trp Ser Gly
    770                 775                 780

Lys Glu Leu Lys Cys Gly Ser Gly Ile Phe Val Val Asp Asn Val His
785                 790                 795                 800

Thr Trp Thr Glu Gln Tyr Lys Phe Gln Pro Glu Ser Pro Ala Arg Leu
                805                 810                 815

Ala Ser Ala Ile Leu Asn Ala His Lys Asp Gly Val Cys Gly Ile Arg
            820                 825                 830

Ser Thr Thr Arg Leu Glu Asn Val Met Trp Lys Gln Ile Thr Asn Glu
        835                 840                 845

Leu Asn Tyr Val Leu Trp Glu Gly Gly His Asp Leu Thr Val Val Ala
    850                 855                 860

Gly Asp Val Lys Gly Val Leu Thr Lys Gly Lys Arg Ala Leu Thr Pro
865                 870                 875                 880

Pro Val Ser Asp Leu Lys Tyr Ser Trp Lys Thr Trp Gly Lys Ala Lys
                885                 890                 895

Ile Phe Thr Pro Glu Ala Arg Asn Ser Thr Phe Leu Ile Asp Gly Pro
```

```
            900                 905                 910

Asp Thr Ser Glu Cys Pro Asn Glu Arg Arg Ala Trp Asn Ser Leu Glu
        915                 920                 925

Val Glu Asp Tyr Gly Phe Gly Met Phe Thr Thr Asn Ile Trp Met Lys
    930                 935                 940

Phe Arg Glu Gly Ser Ser Glu Val Cys Asp His Arg Leu Met Ser Ala
945                 950                 955                 960

Ala Ile Lys Asp Gln Lys Ala Val His Ala Asp Met Gly Tyr Trp Ile
                965                 970                 975

Glu Ser Ser Lys Asn Gln Thr Trp Gln Ile Glu Lys Ala Ser Leu Ile
            980                 985                 990

Glu Val Lys Thr Cys Leu Trp Pro  Lys Thr His Thr Leu  Trp Ser Asn
        995                 1000                1005

Gly Val  Leu Glu Ser Gln Met  Leu Ile Pro Lys Ser  Tyr Ala Gly
    1010                 1015                 1020

Pro Phe  Ser Gln His Asn Tyr  Arg Gln Gly Tyr Ala  Thr Gln Thr
    1025                 1030                 1035

Val Gly  Pro Trp His Leu Gly  Lys Leu Glu Ile Asp  Phe Gly Glu
    1040                 1045                 1050

Cys Pro  Gly Thr Thr Val Thr  Ile Gln Glu Asp Cys  Asp His Arg
    1055                 1060                 1065

Gly Pro  Ser Leu Arg Thr Thr  Thr Ala Ser Gly Lys  Leu Val Thr
    1070                 1075                 1080

Gln Trp  Cys Cys Arg Ser Cys  Thr Met Pro Pro Leu  Arg Phe Leu
    1085                 1090                 1095

Gly Glu  Asp Gly Cys Trp Tyr  Gly Met Glu Ile Arg  Pro Leu Ser
    1100                 1105                 1110

Glu Lys  Glu Glu Asn Met Val  Lys Ser Gln Val Thr  Ala Gly Gln
    1115                 1120                 1125

Gly Thr  Ser Glu Thr Phe Ser  Met Gly Leu Leu Cys  Leu Thr Leu
    1130                 1135                 1140

Phe Val  Glu Glu Cys Leu Arg  Arg Arg Val Thr Arg  Lys His Met
    1145                 1150                 1155

Ile Leu  Val Val Val Ile Thr  Leu Cys Ala Ile Ile  Leu Gly Gly
    1160                 1165                 1170

Leu Thr  Trp Met Asp Leu Leu  Arg Ala Leu Ile Met  Leu Gly Asp
    1175                 1180                 1185

Thr Met  Ser Gly Arg Ile Gly  Gly Gln Ile His Leu  Ala Ile Met
    1190                 1195                 1200

Ala Val  Phe Lys Met Ser Pro  Gly Tyr Val Leu Gly  Val Phe Leu
    1205                 1210                 1215

Arg Lys  Leu Thr Ser Arg Glu  Thr Ala Leu Met Val  Ile Gly Met
    1220                 1225                 1230

Ala Met  Thr Thr Val Leu Ser  Ile Pro His Asp Leu  Met Glu Leu
    1235                 1240                 1245

Ile Asp  Gly Ile Ser Leu Gly  Leu Ile Leu Leu Lys  Ile Val Thr
    1250                 1255                 1260

Gln Phe  Asp Asn Thr Gln Val  Gly Thr Leu Ala Leu  Ser Leu Thr
    1265                 1270                 1275

Phe Ile  Arg Ser Thr Met Pro  Leu Val Met Ala Trp  Arg Thr Ile
    1280                 1285                 1290

Met Ala  Val Leu Phe Val Val  Thr Leu Ile Pro Leu  Cys Arg Thr
    1295                 1300                 1305
```

```
Ser Cys  Leu Gln Lys Gln Ser  His Trp Val Glu Ile  Thr Ala Leu
    1310                 1315                 1320

Ile Leu  Gly Ala Gln Ala Leu  Pro Val Tyr Leu Met  Thr Leu Met
    1325                 1330                 1335

Lys Gly  Ala Ser Arg Arg Ser  Trp Pro Leu Asn Glu  Gly Ile Met
    1340                 1345                 1350

Ala Val  Gly Leu Val Ser Leu  Leu Gly Ser Ala Leu  Leu Lys Asn
    1355                 1360                 1365

Asp Val  Pro Leu Ala Gly Pro  Met Val Ala Gly Gly  Leu Leu Leu
    1370                 1375                 1380

Ala Ala  Tyr Val Met Ser Gly  Ser Ser Ala Asp Leu  Ser Leu Glu
    1385                 1390                 1395

Lys Ala  Ala Asn Val Gln Trp  Asp Glu Met Ala Asp  Ile Thr Gly
    1400                 1405                 1410

Ser Ser  Pro Ile Ile Glu Val  Lys Gln Asp Glu Asp  Gly Ser Phe
    1415                 1420                 1425

Ser Ile  Arg Asp Val Glu Glu  Thr Asn Met Ile Thr  Leu Leu Val
    1430                 1435                 1440

Lys Leu  Ala Leu Ile Thr Val  Ser Gly Leu Tyr Pro  Leu Ala Ile
    1445                 1450                 1455

Pro Val  Thr Met Thr Leu Trp  Tyr Met Trp Gln Val  Lys Thr Gln
    1460                 1465                 1470

Arg Ser  Gly Ala Leu Trp Asp  Val Pro Ser Pro Ala  Ala Thr Lys
    1475                 1480                 1485

Lys Ala  Ala Leu Ser Glu Gly  Val Tyr Arg Ile Met  Gln Arg Gly
    1490                 1495                 1500

Leu Phe  Gly Lys Thr Gln Val  Gly Val Gly Ile His  Met Glu Gly
    1505                 1510                 1515

Val Phe  His Thr Met Trp His  Val Thr Arg Gly Ser  Val Ile Cys
    1520                 1525                 1530

His Glu  Thr Gly Arg Leu Glu  Pro Ser Trp Ala Asp  Val Arg Asn
    1535                 1540                 1545

Asp Met  Ile Ser Tyr Gly Gly  Gly Trp Arg Leu Gly  Asp Lys Trp
    1550                 1555                 1560

Asp Lys  Glu Glu Asp Val Gln  Val Leu Ala Ile Glu  Pro Gly Lys
    1565                 1570                 1575

Asn Pro  Lys His Val Gln Thr  Lys Pro Gly Leu Phe  Lys Thr Leu
    1580                 1585                 1590

Thr Gly  Glu Ile Gly Ala Val  Thr Leu Asp Phe Lys  Pro Gly Thr
    1595                 1600                 1605

Ser Gly  Ser Pro Ile Ile Asn  Arg Lys Gly Lys Val  Ile Gly Leu
    1610                 1615                 1620

Tyr Gly  Asn Gly Val Val Thr  Lys Ser Gly Asp Tyr  Val Ser Ala
    1625                 1630                 1635

Ile Thr  Gln Ala Glu Arg Ile  Gly Glu Pro Asp Tyr  Glu Val Asp
    1640                 1645                 1650

Glu Asp  Ile Phe Arg Lys Lys  Arg Leu Thr Ile Met  Asp Leu His
    1655                 1660                 1665

Pro Gly  Ala Gly Lys Thr Lys  Arg Ile Leu Pro Ser  Ile Val Arg
    1670                 1675                 1680

Glu Ala  Leu Lys Arg Arg Leu  Arg Thr Leu Ile Leu  Ala Pro Thr
    1685                 1690                 1695
```

```
Arg Val  Val Ala Ala Glu Met  Glu Glu Ala Leu Arg  Gly Leu Pro
    1700                 1705                 1710

Ile Arg  Tyr Gln Thr Pro Ala  Val Lys Ser Glu His  Thr Gly Arg
    1715                 1720                 1725

Glu Ile  Val Asp Leu Met Cys  His Ala Thr Phe Thr  Thr Arg Leu
    1730                 1735                 1740

Leu Ser  Ser Thr Arg Val Pro  Asn Tyr Asn Leu Ile  Val Met Asp
    1745                 1750                 1755

Glu Ala  His Phe Thr Asp Pro  Ser Ser Val Ala Ala  Arg Gly Tyr
    1760                 1765                 1770

Ile Ser  Thr Arg Val Glu Met  Gly Glu Ala Ala Ala  Ile Phe Met
    1775                 1780                 1785

Thr Ala  Thr Pro Pro Gly Ala  Thr Asp Pro Phe Pro  Gln Ser Asn
    1790                 1795                 1800

Ser Pro  Ile Glu Asp Ile Glu  Arg Glu Ile Pro Glu  Arg Ser Trp
    1805                 1810                 1815

Asn Thr  Gly Phe Asp Trp Ile  Thr Asp Tyr Gln Gly  Lys Thr Val
    1820                 1825                 1830

Trp Phe  Val Pro Ser Ile Lys  Ala Gly Asn Asp Ile  Ala Asn Cys
    1835                 1840                 1845

Leu Arg  Lys Ser Gly Lys Lys  Val Ile Gln Leu Ser  Arg Lys Thr
    1850                 1855                 1860

Phe Asp  Thr Glu Tyr Pro Lys  Thr Lys Leu Thr Asp  Trp Asp Phe
    1865                 1870                 1875

Val Val  Thr Thr Asp Ile Ser  Glu Met Gly Ala Asn  Phe Arg Ala
    1880                 1885                 1890

Gly Arg  Val Ile Asp Pro Arg  Arg Cys Leu Lys Pro  Val Ile Leu
    1895                 1900                 1905

Pro Asp  Gly Pro Glu Arg Val  Ile Leu Ala Gly Pro  Ile Pro Val
    1910                 1915                 1920

Thr Pro  Ala Ser Ala Ala Gln  Arg Arg Gly Arg Ile  Gly Arg Asn
    1925                 1930                 1935

Pro Ala  Gln Glu Asp Asp Gln  Tyr Val Phe Ser Gly  Asp Pro Leu
    1940                 1945                 1950

Lys Asn  Asp Glu Asp His Ala  His Trp Thr Glu Ala  Lys Met Leu
    1955                 1960                 1965

Leu Asp  Asn Ile Tyr Thr Pro  Glu Gly Ile Ile Pro  Thr Leu Phe
    1970                 1975                 1980

Gly Pro  Glu Arg Glu Lys Thr  Gln Ala Ile Asp Gly  Glu Phe Arg
    1985                 1990                 1995

Leu Arg  Gly Glu Gln Arg Lys  Thr Phe Val Glu Leu  Met Arg Arg
    2000                 2005                 2010

Gly Asp  Leu Pro Val Trp Leu  Ser Tyr Lys Val Ala  Ser Ala Gly
    2015                 2020                 2025

Ile Ser  Tyr Lys Asp Arg Glu  Trp Cys Phe Thr Gly  Glu Arg Asn
    2030                 2035                 2040

Asn Gln  Ile Leu Glu Glu Asn  Met Glu Val Glu Ile  Trp Thr Arg
    2045                 2050                 2055

Glu Gly  Glu Lys Lys Lys Leu  Arg Pro Arg Trp Leu  Asp Ala Arg
    2060                 2065                 2070

Val Tyr  Ala Asp Pro Met Ala  Leu Lys Asp Phe Lys  Glu Phe Ala
    2075                 2080                 2085

Ser Gly  Arg Lys Ser Ile Thr  Leu Asp Ile Leu Thr  Glu Ile Ala
```

```
    2090                2095                2100

Ser Leu  Pro Thr Tyr Leu Ser  Ser Arg Ala Lys Leu  Ala Leu Asp
    2105                2110                2115

Asn Ile  Val Met Leu His Thr  Thr Glu Arg Gly Gly  Arg Ala Tyr
    2120                2125                2130

Gln His  Ala Leu Asn Glu Leu  Pro Glu Ser Leu Glu  Thr Leu Met
    2135                2140                2145

Leu Val  Ala Leu Leu Gly Ala  Met Thr Ala Gly Ile  Phe Leu Phe
    2150                2155                2160

Phe Met  Gln Gly Lys Gly Ile  Gly Lys Leu Ser Met  Gly Leu Ile
    2165                2170                2175

Thr Ile  Ala Val Ala Ser Gly  Leu Leu Trp Val Ala  Glu Ile Gln
    2180                2185                2190

Pro Gln  Trp Ile Ala Ala Ser  Ile Ile Leu Glu Phe  Phe Leu Met
    2195                2200                2205

Val Leu  Leu Ile Pro Glu Pro  Glu Lys Gln Arg Thr  Pro Gln Asp
    2210                2215                2220

Asn Gln  Leu Ile Tyr Val Ile  Leu Thr Ile Leu Thr  Ile Ile Gly
    2225                2230                2235

Leu Ile  Ala Ala Asn Glu Met  Gly Leu Ile Glu Lys  Thr Lys Thr
    2240                2245                2250

Asp Phe  Gly Phe Tyr Gln Val  Lys Thr Glu Thr Thr  Ile Leu Asp
    2255                2260                2265

Val Asp  Leu Arg Pro Ala Ser  Ala Trp Thr Leu Tyr  Ala Val Ala
    2270                2275                2280

Thr Thr  Ile Leu Thr Pro Met  Leu Arg His Thr Ile  Glu Asn Thr
    2285                2290                2295

Ser Ala  Asn Leu Ser Leu Ala  Ala Ile Ala Asn Gln  Ala Ala Val
    2300                2305                2310

Leu Met  Gly Leu Gly Lys Gly  Trp Pro Leu His Arg  Met Asp Leu
    2315                2320                2325

Gly Val  Pro Leu Leu Ala Met  Gly Cys Tyr Ser Gln  Val Asn Pro
    2330                2335                2340

Thr Thr  Leu Thr Ala Ser Leu  Val Met Leu Leu Val  His Tyr Ala
    2345                2350                2355

Ile Ile  Gly Pro Gly Leu Gln  Ala Lys Ala Thr Arg  Glu Ala Gln
    2360                2365                2370

Lys Arg  Thr Ala Ala Gly Ile  Met Lys Asn Pro Thr  Val Asp Gly
    2375                2380                2385

Ile Thr  Val Ile Asp Leu Glu  Pro Ile Ser Tyr Asp  Pro Lys Phe
    2390                2395                2400

Glu Lys  Gln Leu Gly Gln Val  Met Leu Leu Val Leu  Cys Ala Gly
    2405                2410                2415

Gln Leu  Leu Leu Met Arg Thr  Thr Trp Ala Phe Cys  Glu Val Leu
    2420                2425                2430

Thr Leu  Ala Thr Gly Pro Ile  Leu Thr Leu Trp Glu  Gly Asn Pro
    2435                2440                2445

Gly Arg  Phe Trp Asn Thr Thr  Ile Ala Val Ser Thr  Ala Asn Ile
    2450                2455                2460

Phe Arg  Gly Ser Tyr Leu Ala  Gly Ala Gly Leu Ala  Phe Ser Leu
    2465                2470                2475

Ile Lys  Asn Ala Gln Thr Pro  Arg Arg Gly Thr Gly  Thr Thr Gly
    2480                2485                2490
```

```
Glu Thr  Leu Gly Glu Lys Trp  Lys Arg Gln Leu Asn  Ser Leu Asp
    2495                 2500                 2505

Arg Lys  Glu Phe Glu Glu Tyr  Lys Arg Ser Gly Ile  Leu Glu Val
    2510                 2515                 2520

Asp Arg  Thr Glu Ala Lys Ser  Ala Leu Lys Asp Gly  Ser Lys Ile
    2525                 2530                 2535

Lys His  Ala Val Ser Arg Gly  Ser Ser Lys Ile Arg  Trp Ile Val
    2540                 2545                 2550

Glu Arg  Gly Met Val Lys Pro  Lys Gly Lys Val Val  Asp Leu Gly
    2555                 2560                 2565

Cys Gly  Arg Gly Gly Trp Ser  Tyr Tyr Met Ala Thr  Leu Lys Asn
    2570                 2575                 2580

Val Thr  Glu Val Lys Gly Tyr  Thr Lys Gly Gly Pro  Gly His Glu
    2585                 2590                 2595

Glu Pro  Ile Pro Met Ala Thr  Tyr Gly Trp Asn Leu  Val Lys Leu
    2600                 2605                 2610

His Ser  Gly Val Asp Val Phe  Tyr Lys Pro Thr Glu  Gln Val Asp
    2615                 2620                 2625

Thr Leu  Leu Cys Asp Ile Gly  Glu Ser Ser Ser Asn  Pro Thr Ile
    2630                 2635                 2640

Glu Glu  Gly Arg Thr Leu Arg  Val Leu Lys Met Val  Glu Pro Trp
    2645                 2650                 2655

Leu Ser  Ser Lys Pro Glu Phe  Cys Ile Lys Val Leu  Asn Pro Tyr
    2660                 2665                 2670

Met Pro  Thr Val Ile Glu Glu  Leu Glu Lys Leu Gln  Arg Lys His
    2675                 2680                 2685

Gly Gly  Asn Leu Val Arg Cys  Pro Leu Ser Arg Asn  Ser Thr His
    2690                 2695                 2700

Glu Met  Tyr Trp Val Ser Gly  Ala Ser Gly Asn Ile  Val Ser Ser
    2705                 2710                 2715

Val Asn  Thr Thr Ser Lys Met  Leu Leu Asn Arg Phe  Thr Thr Arg
    2720                 2725                 2730

His Arg  Lys Pro Thr Tyr Glu  Lys Asp Val Asp Leu  Gly Ala Gly
    2735                 2740                 2745

Thr Arg  Ser Val Ser Thr Glu  Thr Glu Lys Pro Asp  Met Thr Ile
    2750                 2755                 2760

Ile Gly  Arg Arg Leu Gln Arg  Leu Gln Glu Glu His  Lys Glu Thr
    2765                 2770                 2775

Trp His  Tyr Asp Gln Glu Asn  Pro Tyr Arg Thr Trp  Ala Tyr His
    2780                 2785                 2790

Gly Ser  Tyr Glu Ala Pro Ser  Thr Gly Ser Ala Ser  Ser Met Val
    2795                 2800                 2805

Asn Gly  Val Val Lys Leu Leu  Thr Lys Pro Trp Asp  Val Ile Pro
    2810                 2815                 2820

Met Val  Thr Gln Leu Ala Met  Thr Asp Thr Thr Pro  Phe Gly Gln
    2825                 2830                 2835

Gln Arg  Val Phe Lys Glu Lys  Val Asp Thr Arg Thr  Pro Gln Pro
    2840                 2845                 2850

Lys Pro  Gly Thr Arg Met Val  Met Thr Thr Thr Ala  Asn Trp Leu
    2855                 2860                 2865

Trp Ala  Leu Leu Gly Lys Lys  Lys Asn Pro Arg Leu  Cys Thr Arg
    2870                 2875                 2880
```

```
Glu Glu  Phe Ile Ser Lys Val  Arg Ser Asn Ala Ala  Ile Gly Ala
    2885                 2890                 2895

Val Phe  Gln Glu Glu Gln Gly  Trp Thr Ser Ala Ser  Glu Ala Val
    2900                 2905                 2910

Asn Asp  Ser Arg Phe Trp Glu  Leu Val Asp Lys Glu  Arg Ala Leu
    2915                 2920                 2925

His Gln  Glu Gly Lys Cys Glu  Ser Cys Val Tyr Asn  Met Met Gly
    2930                 2935                 2940

Lys Arg  Glu Lys Lys Leu Gly  Glu Phe Gly Arg Ala  Lys Gly Ser
    2945                 2950                 2955

Arg Ala  Ile Trp Tyr Met Trp  Leu Gly Ala Arg Phe  Leu Glu Phe
    2960                 2965                 2970

Glu Ala  Leu Gly Phe Leu Asn  Glu Asp His Trp Phe  Gly Arg Glu
    2975                 2980                 2985

Asn Ser  Trp Ser Gly Val Glu  Gly Glu Gly Leu His  Arg Leu Gly
    2990                 2995                 3000

Tyr Ile  Leu Glu Glu Ile Asp  Lys Lys Asp Gly Asp  Leu Met Tyr
    3005                 3010                 3015

Ala Asp  Asp Thr Ala Gly Trp  Asp Thr Arg Ile Thr  Glu Asp Asp
    3020                 3025                 3030

Leu Gln  Asn Glu Glu Leu Ile  Thr Glu Gln Met Ala  Pro His His
    3035                 3040                 3045

Lys Ile  Leu Ala Lys Ala Ile  Phe Lys Leu Thr Tyr  Gln Asn Lys
    3050                 3055                 3060

Val Val  Lys Val Leu Arg Pro  Thr Pro Arg Gly Ala  Val Met Asp
    3065                 3070                 3075

Ile Ile  Ser Arg Lys Asp Gln  Arg Gly Ser Gly Gln  Val Gly Thr
    3080                 3085                 3090

Tyr Gly  Leu Asn Thr Phe Thr  Asn Met Glu Val Gln  Leu Ile Arg
    3095                 3100                 3105

Gln Met  Glu Ala Glu Gly Val  Ile Thr Gln Asp Asp  Met Gln Asn
    3110                 3115                 3120

Pro Lys  Gly Leu Lys Glu Arg  Val Glu Lys Trp Leu  Lys Glu Cys
    3125                 3130                 3135

Gly Val  Asp Arg Leu Lys Arg  Met Ala Ile Ser Gly  Asp Asp Cys
    3140                 3145                 3150

Val Val  Lys Pro Leu Asp Glu  Arg Phe Gly Thr Ser  Leu Leu Phe
    3155                 3160                 3165

Leu Asn  Asp Met Gly Lys Val  Arg Lys Asp Ile Pro  Gln Trp Glu
    3170                 3175                 3180

Pro Ser  Lys Gly Trp Lys Asn  Trp Gln Glu Val Pro  Phe Cys Ser
    3185                 3190                 3195

His His  Phe His Lys Ile Phe  Met Lys Asp Gly Arg  Ser Leu Val
    3200                 3205                 3210

Val Pro  Cys Arg Asn Gln Asp  Glu Leu Ile Gly Arg  Ala Arg Ile
    3215                 3220                 3225

Ser Gln  Gly Ala Gly Trp Ser  Leu Arg Glu Thr Ala  Cys Leu Gly
    3230                 3235                 3240

Lys Ala  Tyr Ala Gln Met Trp  Ser Leu Met Tyr Phe  His Arg Arg
    3245                 3250                 3255

Asp Leu  Arg Leu Ala Ser Met  Ala Ile Cys Ser Ala  Val Pro Thr
    3260                 3265                 3270

Glu Trp  Phe Pro Thr Ser Arg  Thr Thr Trp Ser Ile  His Ala His
```

```
    3275                3280                3285

His Gln  Trp Met Thr Thr Glu  Asp Met Leu Lys Val  Trp Asn Arg
    3290                3295                3300

Val Trp  Ile Glu Asp Asn Pro  Asn Met Thr Asp Lys  Thr Pro Val
    3305                3310                3315

His Ser  Trp Glu Asp Ile Pro  Tyr Leu Gly Lys Arg  Glu Asp Leu
    3320                3325                3330

Trp Cys  Gly Ser Leu Ile Gly  Leu Ser Ser Arg Ala  Thr Trp Ala
    3335                3340                3345

Lys Asn  Ile His Thr Ala Ile  Thr Gln Val Arg Asn  Leu Ile Gly
    3350                3355                3360

Lys Glu  Glu Tyr Val Asp Tyr  Met Pro Val Met Lys  Arg Tyr Ser
    3365                3370                3375

Ala Pro  Ser Glu Ser Glu Gly  Val Leu
    3380                3385


<210> SEQ ID NO 14
<211> LENGTH: 10649
<212> TYPE: DNA
<213> ORGANISM: Dengue 4 virus strain 2A

<400> SEQUENCE: 14

agttgttagt ctgtgtggac cgacaaggac agttccaaat cggaagcttg cttaacacag     60

ttctaacagt ttgtttgaat agagagcaga tctctggaaa aatgaaccaa cgaaaaaagg    120

tggttagacc acctttcaat atgctgaaac gcgagagaaa ccgcgtatca acccctcaag    180

ggttggtgaa gagattctca accggacttt tttctgggaa aggaccctta cggatggtgc    240

tagcattcat cacgtttttg cgagtccttt ccatcccacc aacagcaggg attctgaaga    300

gatggggaca gttgaagaaa aataaggcca tcaagatact gattggattc aggaaggaga    360

taggccgcat gctgaacatc ttgaacggga gaaaaaggtc aacgataaca ttgctgtgct    420

tgattcccac cgtaatggcg ttttccttgt caacaagaga tggcgaaccc ctcatgatag    480

tggcaaaaca tgaaaggggg agacctctct tgtttaagac aacagagggg atcaacaaat    540

gcactctcat tgccatggac ttgggtgaaa tgtgtgagga cactgtcacg tataaatgcc    600

ccctactggt caataccgaa cctgaagaca ttgattgctg gtgcaacctc acgtctacct    660

gggtcatgta tgggacatgc acccagagcg gagaacggag acgagagaag cgctcagtag    720

ctttaacacc acattcagga atgggattgg aaacaagagc tgagacatgg atgtcatcgg    780

aaggggcttg gaagcatgct cagagagtag agagctggat actcagaaac ccaggattcg    840

cgctcttggc aggatttatg gcttatatga ttgggcaaac aggaatccag cgaactgtct    900

tctttgtcct aatgatgctg gtcgccccat cctacggaat gcgatgcgta ggagtaggaa    960

acagagactt tgtggaagga gtctcaggtg gagcatgggt cgacctggtg ctagaacatg   1020

gaggatgcgt cacaaccatg gcccagggaa aaccaacctt ggattttgaa ctgactaaga   1080

caacagccaa ggaagtggct ctgttaagaa cctattgcat tgaagcctca atatcaaaca   1140

taactacggc aacaagatgt ccaacgcaag gagagcctta tctgaaagag gaacaggacc   1200

aacagtacat ttgccggaga gatgtggtag acagagggtg gggcaatggc tgtggcttgt   1260

ttggaaaagg aggagttgtg acatgtgcga agttttcatg ttcggggaag ataacaggca   1320

atttggtcca aattgagaac cttgaataca cagtggttgt aacagtccac aatggagaca   1380

cccatgcagt aggaaatgac acatccaatc atggagttac agccatgata actcccaggt   1440
```

-continued caccatcggt ggaagtcaaa ttgccggact atggagaact aacactcgat tgtgaaccca 1500
ggtctggaat tgactttaat gagatgattc tgatgaaaat gaaaaagaaa acatggctcg 1560
tgcataagca atggtttttg gatctgcctc ttccatggac agcaggagca gacacatcag 1620
aggttcactg gaattacaaa gagagaatgg tgacatttaa ggttcctcat gccaagagac 1680
aggatgtgac agtgctggga tctcaggaag gagccatgca ttctgccctc gctggagcca 1740
cagaagtgga ctccggtgat ggaaatcaca tgtttgcagg acatcttaag tgcaaagtcc 1800
gtatggagaa attgagaatc aagggaatgt catacacgat gtgttcagga aagttttcaa 1860
ttgacaaaga gatggcagaa acacagcatg ggacaacagt ggtgaaagtc aagtatgaag 1920
gtgctggagc tccgtgtaaa gtccccatag agataagaga tgtaaacaag gaaaaagtgg 1980
ttgggcgtat catctcatcc accccctttgg ctgagaatac caacagtgta accaacatag 2040
aattagaacc cccctttggg gacagctaca tagtgatagg tgttggaaac agcgcattaa 2100
cactccattg gttcaggaaa gggagttcca ttggcaagat gtttgagtcc acatacagag 2160
gtgcaaaacg aatggccatt ctaggtgaaa cagcttggga ttttggttcc gttggtggac 2220
tgttcacatc attgggaaag gctgtgcacc aggtttttgg aagtgtgtat acaaccatgt 2280
ttggaggagt ctcatggatg attagaatcc taattgggtt cttagtgttg tggattggca 2340
cgaactcaag gaacacttca atggctatga cgtgcatagc tgttggagga atcactctgt 2400
ttctgggctt cacagttcaa gcagacatgg gttgtgtggt gtcatggagt gggaaagaat 2460
tgaagtgtgg aagcggaatt tttgtggttg acaacgtgca cacttggaca gaacagtaca 2520
aatttcaacc agagtcccca gcgagactag cgtctgcaat attaaatgcc cacaaagatg 2580
gggtctgtgg aattagatca accacgaggc tggaaaatgt catgtggaag caaataacca 2640
acgagctaaa ctatgttctc tgggaaggag gacatgacct cactgtagtg gctggggatg 2700
tgaagggggt gttgaccaaa ggcaagagag cactcacacc cccagtgagt gatctgaaat 2760
attcatggaa gacatgggga aaagcaaaaa tcttcacccc agaagcaaga aatagcacat 2820
ttttaataga cggaccagac acctctgaat gccccaatga acgaagagca tggaactctc 2880
ttgaggtgga agactatgga tttggcatgt tcacgaccaa catatggatg aaattccgag 2940
aaggaagttc agaagtgtgt gaccacaggt taatgtcagc tgcaattaaa gatcagaaag 3000
ctgtgcatgc tgacatgggt tattggatag agagctcaaa aaaccagacc tggcagatag 3060
agaaagcatc tcttattgaa gtgaaaacat gtctgtggcc caagacccac acactgtgga 3120
gcaatggagt gctggaaagc cagatgctca ttccaaaatc atatgcgggc cctttttcac 3180
agcacaatta ccgccagggc tatgccacgc aaaccgtggg cccatggcac ttaggcaaat 3240
tagagataga ctttggagaa tgccccggaa caacagtcac aattcaggag gattgtgacc 3300
atagaggccc atctttgagg accaccactg catctggaaa actagtcacg caatggtgct 3360
gccgctcctg cacgatgcct cccttaaggt tcttgggaga agatgggtgc tggtatggga 3420
tggagattag gcccttgagt gaaaaagaag agaacatggt caaatcacag gtgacggccg 3480
gacagggcac atcagaaact tttctatgg gtctgttgtg cctgaccttg tttgtggaag 3540
aatgcttgag gagaagagtc actaggaaac acatgatatt agttgtggtg atcactcttt 3600
gtgctatcat cctgggaggc ctcacatgga tggacttact acgagccctc atcatgttgg 3660
gggacactat gtctggtaga ataggaggac agatccacct agccatcatg gcagtgttca 3720
agatgtcacc aggatacgtg ctgggtgtgt ttttaaggaa actcacttca agagagacag 3780
cactaatggt aataggaatg gccatgacaa cggtgctttc aattccacat gaccttatgg 3840

```
aactcattga tggaatatca ctgggactaa ttttgctaaa aatagtaaca cagtttgaca   3900
acacccaagt gggaacctta gctctttcct tgactttcat aagatcaaca atgccattgg   3960
tcatggcttg gaggaccatt atggctgtgt tgtttgtggt cacactcatt cctttgtgca   4020
ggacaagctg tcttcaaaaa cagtctcatt gggtagaaat aacagcactc atcctaggag   4080
cccaagctct gccagtgtac ctaatgactc ttatgaaagg agcctcaaga agatcttggc   4140
ctcttaacga gggcataatg gctgtgggtt tggttagtct cttaggaagc gctcttttaa   4200
agaatgatgt ccctttagct ggcccaatgg tggcaggagg cttacttctg gcggcttacg   4260
tgatgagtgg tagctcagca gatctgtcac tagagaaggc cgccaacgtg cagtgggatg   4320
aaatggcaga cataacaggc tcaagcccaa tcatagaagt gaagcaggat gaagatggct   4380
ctttctccat acgggacgtc gaggaaacca atatgataac ccttttggtg aaactggcac   4440
tgataacagt gtcaggtctc taccccttgg caattccagt cacaatgacc ttatggtaca   4500
tgtggcaagt gaaaacacaa agatcaggag ccctgtggga cgtcccctca cccgctgcca   4560
ctaaaaaagc cgcactgtct gaaggagtgt acaggatcat gcaaagaggg ttattcggga   4620
aaactcaggt tggagtaggg atacacatgg aaggtgtatt tcacacaatg tggcatgtaa   4680
caagaggatc agtgatctgc cacgagactg ggagattgga gccatcttgg gctgacgtca   4740
ggaatgacat gatatcatac ggtgggggat ggaggcttgg agacaaatgg gacaaagaag   4800
aagacgttca ggtcctcgcc atagaaccag gaaaaaatcc taaacatgtc caaacgaaac   4860
ctggcctttt caagacccta actggagaaa ttggagcagt aacattagat ttcaaacccg   4920
gaacgtctgg ttctcccatc atcaacagga aaggaaaagt catcggactc tatggaaatg   4980
gagtagttac caaatcaggt gattacgtca gtgccataac gcaagccgaa agaattggag   5040
agccagatta tgaagtggat gaggacattt ttcgaaagaa aagattaact ataatggact   5100
tacaccccgg agctggaaag acaaaaagaa ttcttccatc aatagtgaga gaagccttaa   5160
aaaggaggct acgaactttg attttagctc ccacgagagt ggtggcggcc gagatggaag   5220
aggccctacg tggactgcca atccgttatc agaccccagc tgtgaaatca gaacacacag   5280
gaagagagat tgtagacctc atgtgtcatg caaccttcac aacaagactt ttgtcatcaa   5340
ccagggttcc aaattacaac cttatagtga tggatgaagc acatttcacc gatccttcta   5400
gtgtcgcggc tagaggatac atctcgacca gggtggaaat gggagaggca gcagccatct   5460
tcatgaccgc aacccctccc ggagcgacag atccctttcc ccagagcaac agcccaatag   5520
aagacatcga gagggaaatt ccggaaaggt catggaacac agggttcgac tggataacag   5580
actaccaagg gaaaactgtg tggtttgttc ccagcataaa agctggaaat gacattgcaa   5640
attgtttgag aaagtcggga aagaaagtta tccagttgag taggaaaacc tttgatacag   5700
agtatccaaa aacgaaactc acggactggg actttgtggt cactacagac atatctgaaa   5760
tgggggccaa ttttagagcc gggagagtga tagaccctag aagatgcctc aagccagtta   5820
tcctaccaga tgggccagag agagtcattt tagcaggtcc tattccagtg actccagcaa   5880
gcgctgctca gagaagaggg cgaataggaa ggaacccagc acaagaagac gaccaatacg   5940
ttttctccgg agacccacta aaaaatgatg aagatcatgc ccactggaca gaagcaaaga   6000
tgctgcttga caatatctac accccagaag ggatcattcc aacattgttt ggtccggaaa   6060
gggaaaaaac ccaagccatt gatggagagt ttcgcctcag aggggaacaa aggaagactt   6120
ttgtggaatt aatgaggaga ggagaccttc cggtgtggct gagctataag gtagcttctg   6180
```

-continued

```
ctggcatttc ttacaaagat cgggaatggt gcttcacagg ggaaagaaat aaccaaattt   6240
tagaagaaaa catggaggtt gaaatttgga ctagagaggg agaaaagaaa aagctaaggc   6300
caagatggtt agatgcacgt gtatacgctg accccatggc tttgaaggat ttcaaggagt   6360
ttgccagtgg aaggaagagt ataactctcg acatcctaac agagattgcc agtttgccaa   6420
cttacctttc ctctagggcc aagctcgccc ttgataacat agtcatgctc cacacaacag   6480
aaagaggagg gagggcctat caacacgccc tgaacgaact tccggagtca ctggaaacac   6540
tcatgcttgt agctttacta ggtgctatga cagcaggcat cttcctgttt ttcatgcaag   6600
ggaaaggaat agggaaattg tcaatgggtt tgataaccat tgcggtggct agtggcttgc   6660
tctgggtagc agaaattcaa ccccagtgga tagcggcctc aatcatacta gagtttttc    6720
tcatggtact gttgataccg gaaccagaaa aacaaaggac cccacaagac aatcaattga   6780
tctacgtcat attgaccatt ctcaccatca ttggtctaat agcagccaac gagatggggc   6840
tgattgaaaa aacaaaaacg gattttgggt tttaccaggt aaaaacagaa accaccatcc   6900
tcgatgtgga cttgagacca gcttcagcat ggacgctcta tgcagtagcc accacaattc   6960
tgactcccat gctgagacac accatagaaa acacgtcggc caacctatct ctagcagcca   7020
ttgccaacca ggcagccgtc ctaatggggc ttggaaaagg atggccgctc cacagaatgg   7080
acctcggtgt gccgctgtta gcaatgggat gctattctca agtgaaccca acaaccttga   7140
cagcatcctt agtcatgctt ttagtccatt atgcaataat aggcccagga ttgcaggcaa   7200
aagccacaag agaggcccag aaaaggacag ctgctgggat catgaaaaat cccacagtgg   7260
acgggataac agtaatagat ctagaaccaa tatcctatga cccaaaattt gaaaagcaat   7320
tagggcaggt catgctacta gtcttgtgtg ctggacaact actcttgatg agaacaacat   7380
gggctttctg tgaagtcttg actttggcca caggaccaat cttgaccttg tgggagggca   7440
acccgggaag gttttggaac acgaccatag ccgtatccac cgccaacatt ttcaggggaa   7500
gttacttggc gggagctgga ctggcttttt cactcataaa gaatgcacaa acccctagga   7560
ggggaactgg gaccacagga gagacactgg gagagaagtg gaagagacag ctaaactcat   7620
tagacagaaa agagtttgaa gagtataaaa gaagtggaat actagaagtg gacaggactg   7680
aagccaagtc tgccctgaaa gatgggtcta aaatcaagca tgcagtatct agagggtcca   7740
gtaagatcag atggattgtt gagagaggga tggtaaagcc aaaagggaaa gttgtagatc   7800
ttggctgtgg gagaggagga tggtcttatt acatggcgac actcaagaac gtgactgaag   7860
tgaaagggta tacaaaagga ggtccaggac atgaagaacc gattcccatg gctacttatg   7920
gttggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taacccctac atgccaacag tcatagaaga gctggagaaa ctgcagagaa   8160
aacatggtgg gaaccttgtc agatgcccgc tgtccaggaa ctccacccat gagatgtatt   8220
gggtgtcagg agcgtcggga aacattgtga gctctgtgaa cacaacatca aagatgttgt   8280
tgaacaggtt cacaacaagg cataggaaac ccacttatga gaaggacgta gatcttgggg   8340
caggaacgag aagtgtctcc actgaaacag aaaaaccaga catgacaatc attgggagaa   8400
ggcttcagcg attgcaagaa gagcacaaag aaacctggca ttatgatcag gaaaacccat   8460
acagaacctg ggcgtatcat ggaagctatg aagctccttc gacaggctct gcatcctcca   8520
tggtgaacgg ggtggtaaaa ctgctaacaa aaccctggga tgtgattcca atggtgactc   8580
```

```
agttagccat gacagataca accccttttg ggcaacaaag agtgttcaaa gagaaggtgg   8640
ataccagaac accacaacca aaacccggta cacgaatggt tatgaccacg acagccaatt   8700
ggctgtgggc cctccttgga aagaagaaaa atcccagact gtgcacaagg gaagagttca   8760
tctcaaaagt tagatcaaac gcagccatag gcgcagtctt tcaggaagaa cagggatgga   8820
catcagccag tgaagctgtg aatgacagcc ggttttggga actggttgac aaagaaaggg   8880
ccctacacca ggaagggaaa tgtgaatcgt gtgtctataa catgatggga aaacgtgaga   8940
aaaagttagg agagtttggc agagccaagg gaagccgagc aatctggtac atgtggctgg   9000
gagcgcggtt tctggaattt gaagccctgg gtttttttgaa tgaagatcac tggtttggca   9060
gagaaaattc atggagtgga gtggaagggg aaggtctgca cagattggga tatatcctgg   9120
aggagataga caagaaggat ggagacctaa tgtatgctga tgacacagca ggctgggaca   9180
caagaatcac tgaggatgac cttcaaaatg aggaactgat cacggaacag atggctcccc   9240
accacaagat cctagccaaa gccattttca aactaaccta tcaaaacaaa gtggtgaaag   9300
tcctcagacc cacaccgaga ggagcggtga tggatatcat atccaggaaa gaccaaagag   9360
gtagtggaca agttggaaca tatggtttga acacattcac caacatggaa gttcaactca   9420
tccgccaaat ggaagctgaa ggagtcatca cacaagatga catgcagaac ccaaaagggt   9480
tgaaagaaag agttgagaaa tggctgaaag agtgtggtgt cgacaggtta aagaggatgg   9540
caatcagtgg agacgattgc gtggtgaagc ccctagatga gaggtttggc acttccctcc   9600
tcttcttgaa cgacatggga aaggtgagga aagacattcc gcagtgggaa ccatctaagg   9660
gatggaaaaa ctggcaagag gttccttttt gctcccacca ctttcacaag atctttatga   9720
aggatggccg ctcactagtt gttccatgta gaaaccagga tgaactgata gggagagcca   9780
gaatctcgca gggagctgga tggagcttaa gagaaacagc ctgcctgggc aaagcttacg   9840
cccagatgtg gtcgcttatg tacttccaca gaagggatct gcgtttagcc tccatggcca   9900
tatgctcagc agttccaacg gaatggtttc caacaagcag aacaacatgg tcaatccacg   9960
ctcatcacca gtggatgacc actgaagata tgctcaaagt gtggaacaga gtgtggatag  10020
aagacaaccc taatatgact gacaagactc cagtccattc gtgggaagat ataccttacc  10080
tagggaaaag agaggatttg tggtgtggat ccctgattgg actttcttcc agagccacct  10140
gggcgaagaa cattcacacg gccataaccc aggtcaggaa cctgatcgga aaagaggaat  10200
acgtggatta catgccagta atgaaaagat acagtgctcc ttcagagagt gaaggagttc  10260
tgtaattacc aacaacaaac accaaaggct attgaagtca ggccacttgt gccacggttt  10320
gagcaaaccg tgctgcctgt agctccgcca ataatgggag gcgtaataat ccccagggag  10380
gccatgcgcc acggaagctg tacgcgtggc atattggact agcggttaga ggagacccct  10440
cccatcactg acaaaacgca gcaaaagggg gcccgaagcc aggaggaagc tgtactcctg  10500
gtggaaggac tagaggttag aggagacccc cccaacacaa aaacagcata ttgacgctgg  10560
gaaagaccag agatcctgct gtctctgcaa catcaatcca ggcacagagc gccgcaagat  10620
ggattggtgt tgttgatcca acaggttct                                    10649
```

<210> SEQ ID NO 15
<211> LENGTH: 3387
<212> TYPE: PRT
<213> ORGANISM: Recombinant Dengue 4 virus strain rDEN4

<400> SEQUENCE: 15

-continued

Met Asn Gln Arg Lys Lys Val Val Arg Pro Pro Phe Asn Met Leu Lys
1 5 10 15

Arg Glu Arg Asn Arg Val Ser Thr Pro Gln Gly Leu Val Lys Arg Phe
20 25 30

Ser Thr Gly Leu Phe Ser Gly Lys Gly Pro Leu Arg Met Val Leu Ala
35 40 45

Phe Ile Thr Phe Leu Arg Val Leu Ser Ile Pro Pro Thr Ala Gly Ile
50 55 60

Leu Lys Arg Trp Gly Gln Leu Lys Lys Asn Lys Ala Ile Lys Ile Leu
65 70 75 80

Ile Gly Phe Arg Lys Glu Ile Gly Arg Met Leu Asn Ile Leu Asn Gly
85 90 95

Arg Lys Arg Ser Thr Ile Thr Leu Leu Cys Leu Ile Pro Thr Val Met
100 105 110

Ala Phe Ser Leu Ser Thr Arg Asp Gly Glu Pro Leu Met Ile Val Ala
115 120 125

Lys His Glu Arg Gly Arg Pro Leu Leu Phe Lys Thr Thr Glu Gly Ile
130 135 140

Asn Lys Cys Thr Leu Ile Ala Met Asp Leu Gly Glu Met Cys Glu Asp
145 150 155 160

Thr Val Thr Tyr Lys Cys Pro Leu Leu Val Asn Thr Glu Pro Glu Asp
165 170 175

Ile Asp Cys Trp Cys Asn Leu Thr Ser Thr Trp Val Met Tyr Gly Thr
180 185 190

Cys Thr Gln Ser Gly Glu Arg Arg Arg Glu Lys Arg Ser Val Ala Leu
195 200 205

Thr Pro His Ser Gly Met Gly Leu Glu Thr Arg Ala Glu Thr Trp Met
210 215 220

Ser Ser Glu Gly Ala Trp Lys His Ala Gln Arg Val Glu Ser Trp Ile
225 230 235 240

Leu Arg Asn Pro Gly Phe Ala Leu Leu Ala Gly Phe Met Ala Tyr Met
245 250 255

Ile Gly Gln Thr Gly Ile Gln Arg Thr Val Phe Phe Val Leu Met Met
260 265 270

Leu Val Ala Pro Ser Tyr Gly Met Arg Cys Val Gly Val Gly Asn Arg
275 280 285

Asp Phe Val Glu Gly Val Ser Gly Gly Ala Trp Val Asp Leu Val Leu
290 295 300

Glu His Gly Gly Cys Val Thr Thr Met Ala Gln Gly Lys Pro Thr Leu
305 310 315 320

Asp Phe Glu Leu Thr Lys Thr Thr Ala Lys Glu Val Ala Leu Leu Arg
325 330 335

Thr Tyr Cys Ile Glu Ala Ser Ile Ser Asn Ile Thr Thr Ala Thr Arg
340 345 350

Cys Pro Thr Gln Gly Glu Pro Tyr Leu Lys Glu Glu Gln Asp Gln Gln
355 360 365

Tyr Ile Cys Arg Arg Asp Val Val Asp Arg Gly Trp Gly Asn Gly Cys
370 375 380

Gly Leu Phe Gly Lys Gly Gly Val Val Thr Cys Ala Lys Phe Ser Cys
385 390 395 400

Ser Gly Lys Ile Thr Gly Asn Leu Val Gln Ile Glu Asn Leu Glu Tyr
405 410 415

Thr Val Val Val Thr Val His Asn Gly Asp Thr His Ala Val Gly Asn

-continued

```
            420                 425                 430

Asp Thr Ser Asn His Gly Val Thr Ala Met Ile Thr Pro Arg Ser Pro
        435                 440                 445

Ser Val Glu Val Lys Leu Pro Asp Tyr Gly Glu Leu Thr Leu Asp Cys
    450                 455                 460

Glu Pro Arg Ser Gly Ile Asp Phe Asn Glu Met Ile Leu Met Lys Met
465                 470                 475                 480

Lys Lys Lys Thr Trp Leu Val His Lys Gln Trp Phe Leu Asp Leu Pro
                485                 490                 495

Leu Pro Trp Thr Ala Gly Ala Asp Thr Ser Glu Val His Trp Asn Tyr
            500                 505                 510

Lys Glu Arg Met Val Thr Phe Lys Val Pro His Ala Lys Arg Gln Asp
        515                 520                 525

Val Thr Val Leu Gly Ser Gln Glu Gly Ala Met His Ser Ala Leu Ala
    530                 535                 540

Gly Ala Thr Glu Val Asp Ser Gly Asp Gly Asn His Met Phe Ala Gly
545                 550                 555                 560

His Leu Lys Cys Lys Val Arg Met Glu Lys Leu Arg Ile Lys Gly Met
                565                 570                 575

Ser Tyr Thr Met Cys Ser Gly Lys Phe Ser Ile Asp Lys Glu Met Ala
            580                 585                 590

Glu Thr Gln His Gly Thr Thr Val Val Lys Val Lys Tyr Glu Gly Ala
        595                 600                 605

Gly Ala Pro Cys Lys Val Pro Ile Glu Ile Arg Asp Val Asn Lys Glu
    610                 615                 620

Lys Val Val Gly Arg Ile Ile Ser Ser Thr Pro Leu Ala Glu Asn Thr
625                 630                 635                 640

Asn Ser Val Thr Asn Ile Glu Leu Glu Pro Pro Phe Gly Asp Ser Tyr
                645                 650                 655

Ile Val Ile Gly Val Gly Asn Ser Ala Leu Thr Leu His Trp Phe Arg
            660                 665                 670

Lys Gly Ser Ser Ile Gly Lys Met Phe Glu Ser Thr Tyr Arg Gly Ala
        675                 680                 685

Lys Arg Met Ala Ile Leu Gly Glu Thr Ala Trp Asp Phe Gly Ser Val
    690                 695                 700

Gly Gly Leu Phe Thr Ser Leu Gly Lys Ala Val His Gln Val Phe Gly
705                 710                 715                 720

Ser Val Tyr Thr Thr Met Phe Gly Gly Val Ser Trp Met Ile Arg Ile
                725                 730                 735

Leu Ile Gly Phe Leu Val Leu Trp Ile Gly Thr Asn Ser Arg Asn Thr
            740                 745                 750

Ser Met Ala Met Thr Cys Ile Ala Val Gly Gly Ile Thr Leu Phe Leu
        755                 760                 765

Gly Phe Thr Val Gln Ala Asp Met Gly Cys Val Ala Ser Trp Ser Gly
    770                 775                 780

Lys Glu Leu Lys Cys Gly Ser Gly Ile Phe Val Val Asp Asn Val His
785                 790                 795                 800

Thr Trp Thr Glu Gln Tyr Lys Phe Gln Pro Glu Ser Pro Ala Arg Leu
                805                 810                 815

Ala Ser Ala Ile Leu Asn Ala His Lys Asp Gly Val Cys Gly Ile Arg
            820                 825                 830

Ser Thr Thr Arg Leu Glu Asn Val Met Trp Lys Gln Ile Thr Asn Glu
        835                 840                 845
```

```
Leu Asn Tyr Val Leu Trp Glu Gly Gly His Asp Leu Thr Val Val Ala
    850                 855                 860

Gly Asp Val Lys Gly Val Leu Thr Lys Gly Lys Arg Ala Leu Thr Pro
865                 870                 875                 880

Pro Val Ser Asp Leu Lys Tyr Ser Trp Lys Thr Trp Gly Lys Ala Lys
                885                 890                 895

Ile Phe Thr Pro Glu Ala Arg Asn Ser Thr Phe Leu Ile Asp Gly Pro
            900                 905                 910

Asp Thr Ser Glu Cys Pro Asn Glu Arg Arg Ala Trp Asn Ser Leu Glu
        915                 920                 925

Val Glu Asp Tyr Gly Phe Gly Met Phe Thr Thr Asn Ile Trp Met Lys
    930                 935                 940

Phe Arg Glu Gly Ser Ser Glu Val Cys Asp His Arg Leu Met Ser Ala
945                 950                 955                 960

Ala Ile Lys Asp Gln Lys Ala Val His Ala Asp Met Gly Tyr Trp Ile
                965                 970                 975

Glu Ser Ser Lys Asn Gln Thr Trp Gln Ile Glu Lys Ala Ser Leu Ile
            980                 985                 990

Glu Val Lys Thr Cys Leu Trp Pro  Lys Thr His Thr Leu  Trp Ser Asn
        995                 1000                1005

Gly Val  Leu Glu Ser Gln Met  Leu Ile Pro Lys Ser  Tyr Ala Gly
    1010                 1015                 1020

Pro Phe  Ser Gln His Asn Tyr  Arg Gln Gly Tyr Ala  Thr Gln Thr
    1025                 1030                 1035

Val Gly  Pro Trp His Leu Gly  Lys Leu Glu Ile Asp  Phe Gly Glu
    1040                 1045                 1050

Cys Pro  Gly Thr Thr Val Thr  Ile Gln Glu Asp Cys  Asp His Arg
    1055                 1060                 1065

Gly Pro  Ser Leu Arg Thr Thr  Thr Ala Ser Gly Lys  Leu Val Thr
    1070                 1075                 1080

Gln Trp  Cys Cys Arg Ser Cys  Thr Met Pro Pro Leu  Arg Phe Leu
    1085                 1090                 1095

Gly Glu  Asp Gly Cys Trp Tyr  Gly Met Glu Ile Arg  Pro Leu Ser
    1100                 1105                 1110

Glu Lys  Glu Glu Asn Met Val  Lys Ser Gln Val Thr  Ala Gly Gln
    1115                 1120                 1125

Gly Thr  Ser Glu Thr Phe Ser  Met Gly Leu Leu Cys  Leu Thr Leu
    1130                 1135                 1140

Phe Val  Glu Glu Cys Leu Arg  Arg Arg Val Thr Arg  Lys His Met
    1145                 1150                 1155

Ile Leu  Val Val Val Ile Thr  Leu Cys Ala Ile Ile  Leu Gly Gly
    1160                 1165                 1170

Leu Thr  Trp Met Asp Leu Leu  Arg Ala Leu Ile Met  Leu Gly Asp
    1175                 1180                 1185

Thr Met  Ser Gly Arg Ile Gly  Gly Gln Ile His Leu  Ala Ile Met
    1190                 1195                 1200

Ala Val  Phe Lys Met Ser Pro  Gly Tyr Val Leu Gly  Val Phe Leu
    1205                 1210                 1215

Arg Lys  Leu Thr Ser Arg Glu  Thr Ala Leu Met Val  Ile Gly Met
    1220                 1225                 1230

Ala Met  Thr Thr Val Leu Ser  Ile Pro His Asp Leu  Met Glu Leu
    1235                 1240                 1245
```

Ile Asp Gly Ile Ser Leu Gly Leu Ile Leu Leu Lys Ile Val Thr
1250 1255 1260

Gln Phe Asp Asn Thr Gln Val Gly Thr Leu Ala Leu Ser Leu Thr
1265 1270 1275

Phe Ile Arg Ser Thr Met Pro Leu Val Met Ala Trp Arg Thr Ile
1280 1285 1290

Met Ala Val Leu Phe Val Val Thr Leu Ile Pro Leu Cys Arg Thr
1295 1300 1305

Ser Cys Leu Gln Lys Gln Ser His Trp Val Glu Ile Thr Ala Leu
1310 1315 1320

Ile Leu Gly Ala Gln Ala Leu Pro Val Tyr Leu Met Thr Leu Met
1325 1330 1335

Lys Gly Ala Ser Arg Arg Ser Trp Pro Leu Asn Glu Gly Ile Met
1340 1345 1350

Ala Val Gly Leu Val Ser Leu Leu Gly Ser Ala Leu Leu Lys Asn
1355 1360 1365

Asp Val Pro Leu Ala Gly Pro Met Val Ala Gly Gly Leu Leu Leu
1370 1375 1380

Ala Ala Tyr Val Met Ser Gly Ser Ser Ala Asp Leu Ser Leu Glu
1385 1390 1395

Lys Ala Ala Asn Val Gln Trp Asp Glu Met Ala Asp Ile Thr Gly
1400 1405 1410

Ser Ser Pro Ile Val Glu Val Lys Gln Asp Glu Asp Gly Ser Phe
1415 1420 1425

Ser Ile Arg Asp Val Glu Glu Thr Asn Met Ile Thr Leu Leu Val
1430 1435 1440

Lys Leu Ala Leu Ile Thr Val Ser Gly Leu Tyr Pro Leu Ala Ile
1445 1450 1455

Pro Val Thr Met Thr Leu Trp Tyr Met Trp Gln Val Lys Thr Gln
1460 1465 1470

Arg Ser Gly Ala Leu Trp Asp Val Pro Ser Pro Ala Ala Thr Lys
1475 1480 1485

Lys Ala Ala Leu Ser Glu Gly Val Tyr Arg Ile Met Gln Arg Gly
1490 1495 1500

Leu Phe Gly Lys Thr Gln Val Gly Val Gly Ile His Met Glu Gly
1505 1510 1515

Val Phe His Thr Met Trp His Val Thr Arg Gly Ser Val Ile Cys
1520 1525 1530

His Glu Thr Gly Arg Leu Glu Pro Ser Trp Ala Asp Val Arg Asn
1535 1540 1545

Asp Met Ile Ser Tyr Gly Gly Gly Trp Arg Leu Gly Asp Lys Trp
1550 1555 1560

Asp Lys Glu Glu Asp Val Gln Val Leu Ala Ile Glu Pro Gly Lys
1565 1570 1575

Asn Pro Lys His Val Gln Thr Lys Pro Gly Leu Phe Lys Thr Leu
1580 1585 1590

Thr Gly Glu Ile Gly Ala Val Thr Leu Asp Phe Lys Pro Gly Thr
1595 1600 1605

Ser Gly Ser Pro Ile Ile Asn Arg Lys Gly Lys Val Ile Gly Leu
1610 1615 1620

Tyr Gly Asn Gly Val Val Thr Lys Ser Gly Asp Tyr Val Ser Ala
1625 1630 1635

Ile Thr Gln Ala Glu Arg Ile Gly Glu Pro Asp Tyr Glu Val Asp

```
    1640                1645                1650

Glu Asp  Ile Phe Arg Lys Lys  Arg Leu Thr Ile Met  Asp Leu His
    1655                1660                1665

Pro Gly  Ala Gly Lys Thr Lys  Arg Ile Leu Pro Ser  Ile Val Arg
    1670                1675                1680

Glu Ala  Leu Lys Arg Arg Leu  Arg Thr Leu Ile Leu  Ala Pro Thr
    1685                1690                1695

Arg Val  Val Ala Ala Glu Met  Glu Glu Ala Leu Arg  Gly Leu Pro
    1700                1705                1710

Ile Arg  Tyr Gln Thr Pro Ala  Val Lys Ser Glu His  Thr Gly Arg
    1715                1720                1725

Glu Ile  Val Asp Leu Met Cys  His Ala Thr Phe Thr  Thr Arg Leu
    1730                1735                1740

Leu Ser  Ser Thr Arg Val Pro  Asn Tyr Asn Leu Ile  Val Met Asp
    1745                1750                1755

Glu Ala  His Phe Thr Asp Pro  Ser Ser Val Ala Ala  Arg Gly Tyr
    1760                1765                1770

Ile Ser  Thr Arg Val Glu Met  Gly Glu Ala Ala Ala  Ile Phe Met
    1775                1780                1785

Thr Ala  Thr Pro Pro Gly Ala  Thr Asp Pro Phe Pro  Gln Ser Asn
    1790                1795                1800

Ser Pro  Ile Glu Asp Ile Glu  Arg Glu Ile Pro Glu  Arg Ser Trp
    1805                1810                1815

Asn Thr  Gly Phe Asp Trp Ile  Thr Asp Tyr Gln Gly  Lys Thr Val
    1820                1825                1830

Trp Phe  Val Pro Ser Ile Lys  Ala Gly Asn Asp Ile  Ala Asn Cys
    1835                1840                1845

Leu Arg  Lys Ser Gly Lys Lys  Val Ile Gln Leu Ser  Arg Lys Thr
    1850                1855                1860

Phe Asp  Thr Glu Tyr Pro Lys  Thr Lys Leu Thr Asp  Trp Asp Phe
    1865                1870                1875

Val Val  Thr Thr Asp Ile Ser  Glu Met Gly Ala Asn  Phe Arg Ala
    1880                1885                1890

Gly Arg  Val Ile Asp Pro Arg  Arg Cys Leu Lys Pro  Val Ile Leu
    1895                1900                1905

Pro Asp  Gly Pro Glu Arg Val  Ile Leu Ala Gly Pro  Ile Pro Val
    1910                1915                1920

Thr Pro  Ala Ser Ala Ala Gln  Arg Arg Gly Arg Ile  Gly Arg Asn
    1925                1930                1935

Pro Ala  Gln Glu Asp Asp Gln  Tyr Val Phe Ser Gly  Asp Pro Leu
    1940                1945                1950

Lys Asn  Asp Glu Asp His Ala  His Trp Thr Glu Ala  Lys Met Leu
    1955                1960                1965

Leu Asp  Asn Ile Tyr Thr Pro  Glu Gly Ile Ile Pro  Thr Leu Phe
    1970                1975                1980

Gly Pro  Glu Arg Glu Lys Thr  Gln Ala Ile Asp Gly  Glu Phe Arg
    1985                1990                1995

Leu Arg  Gly Glu Gln Arg Lys  Thr Phe Val Glu Leu  Met Arg Arg
    2000                2005                2010

Gly Asp  Leu Pro Val Trp Leu  Ser Tyr Lys Val Ala  Ser Ala Gly
    2015                2020                2025

Ile Ser  Tyr Glu Asp Arg Glu  Trp Cys Phe Thr Gly  Glu Arg Asn
    2030                2035                2040
```

```
Asn Gln  Ile Leu Glu Glu Asn  Met Glu Val Glu Ile  Trp Thr Arg
    2045                 2050                 2055

Glu Gly  Glu Lys Lys Lys Leu  Arg Pro Arg Trp Leu  Asp Ala Arg
    2060                 2065                 2070

Val Tyr  Ala Asp Pro Met Ala  Leu Lys Asp Phe Lys  Glu Phe Ala
    2075                 2080                 2085

Ser Gly  Arg Lys Ser Ile Thr  Leu Asp Ile Leu Thr  Glu Ile Ala
    2090                 2095                 2100

Ser Leu  Pro Thr Tyr Leu Ser  Ser Arg Ala Lys Leu  Ala Leu Asp
    2105                 2110                 2115

Asn Ile  Val Met Leu His Thr  Thr Glu Arg Gly Gly  Arg Ala Tyr
    2120                 2125                 2130

Gln His  Ala Leu Asn Glu Leu  Pro Glu Ser Leu Glu  Thr Leu Met
    2135                 2140                 2145

Leu Val  Ala Leu Leu Gly Ala  Met Thr Ala Gly Ile  Phe Leu Phe
    2150                 2155                 2160

Phe Met  Gln Gly Lys Gly Ile  Gly Lys Leu Ser Met  Gly Leu Ile
    2165                 2170                 2175

Thr Ile  Ala Val Ala Ser Gly  Leu Leu Trp Val Ala  Glu Ile Gln
    2180                 2185                 2190

Pro Gln  Trp Ile Ala Ala Ser  Ile Ile Leu Glu Phe  Phe Leu Met
    2195                 2200                 2205

Val Leu  Leu Ile Pro Glu Pro  Glu Lys Gln Arg Thr  Pro Gln Asp
    2210                 2215                 2220

Asn Gln  Leu Ile Tyr Val Ile  Leu Thr Ile Leu Thr  Ile Ile Gly
    2225                 2230                 2235

Leu Ile  Ala Ala Asn Glu Met  Gly Leu Ile Glu Lys  Thr Lys Thr
    2240                 2245                 2250

Asp Phe  Gly Phe Tyr Gln Val  Lys Thr Glu Thr Thr  Ile Leu Asp
    2255                 2260                 2265

Val Asp  Leu Arg Pro Ala Ser  Ala Trp Thr Leu Tyr  Ala Val Ala
    2270                 2275                 2280

Thr Thr  Ile Leu Thr Pro Met  Leu Arg His Thr Ile  Glu Asn Thr
    2285                 2290                 2295

Ser Ala  Asn Leu Ser Leu Ala  Ala Ile Ala Asn Gln  Ala Ala Val
    2300                 2305                 2310

Leu Met  Gly Leu Gly Lys Gly  Trp Pro Leu His Arg  Met Asp Leu
    2315                 2320                 2325

Gly Val  Pro Leu Leu Ala Met  Gly Cys Tyr Ser Gln  Val Asn Pro
    2330                 2335                 2340

Thr Thr  Leu Thr Ala Ser Leu  Val Met Leu Leu Val  His Tyr Ala
    2345                 2350                 2355

Ile Ile  Gly Pro Gly Leu Gln  Ala Lys Ala Thr Arg  Glu Ala Gln
    2360                 2365                 2370

Lys Arg  Thr Ala Ala Gly Ile  Met Lys Asn Pro Thr  Val Asp Gly
    2375                 2380                 2385

Ile Thr  Val Ile Asp Leu Glu  Pro Ile Ser Tyr Asp  Pro Lys Phe
    2390                 2395                 2400

Glu Lys  Gln Leu Gly Gln Val  Met Leu Leu Val Leu  Cys Ala Gly
    2405                 2410                 2415

Gln Leu  Leu Leu Met Arg Thr  Thr Trp Ala Phe Cys  Glu Val Leu
    2420                 2425                 2430
```

```
Thr Leu Ala Thr Gly Pro Ile Leu Thr Leu Trp Glu Gly Asn Pro
    2435                2440                2445

Gly Arg Phe Trp Asn Thr Thr Ile Ala Val Ser Thr Ala Asn Ile
    2450                2455                2460

Phe Arg Gly Ser Tyr Leu Ala Gly Ala Gly Leu Ala Phe Ser Leu
    2465                2470                2475

Ile Lys Asn Ala Gln Thr Pro Arg Arg Gly Thr Gly Thr Thr Gly
    2480                2485                2490

Glu Thr Leu Gly Glu Lys Trp Lys Arg Gln Leu Asn Ser Leu Asp
    2495                2500                2505

Arg Lys Glu Phe Glu Glu Tyr Lys Arg Ser Gly Ile Leu Glu Val
    2510                2515                2520

Asp Arg Thr Glu Ala Lys Ser Ala Leu Lys Asp Gly Ser Lys Ile
    2525                2530                2535

Lys His Ala Val Ser Arg Gly Ser Ser Lys Ile Arg Trp Ile Val
    2540                2545                2550

Glu Arg Gly Met Val Lys Pro Lys Gly Lys Val Val Asp Leu Gly
    2555                2560                2565

Cys Gly Arg Gly Gly Trp Ser Tyr Tyr Met Ala Thr Leu Lys Asn
    2570                2575                2580

Val Thr Glu Val Lys Gly Tyr Thr Lys Gly Gly Pro Gly His Glu
    2585                2590                2595

Glu Pro Ile Pro Met Ala Thr Tyr Gly Trp Asn Leu Val Lys Leu
    2600                2605                2610

His Ser Gly Val Asp Val Phe Tyr Lys Pro Thr Glu Gln Val Asp
    2615                2620                2625

Thr Leu Leu Cys Asp Ile Gly Glu Ser Ser Ser Asn Pro Thr Ile
    2630                2635                2640

Glu Glu Gly Arg Thr Leu Arg Val Leu Lys Met Val Glu Pro Trp
    2645                2650                2655

Leu Ser Ser Lys Pro Glu Phe Cys Ile Lys Val Leu Asn Pro Tyr
    2660                2665                2670

Met Pro Thr Val Ile Glu Glu Leu Glu Lys Leu Gln Arg Lys His
    2675                2680                2685

Gly Gly Asn Leu Val Arg Cys Pro Leu Ser Arg Asn Ser Thr His
    2690                2695                2700

Glu Met Tyr Trp Val Ser Gly Ala Ser Gly Asn Ile Val Ser Ser
    2705                2710                2715

Val Asn Thr Thr Ser Lys Met Leu Leu Asn Arg Phe Thr Thr Arg
    2720                2725                2730

His Arg Lys Pro Thr Tyr Glu Lys Asp Val Asp Leu Gly Ala Gly
    2735                2740                2745

Thr Arg Ser Val Ser Thr Glu Thr Glu Lys Pro Asp Met Thr Ile
    2750                2755                2760

Ile Gly Arg Arg Leu Gln Arg Leu Gln Glu Glu His Lys Glu Thr
    2765                2770                2775

Trp His Tyr Asp Gln Glu Asn Pro Tyr Arg Thr Trp Ala Tyr His
    2780                2785                2790

Gly Ser Tyr Glu Ala Pro Ser Thr Gly Ser Ala Ser Ser Met Val
    2795                2800                2805

Asn Gly Val Val Lys Leu Leu Thr Lys Pro Trp Asp Val Ile Pro
    2810                2815                2820

Met Val Thr Gln Leu Ala Met Thr Asp Thr Thr Pro Phe Gly Gln
```

-continued

```
    2825                2830                2835

Gln Arg  Val Phe Lys Glu Lys  Val Asp Thr Arg Thr  Pro Gln Pro
    2840                2845                2850

Lys Pro  Gly Thr Arg Met Val  Met Thr Thr Thr Ala  Asn Trp Leu
    2855                2860                2865

Trp Ala  Leu Leu Gly Lys Lys  Lys Asn Pro Arg Leu  Cys Thr Arg
    2870                2875                2880

Glu Glu  Phe Ile Ser Lys Val  Arg Ser Asn Ala Ala  Ile Gly Ala
    2885                2890                2895

Val Phe  Gln Glu Glu Gln Gly  Trp Thr Ser Ala Ser  Glu Ala Val
    2900                2905                2910

Asn Asp  Ser Arg Phe Trp Glu  Leu Val Asp Lys Glu  Arg Ala Leu
    2915                2920                2925

His Gln  Glu Gly Lys Cys Glu  Ser Cys Val Tyr Asn  Met Met Gly
    2930                2935                2940

Lys Arg  Glu Lys Lys Leu Gly  Glu Phe Gly Arg Ala  Lys Gly Ser
    2945                2950                2955

Arg Ala  Ile Trp Tyr Met Trp  Leu Gly Ala Arg Phe  Leu Glu Phe
    2960                2965                2970

Glu Ala  Leu Gly Phe Leu Asn  Glu Asp His Trp Phe  Gly Arg Glu
    2975                2980                2985

Asn Ser  Trp Ser Gly Val Glu  Gly Glu Gly Leu His  Arg Leu Gly
    2990                2995                3000

Tyr Ile  Leu Glu Glu Ile Asp  Lys Lys Asp Gly Asp  Leu Met Tyr
    3005                3010                3015

Ala Asp  Asp Thr Ala Gly Trp  Asp Thr Arg Ile Thr  Glu Asp Asp
    3020                3025                3030

Leu Gln  Asn Glu Glu Leu Ile  Thr Glu Gln Met Ala  Pro His His
    3035                3040                3045

Lys Ile  Leu Ala Lys Ala Ile  Phe Lys Leu Thr Tyr  Gln Asn Lys
    3050                3055                3060

Val Val  Lys Val Leu Arg Pro  Thr Pro Arg Gly Ala  Val Met Asp
    3065                3070                3075

Ile Ile  Ser Arg Lys Asp Gln  Arg Gly Ser Gly Gln  Val Gly Thr
    3080                3085                3090

Tyr Gly  Leu Asn Thr Phe Thr  Asn Met Glu Val Gln  Leu Ile Arg
    3095                3100                3105

Gln Met  Glu Ala Glu Gly Val  Ile Thr Gln Asp Asp  Met Gln Asn
    3110                3115                3120

Pro Lys  Gly Leu Lys Glu Arg  Val Glu Lys Trp Leu  Lys Glu Cys
    3125                3130                3135

Gly Val  Asp Arg Leu Lys Arg  Met Ala Ile Ser Gly  Asp Asp Cys
    3140                3145                3150

Val Val  Lys Pro Leu Asp Glu  Arg Phe Gly Thr Ser  Leu Leu Phe
    3155                3160                3165

Leu Asn  Asp Met Gly Lys Val  Arg Lys Asp Ile Pro  Gln Trp Glu
    3170                3175                3180

Pro Ser  Lys Gly Trp Lys Asn  Trp Gln Glu Val Pro  Phe Cys Ser
    3185                3190                3195

His His  Phe His Lys Ile Phe  Met Lys Asp Gly Arg  Ser Leu Val
    3200                3205                3210

Val Pro  Cys Arg Asn Gln Asp  Glu Leu Ile Gly Arg  Ala Arg Ile
    3215                3220                3225
```

```
Ser Gln Gly Ala Gly Trp Ser Leu Arg Glu Thr Ala Cys Leu Gly
    3230                3235                3240

Lys Ala Tyr Ala Gln Met Trp Ser Leu Met Tyr Phe His Arg Arg
    3245                3250                3255

Asp Leu Arg Leu Ala Ser Met Ala Ile Cys Ser Ala Val Pro Thr
    3260                3265                3270

Glu Trp Phe Pro Thr Ser Arg Thr Thr Trp Ser Ile His Ala His
    3275                3280                3285

His Gln Trp Met Thr Thr Glu Asp Met Leu Lys Val Trp Asn Arg
    3290                3295                3300

Val Trp Ile Glu Asp Asn Pro Asn Met Thr Asp Lys Thr Pro Val
    3305                3310                3315

His Ser Trp Glu Asp Ile Pro Tyr Leu Gly Lys Arg Glu Asp Leu
    3320                3325                3330

Trp Cys Gly Ser Leu Ile Gly Leu Ser Ser Arg Ala Thr Trp Ala
    3335                3340                3345

Lys Asn Ile His Thr Ala Ile Thr Gln Val Arg Asn Leu Ile Gly
    3350                3355                3360

Lys Glu Glu Tyr Val Asp Tyr Met Pro Val Met Lys Arg Tyr Ser
    3365                3370                3375

Ala Pro Ser Glu Ser Glu Gly Val Leu
    3380                3385
```

<210> SEQ ID NO 16
<211> LENGTH: 10649
<212> TYPE: DNA
<213> ORGANISM: Recombinant Dengue 4 virus strain rDEN4

<400> SEQUENCE: 16

```
agttgttagt ctgtgtggac cgacaaggac agttccaaat cggaagcttg cttaacacag      60

ttctaacagt ttgtttgaat agagagcaga tctctggaaa aatgaaccaa cgaaaaaagg     120

tggttagacc acctttcaat atgctgaaac gcgagagaaa ccgcgtatca acccctcaag     180

ggttggtgaa gagattctca accggacttt tttctgggaa aggaccctta cggatggtgc     240

tagcattcat cacgtttttg cgagtccttt ccatcccacc aacagcaggg attctgaaga     300

gatggggaca gttgaagaaa aataaggcca tcaagatact gattggattc aggaaggaga     360

taggccgcat gctgaacatc ttgaacggga gaaaaaggtc aacgataaca ttgctgtgct     420

tgattcccac cgtaatggcg ttttccctca gcacaagaga tggcgaaccc ctcatgatag     480

tggcaaaaca tgaaaggggg agacctctct tgtttaagac aacagagggg atcaacaaat     540

gcactctcat tgccatggac ttgggtgaaa tgtgtgagga cactgtcacg tataaatgcc     600

ccctactggt caataccgaa cctgaagaca ttgattgctg gtgcaacctc acgtctacct     660

gggtcatgta tgggacatgc acccagagcg gagaacggag acgagagaag cgctcagtag     720

ctttaacacc acattcagga atgggattgg aaacaagagc tgagacatgg atgtcatcgg     780

aaggggcttg gaagcatgct cagagagtag agagctggat actcagaaac ccaggattcg     840

cgctcttggc aggatttatg gcttatatga ttgggcaaac aggaatccag cgaactgtct     900

tctttgtcct aatgatgctg gtcgccccat cctacggaat gcgatgcgta ggagtaggaa     960

acagagactt tgtggaagga gtctcaggtg gagcatgggt cgacctggtg ctagaacatg    1020

gaggatgcgt cacaaccatg gcccagggaa aaccaacctt ggattttgaa ctgactaaga    1080

caacagccaa ggaagtggct ctgttaagaa cctattgcat tgaagcctca atatcaaaca    1140
```

taactacggc aacaagatgt ccaacgcaag gagagcctta tctgaaagag gaacaggacc 1200
aacagtacat ttgccggaga gatgtggtag acagagggtg gggcaatggc tgtggcttgt 1260
ttggaaaagg aggagttgtg acatgtgcga agttttcatg ttcggggaag ataacaggca 1320
atttggtcca aattgagaac cttgaataca cagtggttgt aacagtccac aatggagaca 1380
cccatgcagt aggaaatgac acatccaatc atggagttac agccatgata actcccaggt 1440
caccatcggt ggaagtcaaa ttgccggact atggagaact aacactcgat tgtgaaccca 1500
ggtctggaat tgactttaat gagatgattc tgatgaaaat gaaaaagaaa acatggctcg 1560
tgcataagca atggtttttg gatctgcctc ttccatggac agcaggagca gacacatcag 1620
aggttcactg gaattacaaa gagagaatgg tgacatttaa ggttcctcat gccaagagac 1680
aggatgtgac agtgctggga tctcaggaag gagccatgca ttctgccctc gctggagcca 1740
cagaagtgga ctccggtgat ggaaatcaca tgtttgcagg acatcttaag tgcaaagtcc 1800
gtatggagaa attgagaatc aagggaatgt catacacgat gtgttcagga aagttttcaa 1860
ttgacaaaga gatggcagaa acacagcatg ggacaacagt ggtgaaagtc aagtatgaag 1920
gtgctggagc tccgtgtaaa gtccccatag agataagaga tgtaaacaag gaaaaagtgg 1980
ttgggcgtat catctcatcc accccttttgg ctgagaatac caacagtgta accaacatag 2040
aattagaacc cccctttggg gacagctaca tagtgatagg tgttggaaac agcgcattaa 2100
cactccattg gttcaggaaa gggagttcca ttggcaagat gtttgagtcc acatacagag 2160
gtgcaaaacg aatggccatt ctaggtgaaa cagcttggga ttttggttcc gttggtggac 2220
tgttcacatc attgggaaag gctgtgcacc aggtttttgg aagtgtgtat acaaccatgt 2280
ttggaggagt ctcatggatg attagaatcc taattgggtt cttagtgttg tggattggca 2340
cgaactcgag gaacacttca atggctatga cgtgcatagc tgttggagga atcactctgt 2400
ttctgggctt cacagttcaa gcagacatgg gttgtgtggc gtcatggagt gggaaagaat 2460
tgaagtgtgg aagcggaatt tttgtggttg acaacgtgca cacttggaca gaacagtaca 2520
aatttcaacc agagtcccca gcgagactag cgtctgcaat attaaatgcc cacaaagatg 2580
gggtctgtgg aattagatca accacgaggc tggaaaatgt catgtggaag caaataacca 2640
acgagctaaa ctatgttctc tgggaaggag gacatgacct cactgtagtg gctggggatg 2700
tgaagggggt gttgaccaaa ggcaagagag cactcacacc cccagtgagt gatctgaaat 2760
attcatggaa gacatgggga aaagcaaaaa tcttcacccc agaagcaaga aatagcacat 2820
ttttaataga cggaccagac acctctgaat gccccaatga acgaagagca tggaactctc 2880
ttgaggtgga agactatgga tttggcatgt tcacgaccaa catatggatg aaattccgag 2940
aaggaagttc agaagtgtgt gaccacaggt taatgtcagc tgcaattaaa gatcagaaag 3000
ctgtgcatgc tgacatgggt tattggatag agagctcaaa aaaccagacc tggcagatag 3060
agaaagcatc tcttattgaa gtgaaaacat gtctgtggcc caagacccac acactgtgga 3120
gcaatggagt gctggaaagc cagatgctca ttccaaaatc atatgcgggc cctttttcac 3180
agcacaatta ccgccagggc tatgccacgc aaaccgtggg cccatggcac ttaggcaaat 3240
tagagataga ctttggagaa tgccccggaa caacagtcac aattcaggag gattgtgacc 3300
atagaggccc atctttgagg accaccactg catctggaaa actagtcacg caatggtgct 3360
gccgctcctg cacgatgcct cccttaaggt tcttgggaga agatgggtgc tggtatggga 3420
tggagattag gcccttgagt gaaaaagaag agaacatggt caaatcacag gtgacggccg 3480

```
gacagggcac atcagaaact ttttctatgg gtctgttgtg cctgaccttg tttgtggaag   3540
aatgcttgag gagaagagtc actaggaaac acatgatatt agttgtggtg atcactcttt   3600
gtgctatcat cctgggaggc ctcacatgga tggacttact acgagccctc atcatgttgg   3660
gggacactat gtctggtaga ataggaggac agatccacct agccatcatg gcagtgttca   3720
agatgtcacc aggatacgtg ctgggtgtgt ttttaaggaa actcacttca agagagacag   3780
cactaatggt aataggaatg gccatgacaa cggtgctttc aattccacat gaccttatgg   3840
aactcattga tggaatatca ctgggactaa ttttgctaaa aatagtaaca cagtttgaca   3900
acacccaagt gggaacctta gctctttcct tgactttcat aagatcaaca atgccattgg   3960
tcatggcttg gaggaccatt atggctgtgt tgtttgtggt cacactcatt cctttgtgca   4020
ggacaagctg tcttcaaaaa cagtctcatt gggtagaaat aacagcactc atcctaggag   4080
cccaagctct gccagtgtac ctaatgactc ttatgaaagg agcctcaaga agatcttggc   4140
ctcttaacga gggcataatg gctgtgggtt tggttagtct cttaggaagc gctcttttaa   4200
agaatgatgt ccctttagct ggcccaatgg tggcaggagg cttacttctg gcggcttacg   4260
tgatgagtgg tagctcagca gatctgtcac tagagaaggc cgccaacgtg cagtgggatg   4320
aaatggcaga cataacaggc tcaagcccaa tcgtagaagt gaagcaggat gaagatggct   4380
ctttctccat acgggacgtc gaggaaacca atatgataac ccttttggtg aaactggcac   4440
tgataacagt gtcaggtctc taccccttgg caattccagt cacaatgacc ttatggtaca   4500
tgtggcaagt gaaaacacaa agatcaggag ccctgtggga cgtcccctca cccgctgcca   4560
ctaaaaaagc cgcactgtct gaaggagtgt acaggatcat gcaaagaggg ttattcggga   4620
aaactcaggt tggagtaggg atacacatgg aaggtgtatt tcacacaatg tggcatgtaa   4680
caagaggatc agtgatctgc cacgagactg ggagattgga gccatcttgg gctgacgtca   4740
ggaatgacat gatatcatac ggtgggggat ggaggcttgg agacaaatgg gacaaagaag   4800
aagacgttca ggtcctcgcc atagaaccag gaaaaaatcc taaacatgtc caaacgaaac   4860
ctggcctttt caagacccta actggagaaa ttggagcagt aacattagat ttcaaacccg   4920
gaacgtctgg ttctcccatc atcaacagga aaggaaaagt catcggactc tatggaaatg   4980
gagtagttac caaatcaggt gattacgtca gtgccataac gcaagccgaa agaattggag   5040
agccagatta tgaagtggat gaggacattt ttcgaaagaa aagattaact ataatggact   5100
tacaccccgg agctggaaag acaaaaagaa ttcttccatc aatagtgaga gaagccttaa   5160
aaaggaggct acgaactttg attttagctc ccacgagagt ggtggcggcc gagatggaag   5220
aggccctacg tggactgcca atccgttatc agaccccagc tgtgaaatca gaacacacag   5280
gaagagagat tgtagacctc atgtgtcatg caaccttcac aacaagactt ttgtcatcaa   5340
ccagggttcc aaattacaac cttatagtga tggatgaagc acatttcacc gatccttcta   5400
gtgtcgcggc tagaggatac atctcgacca gggtggaaat gggagaggca gcagccatct   5460
tcatgaccgc aacccctccc ggagcgacag atccctttcc ccagagcaac agcccaatag   5520
aagacatcga gagggaaatt ccggaaaggt catggaacac agggttcgac tggataacag   5580
actaccaagg gaaaactgtg tggtttgttc ccagcataaa agctggaaat gacattgcaa   5640
attgtttgag aaagtcggga aagaaagtta tccagttgag taggaaaacc tttgatacag   5700
agtatccaaa aacgaaactc acggactggg actttgtggt cactacagac atatctgaaa   5760
tgggggccaa ttttagagcc gggagagtga tagaccctag aagatgcctc aagccagtta   5820
tcctaccaga tgggccagag agagtcattt tagcaggtcc tattccagtg actccagcaa   5880
```

gcgctgctca gagaagaggg cgaataggaa ggaacccagc acaagaagac gaccaatacg 5940
ttttctccgg agacccacta aaaaatgatg aagatcatgc ccactggaca gaagcaaaga 6000
tgctgcttga caatatctac accccagaag ggatcattcc aacattgttt ggtccggaaa 6060
gggaaaaaac ccaagccatt gatggagagt ttcgcctcag aggggaacaa aggaagactt 6120
ttgtggaatt aatgaggaga ggagaccttc cggtgtggct gagctataag gtagcttctg 6180
ctggcatttc ttacgaagat cgggaatggt gcttcacagg ggaaagaaat aaccaaattt 6240
tagaagaaaa catggaggtt gaaatttgga ctagagaggg agaaaagaaa aagctaaggc 6300
caagatggtt agatgcacgt gtatacgctg accccatggc tttgaaggat ttcaaggagt 6360
ttgccagtgg aaggaagagt ataactctcg acatcctaac agagattgcc agtttgccaa 6420
cttacctttc ctctagggcc aagctcgccc ttgataacat agtcatgctc cacacaacag 6480
aaagaggagg gagggcctat caacacgccc tgaacgaact tccggagtca ctggaaacac 6540
tcatgcttgt agctttacta ggtgctatga cagcaggcat cttcctgttt ttcatgcaag 6600
ggaaaggaat agggaaattg tcaatgggtt tgataaccat tgcggtggct agtggcttgc 6660
tctgggtagc agaaattcaa ccccagtgga tagcggcctc aatcatacta gagttttttc 6720
tcatggtact gttgataccg gaaccagaaa aacaaaggac cccacaagac aatcaattga 6780
tctacgtcat attgaccatt ctcaccatca ttggtctaat agcagccaac gagatggggc 6840
tgattgaaaa aacaaaaacg gattttgggt tttaccaggt aaaaacagaa accaccatcc 6900
tcgatgtgga cttgagacca gcttcagcat ggacgctcta tgcagtagcc accacaattc 6960
tgactcccat gctgagacac accatagaaa acacgtcggc caacctatct ctagcagcca 7020
ttgccaacca ggcagccgtc ctaatggggc ttggaaaagg atggccgctc cacagaatgg 7080
acctcggtgt gccgctgtta gcaatgggat gctattctca agtgaaccca acaaccttga 7140
cagcatcctt agtcatgctt ttagtccatt atgcaataat aggcccagga ttgcaggcaa 7200
aagccacaag agaggcccag aaaaggacag ctgctgggat catgaaaaat cccacagtgg 7260
acgggataac agtaatagat ctagaaccaa tatcctatga cccaaaattt gaaaagcaat 7320
tagggcaggt catgctacta gtcttgtgtg ctggacaact actcttgatg agaacaacat 7380
gggctttctg tgaagtcttg actttggcca caggaccaat cttgaccttg tgggagggca 7440
acccgggaag gttttggaac acgaccatag ccgtatccac cgccaacatt ttcaggggaa 7500
gttacttggc gggagctgga ctggcttttt cactcataaa gaatgcacaa acccctagga 7560
ggggaactgg gaccacagga gagacactgg gagagaagtg gaagagacag ctaaactcat 7620
tagacagaaa agagtttgaa gagtataaaa gaagtggaat actagaagtg gacaggactg 7680
aagccaagtc tgccctgaaa gatgggtcta aaatcaagca tgcagtatca agagggtcca 7740
gtaagatcag atggattgtt gagagaggga tggtaaagcc aaaagggaaa gttgtagatc 7800
ttggctgtgg gagaggagga tggtcttatt acatggcgac actcaagaac gtgactgaag 7860
tgaaagggta tacaaaagga ggtccaggac atgaagaacc gattcccatg gctacttatg 7920
gttggaattt ggtcaaactc cattcagggg ttgacgtgtt ctacaaaccc acagagcaag 7980
tggacaccct gctctgtgat attggggagt catcttctaa tccaacaata gaggaaggaa 8040
gaacattaag agttttgaag atggtggagc catggctctc ttcaaaacct gaattctgca 8100
tcaaagtcct taacccctac atgccaacag tcatagaaga gctggagaaa ctgcagagaa 8160
aacatggtgg gaaccttgtc agatgcccgc tgtccaggaa ctccacccat gagatgtatt 8220

-continued

```
gggtgtcagg agcgtcggga aacattgtga gctctgtgaa cacaacatca aagatgttgt   8280
tgaacaggtt cacaacaagg cataggaaac ccacttatga gaaggacgta gatcttgggg   8340
caggaacgag aagtgtctcc actgaaacag aaaaaccaga catgacaatc attgggagaa   8400
ggcttcagcg attgcaagaa gagcacaaag aaacctggca ttatgatcag gaaaacccat   8460
acagaacctg ggcgtatcat ggaagctatg aagctccttc gacaggctct gcatcctcca   8520
tggtgaacgg ggtggtaaaa ctgctaacaa aaccctggga tgtgattcca atggtgactc   8580
agttagccat gacagataca acccctttg ggcaacaaag agtgttcaaa gagaaggtgg    8640
ataccagaac accacaacca aaacccggta cacgaatggt tatgaccacg acagccaatt   8700
ggctgtgggc cctccttgga aagaagaaaa atcccagact gtgcacaagg gaagagttca   8760
tctcaaaagt tagatcaaac gcagccatag gcgcagtctt tcaggaagaa cagggatgga   8820
catcagccag tgaagctgtg aatgacagcc ggttttggga actggttgac aaagaaaggg   8880
ccctacacca ggaagggaaa tgtgaatcgt gtgtctataa catgatggga aaacgtgaga   8940
aaaagttagg agagtttggc agagccaagg gaagccgagc aatctggtac atgtggctgg   9000
gagcgcggtt tctggaattt gaagccctgg gtttttgaa tgaagatcac tggtttggca    9060
gagaaaattc atggagtgga gtggaagggg aaggtctgca cagattggga tatatcctgg   9120
aggagataga caagaaggat ggagacctaa tgtatgctga tgacacagca ggctgggaca   9180
caagaatcac tgaggatgac cttcaaaatg aggaactgat cacggaacag atggctcccc   9240
accacaagat cctagccaaa gccattttca aactaaccta tcaaaacaaa gtggtgaaag   9300
tcctcagacc cacaccgcgg ggagcggtga tggatatcat atccaggaaa gaccaaagag   9360
gtagtggaca agttggaaca tatggtttga acacattcac caacatggaa gttcaactca   9420
tccgccaaat ggaagctgaa ggagtcatca cacaagatga catgcagaac ccaaaagggt   9480
tgaaagaaag agttgagaaa tggctgaaag agtgtggtgt cgacaggtta aagaggatgg   9540
caatcagtgg agacgattgc gtggtgaagc ccctagatga gaggtttggc acttccctcc   9600
tcttcttgaa cgacatggga aaggtgagga aagacattcc gcagtgggaa ccatctaagg   9660
gatggaaaaa ctggcaagag gttccttttt gctcccacca ctttcacaag atctttatga   9720
aggatggccg ctcactagtt gttccatgta gaaaccagga tgaactgata gggagagcca   9780
gaatctcgca gggagctgga tggagcttaa gagaaacagc ctgcctgggc aaagcttacg   9840
cccagatgtg gtcgcttatg tacttccaca gaagggatct gcgtttagcc tccatggcca   9900
tatgctcagc agttccaacg gaatggtttc caacaagcag aacaacatgg tcaatccacg   9960
ctcatcacca gtggatgacc actgaagata tgctcaaagt gtggaacaga gtgtggatag  10020
aagacaaccc taatatgact gacaagactc cagtccattc gtgggaagat ataccttacc  10080
tagggaaaag agaggatttg tggtgtggat ccctgattgg actttcttcc agagccacct  10140
gggcgaagaa cattcatacg gccataaccc aggtcaggaa cctgatcgga aaagaggaat  10200
acgtggatta catgccagta atgaaaagat acagtgctcc ttcagagagt gaaggagttc  10260
tgtaattacc aacaacaaac accaaaggct attgaagtca ggccacttgt gccacggttt  10320
gagcaaaccg tgctgcctgt agctccgcca ataatgggag gcgtaataat ccccagggag  10380
gccatgcgcc acggaagctg tacgcgtggc atattggact agcggttaga ggagacccct  10440
cccatcactg ataaaacgca gcaaaagggg gcccgaagcc aggaggaagc tgtactcctg  10500
gtggaaggac tagaggttag aggagacccc cccaacacaa aaacagcata ttgacgctgg  10560
gaaagaccag agatcctgct gtctctgcaa catcaatcca ggcacagagc gccgcaagat  10620
```

```
ggattggtgt tgttgatcca acaggttct                                   10649


<210> SEQ ID NO 17
<211> LENGTH: 3388
<212> TYPE: PRT
<213> ORGANISM: Recombinant Dengue rDEN2/4d30

<400> SEQUENCE: 17

Met Asn Asn Gln Arg Lys Lys Ala Arg Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Ala Pro Ser Met Thr Met Arg Cys Ile Gly Ile Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365
```

-continued

```
Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Thr
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Asn
            740                 745                 750

Thr Ser Met Ala Met Thr Cys Ile Ala Val Gly Gly Ile Thr Leu Phe
        755                 760                 765

Leu Gly Phe Thr Val Gln Ala Asp Met Gly Cys Val Ala Ser Trp Ser
    770                 775                 780
```

```
Gly Lys Glu Leu Lys Cys Gly Ser Gly Ile Phe Val Val Asp Asn Val
785                 790                 795                 800

His Thr Trp Thr Glu Gln Tyr Lys Phe Gln Pro Glu Ser Pro Ala Arg
                805                 810                 815

Leu Ala Ser Ala Ile Leu Asn Ala His Lys Asp Gly Val Cys Gly Ile
            820                 825                 830

Arg Ser Thr Thr Arg Leu Glu Asn Val Met Trp Lys Gln Ile Thr Asn
        835                 840                 845

Glu Leu Asn Tyr Val Leu Trp Glu Gly Gly His Asp Leu Thr Val Val
    850                 855                 860

Ala Gly Asp Val Lys Gly Val Leu Thr Lys Gly Lys Arg Ala Leu Thr
865                 870                 875                 880

Pro Pro Val Ser Asp Leu Lys Tyr Ser Trp Lys Thr Trp Gly Lys Ala
                885                 890                 895

Lys Ile Phe Thr Pro Glu Ala Arg Asn Ser Thr Phe Leu Ile Asp Gly
            900                 905                 910

Pro Asp Thr Ser Glu Cys Pro Asn Glu Arg Arg Ala Trp Asn Ser Leu
        915                 920                 925

Glu Val Glu Asp Tyr Gly Phe Gly Met Phe Thr Thr Asn Ile Trp Met
    930                 935                 940

Lys Phe Arg Glu Gly Ser Ser Glu Val Cys Asp His Arg Leu Met Ser
945                 950                 955                 960

Ala Ala Ile Lys Asp Gln Lys Ala Val His Ala Asp Met Gly Tyr Trp
                965                 970                 975

Ile Glu Ser Ser Lys Asn Gln Thr Trp Gln Ile Glu Lys Ala Ser Leu
            980                 985                 990

Ile Glu Val Lys Thr Cys Leu Trp  Pro Lys Thr His Thr  Leu Trp Ser
        995                 1000                 1005

Asn Gly  Val Leu Glu Ser Gln  Met Leu Ile Pro Lys  Ser Tyr Ala
    1010                 1015                 1020

Gly Pro  Phe Ser Gln His Asn  Tyr Arg Gln Gly Tyr  Ala Thr Gln
    1025                 1030                 1035

Thr Val  Gly Pro Trp His Leu  Gly Lys Leu Glu Ile  Asp Phe Gly
    1040                 1045                 1050

Glu Cys  Pro Gly Thr Thr Val  Thr Ile Gln Glu Asp  Cys Asp His
    1055                 1060                 1065

Arg Gly  Pro Ser Leu Arg Thr  Thr Thr Ala Ser Gly  Lys Leu Val
    1070                 1075                 1080

Thr Gln  Trp Cys Cys Arg Ser  Cys Thr Met Pro Pro  Leu Arg Phe
    1085                 1090                 1095

Leu Gly  Glu Asp Gly Cys Trp  Tyr Gly Met Glu Ile  Arg Pro Leu
    1100                 1105                 1110

Ser Glu  Lys Glu Glu Asn Met  Val Lys Ser Gln Val  Thr Ala Gly
    1115                 1120                 1125

Gln Gly  Thr Ser Glu Thr Phe  Ser Met Gly Leu Leu  Cys Leu Thr
    1130                 1135                 1140

Leu Phe  Val Glu Glu Cys Leu  Arg Arg Arg Val Thr  Arg Lys His
    1145                 1150                 1155

Met Ile  Leu Val Val Val Ile  Thr Leu Cys Ala Ile  Ile Leu Gly
    1160                 1165                 1170

Gly Leu  Thr Trp Met Asp Leu  Leu Arg Ala Leu Ile  Met Leu Gly
    1175                 1180                 1185

Asp Thr  Met Ser Gly Arg Ile  Gly Gly Gln Ile His  Leu Ala Ile
```

```
    1190                1195                1200

Met Ala  Val Phe Lys Met Ser  Pro Gly Tyr Val Leu  Gly Val Phe
    1205                1210                1215

Leu Arg  Lys Leu Thr Ser Arg  Glu Thr Ala Leu Met  Val Ile Gly
    1220                1225                1230

Met Ala  Met Thr Thr Val Leu  Ser Ile Pro His Asp  Leu Met Glu
    1235                1240                1245

Leu Ile  Asp Gly Ile Ser Leu  Gly Leu Ile Leu Leu  Lys Ile Val
    1250                1255                1260

Thr Gln  Phe Asp Asn Thr Gln  Val Gly Thr Leu Ala  Leu Ser Leu
    1265                1270                1275

Thr Phe  Ile Arg Ser Thr Met  Pro Leu Val Met Ala  Trp Arg Thr
    1280                1285                1290

Ile Met  Ala Val Leu Phe Val  Val Thr Leu Ile Pro  Leu Cys Arg
    1295                1300                1305

Thr Ser  Cys Leu Gln Lys Gln  Ser His Trp Val Glu  Ile Thr Ala
    1310                1315                1320

Leu Ile  Leu Gly Ala Gln Ala  Leu Pro Val Tyr Leu  Met Thr Leu
    1325                1330                1335

Met Lys  Gly Ala Ser Arg Arg  Ser Trp Pro Leu Asn  Glu Gly Ile
    1340                1345                1350

Met Ala  Val Gly Leu Val Ser  Leu Leu Gly Ser Ala  Leu Leu Lys
    1355                1360                1365

Asn Asp  Val Pro Leu Ala Gly  Pro Met Val Ala Gly  Gly Leu Leu
    1370                1375                1380

Leu Ala  Ala Tyr Val Met Ser  Gly Ser Ser Ala Asp  Leu Ser Leu
    1385                1390                1395

Glu Lys  Ala Ala Asn Val Gln  Trp Asp Glu Met Ala  Asp Ile Thr
    1400                1405                1410

Gly Ser  Ser Pro Ile Val Glu  Val Lys Gln Asp Glu  Asp Gly Ser
    1415                1420                1425

Phe Ser  Ile Arg Asp Val Glu  Glu Thr Asn Met Ile  Thr Leu Leu
    1430                1435                1440

Val Lys  Leu Ala Leu Ile Thr  Val Ser Gly Leu Tyr  Pro Leu Ala
    1445                1450                1455

Ile Pro  Val Thr Met Thr Leu  Trp Tyr Met Trp Gln  Val Lys Thr
    1460                1465                1470

Gln Arg  Ser Gly Ala Leu Trp  Asp Val Pro Ser Pro  Ala Ala Thr
    1475                1480                1485

Lys Lys  Ala Ala Leu Ser Glu  Gly Val Tyr Arg Ile  Met Gln Arg
    1490                1495                1500

Gly Leu  Phe Gly Lys Thr Gln  Val Gly Val Gly Ile  His Met Glu
    1505                1510                1515

Gly Val  Phe His Thr Met Trp  His Val Thr Arg Gly  Ser Val Ile
    1520                1525                1530

Cys His  Glu Thr Gly Arg Leu  Glu Pro Ser Trp Ala  Asp Val Arg
    1535                1540                1545

Asn Asp  Met Ile Ser Tyr Gly  Gly Gly Trp Arg Leu  Gly Asp Lys
    1550                1555                1560

Trp Asp  Lys Glu Glu Asp Val  Gln Val Leu Ala Ile  Glu Pro Gly
    1565                1570                1575

Lys Asn  Pro Lys His Val Gln  Thr Lys Pro Gly Leu  Phe Lys Thr
    1580                1585                1590
```

```
Leu Thr  Gly Glu Ile Gly Ala  Val Thr Leu Asp Phe  Lys Pro Gly
    1595                 1600                 1605

Thr Ser  Gly Ser Pro Ile Ile  Asn Arg Lys Gly Lys  Val Ile Gly
    1610                 1615                 1620

Leu Tyr  Gly Asn Gly Val Val  Thr Lys Ser Gly Asp  Tyr Val Ser
    1625                 1630                 1635

Ala Ile  Thr Gln Ala Glu Arg  Ile Gly Glu Pro Asp  Tyr Glu Val
    1640                 1645                 1650

Asp Glu  Asp Ile Phe Arg Lys  Lys Arg Leu Thr Ile  Met Asp Leu
    1655                 1660                 1665

His Pro  Gly Ala Gly Lys Thr  Lys Arg Ile Leu Pro  Ser Ile Val
    1670                 1675                 1680

Arg Glu  Ala Leu Lys Arg Arg  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Val Lys Ser Glu  His Thr Gly
    1715                 1720                 1725

Arg Glu  Ile Val Asp Leu Met  Cys His Ala Thr Phe  Thr Thr Arg
    1730                 1735                 1740

Leu Leu  Ser Ser Thr Arg Val  Pro Asn Tyr Asn Leu  Ile Val Met
    1745                 1750                 1755

Asp Glu  Ala His Phe Thr Asp  Pro Ser Ser Val Ala  Ala Arg Gly
    1760                 1765                 1770

Tyr Ile  Ser Thr Arg Val Glu  Met Gly Glu Ala Ala  Ala Ile Phe
    1775                 1780                 1785

Met Thr  Ala Thr Pro Pro Gly  Ala Thr Asp Pro Phe  Pro Gln Ser
    1790                 1795                 1800

Asn Ser  Pro Ile Glu Asp Ile  Glu Arg Glu Ile Pro  Glu Arg Ser
    1805                 1810                 1815

Trp Asn  Thr Gly Phe Asp Trp  Ile Thr Asp Tyr Gln  Gly Lys Thr
    1820                 1825                 1830

Val Trp  Phe Val Pro Ser Ile  Lys Ala Gly Asn Asp  Ile Ala Asn
    1835                 1840                 1845

Cys Leu  Arg Lys Ser Gly Lys  Lys Val Ile Gln Leu  Ser Arg Lys
    1850                 1855                 1860

Thr Phe  Asp Thr Glu Tyr Pro  Lys Thr Lys Leu Thr  Asp Trp Asp
    1865                 1870                 1875

Phe Val  Val Thr Thr Asp Ile  Ser Glu Met Gly Ala  Asn Phe Arg
    1880                 1885                 1890

Ala Gly  Arg Val Ile Asp Pro  Arg Arg Cys Leu Lys  Pro Val Ile
    1895                 1900                 1905

Leu Pro  Asp Gly Pro Glu Arg  Val Ile Leu Ala Gly  Pro Ile Pro
    1910                 1915                 1920

Val Thr  Pro Ala Ser Ala Ala  Gln Arg Arg Gly Arg  Ile Gly Arg
    1925                 1930                 1935

Asn Pro  Ala Gln Glu Asp Asp  Gln Tyr Val Phe Ser  Gly Asp Pro
    1940                 1945                 1950

Leu Lys  Asn Asp Glu Asp His  Ala His Trp Thr Glu  Ala Lys Met
    1955                 1960                 1965

Leu Leu  Asp Asn Ile Tyr Thr  Pro Glu Gly Ile Ile  Pro Thr Leu
    1970                 1975                 1980
```

```
Phe Gly  Pro Glu Arg Glu Lys  Thr Gln Ala Ile Asp  Gly Glu Phe
    1985                 1990                 1995

Arg Leu  Arg Gly Glu Gln Arg  Lys Thr Phe Val Glu  Leu Met Arg
    2000                 2005                 2010

Arg Gly  Asp Leu Pro Val Trp  Leu Ser Tyr Lys Val  Ala Ser Ala
    2015                 2020                 2025

Gly Ile  Ser Tyr Glu Asp Arg  Glu Trp Cys Phe Thr  Gly Glu Arg
    2030                 2035                 2040

Asn Asn  Gln Ile Leu Glu Glu  Asn Met Glu Val Glu  Ile Trp Thr
    2045                 2050                 2055

Arg Glu  Gly Glu Lys Lys Lys  Leu Arg Pro Arg Trp  Leu Asp Ala
    2060                 2065                 2070

Arg Val  Tyr Ala Asp Pro Met  Ala Leu Lys Asp Phe  Lys Glu Phe
    2075                 2080                 2085

Ala Ser  Gly Arg Lys Ser Ile  Thr Leu Asp Ile Leu  Thr Glu Ile
    2090                 2095                 2100

Ala Ser  Leu Pro Thr Tyr Leu  Ser Ser Arg Ala Lys  Leu Ala Leu
    2105                 2110                 2115

Asp Asn  Ile Val Met Leu His  Thr Thr Glu Arg Gly  Gly Arg Ala
    2120                 2125                 2130

Tyr Gln  His Ala Leu Asn Glu  Leu Pro Glu Ser Leu  Glu Thr Leu
    2135                 2140                 2145

Met Leu  Val Ala Leu Leu Gly  Ala Met Thr Ala Gly  Ile Phe Leu
    2150                 2155                 2160

Phe Phe  Met Gln Gly Lys Gly  Ile Gly Lys Leu Ser  Met Gly Leu
    2165                 2170                 2175

Ile Thr  Ile Ala Val Ala Ser  Gly Leu Leu Trp Val  Ala Glu Ile
    2180                 2185                 2190

Gln Pro  Gln Trp Ile Ala Ala  Ser Ile Ile Leu Glu  Phe Phe Leu
    2195                 2200                 2205

Met Val  Leu Leu Ile Pro Glu  Pro Glu Lys Gln Arg  Thr Pro Gln
    2210                 2215                 2220

Asp Asn  Gln Leu Ile Tyr Val  Ile Leu Thr Ile Leu  Thr Ile Ile
    2225                 2230                 2235

Gly Leu  Ile Ala Ala Asn Glu  Met Gly Leu Ile Glu  Lys Thr Lys
    2240                 2245                 2250

Thr Asp  Phe Gly Phe Tyr Gln  Val Lys Thr Glu Thr  Thr Ile Leu
    2255                 2260                 2265

Asp Val  Asp Leu Arg Pro Ala  Ser Ala Trp Thr Leu  Tyr Ala Val
    2270                 2275                 2280

Ala Thr  Thr Ile Leu Thr Pro  Met Leu Arg His Thr  Ile Glu Asn
    2285                 2290                 2295

Thr Ser  Ala Asn Leu Ser Leu  Ala Ala Ile Ala Asn  Gln Ala Ala
    2300                 2305                 2310

Val Leu  Met Gly Leu Gly Lys  Gly Trp Pro Leu His  Arg Met Asp
    2315                 2320                 2325

Leu Gly  Val Pro Leu Leu Ala  Met Gly Cys Tyr Ser  Gln Val Asn
    2330                 2335                 2340

Pro Thr  Thr Leu Thr Ala Ser  Leu Val Met Leu Leu  Val His Tyr
    2345                 2350                 2355

Ala Ile  Ile Gly Pro Gly Leu  Gln Ala Lys Ala Thr  Arg Glu Ala
    2360                 2365                 2370

Gln Lys  Arg Thr Ala Ala Gly  Ile Met Lys Asn Pro  Thr Val Asp
```

```
    2375                2380                2385

Gly Ile  Thr Val Ile Asp Leu  Glu Pro Ile Ser Tyr  Asp Pro Lys
    2390                2395                2400

Phe Glu  Lys Gln Leu Gly Gln  Val Met Leu Leu Val  Leu Cys Ala
    2405                2410                2415

Gly Gln  Leu Leu Leu Met Arg  Thr Thr Trp Ala Phe  Cys Glu Val
    2420                2425                2430

Leu Thr  Leu Ala Thr Gly Pro  Ile Leu Thr Leu Trp  Glu Gly Asn
    2435                2440                2445

Pro Gly  Arg Phe Trp Asn Thr  Thr Ile Ala Val Ser  Thr Ala Asn
    2450                2455                2460

Ile Phe  Arg Gly Ser Tyr Leu  Ala Gly Ala Gly Leu  Ala Phe Ser
    2465                2470                2475

Leu Ile  Lys Asn Ala Gln Thr  Pro Arg Arg Gly Thr  Gly Thr Thr
    2480                2485                2490

Gly Glu  Thr Leu Gly Glu Lys  Trp Lys Arg Gln Leu  Asn Ser Leu
    2495                2500                2505

Asp Arg  Lys Glu Phe Glu Glu  Tyr Lys Arg Ser Gly  Ile Leu Glu
    2510                2515                2520

Val Asp  Arg Thr Glu Ala Lys  Ser Ala Leu Lys Asp  Gly Ser Lys
    2525                2530                2535

Ile Lys  His Ala Val Ser Arg  Gly Ser Ser Lys Ile  Arg Trp Ile
    2540                2545                2550

Val Glu  Arg Gly Met Val Lys  Pro Lys Gly Lys Val  Val Asp Leu
    2555                2560                2565

Gly Cys  Gly Arg Gly Gly Trp  Ser Tyr Tyr Met Ala  Thr Leu Lys
    2570                2575                2580

Asn Val  Thr Glu Val Lys Gly  Tyr Thr Lys Gly Gly  Pro Gly His
    2585                2590                2595

Glu Glu  Pro Ile Pro Met Ala  Thr Tyr Gly Trp Asn  Leu Val Lys
    2600                2605                2610

Leu His  Ser Gly Val Asp Val  Phe Tyr Lys Pro Thr  Glu Gln Val
    2615                2620                2625

Asp Thr  Leu Leu Cys Asp Ile  Gly Glu Ser Ser Ser  Asn Pro Thr
    2630                2635                2640

Ile Glu  Glu Gly Arg Thr Leu  Arg Val Leu Lys Met  Val Glu Pro
    2645                2650                2655

Trp Leu  Ser Ser Lys Pro Glu  Phe Cys Ile Lys Val  Leu Asn Pro
    2660                2665                2670

Tyr Met  Pro Thr Val Ile Glu  Glu Leu Glu Lys Leu  Gln Arg Lys
    2675                2680                2685

His Gly  Gly Asn Leu Val Arg  Cys Pro Leu Ser Arg  Asn Ser Thr
    2690                2695                2700

His Glu  Met Tyr Trp Val Ser  Gly Ala Ser Gly Asn  Ile Val Ser
    2705                2710                2715

Ser Val  Asn Thr Thr Ser Lys  Met Leu Leu Asn Arg  Phe Thr Thr
    2720                2725                2730

Arg His  Arg Lys Pro Thr Tyr  Glu Lys Asp Val Asp  Leu Gly Ala
    2735                2740                2745

Gly Thr  Arg Ser Val Ser Thr  Glu Thr Glu Lys Pro  Asp Met Thr
    2750                2755                2760

Ile Ile  Gly Arg Arg Leu Gln  Arg Leu Gln Glu Glu  His Lys Glu
    2765                2770                2775
```

Thr Trp His Tyr Asp Gln Glu Asn Pro Tyr Arg Thr Trp Ala Tyr
2780 2785 2790

His Gly Ser Tyr Glu Ala Pro Ser Thr Gly Ser Ala Ser Ser Met
2795 2800 2805

Val Asn Gly Val Val Lys Leu Leu Thr Lys Pro Trp Asp Val Ile
2810 2815 2820

Pro Met Val Thr Gln Leu Ala Met Thr Asp Thr Thr Pro Phe Gly
2825 2830 2835

Gln Gln Arg Val Phe Lys Glu Lys Val Asp Thr Arg Thr Pro Gln
2840 2845 2850

Pro Lys Pro Gly Thr Arg Met Val Met Thr Thr Thr Ala Asn Trp
2855 2860 2865

Leu Trp Ala Leu Leu Gly Lys Lys Lys Asn Pro Arg Leu Cys Thr
2870 2875 2880

Arg Glu Glu Phe Ile Ser Lys Val Arg Ser Asn Ala Ala Ile Gly
2885 2890 2895

Ala Val Phe Gln Glu Glu Gln Gly Trp Thr Ser Ala Ser Glu Ala
2900 2905 2910

Val Asn Asp Ser Arg Phe Trp Glu Leu Val Asp Lys Glu Arg Ala
2915 2920 2925

Leu His Gln Glu Gly Lys Cys Glu Ser Cys Val Tyr Asn Met Met
2930 2935 2940

Gly Lys Arg Glu Lys Lys Leu Gly Glu Phe Gly Arg Ala Lys Gly
2945 2950 2955

Ser Arg Ala Ile Trp Tyr Met Trp Leu Gly Ala Arg Phe Leu Glu
2960 2965 2970

Phe Glu Ala Leu Gly Phe Leu Asn Glu Asp His Trp Phe Gly Arg
2975 2980 2985

Glu Asn Ser Trp Ser Gly Val Glu Gly Glu Gly Leu His Arg Leu
2990 2995 3000

Gly Tyr Ile Leu Glu Glu Ile Asp Lys Lys Asp Gly Asp Leu Met
3005 3010 3015

Tyr Ala Asp Asp Thr Ala Gly Trp Asp Thr Arg Ile Thr Glu Asp
3020 3025 3030

Asp Leu Gln Asn Glu Glu Leu Ile Thr Glu Gln Met Ala Pro His
3035 3040 3045

His Lys Ile Leu Ala Lys Ala Ile Phe Lys Leu Thr Tyr Gln Asn
3050 3055 3060

Lys Val Val Lys Val Leu Arg Pro Thr Pro Arg Gly Ala Val Met
3065 3070 3075

Asp Ile Ile Ser Arg Lys Asp Gln Arg Gly Ser Gly Gln Val Gly
3080 3085 3090

Thr Tyr Gly Leu Asn Thr Phe Thr Asn Met Glu Val Gln Leu Ile
3095 3100 3105

Arg Gln Met Glu Ala Glu Gly Val Ile Thr Gln Asp Asp Met Gln
3110 3115 3120

Asn Pro Lys Gly Leu Lys Glu Arg Val Glu Lys Trp Leu Lys Glu
3125 3130 3135

Cys Gly Val Asp Arg Leu Lys Arg Met Ala Ile Ser Gly Asp Asp
3140 3145 3150

Cys Val Val Lys Pro Leu Asp Glu Arg Phe Gly Thr Ser Leu Leu
3155 3160 3165

```
Phe Leu  Asn Asp Met Gly Lys  Val Arg Lys Asp Ile  Pro Gln Trp
    3170                 3175                 3180

Glu Pro  Ser Lys Gly Trp Lys  Asn Trp Gln Glu Val  Pro Phe Cys
    3185                 3190                 3195

Ser His  His Phe His Lys Ile  Phe Met Lys Asp Gly  Arg Ser Leu
    3200                 3205                 3210

Val Val  Pro Cys Arg Asn Gln  Asp Glu Leu Ile Gly  Arg Ala Arg
    3215                 3220                 3225

Ile Ser  Gln Gly Ala Gly Trp  Ser Leu Arg Glu Thr  Ala Cys Leu
    3230                 3235                 3240

Gly Lys  Ala Tyr Ala Gln Met  Trp Ser Leu Met Tyr  Phe His Arg
    3245                 3250                 3255

Arg Asp  Leu Arg Leu Ala Ser  Met Ala Ile Cys Ser  Ala Val Pro
    3260                 3265                 3270

Thr Glu  Trp Phe Pro Thr Ser  Arg Thr Thr Trp Ser  Ile His Ala
    3275                 3280                 3285

His His  Gln Trp Met Thr Thr  Glu Asp Met Leu Lys  Val Trp Asn
    3290                 3295                 3300

Arg Val  Trp Ile Glu Asp Asn  Pro Asn Met Thr Asp  Lys Thr Pro
    3305                 3310                 3315

Val His  Ser Trp Glu Asp Ile  Pro Tyr Leu Gly Lys  Arg Glu Asp
    3320                 3325                 3330

Leu Trp  Cys Gly Ser Leu Ile  Gly Leu Ser Ser Arg  Ala Thr Trp
    3335                 3340                 3345

Ala Lys  Asn Ile His Thr Ala  Ile Thr Gln Val Arg  Asn Leu Ile
    3350                 3355                 3360

Gly Lys  Glu Glu Tyr Val Asp  Tyr Met Pro Val Met  Lys Arg Tyr
    3365                 3370                 3375

Ser Ala  Pro Ser Glu Ser Glu  Gly Val Leu
    3380                 3385
```

<210> SEQ ID NO 18
<211> LENGTH: 10616
<212> TYPE: DNA
<213> ORGANISM: Recombinant dengue virus rDEN2/4d30

<400> SEQUENCE: 18

```
agttgttagt ctgtgtggac cgacaaggac agttccaaat cggaagcttg cttaacacag     60

ttctaacagt ttgtttgaat agagagcaga tctctgatga ataaccaacg aaaaaaggcg    120

agaaatacgc ctttcaatat gctgaaacgc gagagaaacc gcgtgtcgac tgtacaacag    180

ctgacaaaga gattctcact tggaatgctg cagggacgag gaccattaaa actgttcatg    240

gccctggtgg cgttccttcg tttcctaaca atcccaccaa cagcagggat actgaagaga    300

tggggaacaa ttaaaaaatc aaaagccatt aatgttttga gagggttcag gaaagagatt    360

ggaaggatgc tgaacatctt gaacaggaga cgcagaactg caggcatgat cattatgctg    420

attccaacag tgatggcgtt ccatttaacc acacgtaacg gagaaccaca catgatcgtc    480

agtagacaag agaaagggaa aagtcttctg tttaaaacag aggatggtgt gaacatgtgt    540

accctcatgg ccatggacct tggtgaattg tgtgaagata caatcacgta caagtgtcct    600

cttctcaggc agaatgaacc agaagacata gattgttggt gcaactctac gtccacatgg    660

gtaacttatg ggacgtgtac caccacagga gaacacagaa gagaaaaaag atcagtggca    720

ctcgttccac atgtgggaat gggactggag acacgaactg aaacatggat gtcatcagaa    780
```

-continued

```
ggggcctgga aacatgccca gagaattgaa acttggatct tgagacatcc aggctttacc    840
ataatggcag caatcctggc atacaccata ggaacgacac atttccaaag agccctgatt    900
ttcatcttac tgacagctgt cgctccttca atgacaatgc gttgcatagg aatatcaaat    960
agagactttg tagaaggggt ttcaggagga agctgggttg acatagtctt agaacatgga   1020
agctgtgtga cgacgatggc aaaaaacaaa ccaacattgg attttgaact gataaaaaca   1080
gaagccaaac aacctgccac tctaaggaag tactgtatag aggcaaagct gaccaacaca   1140
acaacagaat ctcgctgccc aacacaagga gaacctagcc taaatgaaga gcaggacaaa   1200
aggttcgtct gcaaacactc catggtggac agaggatggg gaaatggatg tggattattt   1260
ggaaaaggag gcattgtgac ctgtgctatg ttcacatgca aaaagaacat ggaaggaaaa   1320
gtcgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagagtt gacaggctat ggcactgtca cgatggagtg ctctccgaga   1500
acgggcctcg acttcaatga gatggtgttg ctgcaaatgg aaaataaagc ttggctggtg   1560
cacaggcaat ggttcctaga cctgccgttg ccatggctgc ccggagcgga cacacaagga   1620
tcaaattgga tacagaaaga gacattggtc actttcaaaa atccccatgc gaagaaacag   1680
gatgttgttg ttttgggatc ccaagaaggg gccatgcaca cagcactcac aggggccaca   1740
gaaatccaga tgtcatcagg aaacttactg ttcacaggac atctcaagtg caggctgagg   1800
atggacaaac tacagctcaa aggaatgtca tactctatgt gcacaggaaa gtttaaagtt   1860
gtgaaggaaa tagcagaaac acaacatgga acaatagtta tcagagtaca atatgaaggg   1920
gacggttctc catgtaagat cccttttgag ataatggatt tggaaaaaag acatgtttta   1980
ggtcgcctga ttacagtcaa cccaatcgta acagaaaaag atagcccagt caacatagaa   2040
gcagaacctc cattcggaga cagctacatc atcataggag tagagccggg acaattgaag   2100
ctcaactggt ttaagaaagg aagttctatc ggccaaatgt ttgagacaac aatgagggga   2160
gcgaagagaa tggccatttt aggtgacaca gcttgggatt ttggatccct gggaggagtg   2220
tttacatcta taggaaaggc tctccaccaa gttttcggag caatctatgg ggctgccttc   2280
agtggggtct catggactat gaaaatcctc ataggagtca ttatcacatg gataggaatg   2340
aactcgagga acacttcaat ggctatgacg tgcatagctg ttggaggaat cactctgttt   2400
ctgggcttca cagttcaagc agacatgggt tgtgtggcgt catggagtgg gaaagaattg   2460
aagtgtggaa gcggaatttt tgtggttgac aacgtgcaca cttggacaga acagtacaaa   2520
tttcaaccag agtccccagc gagactagcg tctgcaatat taaatgccca caaagatggg   2580
gtctgtggaa ttagatcaac cacgaggctg gaaaatgtca tgtggaagca aataaccaac   2640
gagctaaact atgttctctg ggaaggagga catgacctca ctgtagtggc tggggatgtg   2700
aagggggtgt tgaccaaagg caagagagca ctcacacccc cagtgagtga tctgaaatat   2760
tcatggaaga catggggaaa agcaaaaatc ttcaccccag aagcaagaaa tagcacattt   2820
ttaatagacg gaccagacac ctctgaatgc cccaatgaac gaagagcatg gaactctctt   2880
gaggtggaag actatggatt tggcatgttc acgaccaaca tatggatgaa attccgagaa   2940
ggaagttcag aagtgtgtga ccacaggtta atgtcagctg caattaaaga tcagaaagct   3000
gtgcatgctg acatgggtta ttggatagag agctcaaaaa accagacctg gcagatagag   3060
aaagcatctc ttattgaagt gaaaacatgt ctgtggccca agacccacac actgtggagc   3120
aatggagtgc tggaaagcca gatgctcatt ccaaaatcat atgcgggccc tttttcacag   3180
```

cacaattacc gccagggcta tgccacgcaa accgtgggcc catggcactt aggcaaatta 3240
gagatagact ttggagaatg ccccggaaca acagtcacaa ttcaggagga ttgtgaccat 3300
agaggcccat ctttgaggac caccactgca tctggaaaac tagtcacgca atggtgctgc 3360
cgctcctgca cgatgcctcc cttaaggttc ttgggagaag atgggtgctg gtatgggatg 3420
gagattaggc ccttgagtga aaaagaagag aacatggtca aatcacaggt gacggccgga 3480
cagggcacat cagaaacttt ttctatgggt ctgttgtgcc tgaccttgtt tgtggaagaa 3540
tgcttgagga gaagagtcac taggaaacac atgatattag ttgtggtgat cactctttgt 3600
gctatcatcc tgggaggcct cacatggatg gacttactac gagccctcat catgttgggg 3660
gacactatgt ctggtagaat aggaggacag atccacctag ccatcatggc agtgttcaag 3720
atgtcaccag gatacgtgct gggtgtgttt ttaaggaaac tcacttcaag agagacagca 3780
ctaatggtaa taggaatggc catgacaacg gtgctttcaa ttccacatga ccttatggaa 3840
ctcattgatg gaatatcact gggactaatt ttgctaaaaa tagtaacaca gtttgacaac 3900
acccaagtgg gaaccttagc tctttccttg actttcataa gatcaacaat gccattggtc 3960
atggcttgga ggaccattat ggctgtgttg tttgtggtca cactcattcc tttgtgcagg 4020
acaagctgtc ttcaaaaaca gtctcattgg gtagaaataa cagcactcat cctaggagcc 4080
caagctctgc cagtgtacct aatgactctt atgaaaggag cctcaagaag atcttggcct 4140
cttaacgagg gcataatggc tgtgggtttg gttagtctct taggaagcgc tcttttaaag 4200
aatgatgtcc ctttagctgg cccaatggtg gcaggaggct tacttctggc ggcttacgtg 4260
atgagtggta gctcagcaga tctgtcacta gagaaggccg ccaacgtgca gtgggatgaa 4320
atggcagaca taacaggctc aagcccaatc atagaagtga agcaggatga agatggctct 4380
ttctccatac gggacgtcga ggaaaccaat atgataaccc ttttggtgaa actggcactg 4440
ataacagtgt caggtctcta ccccttggca attccagtca caatgacctt atggtacatg 4500
tggcaagtga aaacacaaag atcaggagcc ctgtgggacg tcccctcacc cgctgccact 4560
aaaaaagccg cactgtctga aggagtgtac aggatcatgc aaagagggtt attcgggaaa 4620
actcaggttg gagtagggat acacatggaa ggtgtatttc acacaatgtg gcatgtaaca 4680
agaggatcag tgatctgcca cgagactggg agattggagc catcttgggc tgacgtcagg 4740
aatgacatga tatcatacgg tgggggatgg aggcttggag acaaatggga caaagaagaa 4800
gacgttcagg tcctcgccat agaaccagga aaaaatccta aacatgtcca aacgaaacct 4860
ggccttttca agaccctaac tggagaaatt ggagcagtaa cattagattt caaacccgga 4920
acgtctggtt ctcccatcat caacaggaaa ggaaaagtca tcggactcta tggaaatgga 4980
gtagttacca aatcaggtga ttacgtcagt gccataacgc aagccgaaag aattggagag 5040
ccagattatg aagtggatga ggacattttt cgaaagaaaa gattaactat aatggactta 5100
caccccggag ctggaaagac aaaaagaatt cttccatcaa tagtgagaga agccttaaaa 5160
aggaggctac gaactttgat tttagctccc acgagagtgg tggcggccga gatggaagag 5220
gccctacgtg gactgccaat ccgttatcag accccagctg tgaaatcaga acacacagga 5280
agagagattg tagacctcat gtgtcatgca accttcacaa caagactttt gtcatcaacc 5340
agggttccaa attacaacct tatagtgatg gatgaagcac atttcaccga tccttctagt 5400
gtcgcggcta gaggatacat ctcgaccagg gtggaaatgg gagaggcagc agccatcttc 5460
atgaccgcaa cccctcccgg agcgacagat ccctttcccc agagcaacag cccaatagaa 5520

-continued

```
gacatcgaga gggaaattcc ggaaaggtca tggaacacag ggttcgactg gataacagac   5580
taccaaggga aaactgtgtg gtttgttccc agcataaaag ctggaaatga cattgcaaat   5640
tgtttgagaa agtcgggaaa gaaagttatc cagttgagta ggaaaacctt tgatacagag   5700
tatccaaaaa cgaaactcac ggactgggac tttgtggtca ctacagacat atctgaaatg   5760
ggggccaatt ttagagccgg gagagtgata gaccctagaa gatgcctcaa gccagttatc   5820
ctaccagatg ggccagagag agtcatttta gcaggtccta ttccagtgac tccagcaagc   5880
gctgctcaga gaagagggcg aataggaagg aacccagcac aagaagacga ccaatacgtt   5940
ttctccggag acccactaaa aaatgatgaa gatcatgccc actggacaga agcaaagatg   6000
ctgcttgaca atatctacac cccagaaggg atcattccaa cattgtttgg tccggaaagg   6060
gaaaaaaccc aagccattga tggagagttt cgcctcagag gggaacaaag gaagactttt   6120
gtggaattaa tgaggagagg agaccttccg gtgtggctga gctataaggt agcttctgct   6180
ggcatttctt acaaagatcg ggaatggtgc ttcacagggg aaagaaataa ccaaatttta   6240
gaagaaaaca tggaggttga aatttggact agagagggag aaaagaaaaa gctaaggcca   6300
agatggttag atgcacgtgt atacgctgac cccatggctt tgaaggattt caaggagttt   6360
gccagtggaa ggaagagtat aactctcgac atcctaacag agattgccag tttgccaact   6420
tacctttcct ctagggccaa gctcgccctt gataacatag tcatgctcca cacaacagaa   6480
agaggaggga gggcctatca acacgccctg aacgaacttc cggagtcact ggaaacactc   6540
atgcttgtag ctttactagg tgctatgaca gcaggcatct tcctgttttt catgcaaggg   6600
aaaggaatag ggaaattgtc aatgggtttg ataaccattg cggtggctag tggcttgctc   6660
tgggtagcag aaattcaacc ccagtggata gcggcctcaa tcatactaga gtttttctc    6720
atggtactgt tgataccgga accagaaaaa caaaggaccc cacaagacaa tcaattgatc   6780
tacgtcatat tgaccattct caccatcatt ggtctaatag cagccaacga gatggggctg   6840
attgaaaaaa caaaaacgga ttttgggttt taccaggtaa aaacagaaac caccatcctc   6900
gatgtggact tgagaccagc ttcagcatgg acgctctatg cagtagccac cacaattctg   6960
actcccatgc tgagacacac catagaaaac acgtcggcca acctatctct agcagccatt   7020
gccaaccagg cagccgtcct aatggggctt ggaaaaggat ggccgctcca cagaatggac   7080
ctcggtgtgc cgctgttagc aatgggatgc tattctcaag tgaacccaac aaccttgaca   7140
gcatccttag tcatgctttt agtccattat gcaataatag gcccaggatt gcaggcaaaa   7200
gccacaagag aggcccagaa aaggacagct gctgggatca tgaaaaatcc cacagtggac   7260
gggataacag taatagatct agaaccaata tcctatgacc caaaatttga aaagcaatta   7320
gggcaggtca tgctactagt cttgtgtgct ggacaactac tcttgatgag aacaacatgg   7380
gctttctgtg aagtcttgac tttggccaca ggaccaatct tgaccttgtg ggagggcaac   7440
ccgggaaggt tttggaacac gaccatagcc gtatccaccg ccaacatttt caggggaagt   7500
tacttggcgg gagctggact ggctttttca ctcataaaga atgcacaaac ccctaggagg   7560
ggaactggga ccacaggaga gacactggga gagaagtgga agagacagct aaactcatta   7620
gacagaaaag agtttgaaga gtataaaaga agtggaatac tagaagtgga caggactgaa   7680
gccaagtctg ccctgaaaga tgggtctaaa atcaagcatg cagtatcaag agggtccagt   7740
aagatcagat ggattgttga gagagggatg gtaaagccaa aagggaaagt tgtagatctt   7800
ggctgtggga gaggaggatg gtcttattac atggcgacac tcaagaacgt gactgaagtg   7860
aaagggtata caaaaggagg tccaggacat gaagaaccga ttcccatggc tacttatggt   7920
```

```
tggaatttgg tcaaactcca ttcaggggtt gacgtgttct acaaacccac agagcaagtg   7980
gacaccctgc tctgtgatat tggggagtca tcttctaatc caacaataga ggaaggaaga   8040
acattaagag ttttgaagat ggtggagcca tggctctctt caaaacctga attctgcatc   8100
aaagtcctta acccctacat gccaacagtc atagaagagc tggagaaact gcagagaaaa   8160
catggtggga accttgtcag atgcccgctg tccaggaact ccacccatga gatgtattgg   8220
gtgtcaggag cgtcgggaaa cattgtgagc tctgtgaaca caacatcaaa gatgttgttg   8280
aacaggttca caacaaggca taggaaaccc acttatgaga aggacgtaga tcttggggca   8340
ggaacgagaa gtgtctccac tgaaacagaa aaaccagaca tgacaatcat tgggagaagg   8400
cttcagcgat tgcaagaaga gcacaaagaa acctggcatt atgatcagga aaacccatac   8460
agaacctggg cgtatcatgg aagctatgaa gctccttcga caggctctgc atcctccatg   8520
gtgaacgggg tggtaaaact gctaacaaaa ccctgggatg tgattccaat ggtgactcag   8580
ttagccatga cagatacaac cccttttggg caacaaagag tgttcaaaga gaaggtggat   8640
accagaacac cacaaccaaa acccggtaca cgaatggtta tgaccacgac agccaattgg   8700
ctgtgggccc tccttggaaa gaagaaaaat cccagactgt gcacaaggga agagttcatc   8760
tcaaaagtta gatcaaacgc agccataggc gcagtctttc aggaagaaca gggatggaca   8820
tcagccagtg aagctgtgaa tgacagccgg ttttgggaac tggttgacaa agaaagggcc   8880
ctacaccagg aagggaaatg tgaatcgtgt gtctataaca tgatgggaaa acgtgagaaa   8940
aagttaggag agtttggcag agccaaggga agccgagcaa tctggtacat gtggctggga   9000
gcgcggtttc tggaatttga agccctgggt tttttgaatg aagatcactg gtttggcaga   9060
gaaaattcat ggagtggagt ggaaggggaa ggtctgcaca gattgggata tatcctggag   9120
gagatagaca agaaggatgg agacctaatg tatgctgatg acacagcagg ctgggacaca   9180
agaatcactg aggatgacct tcaaaatgag gaactgatca cggaacagat ggctccccac   9240
cacaagatcc tagccaaagc cattttcaaa ctaacctatc aaaacaaagt ggtgaaagtc   9300
ctcagaccca caccgcgggg agcggtgatg gatatcatat ccaggaaaga ccaaagaggt   9360
agtggacaag ttggaacata tggtttgaac acattcacca acatggaagt tcaactcatc   9420
cgccaaatgg aagctgaagg agtcatcaca caagatgaca tgcagaaccc aaaagggttg   9480
aaagaaagag ttgagaaatg gctgaaagag tgtggtgtcg acaggttaaa gaggatggca   9540
atcagtggag acgattgcgt ggtgaagccc ctagatgaga ggtttggcac ttccctcctc   9600
ttcttgaacg acatgggaaa ggtgaggaaa gacattccgc agtgggaacc atctaaggga   9660
tggaaaaact ggcaagaggt tcctttttgc tcccaccact ttcacaagat ctttatgaag   9720
gatggccgct cactagttgt tccatgtaga aaccaggatg aactgatagg gagagccaga   9780
atctcgcagg gagctggatg gagcttaaga gaaacagcct gcctgggcaa agcttacgcc   9840
cagatgtggt cgcttatgta cttccacaga agggatctgc gtttagcctc catggccata   9900
tgctcagcag ttccaacgga atggtttcca acaagcagaa caacatggtc aatccacgct   9960
catcaccagt ggatgaccac tgaagatatg ctcaaagtgt ggaacagagt gtggatagaa  10020
gacaacccta atatgactga caagactcca gtccattcgt gggaagatat accttaccta  10080
gggaaaagag aggatttgtg gtgtggatcc ctgattggac tttcttccag agccacctgg  10140
gcgaagaaca ttcacacggc cataacccag gtcaggaacc tgatcggaaa agaggaatac  10200
gtggattaca tgccagtaat gaaaagatac agtgctcctt cagagagtga aggagttctg  10260
```

```
taattaccaa caacaaacac caaaggctat tgaagtcagg ccacttgtgc cacggtttga  10320

gcaaaccgtg ctgcctgtag ctccgccaat aatgggaggc gtaataatcc ccagggaggc  10380

catgcgccac ggaagctgta cgcgtggcat attggactag cggttagagg agacccctcc  10440

catcactgac aaaacgcagc aaaagggggc ccaagactag aggttagagg agaccccccc  10500

aacacaaaaa cagcatattg acgctgggaa agaccagaga tcctgctgtc tctgcaacat  10560

caatccaggc acagagcgcc gcaagatgga ttggtgttgt tgatccaaca ggttct      10616
```

<210> SEQ ID NO 19
<211> LENGTH: 3387
<212> TYPE: PRT
<213> ORGANISM: Dengue 4 virus

<400> SEQUENCE: 19

```
Met Asn Gln Arg Lys Lys Val Val Arg Pro Pro Phe Asn Met Leu Lys
1               5                   10                  15

Arg Glu Arg Asn Arg Val Ser Thr Pro Gln Gly Leu Val Lys Arg Phe
            20                  25                  30

Ser Thr Gly Leu Phe Ser Gly Lys Gly Pro Leu Arg Met Val Leu Ala
        35                  40                  45

Phe Ile Thr Phe Leu Arg Val Leu Ser Ile Pro Pro Thr Ala Gly Ile
    50                  55                  60

Leu Lys Arg Trp Gly Gln Leu Lys Lys Asn Lys Ala Ile Lys Ile Leu
65                  70                  75                  80

Ile Gly Phe Arg Lys Glu Ile Gly Arg Met Leu Asn Ile Leu Asn Gly
                85                  90                  95

Arg Lys Arg Ser Thr Ile Thr Leu Leu Cys Leu Ile Pro Thr Val Met
            100                 105                 110

Ala Phe Ser Leu Ser Thr Arg Asp Gly Glu Pro Leu Met Ile Val Ala
        115                 120                 125

Lys His Glu Arg Gly Arg Pro Leu Leu Phe Lys Thr Thr Glu Gly Ile
    130                 135                 140

Asn Lys Cys Thr Leu Ile Ala Met Asp Leu Gly Glu Met Cys Glu Asp
145                 150                 155                 160

Thr Val Thr Tyr Lys Cys Pro Leu Leu Val Asn Thr Glu Pro Glu Asp
                165                 170                 175

Ile Asp Cys Trp Cys Asn Leu Thr Ser Thr Trp Val Met Tyr Gly Thr
            180                 185                 190

Cys Thr Gln Ser Gly Glu Arg Arg Arg Glu Lys Arg Ser Val Ala Leu
        195                 200                 205

Thr Pro His Ser Gly Met Gly Leu Glu Thr Arg Ala Glu Thr Trp Met
    210                 215                 220

Ser Ser Glu Gly Ala Trp Lys His Ala Gln Arg Val Glu Ser Trp Ile
225                 230                 235                 240

Leu Arg Asn Pro Gly Phe Ala Leu Leu Ala Gly Phe Met Ala Tyr Met
                245                 250                 255

Ile Gly Gln Thr Gly Ile Gln Arg Thr Val Phe Phe Val Leu Met Met
            260                 265                 270

Leu Val Ala Pro Ser Tyr Gly Met Arg Cys Val Gly Val Gly Asn Arg
        275                 280                 285

Asp Phe Val Glu Gly Val Ser Gly Gly Ala Trp Val Asp Leu Val Leu
    290                 295                 300

Glu His Gly Gly Cys Val Thr Thr Met Ala Gln Gly Lys Pro Thr Leu
305                 310                 315                 320
```

```
Asp Phe Glu Leu Thr Lys Thr Thr Ala Lys Glu Val Ala Leu Leu Arg
                325                 330                 335

Thr Tyr Cys Ile Glu Ala Ser Ile Ser Asn Ile Thr Thr Ala Thr Arg
            340                 345                 350

Cys Pro Thr Gln Gly Glu Pro Tyr Leu Lys Glu Glu Gln Asp Gln Gln
        355                 360                 365

Tyr Ile Cys Arg Arg Asp Val Val Asp Arg Gly Trp Gly Asn Gly Cys
    370                 375                 380

Gly Leu Phe Gly Lys Gly Gly Val Val Thr Cys Ala Lys Phe Ser Cys
385                 390                 395                 400

Ser Gly Lys Ile Thr Gly Asn Leu Val Gln Ile Glu Asn Leu Glu Tyr
                405                 410                 415

Thr Val Val Val Thr Val His Asn Gly Asp Thr His Ala Val Gly Asn
            420                 425                 430

Asp Thr Ser Asn His Gly Val Thr Ala Met Ile Thr Pro Arg Ser Pro
        435                 440                 445

Ser Val Glu Val Lys Leu Pro Asp Tyr Gly Glu Leu Thr Leu Asp Cys
    450                 455                 460

Glu Pro Arg Ser Gly Ile Asp Phe Asn Glu Met Ile Leu Met Lys Met
465                 470                 475                 480

Lys Lys Lys Thr Trp Leu Val His Lys Gln Trp Phe Leu Asp Leu Pro
                485                 490                 495

Leu Pro Trp Thr Ala Gly Ala Asp Thr Ser Glu Val His Trp Asn Tyr
            500                 505                 510

Lys Glu Arg Met Val Thr Phe Lys Val Pro His Ala Lys Arg Gln Asp
        515                 520                 525

Val Thr Val Leu Gly Ser Gln Glu Gly Ala Met His Ser Ala Leu Ala
    530                 535                 540

Gly Ala Thr Glu Val Asp Ser Gly Asp Gly Asn His Met Phe Ala Gly
545                 550                 555                 560

His Leu Lys Cys Lys Val Arg Met Glu Lys Leu Arg Ile Lys Gly Met
                565                 570                 575

Ser Tyr Thr Met Cys Ser Gly Lys Phe Ser Ile Asp Lys Glu Met Ala
            580                 585                 590

Glu Thr Gln His Gly Thr Thr Val Val Lys Val Lys Tyr Glu Gly Ala
        595                 600                 605

Gly Ala Pro Cys Lys Val Pro Ile Glu Ile Arg Asp Val Asn Lys Glu
    610                 615                 620

Lys Val Val Gly Arg Ile Ile Ser Ser Thr Pro Leu Ala Glu Asn Thr
625                 630                 635                 640

Asn Ser Val Thr Asn Ile Glu Leu Glu Pro Pro Phe Gly Asp Ser Tyr
                645                 650                 655

Ile Val Ile Gly Val Gly Asn Ser Ala Leu Thr Leu His Trp Phe Arg
            660                 665                 670

Lys Gly Ser Ser Ile Gly Lys Met Phe Glu Ser Thr Tyr Arg Gly Ala
        675                 680                 685

Lys Arg Met Ala Ile Leu Gly Glu Thr Ala Trp Asp Phe Gly Ser Val
    690                 695                 700

Gly Gly Leu Phe Thr Ser Leu Gly Lys Ala Val His Gln Val Phe Gly
705                 710                 715                 720

Ser Val Tyr Thr Thr Met Phe Gly Gly Val Ser Trp Met Ile Arg Ile
                725                 730                 735
```

```
Leu Ile Gly Phe Leu Val Leu Trp Ile Gly Thr Asn Ser Arg Asn Thr
            740                 745                 750

Ser Met Ala Met Thr Cys Ile Ala Val Gly Gly Ile Thr Leu Phe Leu
        755                 760                 765

Gly Phe Thr Val Gln Ala Asp Met Gly Cys Val Ala Ser Trp Ser Gly
    770                 775                 780

Lys Glu Leu Lys Cys Gly Ser Gly Ile Phe Val Val Asp Asn Val His
785                 790                 795                 800

Thr Trp Thr Glu Gln Tyr Lys Phe Gln Pro Glu Ser Pro Ala Arg Leu
                805                 810                 815

Ala Ser Ala Ile Leu Asn Ala His Lys Asp Gly Val Cys Gly Ile Arg
            820                 825                 830

Ser Thr Thr Arg Leu Glu Asn Val Met Trp Lys Gln Ile Thr Asn Glu
        835                 840                 845

Leu Asn Tyr Val Leu Trp Glu Gly Gly His Asp Leu Thr Val Val Ala
    850                 855                 860

Gly Asp Val Lys Gly Val Leu Thr Lys Gly Lys Arg Ala Leu Thr Pro
865                 870                 875                 880

Pro Val Ser Asp Leu Lys Tyr Ser Trp Lys Thr Trp Gly Lys Ala Lys
                885                 890                 895

Ile Phe Thr Pro Glu Ala Arg Asn Ser Thr Phe Leu Ile Asp Gly Pro
            900                 905                 910

Asp Thr Ser Glu Cys Pro Asn Glu Arg Arg Ala Trp Asn Ser Leu Glu
        915                 920                 925

Val Glu Asp Tyr Gly Phe Gly Met Phe Thr Thr Asn Ile Trp Met Lys
    930                 935                 940

Phe Arg Glu Gly Ser Ser Glu Val Cys Asp His Arg Leu Met Ser Ala
945                 950                 955                 960

Ala Ile Lys Asp Gln Lys Ala Val His Ala Asp Met Gly Tyr Trp Ile
                965                 970                 975

Glu Ser Ser Lys Asn Gln Thr Trp Gln Ile Glu Lys Ala Ser Leu Ile
            980                 985                 990

Glu Val Lys Thr Cys Leu Trp Pro  Lys Thr His Thr Leu  Trp Ser Asn
        995                 1000                 1005

Gly Val  Leu Glu Ser Gln Met  Leu Ile Pro Lys Ser  Tyr Ala Gly
    1010                 1015                 1020

Pro Phe  Ser Gln His Asn Tyr  Arg Gln Gly Tyr Ala  Thr Gln Thr
    1025                 1030                 1035

Val Gly  Pro Trp His Leu Gly  Lys Leu Glu Ile Asp  Phe Gly Glu
    1040                 1045                 1050

Cys Pro  Gly Thr Thr Val Thr  Ile Gln Glu Asp Cys  Asp His Arg
    1055                 1060                 1065

Gly Pro  Ser Leu Arg Thr Thr  Thr Ala Ser Gly Lys  Leu Val Thr
    1070                 1075                 1080

Gln Trp  Cys Cys Arg Ser Cys  Thr Met Pro Pro Leu  Arg Phe Leu
    1085                 1090                 1095

Gly Glu  Asp Gly Cys Trp Tyr  Gly Met Glu Ile Arg  Pro Leu Ser
    1100                 1105                 1110

Glu Lys  Glu Glu Asn Met Val  Lys Ser Gln Val Thr  Ala Gly Gln
    1115                 1120                 1125

Gly Thr  Ser Glu Thr Phe Ser  Met Gly Leu Leu Cys  Leu Thr Leu
    1130                 1135                 1140

Phe Val  Glu Glu Cys Leu Arg  Arg Arg Val Thr Arg  Lys His Met
```

```
    1145                1150                1155

Ile Leu  Val Val Val Ile Thr  Leu Cys Ala Ile Ile  Leu Gly Gly
    1160                1165                1170

Leu Thr  Trp Met Asp Leu Leu  Arg Ala Leu Ile Met  Leu Gly Asp
    1175                1180                1185

Thr Met  Ser Gly Arg Ile Gly  Gly Gln Ile His Leu  Ala Ile Met
    1190                1195                1200

Ala Val  Phe Lys Met Ser Pro  Gly Tyr Val Leu Gly  Val Phe Leu
    1205                1210                1215

Arg Lys  Leu Thr Ser Arg Glu  Thr Ala Leu Met Val  Ile Gly Met
    1220                1225                1230

Ala Met  Thr Thr Val Leu Ser  Ile Pro His Asp Leu  Met Glu Leu
    1235                1240                1245

Ile Asp  Gly Ile Ser Leu Gly  Leu Ile Leu Leu Lys  Ile Val Thr
    1250                1255                1260

Gln Phe  Asp Asn Thr Gln Val  Gly Thr Leu Ala Leu  Ser Leu Thr
    1265                1270                1275

Phe Ile  Arg Ser Thr Met Pro  Leu Val Met Ala Trp  Arg Thr Ile
    1280                1285                1290

Met Ala  Val Leu Phe Val Val  Thr Leu Ile Pro Leu  Cys Arg Thr
    1295                1300                1305

Ser Cys  Leu Gln Lys Gln Ser  His Trp Val Glu Ile  Thr Ala Leu
    1310                1315                1320

Ile Leu  Gly Ala Gln Ala Leu  Pro Val Tyr Leu Met  Thr Leu Met
    1325                1330                1335

Lys Gly  Ala Ser Arg Arg Ser  Trp Pro Leu Asn Glu  Gly Ile Met
    1340                1345                1350

Ala Val  Gly Leu Val Ser Leu  Leu Gly Ser Ala Leu  Leu Lys Asn
    1355                1360                1365

Asp Val  Pro Leu Ala Gly Pro  Met Val Ala Gly Gly  Leu Leu Leu
    1370                1375                1380

Ala Ala  Tyr Val Met Ser Gly  Ser Ser Ala Asp Leu  Ser Leu Glu
    1385                1390                1395

Lys Ala  Ala Asn Val Gln Trp  Asp Glu Met Ala Asp  Ile Thr Gly
    1400                1405                1410

Ser Ser  Pro Ile Ile Glu Val  Lys Gln Asp Glu Asp  Gly Ser Phe
    1415                1420                1425

Ser Ile  Arg Asp Val Glu Glu  Thr Asn Met Ile Thr  Leu Leu Val
    1430                1435                1440

Lys Leu  Ala Leu Ile Thr Val  Ser Gly Leu Tyr Pro  Leu Ala Ile
    1445                1450                1455

Pro Val  Thr Met Thr Leu Trp  Tyr Met Trp Gln Val  Lys Thr Gln
    1460                1465                1470

Arg Ser  Gly Ala Leu Trp Asp  Val Pro Ser Pro Ala  Ala Thr Lys
    1475                1480                1485

Lys Ala  Ala Leu Ser Glu Gly  Val Tyr Arg Ile Met  Gln Arg Gly
    1490                1495                1500

Leu Phe  Gly Lys Thr Gln Val  Gly Val Gly Ile His  Met Glu Gly
    1505                1510                1515

Val Phe  His Thr Met Trp His  Val Thr Arg Gly Ser  Val Ile Cys
    1520                1525                1530

His Glu  Thr Gly Arg Leu Glu  Pro Ser Trp Ala Asp  Val Arg Asn
    1535                1540                1545
```

```
Asp Met  Ile Ser Tyr Gly Gly  Gly Trp Arg Leu Gly  Asp Lys Trp
    1550                 1555                 1560

Asp Lys  Glu Glu Asp Val Gln  Val Leu Ala Ile Glu  Pro Gly Lys
    1565                 1570                 1575

Asn Pro  Lys His Val Gln Thr  Lys Pro Gly Leu Phe  Lys Thr Leu
    1580                 1585                 1590

Thr Gly  Glu Ile Gly Ala Val  Thr Leu Asp Phe Lys  Pro Gly Thr
    1595                 1600                 1605

Ser Gly  Ser Pro Ile Ile Asn  Arg Lys Gly Lys Val  Ile Gly Leu
    1610                 1615                 1620

Tyr Gly  Asn Gly Val Val Thr  Lys Ser Gly Asp Tyr  Val Ser Ala
    1625                 1630                 1635

Ile Thr  Gln Ala Glu Arg Ile  Gly Glu Pro Asp Tyr  Glu Val Asp
    1640                 1645                 1650

Glu Asp  Ile Phe Arg Lys Lys  Arg Leu Thr Ile Met  Asp Leu His
    1655                 1660                 1665

Pro Gly  Ala Gly Lys Thr Lys  Arg Ile Leu Pro Ser  Ile Val Arg
    1670                 1675                 1680

Glu Ala  Leu Lys Arg Arg Leu  Arg Thr Leu Ile Leu  Ala Pro Thr
    1685                 1690                 1695

Arg Val  Val Ala Ala Glu Met  Glu Glu Ala Leu Arg  Gly Leu Pro
    1700                 1705                 1710

Ile Arg  Tyr Gln Thr Pro Ala  Val Lys Ser Glu His  Thr Gly Arg
    1715                 1720                 1725

Glu Ile  Val Asp Leu Met Cys  His Ala Thr Phe Thr  Thr Arg Leu
    1730                 1735                 1740

Leu Ser  Ser Thr Arg Val Pro  Asn Tyr Asn Leu Ile  Val Met Asp
    1745                 1750                 1755

Glu Ala  His Phe Thr Asp Pro  Ser Ser Val Ala Ala  Arg Gly Tyr
    1760                 1765                 1770

Ile Ser  Thr Arg Val Glu Met  Gly Glu Ala Ala Ala  Ile Phe Met
    1775                 1780                 1785

Thr Ala  Thr Pro Pro Gly Ala  Thr Asp Pro Phe Pro  Gln Ser Asn
    1790                 1795                 1800

Ser Pro  Ile Glu Asp Ile Glu  Arg Glu Ile Pro Glu  Arg Ser Trp
    1805                 1810                 1815

Asn Thr  Gly Phe Asp Trp Ile  Thr Asp Tyr Gln Gly  Lys Thr Val
    1820                 1825                 1830

Trp Phe  Val Pro Ser Ile Lys  Ala Gly Asn Asp Ile  Ala Asn Cys
    1835                 1840                 1845

Leu Arg  Lys Ser Gly Lys Lys  Val Ile Gln Leu Ser  Arg Lys Thr
    1850                 1855                 1860

Phe Asp  Thr Glu Tyr Pro Lys  Thr Lys Leu Thr Asp  Trp Asp Phe
    1865                 1870                 1875

Val Val  Thr Thr Asp Ile Ser  Glu Met Gly Ala Asn  Phe Arg Ala
    1880                 1885                 1890

Gly Arg  Val Ile Asp Pro Arg  Arg Cys Leu Lys Pro  Val Ile Leu
    1895                 1900                 1905

Pro Asp  Gly Pro Glu Arg Val  Ile Leu Ala Gly Pro  Ile Pro Val
    1910                 1915                 1920

Thr Pro  Ala Ser Ala Ala Gln  Arg Arg Gly Arg Ile  Gly Arg Asn
    1925                 1930                 1935
```

```
Pro Ala Gln Glu Asp Asp Gln Tyr Val Phe Ser Gly Asp Pro Leu
    1940                1945                1950

Lys Asn Asp Glu Asp His Ala His Trp Thr Glu Ala Lys Met Leu
    1955                1960                1965

Leu Asp Asn Ile Tyr Thr Pro Glu Gly Ile Ile Pro Thr Leu Phe
    1970                1975                1980

Gly Pro Glu Arg Glu Lys Thr Gln Ala Ile Asp Gly Glu Phe Arg
    1985                1990                1995

Leu Arg Gly Glu Gln Arg Lys Thr Phe Val Glu Leu Met Arg Arg
    2000                2005                2010

Gly Asp Leu Pro Val Trp Leu Ser Tyr Lys Val Ala Ser Ala Gly
    2015                2020                2025

Ile Ser Tyr Lys Asp Arg Glu Trp Cys Phe Thr Gly Glu Arg Asn
    2030                2035                2040

Asn Gln Ile Leu Glu Glu Asn Met Glu Val Glu Ile Trp Thr Arg
    2045                2050                2055

Glu Gly Glu Lys Lys Lys Leu Arg Pro Arg Trp Leu Asp Ala Arg
    2060                2065                2070

Val Tyr Ala Asp Pro Met Ala Leu Lys Asp Phe Lys Glu Phe Ala
    2075                2080                2085

Ser Gly Arg Lys Ser Ile Thr Leu Asp Ile Leu Thr Glu Ile Ala
    2090                2095                2100

Ser Leu Pro Thr Tyr Leu Ser Ser Arg Ala Lys Leu Ala Leu Asp
    2105                2110                2115

Asn Ile Val Met Leu His Thr Thr Glu Arg Gly Gly Arg Ala Tyr
    2120                2125                2130

Gln His Ala Leu Asn Glu Leu Pro Glu Ser Leu Glu Thr Leu Met
    2135                2140                2145

Leu Val Ala Leu Leu Gly Ala Met Thr Ala Gly Ile Phe Leu Phe
    2150                2155                2160

Phe Met Gln Gly Lys Gly Ile Gly Lys Leu Ser Met Gly Leu Ile
    2165                2170                2175

Thr Ile Ala Val Ala Ser Gly Leu Leu Trp Val Ala Glu Ile Gln
    2180                2185                2190

Pro Gln Trp Ile Ala Ala Ser Ile Ile Leu Glu Phe Phe Leu Met
    2195                2200                2205

Val Leu Leu Ile Pro Glu Pro Glu Lys Gln Arg Thr Pro Gln Asp
    2210                2215                2220

Asn Gln Leu Ile Tyr Val Ile Leu Thr Ile Leu Thr Ile Ile Gly
    2225                2230                2235

Leu Ile Ala Ala Asn Glu Met Gly Leu Ile Glu Lys Thr Lys Thr
    2240                2245                2250

Asp Phe Gly Phe Tyr Gln Val Lys Thr Glu Thr Thr Ile Leu Asp
    2255                2260                2265

Val Asp Leu Arg Pro Ala Ser Ala Trp Thr Leu Tyr Ala Val Ala
    2270                2275                2280

Thr Thr Ile Leu Thr Pro Met Leu Arg His Thr Ile Glu Asn Thr
    2285                2290                2295

Ser Ala Asn Leu Ser Leu Ala Ala Ile Ala Asn Gln Ala Ala Val
    2300                2305                2310

Leu Met Gly Leu Gly Lys Gly Trp Pro Leu His Arg Met Asp Leu
    2315                2320                2325

Gly Val Pro Leu Leu Ala Met Gly Cys Tyr Ser Gln Val Asn Pro
```

```
    2330                2335                2340

Thr Thr  Leu Thr Ala Ser Leu  Val Met Leu Leu Val  His Tyr Ala
    2345                2350                2355

Ile Ile  Gly Pro Gly Leu Gln  Ala Lys Ala Thr Arg  Glu Ala Gln
    2360                2365                2370

Lys Arg  Thr Ala Ala Gly Ile  Met Lys Asn Pro Thr  Val Asp Gly
    2375                2380                2385

Ile Thr  Val Ile Asp Leu Glu  Pro Ile Ser Tyr Asp  Pro Lys Phe
    2390                2395                2400

Glu Lys  Gln Leu Gly Gln Val  Met Leu Leu Val Leu  Cys Ala Gly
    2405                2410                2415

Gln Leu  Leu Leu Met Arg Thr  Thr Trp Ala Phe Cys  Glu Val Leu
    2420                2425                2430

Thr Leu  Ala Thr Gly Pro Ile  Leu Thr Leu Trp Glu  Gly Asn Pro
    2435                2440                2445

Gly Arg  Phe Trp Asn Thr Thr  Ile Ala Val Ser Thr  Ala Asn Ile
    2450                2455                2460

Phe Arg  Gly Ser Tyr Leu Ala  Gly Ala Gly Leu Ala  Phe Ser Leu
    2465                2470                2475

Ile Lys  Asn Ala Gln Thr Pro  Arg Arg Gly Thr Gly  Thr Thr Gly
    2480                2485                2490

Glu Thr  Leu Gly Glu Lys Trp  Lys Arg Gln Leu Asn  Ser Leu Asp
    2495                2500                2505

Arg Lys  Glu Phe Glu Glu Tyr  Lys Arg Ser Gly Ile  Leu Glu Val
    2510                2515                2520

Asp Arg  Thr Glu Ala Lys Ser  Ala Leu Lys Asp Gly  Ser Lys Ile
    2525                2530                2535

Lys His  Ala Val Ser Arg Gly  Ser Ser Lys Ile Arg  Trp Ile Val
    2540                2545                2550

Glu Arg  Gly Met Val Lys Pro  Lys Gly Lys Val Val  Asp Leu Gly
    2555                2560                2565

Cys Gly  Arg Gly Gly Trp Ser  Tyr Tyr Met Ala Thr  Leu Lys Asn
    2570                2575                2580

Val Thr  Glu Val Lys Gly Tyr  Thr Lys Gly Gly Pro  Gly His Glu
    2585                2590                2595

Glu Pro  Ile Pro Met Ala Thr  Tyr Gly Trp Asn Leu  Val Lys Leu
    2600                2605                2610

His Ser  Gly Val Asp Val Phe  Tyr Lys Pro Thr Glu  Gln Val Asp
    2615                2620                2625

Thr Leu  Leu Cys Asp Ile Gly  Glu Ser Ser Ser Asn  Pro Thr Ile
    2630                2635                2640

Glu Glu  Gly Arg Thr Leu Arg  Val Leu Lys Met Val  Glu Pro Trp
    2645                2650                2655

Leu Ser  Ser Lys Pro Glu Phe  Cys Ile Lys Val Leu  Asn Pro Tyr
    2660                2665                2670

Met Pro  Thr Val Ile Glu Glu  Leu Glu Lys Leu Gln  Arg Lys His
    2675                2680                2685

Gly Gly  Asn Leu Val Arg Cys  Pro Leu Ser Arg Asn  Ser Thr His
    2690                2695                2700

Glu Met  Tyr Trp Val Ser Gly  Ala Ser Gly Asn Ile  Val Ser Ser
    2705                2710                2715

Val Asn  Thr Thr Ser Lys Met  Leu Leu Asn Arg Phe  Thr Thr Arg
    2720                2725                2730
```

His Arg Lys Pro Thr Tyr Glu Lys Asp Val Asp Leu Gly Ala Gly
2735 2740 2745

Thr Arg Ser Val Ser Thr Glu Thr Glu Lys Pro Asp Met Thr Ile
2750 2755 2760

Ile Gly Arg Arg Leu Gln Arg Leu Gln Glu Glu His Lys Glu Thr
2765 2770 2775

Trp His Tyr Asp Gln Glu Asn Pro Tyr Arg Thr Trp Ala Tyr His
2780 2785 2790

Gly Ser Tyr Glu Ala Pro Ser Thr Gly Ser Ala Ser Ser Met Val
2795 2800 2805

Asn Gly Val Val Lys Leu Leu Thr Lys Pro Trp Asp Val Ile Pro
2810 2815 2820

Met Val Thr Gln Leu Ala Met Thr Asp Thr Thr Pro Phe Gly Gln
2825 2830 2835

Gln Arg Val Phe Lys Glu Lys Val Asp Thr Arg Thr Pro Gln Pro
2840 2845 2850

Lys Pro Gly Thr Arg Met Val Met Thr Thr Thr Ala Asn Trp Leu
2855 2860 2865

Trp Ala Leu Leu Gly Lys Lys Lys Asn Pro Arg Leu Cys Thr Arg
2870 2875 2880

Glu Glu Phe Ile Ser Lys Val Arg Ser Asn Ala Ala Ile Gly Ala
2885 2890 2895

Val Phe Gln Glu Glu Gln Gly Trp Thr Ser Ala Ser Glu Ala Val
2900 2905 2910

Asn Asp Ser Arg Phe Trp Glu Leu Val Asp Lys Glu Arg Ala Leu
2915 2920 2925

His Gln Glu Gly Lys Cys Glu Ser Cys Val Tyr Asn Met Met Gly
2930 2935 2940

Lys Arg Glu Lys Lys Leu Gly Glu Phe Gly Arg Ala Lys Gly Ser
2945 2950 2955

Arg Ala Ile Trp Tyr Met Trp Leu Gly Ala Arg Phe Leu Glu Phe
2960 2965 2970

Glu Ala Leu Gly Phe Leu Asn Glu Asp His Trp Phe Gly Arg Glu
2975 2980 2985

Asn Ser Trp Ser Gly Val Glu Gly Glu Gly Leu His Arg Leu Gly
2990 2995 3000

Tyr Ile Leu Glu Glu Ile Asp Lys Lys Asp Gly Asp Leu Met Tyr
3005 3010 3015

Ala Asp Asp Thr Ala Gly Trp Asp Thr Arg Ile Thr Glu Asp Asp
3020 3025 3030

Leu Gln Asn Glu Glu Leu Ile Thr Glu Gln Met Ala Pro His His
3035 3040 3045

Lys Ile Leu Ala Lys Ala Ile Phe Lys Leu Thr Tyr Gln Asn Lys
3050 3055 3060

Val Val Lys Val Leu Arg Pro Thr Pro Arg Gly Ala Val Met Asp
3065 3070 3075

Ile Ile Ser Arg Lys Asp Gln Arg Gly Ser Gly Gln Val Gly Thr
3080 3085 3090

Tyr Gly Leu Asn Thr Phe Thr Asn Met Glu Val Gln Leu Ile Arg
3095 3100 3105

Gln Met Glu Ala Glu Gly Val Ile Thr Gln Asp Asp Met Gln Asn
3110 3115 3120

Pro Lys Gly Leu Lys Glu Arg Val Glu Lys Trp Leu Lys Glu Cys
3125 3130 3135

Gly Val Asp Arg Leu Lys Arg Met Ala Ile Ser Gly Asp Asp Cys
3140 3145 3150

Val Val Lys Pro Leu Asp Glu Arg Phe Gly Thr Ser Leu Leu Phe
3155 3160 3165

Leu Asn Asp Met Gly Lys Val Arg Lys Asp Ile Pro Gln Trp Glu
3170 3175 3180

Pro Ser Lys Gly Trp Lys Asn Trp Gln Glu Val Pro Phe Cys Ser
3185 3190 3195

His His Phe His Lys Ile Phe Met Lys Asp Gly Arg Ser Leu Val
3200 3205 3210

Val Pro Cys Arg Asn Gln Asp Glu Leu Ile Gly Arg Ala Arg Ile
3215 3220 3225

Ser Gln Gly Ala Gly Trp Ser Leu Arg Glu Thr Ala Cys Leu Gly
3230 3235 3240

Lys Ala Tyr Ala Gln Met Trp Ser Leu Met Tyr Phe His Arg Arg
3245 3250 3255

Asp Leu Arg Leu Ala Ser Met Ala Ile Cys Ser Ala Val Pro Thr
3260 3265 3270

Glu Trp Phe Pro Thr Ser Arg Thr Thr Trp Ser Ile His Ala His
3275 3280 3285

His Gln Trp Met Thr Thr Glu Asp Met Leu Lys Val Trp Asn Arg
3290 3295 3300

Val Trp Ile Glu Asp Asn Pro Asn Met Thr Asp Lys Thr Pro Val
3305 3310 3315

His Ser Trp Glu Asp Ile Pro Tyr Leu Gly Lys Arg Glu Asp Leu
3320 3325 3330

Trp Cys Gly Ser Leu Ile Gly Leu Ser Ser Arg Ala Thr Trp Ala
3335 3340 3345

Lys Asn Ile His Thr Ala Ile Thr Gln Val Arg Asn Leu Ile Gly
3350 3355 3360

Lys Glu Glu Tyr Val Asp Tyr Met Pro Val Met Lys Arg Tyr Ser
3365 3370 3375

Ala Pro Ser Glu Ser Glu Gly Val Leu
3380 3385

<210> SEQ ID NO 20
<211> LENGTH: 3392
<212> TYPE: PRT
<213> ORGANISM: Dengue 1 virus strain WP

<400> SEQUENCE: 20

Met Asn Asn Gln Arg Lys Lys Thr Gly Arg Pro Ser Phe Asn Met Leu
1 5 10 15

Lys Arg Ala Arg Asn Arg Val Ser Thr Val Ser Gln Leu Ala Lys Arg
20 25 30

Phe Ser Lys Gly Leu Leu Ser Gly Gln Gly Pro Met Lys Leu Val Met
35 40 45

Ala Phe Ile Ala Phe Leu Arg Phe Leu Ala Ile Pro Pro Thr Ala Gly
50 55 60

Ile Leu Ala Arg Trp Gly Ser Phe Lys Lys Asn Gly Ala Ile Lys Val
65 70 75 80

Leu Arg Gly Phe Lys Lys Glu Ile Ser Asn Met Leu Asn Ile Met Asn
85 90 95

```
Arg Arg Lys Arg Ser Val Thr Met Leu Leu Met Leu Leu Pro Thr Ala
            100                 105                 110

Leu Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Thr Glu Pro Asp
                165                 170                 175

Asp Val Asp Cys Trp Cys Asn Ala Thr Glu Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Thr Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asp Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Thr
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Ala Leu Thr Leu Asp
    450                 455                 460

Cys Ser Pro Arg Thr Gly Leu Asp Phe Asn Glu Met Val Leu Leu Thr
465                 470                 475                 480

Met Glu Lys Lys Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510
```

-continued

```
Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Ser Gln Asp Glu Lys Gly
    610                 615                 620

Val Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Val Gly Lys Leu Ile His Gln Ile Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Ser
            740                 745                 750

Thr Ser Leu Ser Met Thr Cys Ile Ala Val Gly Met Val Thr Leu Tyr
        755                 760                 765

Leu Gly Val Met Val Gln Ala Asp Ser Gly Cys Val Ile Asn Trp Lys
    770                 775                 780

Gly Arg Glu Leu Lys Cys Gly Ser Gly Ile Phe Val Thr Asn Glu Val
785                 790                 795                 800

His Thr Trp Thr Glu Gln Tyr Lys Phe Gln Ala Asp Ser Pro Lys Arg
                805                 810                 815

Leu Ser Ala Ala Ile Gly Lys Ala Trp Glu Glu Gly Val Cys Gly Ile
            820                 825                 830

Arg Ser Ala Thr Arg Leu Glu Asn Ile Met Trp Lys Gln Ile Ser Asn
        835                 840                 845

Glu Leu Asn His Ile Leu Leu Glu Asn Asp Met Lys Phe Thr Val Val
    850                 855                 860

Val Gly Asp Val Ser Gly Ile Leu Ala Gln Gly Lys Lys Met Ile Arg
865                 870                 875                 880

Pro Gln Pro Met Glu His Lys Tyr Ser Trp Lys Ser Trp Gly Lys Ala
                885                 890                 895

Lys Ile Ile Gly Ala Asp Val Gln Asn Thr Thr Phe Ile Ile Asp Gly
            900                 905                 910

Pro Asn Thr Pro Glu Cys Pro Asp Asn Gln Arg Ala Trp Asn Ile Trp
        915                 920                 925

Glu Val Glu Asp Tyr Gly Phe Gly Ile Phe Thr Thr Asn Ile Trp Leu
```

```
    930                 935                 940

Lys Leu Arg Asp Ser Tyr Thr Gln Val Cys Asp His Arg Leu Met Ser
945                 950                 955                 960

Ala Ala Ile Lys Asp Ser Lys Ala Val His Ala Asp Met Gly Tyr Trp
                965                 970                 975

Ile Glu Ser Glu Lys Asn Glu Thr Trp Lys Leu Ala Arg Ala Ser Phe
            980                 985                 990

Ile Glu Val Lys Thr Cys Ile Trp  Pro Lys Ser His Thr  Leu Trp Ser
        995                 1000                1005

Asn Gly  Val Leu Glu Ser Glu  Met Ile Ile Pro Lys  Ile Tyr Gly
    1010                1015                1020

Gly Pro  Ile Ser Gln His Asn  Tyr Arg Pro Gly Tyr  Phe Thr Gln
    1025                1030                1035

Thr Ala  Gly Pro Trp His Leu  Gly Lys Leu Glu Leu  Asp Phe Asp
    1040                1045                1050

Leu Cys  Glu Gly Thr Thr Val  Val Val Asp Glu His  Cys Gly Asn
    1055                1060                1065

Arg Gly  Pro Ser Leu Arg Thr  Thr Thr Val Thr Gly  Lys Thr Ile
    1070                1075                1080

His Glu  Trp Cys Cys Arg Ser  Cys Thr Leu Pro Pro  Leu Arg Phe
    1085                1090                1095

Lys Gly  Glu Asp Gly Cys Trp  Tyr Gly Met Glu Ile  Arg Pro Val
    1100                1105                1110

Lys Glu  Lys Glu Glu Asn Leu  Val Lys Ser Met Val  Ser Ala Gly
    1115                1120                1125

Ser Gly  Glu Val Asp Ser Phe  Ser Leu Gly Leu Leu  Cys Ile Ser
    1130                1135                1140

Ile Met  Ile Glu Glu Val Met  Arg Ser Arg Trp Ser  Arg Lys Met
    1145                1150                1155

Leu Met  Thr Gly Thr Leu Ala  Val Phe Leu Leu Leu  Thr Met Gly
    1160                1165                1170

Gln Leu  Thr Trp Asn Asp Leu  Ile Arg Leu Cys Ile  Met Val Gly
    1175                1180                1185

Ala Asn  Ala Ser Asp Lys Met  Gly Met Gly Thr Thr  Tyr Leu Ala
    1190                1195                1200

Leu Met  Ala Thr Phe Arg Met  Arg Pro Met Phe Ala  Val Gly Leu
    1205                1210                1215

Leu Phe  Arg Arg Leu Thr Ser  Arg Glu Val Leu Leu  Leu Thr Val
    1220                1225                1230

Gly Leu  Ser Leu Val Ala Ser  Val Glu Leu Pro Asn  Ser Leu Glu
    1235                1240                1245

Glu Leu  Gly Asp Gly Leu Ala  Met Gly Ile Met Met  Leu Lys Leu
    1250                1255                1260

Leu Thr  Asp Phe Gln Ser His  Gln Leu Trp Ala Thr  Leu Leu Ser
    1265                1270                1275

Leu Thr  Phe Val Lys Thr Thr  Phe Ser Leu His Tyr  Ala Trp Lys
    1280                1285                1290

Thr Met  Ala Met Ile Leu Ser  Ile Val Ser Leu Phe  Pro Leu Cys
    1295                1300                1305

Leu Ser  Thr Thr Ser Gln Lys  Thr Thr Trp Leu Pro  Val Leu Leu
    1310                1315                1320

Gly Ser  Leu Gly Cys Lys Pro  Leu Thr Met Phe Leu  Ile Thr Glu
    1325                1330                1335
```

Asn Lys Ile Trp Gly Arg Lys Ser Trp Pro Leu Asn Glu Gly Ile
1340 1345 1350

Met Ala Val Gly Ile Val Ser Ile Leu Leu Ser Ser Leu Leu Lys
1355 1360 1365

Asn Asp Val Pro Leu Ala Gly Pro Leu Ile Ala Gly Gly Met Leu
1370 1375 1380

Ile Ala Cys Tyr Val Ile Ser Gly Ser Ser Ala Asp Leu Ser Leu
1385 1390 1395

Glu Lys Ala Ala Glu Val Ser Trp Glu Glu Glu Ala Glu His Ser
1400 1405 1410

Gly Ala Ser His Asn Ile Leu Val Glu Val Gln Asp Asp Gly Thr
1415 1420 1425

Met Lys Ile Lys Asp Glu Glu Arg Asp Asp Thr Leu Thr Ile Leu
1430 1435 1440

Leu Lys Ala Thr Leu Leu Ala Ile Ser Gly Val Tyr Pro Met Ser
1445 1450 1455

Ile Pro Ala Thr Leu Phe Val Trp Tyr Phe Trp Gln Lys Lys Lys
1460 1465 1470

Gln Arg Ser Gly Val Leu Trp Asp Thr Pro Ser Pro Pro Glu Val
1475 1480 1485

Glu Arg Ala Val Leu Asp Asp Gly Ile Tyr Arg Ile Leu Gln Arg
1490 1495 1500

Gly Leu Leu Gly Arg Ser Gln Val Gly Val Gly Val Phe Gln Glu
1505 1510 1515

Gly Val Phe His Thr Met Trp His Val Thr Arg Gly Ala Val Leu
1520 1525 1530

Met Tyr Gln Gly Lys Arg Leu Glu Pro Ser Trp Ala Ser Val Lys
1535 1540 1545

Lys Asp Leu Ile Ser Tyr Gly Gly Gly Trp Arg Phe Gln Gly Ser
1550 1555 1560

Trp Asn Ala Gly Glu Glu Val Gln Val Ile Ala Val Glu Pro Gly
1565 1570 1575

Lys Asn Pro Lys Asn Val Gln Thr Ala Pro Gly Thr Phe Lys Thr
1580 1585 1590

Pro Glu Gly Glu Val Gly Ala Ile Ala Leu Asp Phe Lys Pro Gly
1595 1600 1605

Thr Ser Gly Ser Pro Ile Val Asn Arg Glu Gly Lys Ile Val Gly
1610 1615 1620

Leu Tyr Gly Asn Gly Val Val Thr Thr Ser Gly Thr Tyr Val Ser
1625 1630 1635

Ala Ile Ala Gln Ala Lys Ala Ser Gln Glu Gly Pro Leu Pro Glu
1640 1645 1650

Ile Glu Asp Glu Val Phe Arg Lys Arg Asn Leu Thr Ile Met Asp
1655 1660 1665

Leu His Pro Gly Ser Gly Lys Thr Arg Arg Tyr Leu Pro Ala Ile
1670 1675 1680

Val Arg Glu Ala Ile Arg Arg Asn Val Arg Thr Leu Val Leu Ala
1685 1690 1695

Pro Thr Arg Val Val Ala Ser Glu Met Ala Glu Ala Leu Lys Gly
1700 1705 1710

Met Pro Ile Arg Tyr Gln Thr Thr Ala Val Lys Ser Glu His Thr
1715 1720 1725

```
Gly Lys  Glu Ile Val Asp Leu  Met Cys His Ala Thr  Phe Thr Met
    1730                 1735                 1740

Arg Leu  Leu Ser Pro Val Arg  Val Pro Asn Tyr Asn  Met Ile Ile
    1745                 1750                 1755

Met Asp  Glu Ala His Phe Thr  Asp Pro Ala Ser Ile  Ala Ala Arg
    1760                 1765                 1770

Gly Tyr  Ile Ser Thr Arg Val  Gly Met Gly Glu Ala  Ala Ala Ile
    1775                 1780                 1785

Phe Met  Thr Ala Thr Pro Pro  Gly Ser Val Glu Ala  Phe Pro Gln
    1790                 1795                 1800

Ser Asn  Ala Val Ile Gln Asp  Glu Glu Arg Asp Ile  Pro Glu Arg
    1805                 1810                 1815

Ser Trp  Asn Ser Gly Tyr Asp  Trp Ile Thr Asp Phe  Pro Gly Lys
    1820                 1825                 1830

Thr Val  Trp Phe Val Pro Ser  Ile Lys Ser Gly Asn  Asp Ile Ala
    1835                 1840                 1845

Asn Cys  Leu Arg Lys Asn Gly  Lys Arg Val Val Gln  Leu Ser Arg
    1850                 1855                 1860

Lys Thr  Phe Asp Thr Glu Tyr  Gln Lys Thr Lys Asn  Asn Asp Trp
    1865                 1870                 1875

Asp Tyr  Val Val Thr Thr Asp  Ile Ser Glu Met Gly  Ala Asn Phe
    1880                 1885                 1890

Arg Ala  Asp Arg Val Ile Asp  Pro Arg Arg Cys Leu  Lys Pro Val
    1895                 1900                 1905

Ile Leu  Lys Asp Gly Pro Glu  Arg Val Ile Leu Ala  Gly Pro Met
    1910                 1915                 1920

Pro Val  Thr Val Ala Ser Ala  Ala Gln Arg Arg Gly  Arg Ile Gly
    1925                 1930                 1935

Arg Asn  Gln Asn Lys Glu Gly  Asp Gln Tyr Ile Tyr  Met Gly Gln
    1940                 1945                 1950

Pro Leu  Asn Asn Asp Glu Asp  His Ala His Trp Thr  Glu Ala Lys
    1955                 1960                 1965

Met Leu  Leu Asp Asn Ile Asn  Thr Pro Glu Gly Ile  Ile Pro Ala
    1970                 1975                 1980

Leu Phe  Glu Pro Glu Arg Glu  Lys Ser Ala Ala Ile  Asp Gly Glu
    1985                 1990                 1995

Tyr Arg  Leu Arg Gly Glu Ala  Arg Lys Thr Phe Val  Glu Leu Met
    2000                 2005                 2010

Arg Arg  Gly Asp Leu Pro Val  Trp Leu Ser Tyr Lys  Val Ala Ser
    2015                 2020                 2025

Glu Gly  Phe Gln Tyr Ser Asp  Arg Arg Trp Cys Phe  Asp Gly Glu
    2030                 2035                 2040

Arg Asn  Asn Gln Val Leu Glu  Glu Asn Met Asp Val  Glu Ile Trp
    2045                 2050                 2055

Thr Lys  Glu Gly Glu Arg Lys  Lys Leu Arg Pro Arg  Trp Leu Asp
    2060                 2065                 2070

Ala Arg  Thr Tyr Ser Asp Pro  Leu Ala Leu Arg Glu  Phe Lys Glu
    2075                 2080                 2085

Phe Ala  Ala Gly Arg Arg Ser  Val Ser Gly Asp Leu  Ile Leu Glu
    2090                 2095                 2100

Ile Gly  Lys Leu Pro Gln His  Leu Thr Gln Arg Ala  Gln Asn Ala
    2105                 2110                 2115

Leu Asp  Asn Leu Val Met Leu  His Asn Ser Glu Gln  Gly Gly Lys
```

```
    2120                2125                2130

Ala Tyr  Arg His Ala Met Glu  Glu Leu Pro Asp Thr  Ile Glu Thr
    2135                2140                2145

Leu Met  Leu Leu Ala Leu Ile  Ala Val Leu Thr Gly  Gly Val Thr
    2150                2155                2160

Leu Phe  Phe Leu Ser Gly Arg  Gly Leu Gly Lys Thr  Ser Ile Gly
    2165                2170                2175

Leu Leu  Cys Val Ile Ala Ser  Ser Ala Leu Leu Trp  Met Ala Ser
    2180                2185                2190

Val Glu  Pro His Trp Ile Ala  Ala Ser Ile Ile Leu  Glu Phe Phe
    2195                2200                2205

Leu Met  Val Leu Leu Ile Pro  Glu Pro Asp Arg Gln  Arg Thr Pro
    2210                2215                2220

Gln Asp  Asn Gln Leu Ala Tyr  Val Val Ile Gly Leu  Leu Phe Met
    2225                2230                2235

Ile Leu  Thr Ala Ala Ala Asn  Glu Met Gly Leu Leu  Glu Thr Thr
    2240                2245                2250

Lys Lys  Asp Leu Gly Ile Gly  His Ala Ala Ala Glu  Asn His His
    2255                2260                2265

His Ala  Ala Met Leu Asp Val  Asp Leu His Pro Ala  Ser Ala Trp
    2270                2275                2280

Thr Leu  Tyr Ala Val Ala Thr  Thr Ile Ile Thr Pro  Met Met Arg
    2285                2290                2295

His Thr  Ile Glu Asn Thr Thr  Ala Asn Ile Ser Leu  Thr Ala Ile
    2300                2305                2310

Ala Asn  Gln Ala Ala Ile Leu  Met Gly Leu Asp Lys  Gly Trp Pro
    2315                2320                2325

Ile Ser  Lys Met Asp Ile Gly  Val Pro Leu Leu Ala  Leu Gly Cys
    2330                2335                2340

Tyr Ser  Gln Val Asn Pro Leu  Thr Leu Thr Ala Ala  Val Phe Met
    2345                2350                2355

Leu Val  Ala His Tyr Ala Ile  Ile Gly Pro Gly Leu  Gln Ala Lys
    2360                2365                2370

Ala Thr  Arg Glu Ala Gln Lys  Arg Thr Ala Ala Gly  Ile Met Lys
    2375                2380                2385

Asn Pro  Thr Val Asp Gly Ile  Val Ala Ile Asp Leu  Asp Pro Val
    2390                2395                2400

Val Tyr  Asp Ala Lys Phe Glu  Lys Gln Leu Gly Gln  Ile Met Leu
    2405                2410                2415

Leu Ile  Leu Cys Thr Ser Gln  Ile Leu Leu Met Arg  Thr Thr Trp
    2420                2425                2430

Ala Leu  Cys Glu Ser Ile Thr  Leu Ala Thr Gly Pro  Leu Thr Thr
    2435                2440                2445

Leu Trp  Glu Gly Ser Pro Gly  Lys Phe Trp Asn Thr  Thr Ile Ala
    2450                2455                2460

Val Ser  Met Ala Asn Ile Phe  Arg Gly Ser Tyr Leu  Ala Gly Ala
    2465                2470                2475

Gly Leu  Ala Phe Ser Leu Met  Lys Ser Leu Gly Gly  Gly Arg Arg
    2480                2485                2490

Gly Thr  Gly Ala Gln Gly Glu  Thr Leu Gly Glu Lys  Trp Lys Arg
    2495                2500                2505

Gln Leu  Asn Gln Leu Ser Lys  Ser Glu Phe Asn Thr  Tyr Lys Arg
    2510                2515                2520
```

```
Ser Gly Ile Ile Glu Val Asp Arg Ser Glu Ala Lys Glu Gly Leu
    2525                2530                2535

Lys Arg Gly Glu Pro Thr Lys His Ala Val Ser Arg Gly Thr Ala
    2540                2545                2550

Lys Leu Arg Trp Phe Val Glu Arg Asn Leu Val Lys Pro Glu Gly
    2555                2560                2565

Lys Val Ile Asp Leu Gly Cys Gly Arg Gly Gly Trp Ser Tyr Tyr
    2570                2575                2580

Cys Ala Gly Leu Lys Lys Val Thr Glu Val Lys Gly Tyr Thr Lys
    2585                2590                2595

Gly Gly Pro Gly His Glu Glu Pro Ile Pro Met Ala Thr Tyr Gly
    2600                2605                2610

Trp Asn Leu Val Lys Leu Tyr Ser Gly Lys Asp Val Phe Phe Thr
    2615                2620                2625

Pro Pro Glu Lys Cys Asp Thr Leu Leu Cys Asp Ile Gly Glu Ser
    2630                2635                2640

Ser Pro Asn Pro Thr Ile Glu Glu Gly Arg Thr Leu Arg Val Leu
    2645                2650                2655

Lys Met Val Glu Pro Trp Leu Arg Gly Asn Gln Phe Cys Ile Lys
    2660                2665                2670

Ile Leu Asn Pro Tyr Met Pro Ser Val Val Glu Thr Leu Glu Gln
    2675                2680                2685

Met Gln Arg Lys His Gly Gly Met Leu Val Arg Asn Pro Leu Ser
    2690                2695                2700

Arg Asn Ser Thr His Glu Met Tyr Trp Val Ser Cys Gly Thr Gly
    2705                2710                2715

Asn Ile Val Ser Ala Val Asn Met Thr Ser Arg Met Leu Leu Asn
    2720                2725                2730

Arg Phe Thr Met Ala His Arg Lys Pro Thr Tyr Glu Arg Asp Val
    2735                2740                2745

Asp Leu Gly Ala Gly Thr Arg His Val Ala Val Glu Pro Glu Val
    2750                2755                2760

Ala Asn Leu Asp Ile Ile Gly Gln Arg Ile Glu Asn Ile Lys Asn
    2765                2770                2775

Gly His Lys Ser Thr Trp His Tyr Asp Glu Asp Asn Pro Tyr Lys
    2780                2785                2790

Thr Trp Ala Tyr His Gly Ser Tyr Glu Val Lys Pro Ser Gly Ser
    2795                2800                2805

Ala Ser Ser Met Val Asn Gly Val Val Arg Leu Leu Thr Lys Pro
    2810                2815                2820

Trp Asp Val Ile Pro Met Val Thr Gln Ile Ala Met Thr Asp Thr
    2825                2830                2835

Thr Pro Phe Gly Gln Gln Arg Val Phe Lys Glu Lys Val Asp Thr
    2840                2845                2850

Arg Thr Pro Lys Ala Lys Arg Gly Thr Ala Gln Ile Met Glu Val
    2855                2860                2865

Thr Ala Arg Trp Leu Trp Gly Phe Leu Ser Arg Asn Lys Lys Pro
    2870                2875                2880

Arg Ile Cys Thr Arg Glu Glu Phe Thr Arg Lys Val Arg Ser Asn
    2885                2890                2895

Ala Ala Ile Gly Ala Val Phe Val Asp Glu Asn Gln Trp Asn Ser
    2900                2905                2910
```

Ala Lys Glu Ala Val Glu Asp Glu Arg Phe Trp Asp Leu Val His
2915 2920 2925

Arg Glu Arg Glu Leu His Lys Gln Gly Lys Cys Ala Thr Cys Val
2930 2935 2940

Tyr Asn Met Met Gly Lys Arg Glu Lys Lys Leu Gly Glu Phe Gly
2945 2950 2955

Lys Ala Lys Gly Ser Arg Ala Ile Trp Tyr Met Trp Leu Gly Ala
2960 2965 2970

Arg Phe Leu Glu Phe Glu Ala Leu Gly Phe Met Asn Glu Asp His
2975 2980 2985

Trp Phe Ser Arg Glu Asn Ser Leu Ser Gly Val Glu Gly Glu Gly
2990 2995 3000

Leu His Lys Leu Gly Tyr Ile Leu Arg Asp Ile Ser Lys Ile Pro
3005 3010 3015

Gly Gly Asn Met Tyr Ala Asp Asp Thr Ala Gly Trp Asp Thr Arg
3020 3025 3030

Ile Thr Glu Asp Asp Leu Gln Asn Glu Ala Lys Ile Thr Asp Ile
3035 3040 3045

Met Glu Pro Glu His Ala Leu Leu Ala Thr Ser Ile Phe Lys Leu
3050 3055 3060

Thr Tyr Gln Asn Lys Val Val Arg Val Gln Arg Pro Ala Lys Asn
3065 3070 3075

Gly Thr Val Met Asp Val Ile Ser Arg Arg Asp Gln Arg Gly Ser
3080 3085 3090

Gly Gln Val Gly Thr Tyr Gly Leu Asn Thr Phe Thr Asn Met Glu
3095 3100 3105

Ala Gln Leu Ile Arg Gln Met Glu Ser Glu Gly Ile Phe Ser Pro
3110 3115 3120

Ser Glu Leu Glu Thr Pro Asn Leu Ala Glu Arg Val Leu Asp Trp
3125 3130 3135

Leu Lys Lys His Gly Thr Glu Arg Leu Lys Arg Met Ala Ile Ser
3140 3145 3150

Gly Asp Asp Cys Val Val Lys Pro Ile Asp Asp Arg Phe Ala Thr
3155 3160 3165

Ala Leu Thr Ala Leu Asn Asp Met Gly Lys Val Arg Lys Asp Ile
3170 3175 3180

Pro Gln Trp Glu Pro Ser Lys Gly Trp Asn Asp Trp Gln Gln Val
3185 3190 3195

Pro Phe Cys Ser His His Phe His Gln Leu Ile Met Lys Asp Gly
3200 3205 3210

Arg Glu Ile Val Val Pro Cys Arg Asn Gln Asp Glu Leu Val Gly
3215 3220 3225

Arg Ala Arg Val Ser Gln Gly Ala Gly Trp Ser Leu Arg Glu Thr
3230 3235 3240

Ala Cys Leu Gly Lys Ser Tyr Ala Gln Met Trp Gln Leu Met Tyr
3245 3250 3255

Phe His Arg Arg Asp Leu Arg Leu Ala Ala Asn Ala Ile Cys Ser
3260 3265 3270

Ala Val Pro Val Asp Trp Val Pro Thr Ser Arg Thr Thr Trp Ser
3275 3280 3285

Ile His Ala His His Gln Trp Met Thr Thr Glu Asp Met Leu Ser
3290 3295 3300

Val Trp Asn Arg Val Trp Ile Glu Glu Asn Pro Trp Met Glu Asp

```
    3305                3310                3315

Lys Thr  His Val Ser Ser Trp  Glu Asp Val Pro Tyr  Leu Gly Lys
    3320                3325                3330

Arg Glu  Asp Arg Trp Cys Gly  Ser Leu Ile Gly Leu  Thr Ala Arg
    3335                3340                3345

Ala Thr  Trp Ala Thr Asn Ile  Gln Val Ala Ile Asn  Gln Val Arg
    3350                3355                3360

Arg Leu  Ile Gly Asn Glu Asn  Tyr Leu Asp Phe Met  Thr Ser Met
    3365                3370                3375

Lys Arg  Phe Lys Asn Glu Ser  Asp Pro Glu Gly Ala  Leu Trp
    3380                3385                3390


<210> SEQ ID NO 21
<211> LENGTH: 3391
<212> TYPE: PRT
<213> ORGANISM: Dengue 2 virus strain NGC

<400> SEQUENCE: 21

Met Asn Asn Gln Arg Lys Lys Ala Arg Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Phe Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Ala Pro Ser Met Thr Met Arg Cys Ile Gly Ile Ser Asn
        275                 280                 285
```

-continued

```
Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Asp Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Thr
385                 390                 395                 400

Cys Lys Lys Asn Met Lys Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Ile Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
```

-continued

```
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Ser Leu Val Leu Val Gly Val Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Gly Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Gln
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Arg Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Ser Cys His Trp  Pro Lys Ser His Thr  Leu Trp Ser
        995                 1000                1005

Asn Gly  Val Leu Glu Ser Glu  Met Ile Ile Pro Lys  Asn Phe Ala
    1010                 1015                 1020

Gly Pro  Val Ser Gln His Asn  Tyr Arg Pro Gly Tyr  His Thr Gln
    1025                 1030                 1035

Thr Ala  Gly Pro Trp His Leu  Gly Lys Leu Glu Met  Asp Phe Asp
    1040                 1045                 1050

Phe Cys  Glu Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125
```

```
His Gly  Gln Ile Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Lys Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Ala Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Asn Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Val
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515
```

-continued

```
Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Lys Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Glu  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Met Asp Glu  Glu Arg Glu Ile Pro  Glu Arg Ser
    1805                 1810                 1815

Trp Ser  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
```

```
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Ile Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Thr Leu Lys Glu Phe  Lys Glu Phe
    2075                2080                2085

Ala Ala  Gly Arg Lys Ser Leu  Thr Leu Asn Leu Ile  Thr Glu Met
    2090                2095                2100

Gly Arg  Leu Pro Thr Phe Met  Thr Gln Lys Ala Arg  Asp Ala Leu
    2105                2110                2115

Asp Asn  Leu Ala Val Leu His  Thr Ala Glu Ala Gly  Gly Arg Ala
    2120                2125                2130

Tyr Asn  His Ala Leu Ser Glu  Leu Pro Glu Thr Leu  Glu Thr Leu
    2135                2140                2145

Leu Leu  Leu Thr Leu Leu Ala  Thr Val Thr Gly Gly  Ile Phe Leu
    2150                2155                2160

Phe Leu  Met Ser Gly Arg Gly  Ile Gly Lys Met Thr  Leu Gly Met
    2165                2170                2175

Cys Cys  Ile Ile Thr Ala Ser  Ile Leu Leu Trp Tyr  Ala Gln Ile
    2180                2185                2190

Gln Pro  His Trp Ile Ala Ala  Ser Ile Ile Leu Glu  Phe Phe Leu
    2195                2200                2205

Ile Val  Leu Leu Ile Pro Glu  Pro Glu Lys Gln Arg  Thr Pro Gln
    2210                2215                2220

Asp Asn  Gln Leu Thr Tyr Val  Val Ile Ala Ile Leu  Thr Val Val
    2225                2230                2235

Ala Ala  Thr Met Ala Asn Glu  Met Gly Phe Leu Glu  Lys Thr Lys
    2240                2245                2250

Lys Asp  Leu Gly Leu Gly Ser  Ile Thr Thr Gln Gln  Pro Glu Ser
    2255                2260                2265

Asn Ile  Leu Asp Ile Asp Leu  Arg Pro Ala Ser Ala  Trp Thr Leu
    2270                2275                2280

Tyr Ala  Val Ala Thr Thr Phe  Val Thr Pro Met Leu  Arg His Ser
    2285                2290                2295

Ile Glu  Asn Ser Ser Val Asn  Val Ser Leu Thr Ala  Ile Ala Asn
    2300                2305                2310
```

```
Gln Ala Thr Val Leu Met Gly Leu Gly Lys Gly Trp Pro Leu Ser
    2315                2320                2325

Lys Met Asp Ile Gly Val Pro Leu Leu Ala Ile Gly Cys Tyr Ser
    2330                2335                2340

Gln Val Asn Pro Ile Thr Leu Thr Ala Ala Leu Phe Leu Leu Val
    2345                2350                2355

Ala His Tyr Ala Ile Ile Gly Pro Gly Leu Gln Ala Lys Ala Thr
    2360                2365                2370

Arg Glu Ala Gln Lys Arg Ala Ala Ala Gly Ile Met Lys Asn Pro
    2375                2380                2385

Thr Val Asp Gly Ile Thr Val Ile Asp Leu Asp Pro Ile Pro Tyr
    2390                2395                2400

Asp Pro Lys Phe Glu Lys Gln Leu Gly Gln Val Met Leu Leu Val
    2405                2410                2415

Leu Cys Val Thr Gln Val Leu Met Met Arg Thr Thr Trp Ala Leu
    2420                2425                2430

Cys Glu Ala Leu Thr Leu Ala Thr Gly Pro Ile Ser Thr Leu Trp
    2435                2440                2445

Glu Gly Asn Pro Gly Arg Phe Trp Asn Thr Thr Ile Ala Val Ser
    2450                2455                2460

Met Ala Asn Ile Phe Arg Gly Ser Tyr Leu Ala Gly Ala Gly Leu
    2465                2470                2475

Leu Phe Ser Ile Met Lys Asn Thr Thr Asn Thr Arg Arg Gly Thr
    2480                2485                2490

Gly Asn Ile Gly Glu Thr Leu Gly Glu Lys Trp Lys Ser Arg Leu
    2495                2500                2505

Asn Ala Leu Gly Lys Ser Glu Phe Gln Ile Tyr Lys Lys Ser Gly
    2510                2515                2520

Ile Gln Glu Val Asp Arg Thr Leu Ala Lys Glu Gly Ile Lys Arg
    2525                2530                2535

Gly Glu Thr Asp His His Ala Val Ser Arg Gly Ser Ala Lys Leu
    2540                2545                2550

Arg Trp Phe Val Glu Arg Asn Met Val Thr Pro Glu Gly Lys Val
    2555                2560                2565

Val Asp Leu Gly Cys Gly Arg Gly Gly Trp Ser Tyr Tyr Cys Gly
    2570                2575                2580

Gly Leu Lys Asn Val Arg Glu Val Lys Gly Leu Thr Lys Gly Gly
    2585                2590                2595

Pro Gly His Glu Glu Pro Ile Pro Met Ser Thr Tyr Gly Trp Asn
    2600                2605                2610

Leu Val Arg Leu Gln Ser Gly Val Asp Val Phe Phe Thr Pro Pro
    2615                2620                2625

Glu Lys Cys Asp Thr Leu Leu Cys Asp Ile Gly Glu Ser Ser Pro
    2630                2635                2640

Asn Pro Thr Val Glu Ala Gly Arg Thr Leu Arg Val Leu Asn Leu
    2645                2650                2655

Val Glu Asn Trp Leu Asn Asn Asn Thr Gln Phe Cys Ile Lys Val
    2660                2665                2670

Leu Asn Pro Tyr Met Pro Ser Val Ile Glu Lys Met Glu Ala Leu
    2675                2680                2685

Gln Arg Lys Tyr Gly Gly Ala Leu Val Arg Asn Pro Leu Ser Arg
    2690                2695                2700
```

```
Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730

Phe Thr  Met Arg His Lys Lys  Ala Thr Tyr Glu Pro  Asp Val Asp
    2735                 2740                 2745

Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805

Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
    2870                 2875                 2880

Met Cys  Thr Arg Glu Glu Phe  Thr Arg Lys Val Arg  Ser Asn Ala
    2885                 2890                 2895

Ala Leu  Gly Ala Ile Phe Thr  Asp Glu Asn Lys Trp  Lys Ser Ala
    2900                 2905                 2910

Arg Glu  Ala Val Glu Asp Ser  Arg Phe Trp Glu Leu  Val Asp Lys
    2915                 2920                 2925

Glu Arg  Asn Leu His Leu Glu  Gly Lys Cys Glu Thr  Cys Val Tyr
    2930                 2935                 2940

Asn Met  Met Gly Lys Arg Glu  Lys Lys Leu Gly Glu  Phe Gly Lys
    2945                 2950                 2955

Ala Lys  Gly Ser Arg Ala Ile  Trp Tyr Met Trp Leu  Gly Ala Arg
    2960                 2965                 2970

Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Arg Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
```

```
    3095                3100                3105

Gln Leu  Ile Arg Gln Met Glu  Gly Glu Gly Val Phe  Lys Ser Ile
    3110                3115                3120

Gln His  Leu Thr Val Thr Glu  Glu Ile Ala Val Gln  Asn Trp Leu
    3125                3130                3135

Ala Arg  Val Gly Arg Glu Arg  Leu Ser Arg Met Ala  Ile Ser Gly
    3140                3145                3150

Asp Asp  Cys Val Val Lys Pro  Leu Asp Asp Arg Phe  Ala Ser Ala
    3155                3160                3165

Leu Thr  Ala Leu Asn Asp Met  Gly Lys Val Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Val Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270

Val Pro  Ser His Trp Val Pro  Thr Ser Arg Thr Thr  Trp Ser Ile
    3275                3280                3285

His Ala  Lys His Glu Trp Met  Thr Thr Glu Asp Met  Leu Thr Val
    3290                3295                3300

Trp Asn  Arg Val Trp Ile Gln  Glu Asn Pro Trp Met  Glu Asp Lys
    3305                3310                3315

Thr Pro  Val Glu Ser Trp Glu  Glu Ile Pro Tyr Leu  Gly Lys Arg
    3320                3325                3330

Glu Asp  Gln Trp Cys Gly Ser  Leu Ile Gly Leu Thr  Ser Arg Ala
    3335                3340                3345

Thr Trp  Ala Lys Asn Ile Gln  Thr Ala Ile Asn Gln  Val Arg Ser
    3350                3355                3360

Leu Ile  Gly Asn Glu Glu Tyr  Thr Asp Tyr Met Pro  Ser Met Lys
    3365                3370                3375

Arg Phe  Arg Arg Glu Glu Glu  Glu Ala Gly Val Leu  Trp
    3380                3385                3390


<210> SEQ ID NO 22
<211> LENGTH: 3390
<212> TYPE: PRT
<213> ORGANISM: Dengue 3 virus strain H87

<400> SEQUENCE: 22

Met Asn Asn Gln Arg Lys Lys Thr Gly Lys Pro Ser Ile Asn Met Leu
1               5                   10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60
```

```
Val Leu Ala Arg Trp Gly Thr Phe Lys Lys Ser Gly Ala Ile Lys Val
65                  70                  75                  80

Leu Lys Gly Phe Lys Lys Glu Ile Ser Asn Met Leu Ser Ile Ile Asn
                85                  90                  95

Lys Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Ser Gln Ala Ser Thr
        435                 440                 445

Ala Glu Ala Ile Leu Pro Glu Tyr Gly Thr Leu Gly Leu Glu Cys Ser
    450                 455                 460

Pro Arg Thr Gly Leu Asp Phe Asn Glu Met Ile Leu Leu Thr Met Lys
465                 470                 475                 480

Asn Lys Ala Trp Met Val His Arg Gln Trp Phe Phe Asp Leu Pro Leu
```

```
                485                 490                 495

Pro Trp Thr Ser Gly Ala Thr Thr Lys Thr Pro Thr Trp Asn Arg Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Lys Leu Lys Gly Met Ser
                565                 570                 575

Tyr Ala Met Cys Leu Asn Thr Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Arg Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Ser Gly Val Ser Trp Ile Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ile Gly Ile Ile Thr Leu Tyr Leu Gly
        755                 760                 765

Val Val Val Gln Ala Asp Met Gly Cys Val Ile Asn Trp Lys Gly Lys
    770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Val Ala
                805                 810                 815

Thr Ala Ile Ala Gly Ala Trp Glu Asn Gly Val Cys Gly Ile Arg Ser
            820                 825                 830

Thr Thr Arg Met Glu Asn Leu Leu Trp Lys Gln Ile Ala Asn Glu Leu
        835                 840                 845

Asn Tyr Ile Leu Trp Glu Asn Asp Ile Lys Leu Thr Val Val Val Gly
    850                 855                 860

Asp Ile Thr Gly Val Leu Glu Gln Gly Lys Arg Thr Leu Thr Pro Gln
865                 870                 875                 880

Pro Met Glu Leu Lys Tyr Ser Trp Lys Thr Trp Gly Leu Ala Lys Ile
                885                 890                 895

Val Thr Ala Glu Thr Gln Asn Ser Ser Phe Ile Ile Asp Gly Pro Ser
            900                 905                 910
```

Thr Pro Glu Cys Pro Ser Ala Ser Arg Ala Trp Asn Val Trp Glu Val
915 920 925

Glu Asp Tyr Gly Phe Gly Val Phe Thr Thr Asn Ile Trp Leu Lys Leu
930 935 940

Arg Glu Val Tyr Thr Gln Leu Cys Asp His Arg Leu Met Ser Ala Ala
945 950 955 960

Val Lys Asp Glu Arg Ala Val His Ala Asp Met Gly Tyr Trp Ile Glu
965 970 975

Ser Gln Lys Asn Gly Ser Trp Lys Leu Glu Lys Ala Ser Leu Ile Glu
980 985 990

Val Lys Thr Cys Thr Trp Pro Lys Ser His Thr Leu Trp Ser Asn Gly
995 1000 1005

Val Leu Glu Ser Asp Met Ile Ile Pro Lys Ser Leu Ala Gly Pro
1010 1015 1020

Ile Ser Gln His Asn His Arg Pro Gly Tyr His Thr Gln Thr Ala
1025 1030 1035

Gly Pro Trp His Leu Gly Lys Leu Glu Leu Asp Phe Asn Tyr Cys
1040 1045 1050

Glu Gly Thr Thr Val Val Ile Ser Glu Asn Cys Gly Thr Arg Gly
1055 1060 1065

Pro Ser Leu Arg Thr Thr Thr Val Ser Gly Lys Leu Ile His Glu
1070 1075 1080

Trp Cys Cys Arg Ser Cys Thr Leu Pro Pro Leu Arg Tyr Met Gly
1085 1090 1095

Glu Asp Gly Cys Trp Tyr Gly Met Glu Ile Arg Pro Ile Asn Glu
1100 1105 1110

Lys Glu Glu Asn Met Val Lys Ser Leu Ala Ser Ala Gly Ser Gly
1115 1120 1125

Lys Val Asp Asn Phe Thr Met Gly Val Leu Cys Leu Ala Ile Leu
1130 1135 1140

Phe Glu Glu Val Met Arg Gly Lys Phe Gly Lys Lys His Met Ile
1145 1150 1155

Ala Gly Val Leu Phe Thr Phe Val Leu Leu Leu Ser Gly Gln Ile
1160 1165 1170

Thr Trp Arg Gly Met Ala His Thr Leu Ile Met Ile Gly Ser Asn
1175 1180 1185

Ala Ser Asp Arg Met Gly Met Gly Val Thr Tyr Leu Ala Leu Ile
1190 1195 1200

Ala Thr Phe Lys Ile Gln Pro Phe Leu Ala Leu Gly Phe Phe Leu
1205 1210 1215

Arg Lys Leu Thr Ser Arg Glu Asn Leu Leu Leu Gly Val Gly Leu
1220 1225 1230

Ala Met Ala Ala Thr Leu Arg Leu Pro Glu Asp Ile Glu Gln Met
1235 1240 1245

Ala Asn Gly Ile Ala Leu Gly Leu Met Ala Leu Lys Leu Ile Thr
1250 1255 1260

Gln Phe Glu Thr Tyr Gln Leu Trp Thr Ala Leu Val Ser Leu Thr
1265 1270 1275

Cys Ser Asn Thr Ile Phe Thr Leu Thr Val Ala Trp Arg Thr Ala
1280 1285 1290

Thr Leu Ile Leu Ala Gly Ile Ser Leu Leu Pro Val Cys Gln Ser
1295 1300 1305

```
Ser Ser  Met Arg Lys Thr Asp  Trp Leu Pro Met Thr  Val Ala Ala
    1310                 1315                 1320

Met Gly  Val Pro Pro Leu Pro  Leu Phe Ile Phe Ser  Leu Lys Asp
    1325                 1330                 1335

Thr Leu  Lys Arg Arg Ser Trp  Pro Leu Asn Glu Gly  Val Met Ala
    1340                 1345                 1350

Val Gly  Leu Val Ser Ile Leu  Ala Ser Ser Leu Leu  Arg Asn Asp
    1355                 1360                 1365

Val Pro  Met Ala Gly Pro Leu  Val Ala Gly Gly Leu  Leu Ile Ala
    1370                 1375                 1380

Cys Tyr  Val Ile Thr Gly Thr  Ser Ala Asp Leu Thr  Val Glu Lys
    1385                 1390                 1395

Ala Ala  Asp Val Thr Trp Glu  Glu Glu Ala Glu Gln  Thr Gly Val
    1400                 1405                 1410

Ser His  Asn Leu Met Ile Thr  Val Asp Asp Asp Gly  Thr Met Arg
    1415                 1420                 1425

Ile Lys  Asp Asp Glu Thr Glu  Asn Ile Leu Thr Val  Leu Leu Lys
    1430                 1435                 1440

Thr Ala  Leu Leu Ile Val Ser  Gly Ile Phe Pro Tyr  Ser Ile Pro
    1445                 1450                 1455

Ala Thr  Met Leu Val Trp His  Thr Trp Gln Lys Gln  Thr Gln Arg
    1460                 1465                 1470

Ser Gly  Val Leu Trp Asp Val  Pro Ser Pro Pro Glu  Thr Gln Lys
    1475                 1480                 1485

Ala Glu  Leu Glu Glu Gly Val  Tyr Arg Ile Lys Gln  Gln Gly Ile
    1490                 1495                 1500

Phe Gly  Lys Thr Gln Val Gly  Val Gly Val Gln Lys  Glu Gly Val
    1505                 1510                 1515

Phe His  Thr Met Trp His Val  Thr Arg Gly Ala Val  Leu Thr His
    1520                 1525                 1530

Asn Gly  Lys Arg Leu Glu Pro  Asn Trp Ala Ser Val  Lys Lys Asp
    1535                 1540                 1545

Leu Ile  Ser Tyr Gly Gly Gly  Trp Arg Leu Ser Ala  Gln Trp Gln
    1550                 1555                 1560

Lys Gly  Glu Glu Val Gln Val  Ile Ala Val Glu Pro  Gly Lys Asn
    1565                 1570                 1575

Pro Lys  Asn Phe Gln Thr Met  Pro Gly Ile Phe Gln  Thr Thr Thr
    1580                 1585                 1590

Gly Glu  Ile Gly Ala Ile Ala  Leu Asp Phe Lys Pro  Gly Thr Ser
    1595                 1600                 1605

Gly Ser  Pro Ile Ile Asn Arg  Glu Gly Lys Val Val  Gly Leu Tyr
    1610                 1615                 1620

Gly Asn  Gly Val Val Thr Lys  Asn Gly Gly Tyr Val  Ser Gly Ile
    1625                 1630                 1635

Ala Gln  Thr Asn Ala Glu Pro  Asp Gly Pro Thr Pro  Glu Leu Glu
    1640                 1645                 1650

Glu Glu  Met Phe Lys Lys Arg  Asn Leu Thr Ile Met  Asp Leu His
    1655                 1660                 1665

Pro Gly  Ser Gly Lys Thr Arg  Lys Tyr Leu Pro Ala  Ile Val Arg
    1670                 1675                 1680

Glu Ala  Ile Lys Arg Arg Leu  Arg Thr Leu Ile Leu  Ala Pro Thr
    1685                 1690                 1695

Arg Val  Val Ala Ala Glu Met  Glu Glu Ala Met Lys  Gly Leu Pro
```

-continued

```
    1700                1705                1710

Ile Arg  Tyr Gln Thr Thr Ala  Thr Lys Ser Glu His  Thr Gly Arg
    1715                1720                1725

Glu Ile  Val Asp Leu Met Cys  His Ala Thr Phe Thr  Met Arg Leu
    1730                1735                1740

Leu Ser  Pro Val Arg Val Pro  Asn Tyr Asn Leu Ile  Ile Met Asp
    1745                1750                1755

Glu Ala  His Phe Thr Asp Pro  Ala Ser Ile Ala Ala  Arg Gly Tyr
    1760                1765                1770

Ile Ser  Thr Arg Val Gly Met  Gly Glu Ala Ala Ala  Ile Phe Met
    1775                1780                1785

Thr Ala  Thr Pro Pro Gly Thr  Ala Asp Ala Phe Pro  Gln Ser Asn
    1790                1795                1800

Ala Pro  Ile Gln Asp Glu Glu  Arg Asp Ile Pro Glu  Arg Ser Trp
    1805                1810                1815

Asn Ser  Gly Asn Glu Trp Ile  Thr Asp Phe Val Gly  Lys Thr Val
    1820                1825                1830

Trp Phe  Val Pro Ser Ile Lys  Ala Gly Asn Val Ile  Ala Asn Cys
    1835                1840                1845

Leu Arg  Lys Asn Gly Lys Lys  Val Ile Gln Leu Ser  Arg Lys Thr
    1850                1855                1860

Phe Asp  Thr Glu Tyr Gln Lys  Thr Lys Leu Asn Asp  Trp Asp Phe
    1865                1870                1875

Val Val  Thr Thr Asp Ile Ser  Glu Met Gly Ala Asn  Phe Ile Ala
    1880                1885                1890

Asp Arg  Val Ile Asp Pro Arg  Arg Cys Leu Lys Pro  Val Ile Leu
    1895                1900                1905

Thr Asp  Gly Pro Glu Arg Val  Ile Leu Ala Gly Pro  Met Pro Val
    1910                1915                1920

Thr Val  Ala Ser Ala Ala Gln  Arg Arg Gly Arg Val  Gly Arg Asn
    1925                1930                1935

Pro Gln  Lys Glu Asn Asp Gln  Tyr Ile Phe Met Gly  Gln Pro Leu
    1940                1945                1950

Asn Lys  Asp Glu Asp His Ala  His Trp Thr Glu Ala  Lys Met Leu
    1955                1960                1965

Leu Asp  Asn Ile Asn Thr Pro  Glu Gly Ile Ile Pro  Ala Leu Phe
    1970                1975                1980

Glu Pro  Glu Arg Glu Lys Ser  Ala Ala Ile Asp Gly  Glu Tyr Arg
    1985                1990                1995

Leu Lys  Gly Glu Ser Arg Lys  Thr Phe Val Glu Leu  Met Arg Arg
    2000                2005                2010

Gly Asp  Leu Pro Val Trp Leu  Ala His Lys Val Ala  Ser Glu Gly
    2015                2020                2025

Ile Lys  Tyr Thr Asp Arg Lys  Trp Cys Phe Asp Gly  Glu Arg Asn
    2030                2035                2040

Asn Gln  Ile Leu Glu Glu Asn  Met Asp Val Glu Ile  Trp Thr Lys
    2045                2050                2055

Glu Gly  Glu Lys Lys Lys Leu  Arg Pro Arg Trp Leu  Asp Ala Arg
    2060                2065                2070

Thr Tyr  Ser Asp Pro Leu Ala  Leu Lys Glu Phe Lys  Asp Phe Ala
    2075                2080                2085

Ala Gly  Arg Lys Ser Ile Ala  Leu Asp Leu Val Thr  Glu Ile Gly
    2090                2095                2100
```

```
Arg Val  Pro Ser His Leu Ala  His Arg Thr Arg Asn  Ala Leu Asp
    2105                 2110                 2115

Asn Leu  Val Met Leu His Thr  Ser Glu His Gly Gly  Arg Ala Tyr
    2120                 2125                 2130

Arg His  Ala Val Glu Glu Leu  Pro Glu Thr Met Glu  Thr Leu Leu
    2135                 2140                 2145

Leu Leu  Gly Leu Met Ile Leu  Leu Thr Gly Gly Ala  Met Leu Phe
    2150                 2155                 2160

Leu Ile  Ser Gly Lys Gly Ile  Gly Lys Thr Ser Ile  Gly Leu Ile
    2165                 2170                 2175

Cys Val  Ile Ala Ser Ser Gly  Met Leu Trp Met Ala  Asp Val Pro
    2180                 2185                 2190

Leu Gln  Trp Ile Ala Ser Ala  Ile Val Leu Glu Phe  Phe Met Met
    2195                 2200                 2205

Val Leu  Leu Ile Pro Glu Pro  Glu Lys Gln Arg Thr  Pro Gln Asp
    2210                 2215                 2220

Asn Gln  Leu Ala Tyr Val Val  Ile Gly Ile Leu Thr  Leu Ala Ala
    2225                 2230                 2235

Ile Val  Ala Ala Asn Glu Met  Gly Leu Leu Glu Thr  Thr Lys Arg
    2240                 2245                 2250

Asp Leu  Gly Met Ser Lys Glu  Pro Gly Val Val Ser  Pro Thr Ser
    2255                 2260                 2265

Tyr Leu  Asp Val Asp Leu His  Pro Ala Ser Ala Trp  Thr Leu Tyr
    2270                 2275                 2280

Ala Val  Ala Thr Thr Val Ile  Thr Pro Met Leu Arg  His Thr Ile
    2285                 2290                 2295

Glu Asn  Ser Thr Ala Asn Val  Ser Leu Ala Ala Ile  Ala Asn Gln
    2300                 2305                 2310

Ala Val  Val Leu Met Gly Leu  Asp Lys Gly Trp Pro  Ile Ser Lys
    2315                 2320                 2325

Met Asp  Leu Gly Val Pro Leu  Leu Ala Leu Gly Cys  Tyr Ser Gln
    2330                 2335                 2340

Val Asn  Pro Leu Thr Leu Ile  Ala Ala Val Leu Leu  Leu Val Thr
    2345                 2350                 2355

His Tyr  Ala Ile Ile Gly Pro  Gly Leu Gln Ala Lys  Ala Thr Arg
    2360                 2365                 2370

Glu Ala  Gln Lys Arg Thr Ala  Ala Gly Ile Met Lys  Asn Pro Thr
    2375                 2380                 2385

Val Asp  Gly Ile Met Thr Ile  Asp Leu Asp Pro Val  Ile Tyr Asp
    2390                 2395                 2400

Ser Lys  Phe Glu Lys Gln Leu  Gly Gln Val Met Leu  Leu Val Leu
    2405                 2410                 2415

Cys Ala  Val Gln Leu Leu Leu  Met Arg Thr Ser Trp  Ala Leu Cys
    2420                 2425                 2430

Glu Val  Leu Thr Leu Ala Thr  Gly Pro Ile Thr Thr  Leu Trp Glu
    2435                 2440                 2445

Gly Ser  Pro Gly Lys Phe Trp  Asn Thr Thr Ile Ala  Val Ser Met
    2450                 2455                 2460

Ala Asn  Ile Phe Arg Gly Ser  Tyr Leu Ala Gly Ala  Gly Leu Ala
    2465                 2470                 2475

Leu Ser  Ile Met Lys Ser Val  Gly Thr Gly Lys Arg  Gly Thr Gly
    2480                 2485                 2490
```

Ser Gln Gly Glu Thr Leu Gly Glu Lys Trp Lys Lys Lys Leu Asn
2495 2500 2505

Gln Leu Ser Arg Lys Glu Phe Asp Leu Tyr Lys Lys Ser Gly Ile
2510 2515 2520

Thr Glu Val Asp Arg Thr Glu Ala Lys Glu Gly Leu Lys Arg Gly
2525 2530 2535

Glu Ile Thr His His Ala Val Ser Arg Gly Ser Ala Lys Leu Gln
2540 2545 2550

Trp Phe Val Glu Arg Asn Met Val Ile Pro Glu Gly Arg Val Ile
2555 2560 2565

Asp Leu Gly Cys Gly Arg Gly Gly Trp Ser Tyr Tyr Cys Ala Gly
2570 2575 2580

Leu Lys Lys Val Thr Glu Val Arg Gly Tyr Thr Lys Gly Gly Pro
2585 2590 2595

Gly His Glu Glu Pro Val Pro Met Ser Thr Tyr Gly Trp Asn Ile
2600 2605 2610

Val Lys Leu Met Ser Gly Lys Asp Val Phe Tyr Leu Pro Pro Glu
2615 2620 2625

Lys Cys Asp Thr Leu Leu Cys Asp Ile Gly Glu Ser Ser Pro Ser
2630 2635 2640

Pro Thr Val Glu Glu Ser Arg Thr Ile Arg Val Leu Lys Met Val
2645 2650 2655

Glu Pro Trp Leu Lys Asn Asn Gln Phe Cys Ile Lys Val Leu Asn
2660 2665 2670

Pro Tyr Met Pro Thr Val Ile Glu His Leu Glu Arg Leu Gln Arg
2675 2680 2685

Lys His Gly Gly Met Leu Val Arg Asn Pro Leu Ser Arg Asn Ser
2690 2695 2700

Thr His Glu Met Tyr Trp Ile Ser Asn Gly Thr Gly Asn Ile Val
2705 2710 2715

Ser Ser Val Asn Met Val Ser Arg Leu Leu Leu Asn Arg Phe Thr
2720 2725 2730

Met Thr His Arg Arg Pro Thr Ile Glu Lys Asp Val Asp Leu Gly
2735 2740 2745

Ala Gly Thr Arg His Val Asn Ala Glu Pro Glu Thr Pro Asn Met
2750 2755 2760

Asp Val Ile Gly Glu Arg Ile Lys Arg Ile Lys Glu Glu His Ser
2765 2770 2775

Ser Thr Trp His Tyr Asp Asp Glu Asn Pro Tyr Lys Thr Trp Ala
2780 2785 2790

Tyr His Gly Ser Tyr Glu Val Lys Ala Thr Gly Ser Ala Ser Ser
2795 2800 2805

Met Ile Asn Gly Val Val Lys Leu Leu Thr Lys Pro Trp Asp Val
2810 2815 2820

Val Pro Met Val Thr Gln Met Ala Met Thr Asp Thr Thr Pro Phe
2825 2830 2835

Gly Gln Gln Arg Val Phe Lys Glu Lys Val Asp Thr Arg Thr Pro
2840 2845 2850

Arg Pro Met Pro Gly Thr Arg Lys Val Met Glu Ile Thr Ala Glu
2855 2860 2865

Trp Leu Trp Arg Thr Leu Gly Arg Asn Lys Arg Pro Arg Leu Cys
2870 2875 2880

Thr Arg Glu Glu Phe Thr Lys Lys Val Arg Thr Asn Ala Ala Met

```
    2885                2890                2895

Gly Ala  Val Phe Thr Glu Glu  Asn Gln Trp Asp Ser  Ala Arg Ala
    2900                2905                2910

Ala Val  Glu Asp Glu Glu Phe  Trp Lys Leu Val Asp  Arg Glu Arg
    2915                2920                2925

Glu Leu  His Lys Leu Gly Lys  Cys Gly Ser Cys Val  Tyr Asn Met
    2930                2935                2940

Met Gly  Lys Arg Glu Lys Lys  Leu Gly Glu Phe Gly  Lys Ala Lys
    2945                2950                2955

Gly Ser  Arg Ala Ile Trp Tyr  Met Trp Leu Gly Ala  Arg Tyr Leu
    2960                2965                2970

Glu Phe  Glu Ala Leu Gly Phe  Leu Asn Glu Asp His  Trp Phe Ser
    2975                2980                2985

Arg Glu  Asn Ser Tyr Ser Gly  Val Glu Gly Glu Gly  Leu His Lys
    2990                2995                3000

Leu Gly  Tyr Ile Leu Arg Asp  Ile Ser Lys Ile Pro  Gly Gly Ala
    3005                3010                3015

Met Tyr  Ala Asp Asp Thr Ala  Gly Trp Asp Thr Arg  Ile Thr Glu
    3020                3025                3030

Asp Asp  Leu His Asn Glu Glu  Lys Ile Thr Gln Gln  Met Asp Pro
    3035                3040                3045

Glu His  Arg Gln Leu Ala Asn  Ala Ile Phe Lys Leu  Thr Tyr Gln
    3050                3055                3060

Asn Lys  Val Val Lys Val Gln  Arg Pro Thr Pro Lys  Gly Thr Val
    3065                3070                3075

Met Asp  Ile Ile Ser Arg Lys  Asp Gln Arg Gly Ser  Gly Gln Val
    3080                3085                3090

Gly Thr  Tyr Gly Leu Asn Thr  Phe Thr Asn Met Glu  Ala Gln Leu
    3095                3100                3105

Ile Arg  Gln Met Glu Gly Glu  Gly Val Leu Ser Lys  Ala Asp Leu
    3110                3115                3120

Glu Asn  Pro His Pro Leu Glu  Lys Lys Ile Thr Gln  Trp Leu Glu
    3125                3130                3135

Thr Lys  Gly Val Glu Arg Leu  Lys Arg Met Ala Ile  Ser Gly Asp
    3140                3145                3150

Asp Cys  Val Val Lys Pro Ile  Asp Asp Arg Phe Ala  Asn Ala Leu
    3155                3160                3165

Leu Ala  Leu Asn Asp Met Gly  Lys Val Arg Lys Asp  Ile Pro Gln
    3170                3175                3180

Trp Gln  Pro Ser Lys Gly Trp  His Asp Trp Gln Gln  Val Pro Phe
    3185                3190                3195

Cys Ser  His His Phe His Glu  Leu Ile Met Lys Asp  Gly Arg Lys
    3200                3205                3210

Leu Val  Val Pro Cys Arg Pro  Gln Asp Glu Leu Ile  Gly Arg Ala
    3215                3220                3225

Arg Ile  Ser Gln Gly Ala Gly  Trp Ser Leu Arg Glu  Thr Ala Cys
    3230                3235                3240

Leu Gly  Lys Ala Tyr Ala Gln  Met Trp Thr Leu Met  Tyr Phe His
    3245                3250                3255

Arg Arg  Asp Leu Arg Leu Ala  Ser Asn Ala Ile Cys  Ser Ala Val
    3260                3265                3270

Pro Val  His Trp Val Pro Thr  Ser Arg Thr Thr Trp  Ser Ile His
    3275                3280                3285
```

```
Ala His His Gln Trp Met Thr Thr Glu Asp Met Leu Thr Val Trp
    3290                3295                3300

Asn Arg Val Trp Ile Glu Asp Asn Pro Trp Met Glu Asp Lys Thr
    3305                3310                3315

Pro Val Thr Thr Trp Glu Asp Val Pro Tyr Leu Gly Lys Arg Glu
    3320                3325                3330

Asp Gln Trp Cys Gly Ser Leu Ile Gly Leu Thr Ser Arg Ala Thr
    3335                3340                3345

Trp Ala Gln Asn Ile Leu Thr Ala Ile Gln Gln Val Arg Ser Leu
    3350                3355                3360

Ile Gly Asn Glu Glu Phe Leu Asp Tyr Met Pro Ser Met Lys Arg
    3365                3370                3375

Phe Arg Lys Glu Glu Glu Ser Glu Gly Ala Ile Trp
    3380                3385                3390
```

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide

<400> SEQUENCE: 23
cagttccaaa ccggaagctt g 21

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide

<400> SEQUENCE: 24
ccaacgagct atcgtacgtt ctctggg 27

<210> SEQ ID NO 25
<211> LENGTH: 27
<212> TYPE: DNA
<213> ORGANISM: Artificial Sequence
<220> FEATURE:
<223> OTHER INFORMATION: Oligonucleotide

<400> SEQUENCE: 25
gattgtgacc atggcggccc atctttg 27

<210> SEQ ID NO 26
<211> LENGTH: 31
<212> TYPE: DNA
<213> ORGANISM: Artificial Sequence
<220> FEATURE:
<223> OTHER INFORMATION: Oligonucleotide

<400> SEQUENCE: 26
ggagattagg ccgctgagcg gtaaagaaga g 31

<210> SEQ ID NO 27
<211> LENGTH: 26
<212> TYPE: DNA
<213> ORGANISM: Artificial Sequence
<220> FEATURE:
<223> OTHER INFORMATION: Oligonucleotide

<400> SEQUENCE: 27
gtttgtggaa aaatgtctga ggagaa 26

<210> SEQ ID NO 28
<211> LENGTH: 27
<212> TYPE: DNA
<213> ORGANISM: Artificial Sequence
<220> FEATURE:
<223> OTHER INFORMATION: Oligonucleotide

<400> SEQUENCE: 28
ctaggaaaca cataatatta gttgtgg 27

<210> SEQ ID NO 29
<211> LENGTH: 27
<212> TYPE: DNA
<213> ORGANISM: Artificial Sequence
<220> FEATURE:
<223> OTHER INFORMATION: Oligonucleotide

<400> SEQUENCE: 29
cagatccacc taaccataat ggcagtg 27

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide

<400> SEQUENCE: 30
ggaaactcac ctcgggagag acagc 25

<210> SEQ ID NO 31
<211> LENGTH: 26
<212> TYPE: DNA
<213> ORGANISM: Artificial Sequence
<220> FEATURE:
<223> OTHER INFORMATION: Oligonucleotide

<400> SEQUENCE: 31
ttgggtagag gtcaccgcac tcatcc 26

<210> SEQ ID NO 32
<211> LENGTH: 25
<212> TYPE: DNA
<213> ORGANISM: Artificial Sequence
<220> FEATURE:
<223> OTHER INFORMATION: Oligonucleotide

<400> SEQUENCE: 32
gtagaaatag ccgctctcat cctag 25

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide

<400> SEQUENCE: 33
ggcggcttac gtaatgggag gtagctcagc 30

<210> SEQ ID NO 34
<211> LENGTH: 27
<212> TYPE: DNA

<213> ORGANISM: Artificial Sequence
<220> FEATURE:
<223> OTHER INFORMATION: Oligonucleotide

<400> SEQUENCE: 34
ctagagaagg cagcttctgt gcagtgg 27

<210> SEQ ID NO 35
<211> LENGTH: 25
<212> TYPE: DNA
<213> ORGANISM: Artificial Sequence
<220> FEATURE:
<223> OTHER INFORMATION: Oligonucleotide

<400> SEQUENCE: 35
ccttggccat tccagcaaca atgac 25

<210> SEQ ID NO 36
<211> LENGTH: 26
<212> TYPE: DNA
<213> ORGANISM: Artificial Sequence
<220> FEATURE:
<223> OTHER INFORMATION: Oligonucleotide

<400> SEQUENCE: 36
gacgttcaaa ttttagccat agaacc 26

<210> SEQ ID NO 37
<211> LENGTH: 27
<212> TYPE: DNA
<213> ORGANISM: Artificial Sequence
<220> FEATURE:
<223> OTHER INFORMATION: Oligonucleotide

<400> SEQUENCE: 37
ctggagaaac gggcgccgta acattag 27

<210> SEQ ID NO 38
<211> LENGTH: 27
<212> TYPE: DNA
<213> ORGANISM: Artificial Sequence
<220> FEATURE:
<223> OTHER INFORMATION: Oligonucleotide

<400> SEQUENCE: 38
gaaattggat cggtaacctt agatttc 27

<210> SEQ ID NO 39
<211> LENGTH: 27
<212> TYPE: DNA
<213> ORGANISM: Artificial Sequence
<220> FEATURE:
<223> OTHER INFORMATION: Oligonucleotide

<400> SEQUENCE: 39
ggagcagtaa cgtttgattt caaaccc 27

<210> SEQ ID NO 40
<211> LENGTH: 24
<212> TYPE: DNA
<213> ORGANISM: Artificial Sequence
<220> FEATURE:
<223> OTHER INFORMATION: Oligonucleotide

<400> SEQUENCE: 40
gttaccaaac ctggggatta cgtc 24

<210> SEQ ID NO 41
<211> LENGTH: 25
<212> TYPE: DNA
<213> ORGANISM: Artificial Sequence
<220> FEATURE:
<223> OTHER INFORMATION: Oligonucleotide

<400> SEQUENCE: 41
gattaactat catgaactta caccc 25

<210> SEQ ID NO 42
<211> LENGTH: 25
<212> TYPE: DNA
<213> ORGANISM: Artificial Sequence
<220> FEATURE:
<223> OTHER INFORMATION: Oligonucleotide

<400> SEQUENCE: 42
ggaaaacctt tggcaccgag tatcc 25

<210> SEQ ID NO 43
<211> LENGTH: 26
<212> TYPE: DNA
<213> ORGANISM: Artificial Sequence
<220> FEATURE:
<223> OTHER INFORMATION: Oligonucleotide

<400> SEQUENCE: 43
tccagtgata ccggctagcg ctgctc 26

<210> SEQ ID NO 44
<211> LENGTH: 23
<212> TYPE: DNA
<213> ORGANISM: Artificial Sequence
<220> FEATURE:
<223> OTHER INFORMATION: Oligonucleotide

<400> SEQUENCE: 44
gcctcagagg tggccaaagg aag 23

<210> SEQ ID NO 45
<211> LENGTH: 26
<212> TYPE: DNA
<213> ORGANISM: Artificial Sequence
<220> FEATURE:
<223> OTHER INFORMATION: Oligonucleotide

<400> SEQUENCE: 45
acatggaggc agagatctgg actaga 26

<210> SEQ ID NO 46
<211> LENGTH: 23
<212> TYPE: DNA
<213> ORGANISM: Artificial Sequence
<220> FEATURE:
<223> OTHER INFORMATION: Oligonucleotide

<400> SEQUENCE: 46
aaagcatggc caaggatgct gtc 23

<210> SEQ ID NO 47
<211> LENGTH: 28
<212> TYPE: DNA
<213> ORGANISM: Artificial Sequence
<220> FEATURE:

<223> OTHER INFORMATION: Oligonucleotide

<400> SEQUENCE: 47
gcataatgga cgctaagcat gactaagg 28

<210> SEQ ID NO 48
<211> LENGTH: 26
<212> TYPE: DNA
<213> ORGANISM: Artificial Sequence
<220> FEATURE:
<223> OTHER INFORMATION: Oligonucleotide

<400> SEQUENCE: 48
ttattgcata gtgcacgaaa agcatg 26

<210> SEQ ID NO 49
<211> LENGTH: 23
<212> TYPE: DNA
<213> ORGANISM: Artificial Sequence
<220> FEATURE:
<223> OTHER INFORMATION: Oligonucleotide

<400> SEQUENCE: 49
gggcctatta ttacgtaatg gac 23

<210> SEQ ID NO 50
<211> LENGTH: 24
<212> TYPE: DNA
<213> ORGANISM: Artificial Sequence
<220> FEATURE:
<223> OTHER INFORMATION: Oligonucleotide

<400> SEQUENCE: 50
ctgcaatcct ggtgatatta ttgc 24

<210> SEQ ID NO 51
<211> LENGTH: 23
<212> TYPE: DNA
<213> ORGANISM: Artificial Sequence
<220> FEATURE:
<223> OTHER INFORMATION: Oligonucleotide

<400> SEQUENCE: 51
ctcataaaga acgttcaaac cct 23

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide

<400> SEQUENCE: 52
cattagacag acgcgagttt gaag 24

<210> SEQ ID NO 53
<211> LENGTH: 27
<212> TYPE: DNA
<213> ORGANISM: Artificial Sequence
<220> FEATURE:
<223> OTHER INFORMATION: Oligonucleotide

<400> SEQUENCE: 53
tggcgacgct caagatagtg actgaag 27

<210> SEQ ID NO 54
<211> LENGTH: 25
<212> TYPE: DNA
<213> ORGANISM: Artificial Sequence
<220> FEATURE:
<223> OTHER INFORMATION: Oligonucleotide

<400> SEQUENCE: 54
gagtcatcat cgataccaac aatag 25

<210> SEQ ID NO 55
<211> LENGTH: 27
<212> TYPE: DNA
<213> ORGANISM: Artificial Sequence
<220> FEATURE:
<223> OTHER INFORMATION: Oligonucleotide

<400> SEQUENCE: 55
cttcaaaacc tggcttctgc atcaaag 27

<210> SEQ ID NO 56
<211> LENGTH: 28
<212> TYPE: DNA
<213> ORGANISM: Artificial Sequence
<220> FEATURE:
<223> OTHER INFORMATION: Oligonucleotide

<400> SEQUENCE: 56
caaagatgtt gagcaacagg ttcacaac 28

<210> SEQ ID NO 57
<211> LENGTH: 27
<212> TYPE: DNA
<213> ORGANISM: Artificial Sequence
<220> FEATURE:
<223> OTHER INFORMATION: Oligonucleotide

<400> SEQUENCE: 57
ggaaagaaga aacacccgag actgtgc 27

<210> SEQ ID NO 58
<211> LENGTH: 25
<212> TYPE: DNA
<213> ORGANISM: Artificial Sequence
<220> FEATURE:
<223> OTHER INFORMATION: Oligonucleotide

<400> SEQUENCE: 58
gggaactggt cgatcgagaa agggc 25

<210> SEQ ID NO 59
<211> LENGTH: 28
<212> TYPE: DNA
<213> ORGANISM: Artificial Sequence
<220> FEATURE:
<223> OTHER INFORMATION: Oligonucleotide

<400> SEQUENCE: 59
ccagtggatt actacagaag atatgctc 28

<210> SEQ ID NO 60
<211> LENGTH: 29
<212> TYPE: DNA
<213> ORGANISM: Artificial Sequence
<220> FEATURE:
<223> OTHER INFORMATION: Oligonucleotide

<400> SEQUENCE: 60
caggaacctg accggtaaag aggaatacg 29

<210> SEQ ID NO 61
<211> LENGTH: 28
<212> TYPE: DNA
<213> ORGANISM: Artificial Sequence
<220> FEATURE:
<223> OTHER INFORMATION: Oligonucleotide

<400> SEQUENCE: 61
ctgtaattac caacatcaaa caccaaag 28

<210> SEQ ID NO 62
<211> LENGTH: 26
<212> TYPE: DNA
<213> ORGANISM: Artificial Sequence
<220> FEATURE:
<223> OTHER INFORMATION: Oligonucleotide

<400> SEQUENCE: 62
ccaacaacaa ccaccaaagg ctattg 26

<210> SEQ ID NO 63
<211> LENGTH: 25
<212> TYPE: DNA
<213> ORGANISM: Artificial Sequence
<220> FEATURE:
<223> OTHER INFORMATION: Oligonucleotide

<400> SEQUENCE: 63
ggattggtgt tgtcgatcca acagg 25

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
ctggtggaag cccaacacaa aaac 24

<210> SEQ ID NO 65
<211> LENGTH: 45
<212> TYPE: DNA
<213> ORGANISM: Artificial Sequence
<220> FEATURE:
<223> OTHER INFORMATION: Primer

<400> SEQUENCE: 65
ctggtggaag gaagagagaa attggcaact ccccaacaca aaaac 45

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
agaccccccc aagcatattg ac 22

<210> SEQ ID NO 67
<211> LENGTH: 39

-continued

```
<212> TYPE: DNA
<213> ORGANISM: Artificial Sequence
<220> FEATURE:
<223> OTHER INFORMATION: Primer

<400> SEQUENCE: 67

agaccccccc aatatttcct cctcctatag catattgac                             39


<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68

cccaacacaa agcatattga c                                                21


<210> SEQ ID NO 69
<211> LENGTH: 6
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(6)
<223> OTHER INFORMATION: n = A,T,C or G

<400> SEQUENCE: 69

gcagcn                                                                  6


<210> SEQ ID NO 70
<211> LENGTH: 5
<212> TYPE: DNA
<213> ORGANISM: Artificial Sequence
<220> FEATURE:
<223> OTHER INFORMATION: Oligonucleotide

<400> SEQUENCE: 70

gcagc                                                                   5
```

DEVELOPMENT OF MUTATIONS USEFUL FOR ATTENUATING DENGUE VIRUSES AND CHIMERIC DENGUE VIRUSES

RELATED APPLICATIONS

This application is a divisional of U.S. patent application Ser. No. 14/096,424, filed Dec. 4, 2013, which is a divisional of U.S. application Ser. No. 13/240,849, filed Sep. 22, 2011, now U.S. Pat. No. 8,632,782, which is a divisional of U.S. application Ser. No. 12/396,376, filed Mar. 2, 2009, now U.S. Pat. No. 8,039,003, which is a continuation of U.S. application Ser. No. 11/446,050, filed Jun. 2, 2006, now U.S. Pat. No. 7,560,118, which is a divisional of U.S. application Ser. No. 10/719,547, filed Nov. 21, 2003, now U.S. Pat. No. 7,226,602, which is a continuation and claims the benefit of priority of International Application No. PCT/US02/16308 filed May 22, 2002, designating the United States of America and published in English as WO 02/095075 on Nov. 28, 2002, which claims the benefit of priority of U.S. Provisional Application No. 60/293,049 filed May 22, 2001, all of which are hereby expressly incorporated by reference in their entireties.

FIELD OF THE INVENTION

A menu of mutations was developed that is useful in fine-tuning the attenuation and growth characteristics of dengue virus vaccines.

BACKGROUND OF THE INVENTION

Dengue virus is a positive-sense RNA virus belonging to the *Flavivirus* genus of the family Flaviviridae. Dengue virus is widely distributed throughout the tropical and semi-tropical regions of the world and is transmitted to humans by mosquito vectors. Dengue virus is a leading cause of hospitalization and death in children in at least eight tropical Asian countries (WHO, 1997. *Dengue haemorrhagic fever: diagnosis, treatment prevention and control*—2nd ed. Geneva: WHO). There are four serotypes of dengue virus (DEN-1, DEN-2, DEN-3, and DEN-4) which annually cause an estimated 50-100 million cases of dengue fever and 500,000 cases of the more severe form of dengue virus infection, dengue hemorrhagic fever/dengue shock syndrome (DHF/DSS) (Gubler, D. J. & Meltzer, M. 1999 *Adv Virus Res* 53:35-70). DHF/DSS is seen predominately in children and adults experiencing a second dengue virus infection with a serotype different than that of their first dengue virus infection and in primary infection of infants who still have circulating dengue-specific maternal antibody (Burke, D. S. et al. 1988 *Am J Trop Med Hyg* 38:172-80; Halstead, S. B. et al. 1969 *Am J Trop Med Hyg* 18:997-1021; Thein, S. et al. 1997 *Am J Trop Med Hyg* 56:566-72). A vaccine is needed to lessen the disease burden caused by dengue virus, but none is licensed. Because of the association of more severe disease with secondary dengue virus infection, a successful vaccine must induce immunity to all four serotypes. Immunity is primarily mediated by neutralizing antibody directed against the envelope E glycoprotein, a virion structural protein. Infection with one serotype induces long-lived homotypic immunity and a short-lived heterotypic immunity (Sabin, A. 1955 *Amer J Trop Med Hyg* 4:198-207). Therefore, the goal of immunization is to induce a long-lived neutralizing antibody response against DEN-1, DEN-2, DEN-3, and DEN-4, which can best be achieved economically using live attenuated virus vaccines. This is a reasonable goal since a live attenuated vaccine has already been developed for the related yellow fever virus, another mosquito-borne flavivirus present in tropical and semitropical regions of the world (Monath, T. P. & Heinz, F. X. 1996 in: Fields B. N. et al. eds. *Fields Virology* Philadelphia: Lippincott-Ravan Publishers, 961-1034).

Several live attenuated dengue vaccine candidates have been developed and evaluated in humans or non-human primates. The first live attenuated dengue vaccine candidates were host range mutants developed by serial passage of wild type dengue viruses in the brains of mice and selection of mutants attenuated for humans (Kimura, R. & Hotta, S. 1944 *Japanese J Bacteriology* 1:96-99; Sabin, A. B. & Schlesinger, R. W. 1945 *Science* 101:640; Wisseman, C. L. Jr. et al. 1963 *Am J Trop Med* 12:620-623). Although these candidate vaccine viruses were immunogenic in humans, their poor growth in cell culture discouraged further development. Additional live attenuated DEN-1, DEN-2, DEN-3, and DEN-4 vaccine candidates have been developed by serial passage in tissue culture (Angsubhakom, S. et al. 1994 *Southeast Asian J Trop Med Public Health* 25:554-9; Bancroft, W. H. et al. 1981 *Infect Immun* 31:698-703; Bhamarapravati, N. et al. 1987 *Bull World Health Organ* 65:189-95; Eckels, K. H. et al. 1984 *Am J Trop Med Hyg* 33:684-9; Hoke, C. H. Jr. et al. 1990 *Am J Trop Med Hyg* 43:219-26; Kanesa-thasan, N. et al. 2001 *Vaccine* 19:3179-88) or by chemical mutagenesis (McKee, K. T. Jr. et al. 1987 *Am J Trop Med Hyg* 36:435-42). It has proven very difficult to achieve a satisfactory balance between attenuation and immunogenicity for each of the four serotypes of dengue virus using these approaches and to formulate a tetravalent vaccine that is safe and satisfactorily immunogenic against each of the four dengue viruses (Kanesa-thasan, N. et al. 2001 *Vaccine* 19:3179-88; Bhamarapravati, N. & Sutee, Y. 2000 *Vaccine* 18 Suppl 2: 44-7).

Two major advances utilizing recombinant DNA technology have recently made it possible to develop additional promising live attenuated dengue virus vaccine candidates. First, methods have been developed to recover infectious dengue virus from cells transfected with RNA transcripts derived from a full-length cDNA clone of the dengue virus genome, thus making it possible to derive infectious viruses bearing attenuating mutations which have been introduced into the cDNA clone by site-directed mutagenesis (Lai, C. J. et al. 1991 *PNAS USA* 88: 10342-6; Chen, W. et al. 1995 *J Virol* 69:5186-90; Huang, C. Y. et al. 2000 *J Virol* 74:3020-8; Pletnev, A. G. & Men, R. 1998 *PNAS USA* 95:1746-51). These techniques have been used to construct intertypic chimeric dengue viruses which have been shown to be effective in protecting monkeys against homologous dengue virus challenge (Bray, M. et al. 1996 *J Virol* 70:4162-6). Despite these advances, there is a need to develop attenuated antigenic dengue virus vaccines that specify a satisfactory balance between attenuation and immunogenicity for humans.

SUMMARY OF THE INVENTION

The invention provides mutations that confer temperature sensitivity in Vero cells or human liver cells, host-cell restriction in mosquito or human liver cells, host-cell adaptation for improved replication in Vero cells, or attenuation in mice, which mutations are useful in fine tuning the attenuation and growth characteristics of dengue virus vaccines.

BRIEF DESCRIPTION OF THE DRAWINGS

FIGS. 4A and 4B show generation of recombinant DEN4 viruses. In FIG. 4A, the p4 cDNA clone is represented which was constructed from the 2A cDNA clone (derived from DEN4 814669) by site-directed mutagenesis. Restriction enzyme sites were introduced or removed to facilitate subsequent cloning of DEN4 recombinants bearing introduced attenuating mutations. Restriction enzyme sites are shown and define fragments of the genome that were sub-cloned into modified pUC-119 vectors for site-directed mutagenesis to introduce mutations identified in the 5-FU mutant viruses. FIG. 4B is an outline of the methods used to generate rDEN4 viruses and is also represented and described in Example 1.

FIG. 5 shows amino acid sequence of the rDEN4 NS5 gene (SEQ ID NO: 1). Eighty underlined amino acid pairs were mutagenized to alanine pairs; 32 pairs in boldface represent mutant viruses that could not be recovered in either Vero or C6/36 cells; pairs in normal type represent mutant viruses that could be recovered in either Vero or C6/36 cells. Boxed regions indicate putative functional domains, including an S-adenosylmethionine utilizing methyltransferase domain (SAM), an importin-β binding domain adjacent to a nuclear localization sequence (importin-β-binding+NLS) and an RNA-dependent RNA polymerase domain (Polymerase).

BRIEF DESCRIPTION OF THE TABLES

Figures 1A, 1B:
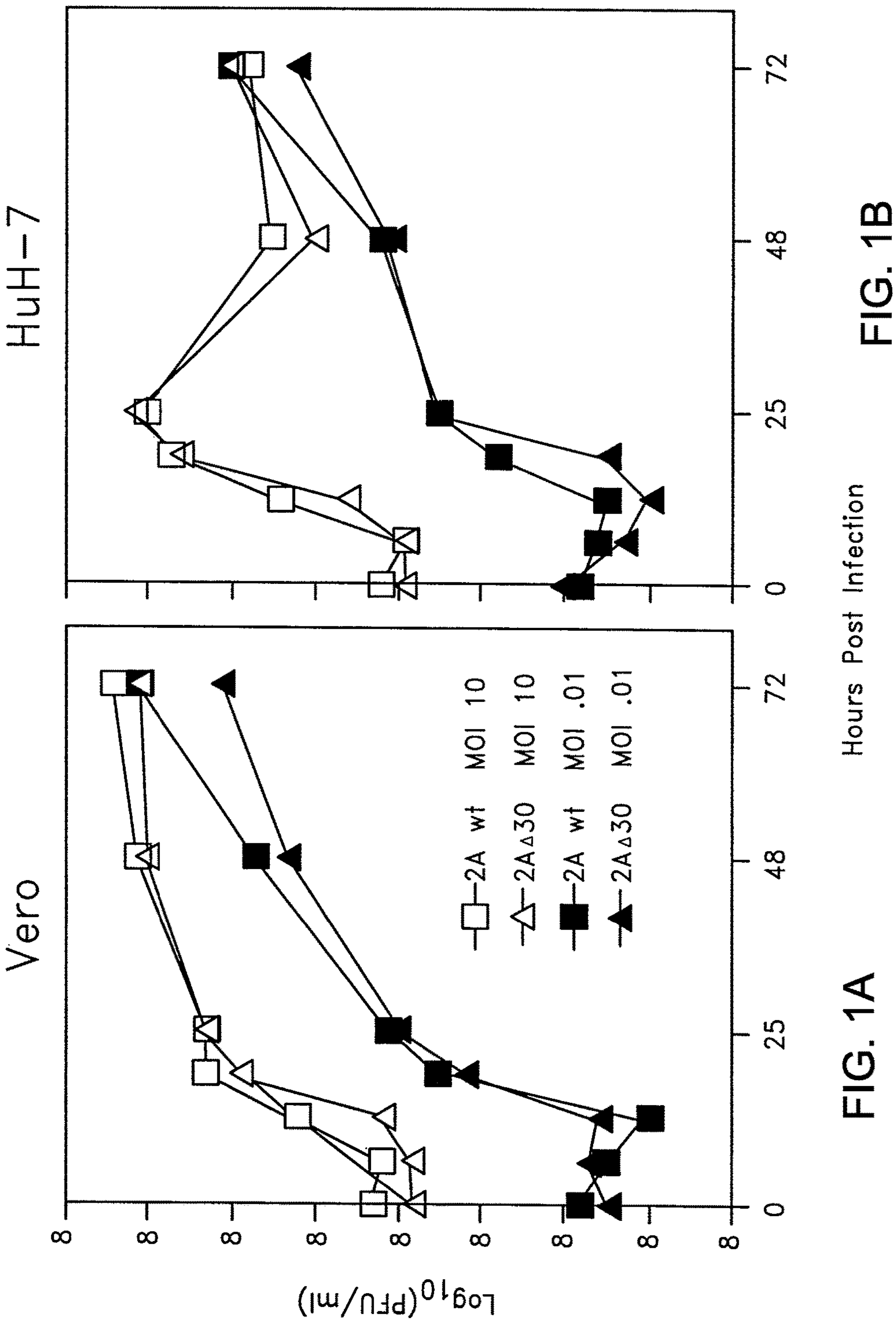
FIGS. 1A and 1B show growth of wt DEN4 2A and vaccine candidate, 2AΔ30, in Vero and HuH-7 cells. Vero (FIG. 1A) or HuH-7 (FIG. 1B) cells were infected with DEN4 2A or 2AΔ30 at a multiplicity of infection (MOI) of 10 or 0.01. Confluent cell monolayers in 25-mm tissue culture flasks were washed and overlaid with a 1.5 ml inoculum containing the indicated virus. After a two hour incubation at 37° C., cells were washed three times in PBS and 7 ml of culture media supplemented with 2% FBS was added. A 1 ml aliquot of tissue culture medium was removed, replaced with fresh medium, and designated the 0 hour time-point. At the indicated time points post-infection, samples of tissue culture media were removed and frozen at −70° C. The level of viral replication was assayed by plaque titration in Vero cells. Briefly, serial ten-fold dilutions of cell culture media samples were inoculated onto confluent Vero cell monolayers in 24-well plates in duplicate and overlaid with Opti-MEM containing 0.8% methylcellulose. After five days, plaques were visualized by immunoperoxidase staining as described in Example 1.

Table 1. Susceptibility of mice to intracerebral DEN4 infection is age-dependent.

Table 2. Temperature-sensitive (ts) and mouse brain attenuation (att) phenotypes of 5-FU mutant DEN4 viruses.

Table 3. Nucleotide and amino acid differences of the 5-FU mutant viruses which are ts in both Vero and HuH-7 cells.

Table 4. Nucleotide and amino acid differences of the 5-FU mutant viruses which are ts in only HuH-7 cells.

Table 5. Mutations which are represented in multiple 5-FU mutant DEN4 viruses.

Table 6. Addition of ts mutation 4995 to rDEN4Δ30 confers a ts phenotype and further attenuates its replication in suckling mouse brain.

Table 7. Temperature-sensitive (ts) and mouse brain attenuation (raft) phenotypes of 5-FU DEN4 mutant viruses which exhibit a small plaque (sp) phenotype.

Table 8. Viruses with both ts and sp phenotypes are more restricted in replication in mouse brain than those with only a ts phenotype.

Table 9. Nucleotide and amino acid differences of the 5-FU mutant DEN4 viruses which produce small plaques in both Vero and HuH-7 cells.

Table 10. Nucleotide and amino acid differences of the 5-FU mutant DEN4 viruses which produce small plaques in only HuH-7 cells.

Table 11. Putative Vero cell adaptation mutations derived from the full set of 5-FU mutant viruses.

Table 12. Mutagenic oligonucleotides used to generate recombinant DEN4 viruses containing single 5-FU mutations.

Table 13, sp, ts and mouse attenuation phenotypes of rDEN4 mutant viruses encoding single mutations identified in six sp 5-FU mutant viruses.

Table 14. Phenotypes of rDEN4 mutant viruses encoding single mutations identified in 10 5-FU mutant viruses that are ts in both Vero and HuH-7 cells.

Table 15. sp, ts and mouse attenuation phenotypes of rDEN4 mutant viruses encoding single mutations identified in 3 HuH-7 cell-specific ts 5-FU mutant viruses.

Table 16. Temperature-sensitive (ts) and mouse brain attenuation (att) phenotypes of additional rDEN4 viruses encoding single 5-FU mutations.

Table 17. Growth of wt DEN-4 2A-13 in SCID mice transplanted with HuH-7 cells.

Table 18. Combination of ts mutations, NS3 4995 and NS5 7849, in rDEN4 results in an additive ts phenotype.

Table 19. The 5-FU mutations are compatible with the Δ30 mutation for replication in the brain of suckling mice.

Table 20. Temperature-sensitive and mouse brain attenuation phenotypes of viruses bearing charge-cluster-to-alanine mutations in the NS5 gene of DEN4.

Table 21. SCID-HuH-7 attenuation phenotypes of viruses bearing charge-cluster-to-alanine mutations in the NS5 gene of DEN4.

Table 22. Combination of paired charge-cluster-to-alanine mutations into double-pair mutant viruses.

Table 23. Temperature-sensitive and mouse brain attenuation phenotypes of double charge-cluster-to-alanine mutants of the NS5 gene of rDEN4.

Table 24. SCID-HuH-7 attenuation phenotypes of double charge-cluster-to-alanine mutants of the NS5 gene of rDEN4.

Table 25. Phenotypes (temperature sensitivity, plaque size and replication in mouse brain and SCID-HuH-7 mice) of wt DEN4 and viruses containing the Δ30 and 7129 mutations.

Table 26. The 5-fluorouracil 5-1A1 small plaque mutant demonstrates a restriction of midgut infection following oral infection of *Aedes aegypti* mosquitoes.

Table 27. The 5-fluorouracil 5-1A1 small plaque mutant demonstrates a restriction of infection following intrathoracic inoculation of *Toxorhynchites splendens* mosquitoes.

Table 28. Mutagenesis primers for the deletion or swap of sequences in DEN4 showing conserved differences from tick-borne flaviviruses.

Table 29. Virus titer and plaque size of 3' UTR mutant viruses in Vero and C6/36 cells.

Table 30. Infectivity of wt DEN4 and 3' UTR mutants for *Toxorhynchites splendens* via intrathoracic inoculation.

Table 31. Infectivity of 3' UTR swap mutant viruses for *Aedes aegypti* fed on an infectious bloodmeal.

Table 32. Putative Vero cell adaptation mutations derived from the set of 5-FU mutant viruses and other DEN4 viruses passaged in Vero cells.

Table 33. Sequence analysis of rDEN2/4Δ30 clone 27(p4)-2-2A2.

Table 34. Sequence analysis of rDEN2/4Δ30 clone 27(p3)-2-1A1.

Table 35. Recombinant virus rDEN2/4Δ30 bearing Vero adaptation mutations can be recovery and titered on Vero cells.

Table 36. Putative Vero cell adaptation mutations of dengue type 4 virus and the corresponding wildtype amino acid residue in other dengue viruses.

Table 37. Mutations known to attenuate dengue type 4 virus and the corresponding wildtype amino acid residue in other dengue virus.

BRIEF DESCRIPTION OF THE APPENDICES

Appendix 1. Sequence of recombinant dengue type 4 virus strain 2A (amino acid sequence SEQ ID NO: 13 and nucleotide sequence SEQ ID NO: 14).

Appendix 2. Sequence of recombinant dengue type 4 virus strain rDEN4 (amino acid sequence SEQ ID NO: 15 and nucleotide sequence SEQ ID NO: 16).

Appendix 3. Sequence of recombinant dengue type 2 chimeric virus strain rDEN2/4Δ30 (amino acid sequence SEQ ID NO: 17 and nucleotide sequence SEQ ID NO: 18).

Appendix 4. Alignment of dengue virus polyproteins. DEN4 (SEQ ID NO: 19); DEN1-WP (SEQ ID NO: 20); DEN2-NGC (SEQ ID NO: 21); DEN3-H87 (SEQ ID NO: 22).

The Sequence Listing is submitted as an ASCII text file in the form of the file named Sequence_Listing.txt, which was created on Jul. 11, 2017, and is 273,594 bytes, which is incorporated by reference herein.

DETAILED DESCRIPTION OF THE PREFERRED EMBODIMENT

To assemble a collection of useful mutations for incorporation in recombinant live dengue virus vaccines, site-directed and random mutagenesis techniques were used to introduce mutations into the dengue virus genome. The resulting mutant viruses were screened for several valuable phenotypes, including temperature sensitivity in Vero cells or human liver cells, host cell restriction in mosquito cells or human liver cells, host-cell adaptation for improved replication in Vero cells, and attenuation in mice. The genetic basis for each observed phenotype was determined by direct sequence analysis of the virus genome. Mutations identified through these sequencing efforts have been further evaluated by their re-introduction, singly, or in combination, into recombinant dengue virus and characterization of the resulting phenotypes. In this manner, a menu of mutations was developed that is useful in fine-tuning the attenuation and growth characteristics of dengue virus vaccines.

Example 1

Chemical Mutagenesis of Dengue Virus Type 4 Yields Temperature-Sensitive and Attenuated Mutant Viruses A recombinant live attenuated dengue virus type 4 (DEN4) vaccine candidate, 2AΔ30, was found previously to be generally well-tolerated in humans, but a rash and an elevation of liver enzymes in the serum occurred in some vaccinees. 2AΔ30, a non-temperature-sensitive (ts) virus, contains a 30 nucleotide deletion in the 3' untranslated region (UTR) of the viral genome. In the present study, chemical mutagenesis of DEN4 has been utilized to generate attenuating mutations which may be useful to further attenuate the incompletely attenuated 2AΔ30 candidate vaccine. Wild-type DEN4 2A virus was grown in Vero cells in the presence of 5-fluorouracil, and, from a panel of 1,248 clones that were isolated in Vero cells, twenty ts mutant viruses were identified which were ts in both Vero and HuH-7 cells (n=13) or in HuH-7 cells only (n=7). Each of the twenty ts mutations possessed an attenuation (att) phenotype as indicated by restricted replication in the brains of seven day old mice. The complete nucleotide sequence of the 20 ts mutant viruses identified nucleotide substitutions in structural and non-structural genes as well as in the 5' and 3' UTR with more than one change occurring, in general, per mutant virus. A ts mutation in the NS3 protein (nucleotide position 4,995) was introduced into a recombinant DEN4 virus possessing the Δ30 deletion creating the rDEN4Δ30-4995 recombinant virus which was found to be ts and to be more attenuated than rDEN4Δ30 in the brains of mice. A menu of attenuating mutations is being assembled that should be useful in generating satisfactorily attenuated recombinant dengue vaccine viruses and in increasing our understanding of the pathogenesis of dengue virus.

The mosquito-borne dengue (DEN) viruses (serotypes 1 to 4) are members of the *Flavivirus* genus and contain a single-stranded positive-sense RNA genome of approximately 10,600 nucleotides (nt) (Monath, T. P. & Heinz, F. X. 1996 in: *Fields Virology* B. N. Fields, et al. Eds. pp. 961-1034 Lippincott-Ravan Publishers, Philadelphia). The genome organization of DEN viruses is 5'-UTR-C-prM-E-NS1-NS2A-NS2B-NS3-NS4A-NS4B-NS5-UTR-3' (UTR—untranslated region, C—capsid, PrM—pre-membrane, E—envelope, NS—non-structural) (Chang, G.-J. 1997 in: *Dengue and dengue hemorrhagic fever* D. J. Gubler & G. Kuno, eds. pp. 175-198 CAB International, New York; Rice, C. M. 1996 in: *Fields Virology* B. N. Fields et al. Eds. pp. 931-959 Lippincott-Raven Publishers, Philadelphia). A single viral polypeptide is co-translationally processed by viral and cellular proteases generating three structural proteins (C, M, and E) and seven NS proteins. The disease burden associated with DEN virus infection has increased over the past several decades in tropical and semitropical countries. Annually, there are an estimated 50-100 million cases of dengue fever (DF) and 500,000 cases of the more severe and potentially lethal dengue hemorrhagic fever/dengue shock syndrome (DHF/DSS) (Gubler, D. J. & Meltzer, M. 1999 *Adv Virus Res* 53:35-70).

The site of viral replication in DEN virus-infected humans and the pathogenesis of DF and DHF/DSS are still incompletely understood (Innis, B. L. 1995 in: *Exotic viral infections* J. S. Porterfield, ed. pp. 103-146 Chapman and Hall, London). In humans, DEN virus infects lymphocytes (Kurane, I. et al. 1990 *Arch Virol* 110:91-101; Theofilopoulos, A. N. et al. 1976 *J Immunol* 117:953-61), macrophages (Halstead, S. B. et al. 1977 *J Exp Med* 146:218-29; Scott, R. M. et al. 1980 *J Infect Dis* 141:1-6), dendritic cells (Libraty, D. H. et al. 2001 *J Virol* 75:3501-8; \Wu, S. J. et al. 2000 *Nat Med* 6:816-20), and hepatocytes (Lin, Y. L. et al. 2000 *J Med Virol* 60:425-31; Marianneau, P. et al. 1996 *J Gen Virol* 77:2547-54). The liver is clearly involved in DEN virus infection of humans, as indicated by the occurrence of transient elevations in serum alanine aminotransferase (ALT) and aspartate aminotransferase (AST) levels in the majority of dengue virus-infected patients and by the presence of hepatomegaly in some patients (Kalayanarooj, S. et al. 1997 *J Infect Dis* 176:313-21; Kuo, C. H. et al. 1992 *Am J Trop Med Hyg* 47:265-70; Mohan, B. et al. 2000 *J Trop Pediatr* 46:40-3; Wahid, S. F. et al. 2000 *Southeast Asian J Trop Med Public Health* 31:259-63). DEN virus antigen-positive hepatocytes are seen surrounding areas of necrosis in the liver of fatal cases (Couvelard, A. et al. 1999 *Hum Pathol* 30:1106-10; Huerre, M. R. et al. 2001 *Virchows Arch* 438:107-15), and dengue virus sequences were identified in such cases using RT-PCR (Rosen, L. et al. 1999 *Am J Trop Med Hyg* 61:720-4). Of potential importance to the etiology of severe dengue virus infection, three studies have demonstrated that the mean levels of serum ALT/AST were significantly increased in patients with DHF/DSS versus those with DF (Kalayanarooj, S. et al. 1997 *J Infect Dis* 176:313-21; Mohan, B. et al. 2000 *J Trop Pediatr* 46:40-3; Wahid, S. F. et al. 2000 *Southeast Asian J Trop Med Public Health* 31:259-63).

A vaccine for DEN viruses is not presently licensed. Since previous infection with one dengue virus serotype can increase the risk for DHF/DSS following infection with a different serotype (Burke, D. S. et al. 1988 *Am J Trop Med Hyg* 38:172-80; Halstead, S. B. et al. 1969 *Am J Trop Med Hyg* 18:997-1021; Thein, S. et al. 1997 *Am J Trop Med Hyg* 56:566-72), it is clear that a dengue virus vaccine will need to protect against each of the four dengue virus serotypes, namely DEN1, DEN2, DEN3, and DEN4. Several strategies are currently being actively pursued in the development of a live attenuated tetravalent DEN virus vaccine (Bancroft, W. H. et al. 1984 *J Infect Dis* 149:1005-10; Bhamarapravati, N. & Sutee, Y. 2000 *Vaccine* 18:44-7; Guirakhoo, F. et al. 2000 *J Virol* 74:5477-85; Huang, C. Y. et al. 2000 *J Virol* 74:3020-8). Recently, we demonstrated that a live attenuated DEN4 vaccine candidate, 2AΔ30, was attenuated and immunogenic in a group of 20 human volunteers (see Example 8). This recombinant DEN4 virus contains a 30 nt deletion in the 3' UTR which removes nucleotides 10,478-10,507 and was restricted in replication in rhesus monkeys. Levels of viremia in humans were low or undetectable, and virus recovered from the vaccinees retained the Δ30 mutation. An asymptomatic rash was reported in 50% of patients. The only laboratory abnormality observed was an asymptomatic, transient rise in the serum ALT level in 5 of 20 vaccinees. All vaccinees developed serum-neutralizing antibody against DEN4 virus (mean titer: 1:580). Importantly, 2AΔ30 was not transmitted to mosquitoes fed on vaccinees and has restricted growth properties in mosquitoes (Troyer, J. M. et al. 2001 *Am J Trop Med Hyg* 65:414-9). The presence of a rash and of the elevated ALT levels suggests that the 2AΔ30 vaccine candidate is slightly under-attenuated in humans. Because of the overall set of desirable properties conferred by the Δ30 mutation, chimeric vaccine candidates are being constructed which contain the structural genes of dengue virus type 1, 2, and 3 and the DEN4 attenuated backbone bearing the genetically stable Δ30 mutation.

Although the initial findings indicate the utility of the 2AΔ30 vaccine candidate, many previous attempts to develop live attenuated dengue virus vaccines have yielded vaccine candidates that were either over- or under-attenuated in humans (Eckels, K. H. et al. 1984 *Am J Trop Med Hyg* 33:684-9; Bhamarapravati, N. & Yoksan, S. 1997 in: *Dengue and dengue hemorrhagic fever* D. J. Gubler & G. Kuno eds. pp. 367-377 CAB International, New York; Innis, B. L. et al. 1988 *J Infect Dis* 158:876-80; McKee, K. T., Jr. et al. 1987 *Am J Trop Med Hyg* 36:435-42). Therefore, we developed a menu of point mutations which confer temperature-sensitive (ts) and attenuation (att) phenotypes upon DEN4. These mutations are envisioned as being useful to attenuate DEN4 viruses to different degrees and therefore as having purpose in fine-tuning the level of attenuation of vaccine candidates such as 2AΔ30. Addition of such mutations to 2AΔ30 or to other dengue virus vaccine candidates is envisioned as resulting in the generation of a vaccine candidate that exhibits a satisfactory balance between attenuation and immunogenicity for humans.

In the present example, chemical mutagenesis of DEN4 has been utilized to identify point mutations which confer the ts phenotype, since such viruses often are attenuated in humans. Additionally, because of the reported involvement of the liver in natural dengue infection and the elevated ALT levels in a subset of 2AΔ30 vaccinees, mutagenized DEN4 viruses were also evaluated for ts phenotype in HuH-7 liver cells derived from a human hepatoma. Here, we describe the identification of 20 DEN4 ts mutant viruses each of which replicates efficiently in Vero cells, the proposed substrate for vaccine manufacture, and each of which is attenuated in mice. Finally, the feasibility of modifying the attenuation phenotype of the 2AΔ30 vaccine candidate by introduction of a point mutation in NS3 is demonstrated.

Cells and viruses. WHO Vero cells (African green monkey kidney cells) were maintained in MEM (Life Technologies, Grand Island, N.Y.) supplemented with 10% fetal bovine serum (FBS) (Summit Biotechnologies, Fort Collins, Colo.), 2 mM L-glutamine (Life Technologies), and 0.05 mg/ml gentamicin (Life Technologies). HuH-7 cells (human hepatoma cells) (Nakabayashi, H. et al. 1982 *Cancer Res* 42:3858-63) were maintained in D-MEM/F-12 (Life Technologies) supplemented with 10% FBS, 1 mM L-glutamine and 0.05 mg/ml gentamicin. C6/36 cells (*Aedes albopictus* mosquito cells) were maintained in complete MEM as described above supplemented with 2 mM non-essential amino acids (Life Technologies).

The wild type (wt) DEN4 2A virus was derived from a cDNA clone of DEN4 strain 814669 (Dominica, 1981) (Men, R. et al. 1996 *Virol* 70:3930-7). Sequence of the cDNA of DEN 4 2A virus is presented in Appendix 1. The full-length 2A cDNA clone has undergone several subsequent modifications to improve its ability to be genetically manipulated. As previously described, a translationally-silent XhoI restriction enzyme site was engineered near the end of the E region at nucleotide 2348 to create clone 2A-XhoI (Bray, M. & Lai, C. J. 1991 *PNAS USA* 88:10342-6). The viral coding sequence of the 2A-XhoI clone was further modified using site-directed mutagenesis to create clone p4: a unique BbvCI restriction site was introduced near the C-prM junction (nucleotides 447-452); an extra XbaI restriction site was ablated by mutation of nucleotide 7730; and a unique SacII restriction site was created in the NS5 region (nucleotides 9318-9320). Each of these engineered mutations is translationally silent and does not change the amino acid sequence of the viral polypeptide. Also, several mutations were made in the vector region of clone p4 to introduce or ablate additional restriction sites. The cDNA clone p4Δ30 was generated by introducing the Δ30 mutation into clone p4. This was accomplished by replacing the MluI-KpnI fragment of p4 (nucleotides 10403-10654) with that derived from plasmid 2AΔ30 containing the 30 nucleotide deletion. The cDNA clones p4 and p4Δ30 were subsequently used to generate recombinant viruses rDEN4 (Appendix 2) and rDEN4Δ30, respectively. (The GenBank accession number for rDEN4 is AF326825 and the accession for rDEN4Δ30 is AF326827).

Chemical mutagenesis of DEN4. Confluent monolayers of Vero cells were infected with wt DEN4 2A at an multiplicity of infection (MOI) of 0.01 and incubated for 2 hours at 32° C. Infected cells were then overlaid with MEM supplemented with 2% FBS and 5-fluorouracil (5-FU) (Sigma, St. Louis, Mo.) at concentrations ranging from 10 mM to 10 nM. After incubation at 32° C. for five days, cell culture medium was harvested, clarified by centrifugation, and frozen at −70° C. Clarified supernatants were then assayed for virus titer by plaque titration in Vero cells. Serial ten-fold dilutions of the clarified supernatant were prepared in Opti-MEM I (Life Technologies) and inoculated onto confluent Vero cell monolayers in 24-well plates. After incubation at 35° C. for two hours, monolayers were overlaid with 0.8% methylcellulose (EM Science, Gibbstown, N.J.) in Opti-MEM I supplemented with 2% FBS, gentamicin, and L-glutamine. Following incubation at 35° C. for five days, plaques were visualized by immunoperoxidase staining. Vero cell monolayers were fixed in 80% methanol for 30 minutes and washed for 10 minutes with antibody buffer which consists of 3.5% (w/v) nonfat dry milk (Nestle, Solon, Ohio) in phosphate buffered saline (PBS). Cells were then incubated for one hour at 37° C. with an anti-DEN4 rabbit polyclonal antibody preparation ($PRNT_{50}$ of >1:2000) diluted 1:1,000 in antibody buffer. After one wash with antibody buffer, cells were incubated for one hour with peroxidase-labeled goat-anti-rabbit IgG (KPL, Gaithersburg, Md.) diluted 1:500 in antibody buffer. Monolayers were washed with PBS, allowed to dry briefly, overlaid with peroxidase substrate (KPL), and plaques were counted.

Virus yields in cultures treated with 1 mM 5-FU were reduced 100-fold compared to untreated cultures, and the virus present in the supernatant from the 1 mM 5-FU-treated culture was terminally diluted to derive clones for phenotypic characterization. Briefly, 96 well plates of Vero cells were inoculated with the 5-FU-treated virus at an MOI that yielded 10 or fewer virus-positive wells per plate. After a five-day incubation at 35° C., cell culture media from the 96 well plates were temporarily transferred to 96 well plates lacking cells, and the positive cultures were identified by immunoperoxidase staining of the infected-cell monolayers. Virus from each positive well was transferred to confluent Vero cell monolayers in 12 well plates for amplification. Cell culture medium was harvested from individual wells five or six days later, clarified by centrifugation, aliquoted to 96 deep-well polypropylene plates (Beckman, Fullerton, Calif.) and frozen at −70° C. A total of 1,248 virus clones were prepared from the 1 mM 5-FU-treated cultures. Two wt virus clones, 2A-1 and 2A-13, were generated in the same manner from the 5-FU untreated control cultures.

Screening of clones for ts and att phenotypes. The 1,248 virus clones were screened for ts phenotype by assessing virus replication at 35° C. and 39° C. in Vero and HuH-7 cells. Cell monolayers in 96 well plates were inoculated with serial ten-fold dilutions of virus in L-15 media (Quality Biologicals, Gaithersburg, Md.) supplemented with 2% FBS, L-glutamine and gentamicin. Cells were incubated at the indicated temperatures for five days in temperature-controlled water baths, and presence of virus was determined by immunoperoxidase staining as described above. Virus clones which demonstrated a 100-fold or greater reduction in titer at 39° C. were terminally diluted an additional two times and amplified in Vero cells. The efficiency of plaque formation (EOP) at permissive and restrictive temperatures of each triply biologically cloned virus suspension was determined as follows. Plaque titration in Vero and HuH-7 cells was performed as described above except virus-infected monolayers were overlaid with 0.8% methylcellulose in L-15 medium supplemented with 5% FBS, gentamicin, and L-glutamine. After incubation of replicate plates for five days at 35, 37, 38, or 39° C. in temperature-controlled water baths, plaques were visualized by immunoperoxidase staining and counted.

The replication of DEN4 5-FU ts mutant viruses was evaluated in Swiss Webster suckling mice (Taconic Farms, Germantown, N.Y.). Groups of six one-week-old mice were inoculated intracranially with $10^4$ PFU of virus diluted in 30 μl Opti-MEM I. Five days later, mice were sacrificed and brains were removed and individually homogenized in a 10% suspension of phosphate-buffered Hank's balanced salt solution containing 7.5% sucrose, 5 mM sodium glutamate, 0.05 mg/ml ciprofloxacin, 0.06 mg/ml clindamycin, and 0.0025 mg/ml amphotericin B. Clarified supernatants were frozen at −70° C. and subsequently virus titer was determined by titration in Vero cells, and plaques were stained by the immunoperoxidase method described above.

Sequence analysis of viral genomes. The nucleotide sequence of the 5-FU-mutagenized DEN4 viruses was determined. Briefly, genomic viral RNA was isolated from virus clones with the QIAamp viral RNA mini kit (Qiagen, Valencia, Calif.) and reverse transcription was performed using the SuperScript First Strand Synthesis System for RT-PCR (Life Technologies) and random hexamer primers. Advantage cDNA polymerase (Clontech, Palo Alto, Calif.) was used to generate overlapping PCR fragments of approximately 2,000 nt which were purified by HighPure PCR Product Purification System (Roche Diagnostics, Indianapolis, Ind.). DEN-specific primers were used in BigDye terminator cycle sequencing reactions (Applied Biosystems, Foster City, Calif.) and reactions were analyzed on a 3100 genetic analyzer (Applied Biosystems). Primers were designed to sequence both strands of the PCR product from which consensus sequences were assembled.

The nucleotide sequence of the 5' and 3' regions of the viral genome were determined as above after circularization of the RNA genome. The 5' cap nucleoside of the viral RNA was excised using tobacco acid pyrophosphatase (Epicentre Technologies, Madison, Wis.) and the genome was circularized by RNA ligase (Epicentre Technologies). A RT-PCR fragment was generated which overlapped the ligation junction (5' and 3' ends) and was sequenced as described above.

Generation of recombinant DEN4 viruses. The mutation at nt position 4,995 in NS3 was introduced into the p4 cDNA construct by site-directed mutagenesis (Kunkel, T. A. 1985 *PNAS USA* 82:488-92). The StuI-BstBI (nt 3,619-5,072) fragment of p4 was sub-cloned into a modified pUC119 vector. The U>C mutation at nt position 4,995 was engineered by site-directed mutagenesis into the p4 fragment, cloned back into the p4 cDNA construct, and the presence of the mutation was confirmed by sequence analysis. The Δ30 mutation was introduced into the 3' UTR of the p4-4995 cDNA clone by replacing the MluI-KpnI fragment with that derived from the p4Δ30 cDNA clone, and the presence of the deletion was confirmed by sequence analysis. Full length RNA transcripts were prepared from the above cDNA clones by in vitro transcription. Briefly, transcription consisted of a 50 μl reaction mixture containing 1 μg linearized plasmid, 60 U SP6 polymerase (New England Biolabs (NEB), Beverly, Mass.), 1×RNA polymerase buffer (40 mM Tris-HCl, pH 7.9, 6 mM $MgCl_2$, 2 mM spermidine, 10 mM dithiothreitol), 0.5 mM m7G(5')ppp(5')G cap analog (NEB), 1 mM each nucleotide triphosphate, 1 U pyrophosphatase (NEB), and 80 U RNAse inhibitor (Roche, Indianapolis, Ind.). This reaction mixture was incubated at 40° C. for 90 min and the resulting transcripts were purified using RNeasy mini kit (Qiagen, Valencia, Calif.).

For transfection of C6/36 cells, RNA transcripts were combined with DOTAP liposomal transfection reagent (Roche) in HEPES-buffered saline (pH 7.6) and added to cell monolayers in 6 well plates. After incubation at 32° C. for 12-18 hours, the cell culture media were removed and replaced with MEM supplemented with 5% FBS, L-glutantine, gentamicin and non-essential amino acids. Cell monolayers were incubated for an additional 5 to 7 days and cell culture media were harvested, clarified by centrifugation, and assayed for the presence of virus by plaque titration in Vero cells. Recovered viruses were terminally diluted twice as described above, and virus suspensions for further analysis were prepared in Vero cells.

In vitro (tissue culture) and in vivo replication of wt DEN4 and DEN4Δ30. The level of replication of both wt DEN4 2A and the vaccine candidate, 2AΔ30, was evaluated in Vero (monkey kidney) and HuH-7 (human hepatoma) cells (FIG. 1), the latter of which has recently been found to efficiently support the replication of DEN2 virus (Lin, Y. L. et al. 2000 *J Med Virol* 60:425-31). The pattern of replication of wt DEN4 2A and 2AΔ30 was similar in both cell lines. Viral titers from cultures infected with 2AΔ30 at an MOI of 0.01 were slightly reduced compared to wt DEN4 2A at 72 hours, but at later time points their level of replication was equivalent. The efficient replication of both DEN4 viruses in each cell line indicated that these continuous lines of cells would be useful for characterization of the ts phenotype of the 1248 potential mutant viruses.

The level of replication of DEN4 virus administered intracerebrally to Swiss Webster mice was first determined to assess whether mice could be used to efficiently evaluate and quantitate the attenuation phenotype of a large set of mutant viruses. Since the susceptibility of mice to DEN infection is age dependent (Cole, G. A. & Wisseman, C. L. Jr. 1969 *Am J Epidemical* 89:669-80; Cole, G. A. et al. 1973 *J Comp Pathol* 83:243-52), mice aged 7 to 21 days were infected with 2A-13 (a clone of DEN4 wild type virus—see below), rDEN4 or rDEN4Δ30, and after five days the brain of each mouse was removed, and the level of viral replication was quantitated by plaque assay (Table 1). The results indicated that the two wt DEN4 viruses and the rDEN4Δ30 vaccine candidate replicated to high titer (>6.0 $\log_{10}$PFU/g brain) in 7-day old mice and that the mean viral titers were similar among the three viruses. These results demonstrated the feasibility of using 7-day old mice to screen a large set of mutant viruses, and the high level of replication of wild type and vaccine candidate permits one to quantitate the magnitude of the restriction of replication specified by an attenuating mutation over a 10,000-fold range.

Figure 2:
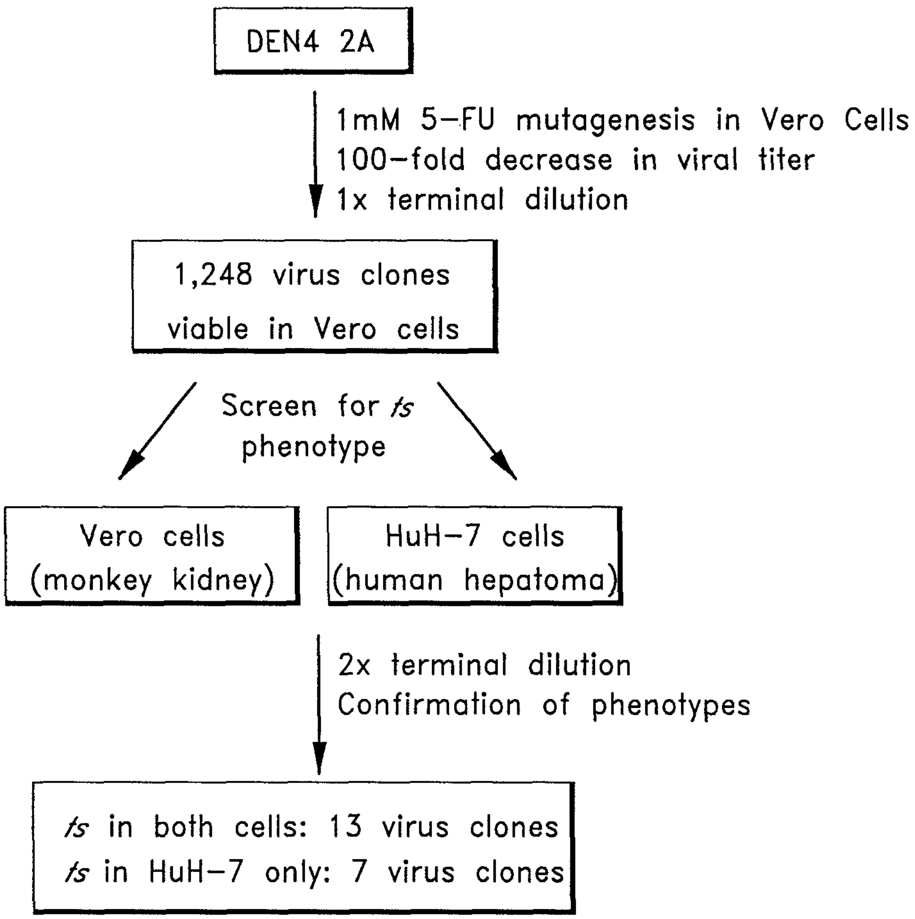
FIG. 2 shows generation of temperature-sensitive (ts) DEN4 viruses by 5-fluorouracil (5-FU) chemical mutagenesis. The wild-type DEN4 2A virus was derived from a cDNA clone of DEN4 strain 814669 (Dominica, 1981). Vero cells were infected with DEN4 2A and overlaid with culture media containing 1 mM 5-fluorouracil (5-FU) which resulted in a reduction of approximately 100-fold in viral replication when compared to untreated controls. Viral progeny from the 1 mM 5-FU-treated cultures were subjected to a single round of terminal dilutions generating 1,248 biologically cloned viruses which were screened for ts phenotypes by assessing virus replication at 35° C. and 39° C. in Vero and HuH-7 cells. Virus clones which demonstrated a 100-fold or greater reduction in titer at 39° C. were terminally diluted an additional two times and amplified in Vero cells. Temperature-sensitive phenotypes of the 3× biologically cloned viruses were confirmed by evaluating efficiency of plaque formation (EOP) in the indicated cells as described in Example 1.

Generation and in vitro characterization of DEN4 5-FU mutant viruses. A panel of 1,248 DEN4 virus clones was generated from a 5-FU-mutagenized suspension of wt DEN4 2A as described above (FIG. 2). Each clone was tested in Vero and HuH-7 cells for the ts phenotype at 39° C., and putative ts mutant viruses were subjected to two additional rounds of biological cloning by terminal dilution, and the ts phenotype of each further cloned virus population was examined in more detail by determining their efficiency of plating (EOP) at permissive temperature (35° C.) and at various restrictive temperatures (Table 2). One virus (clone 2A-13) without a ts phenotype, which was passaged in an identical fashion as the ts mutant viruses, served as the virus to which each of the ts mutant viruses was directly compared for both the ts and att phenotypes.

Thirteen 5-FU mutant viruses were identified which have a ts phenotype in both Vero and HuH-7 cells, and seven mutant viruses were ts only in HuH-7 cells (Table 2). Mutant viruses which were ts in Vero cells but not in HuH-7 cells were not identified. Temperature-sensitivity was defined as a ≥2.5 or ≥3.5 $\log_{10}$PFU/ml reduction in virus titer in Vero or HuH-7 cells, respectively, at an indicated temperature when compared to the permissive temperature of 35° C. Wild type DEN4 2A was found to have approximately a 0.5 and 1.5 $\log_{10}$PFU/ml reduction in virus titer in Vero or HuH-7 cells at 39° C., respectively. The Δ30 deletion did not confer a ts phenotype in Vero or HuH-7 cells and exhibited only a slight reduction in virus titer (2.2 $\log_{10}$PFU/ml) at 39° C. in HuH-7 cells, which was less than 10-fold greater than the reduction of wt DEN4 2A at that temperature. Several 5-FU mutant viruses had a greater than 10,000-fold reduction in virus titer at 39° C. in both Vero and HuH-7 cells. A complete shut-off in viral replication at 39° C. in HuH-7 cells was observed in five virus clones (#571, 605, 631, 967, and 992) which were not ts in Vero cells. Mutations that selectively restrict replication in HuH-7 liver cells may be particularly useful in controlling the replication of dengue virus vaccine candidates in the liver of vaccinees.

Replication of DEN4 5-FU mutant viruses in suckling mice. The level of replication of each of the 20 ts DEN4 mutant viruses in mouse brain was determined (Table 2). The titers obtained were compared to that of the two wt viruses, 2A-13 and rDEN4, which each replicated to a level of greater than $10^6$ PFU/g of brain tissue, and to that of the 2AΔ30 mutant, which conferred only a limited 0.5 $\log_{10}$PFU/g reduction in mean virus titer compared to the wt controls. The observed reduction in the level of rDEN4Δ30 replication was consistent among 11 separate experiments. Interestingly, the rDEN4Δ30 virus, which was attenuated in both rhesus monkeys and humans (Example 8), was only slightly restricted in replication in mouse brain. Varying levels of restriction of replication were observed among the mutant viruses ranging from a 10-fold (#473) to over 6,000-fold (#686) reduction. Mutant viruses with ts phenotypes in both Vero and HuH-7 cells, as well as in HuH-7 cells alone, were found to have significant att phenotypes. Five of 13 5-FU mutant viruses with ts phenotypes in both Vero and HuH-7 cells and five of seven mutant viruses with ts phenotypes in HuH-7 cells alone had greater than a 100-fold reduction in virus replication. There appeared to be no direct correlation between the magnitude of the reduction in replication at restrictive temperature in tissue culture and the level of attenuation in vivo. The similar level of temperature sensitivity and replication of the rDEN4 wt and clone 2A-13 in mouse brain indicated that observed differences in replication between the ts mutant viruses and clone 2A-13 was not simply a function of passage in Vero cells, but reflects the sequence differences between these viruses.

Sequence analysis of DEN4 5-FU mutant viruses. To determine the genetic basis of the observed ts and att phenotypes, the complete nucleotide sequence of each ts mutant and of clone 2A-13 was determined and summarized in Table 3 (ts in Vero and HuH-7 cells) and Table 4 (ts in only HuH-7 cells).

The only type of mutation identified in the 20 mutant viruses sequenced was a nucleotide substitution (no deletions or insertions occurred), and these were present in each of the coding regions except C and NS4A. Three mutant viruses (#239, 489, and 773) contained only a single missense point mutation in NS3 at nt position 4,995 resulting in a Ser to Pro amino acid (a.a.) change at a.a. position 1,632. For #773, this was the sole mutation present (Table 3). The non-coding mutations in coding regions are not considered to be significant. The 17 additional mutant viruses had multiple mutations (two to five) in a coding region or in an UTR which could potentially confer the observed ts or att phenotypes. Five of the 17 mutant viruses with multiple mutations (#473, 718, 759, 816, and 938) also encoded the point mutation at nt position 4,995. The presence of the 4,995 mutation was found in only DEN4 mutant viruses with ts phenotypes in both Vero and HuH-7 cells.

The sequence analysis indicated that 10 mutant viruses which were ts in Vero and HuH-7 cells and three mutant viruses which were ts in only HuH-7 cells contained mutations in only the 5' and 3' UTR and/or in a nonstructural protein. These mutations are especially suitable for inclusion in chimeric dengue virus vaccine candidates in which the structural genes derive from a DEN1, DEN2, or DEN3 serotype and the remaining coding and non-coding regions come from an attenuated DEN4 vector. Mutations identified in 5-FU DEN4 mutant viruses which were ts in only HuH-7 cells (Table 4) may potentially be utilized in vaccine candidates, such as rDEN4Δ30, to selectively control the replication and pathogenesis of DEN4 in the liver. These combined results from the sequence analysis of 5-FU mutant viruses demonstrate the utility of chemical mutagenesis as a means of introducing attenuating mutations into the dengue virus genome.

The presence of a point mutation at nt position 4,995 in eight separate mutant viruses was described above. Five additional point mutations were also represented in multiple viruses including nt changes at position 1,455 in E, 7,162, 7,163 and 7,564 in NS4B, and 10,275 in the 3' UTR (Table 5). The significance of the occurrence of these "sister" mutations in multiple viruses is discussed in Example 6. Interestingly, the wild-type, parallel-passaged virus, 2A-13, also contained a single mutation at the 7,163 nt position in NS4B.

Introduction of a ts mutation into rDEN4 and rDEN4Δ30. The presence of a single nucleotide substitution (U>C mutation at nt position 4,995 in NS3) in three separate mutant viruses (clones 239, 489, and 773) indicated that this mutation specified the ts and att phenotypes in each of the three mutant viruses. This mutation was cloned into cDNA construct of p4 and p4Δ30 and recombinant viruses were recovered and designated rDEN4-4995 and rDEN4Δ30-4995, respectively. These recombinant viruses were tested for ts and att phenotypes as described above (Table 6). As expected, introduction of mutation 4995 into rDEN4 wt resulted in a significant ts phenotype at 39° C. in both Vero and HuH-7 cells. rDEN4-4995 grew to nearly wild-type levels at the permissive temperature, 35° C., in both cell types, but demonstrated a greater than 10,000-fold reduction at 39° C. (shut-off temperature) in both Vero and HuH-7 cells. The addition of the 4995 mutation to rDEN4Δ30 yields a recombinant virus, rDEN4Δ30-4995, that exhibits the same level of temperature sensitivity as rDEN4-4995 (Table 6).

The rDEN4 viruses encoding the 4995 mutation were next tested for replication in the brains of suckling mice (Table 6). The 4995 mutation conferred an att phenotype upon both rDEN4 and rDEN4Δ30. There was an approximately 1,000-fold reduction in virus replication compared to that of wt virus. The combination of point mutation 4995 and the Δ30 deletion did not appear to result in an additive reduction of virus replication. These results confirmed that the 4995 point mutation indeed specifies the ts and att phenotypes. Importantly, the utility of modifying tissue culture and in vivo phenotypes of the rDEN4Δ30 vaccine candidate by introduction of additional mutations was also demonstrated.

Discussion. Herein we teach how to prepare a tetravalent, live-attenuated dengue virus vaccine using rDEN4Δ30 as the DEN4 component and three antigenic chimeric viruses expressing the structural proteins (C, prM, and E) of DEN1, DEN2, and DEN3 from the attenuated rDEN4Δ30 vector (Example 8). DEN4 virus rDEN4Δ30 containing the Δ30 deletion mutation in the 3' UTR manifests restricted replication in humans while retaining immunogenicity. Since rDEN4Δ30 retains a low level of residual virulence for humans despite this restricted replication, the present study was initiated to generate additional attenuating mutations that are envisioned as being useful to further attenuate rDEN4Δ30 or other dengue viruses and that are envisioned as being incorporated into any of the three antigenic chimeric viruses or other dengue viruses as needed. Temperature-sensitive mutants of dengue viruses (Bhamarapravati, N. & Yoksan, S. 1997 in: *Dengue and Dengue Hemorrhagic Fever* D. J. Gubler & G. Kuno eds. pp. 367-377 CAB International, New York; Eckels, K. H. et al. 1980 *Infect Immun* 27:175-80) as well of other viruses (Skiadopoulos, M. H. et al. 1998 *J Virol* 72:1762-8; Whitehead, S. S. et al. 1999 *J Virol* 73:871-7) manifest restricted replication in vivo. We have generated a panel of 20 ts DEN4 mutant viruses, determined their genomic sequence, and assessed their in vivo attenuation phenotypes. The 20 ts DEN4 mutant viruses were generated by growth in the presence of 5-FU and were first selected for viability in Vero cells, the substrate planned for use in the manufacture of these vaccines, to ensure that the mutant viruses can be grown efficiently in a suitable substrate.

Two classes of mutant viruses were obtained; those ts in both Vero and HuH-7 cells (n=13) or those ts in only HuH-7 cells (n=7). The viruses exhibited a range in their level of temperature sensitivity from a 100- to 1,000,000-fold reduction in replication at the restrictive temperature of 39° C. Since our DEN4 vaccine candidate retains a low level of virulence for the liver and other findings support the ability of dengue viruses to infect hepatocytes (Lin, Y. L. et al. 2000 *J Med Virol* 60:425-31; Marianneau, P. et al. 1997 *J Virol* 71:3244-9) and cause liver pathology (Couvelard, A. et al. 1999 *Hum Pathol* 30:1106-10; Huerre, M. R. et al. 2001 *Virchows Arch* 438:107-15), we sought to develop mutations that would selectively restrict replication of dengue 4 virus in liver cells. Toward this end, we identified seven mutant viruses which have a HuH-7 cell-specific ts phenotype. The mutations present in these viruses are the first reported in DEN viruses that confer restricted replication in liver cells and are envisioned as being useful in limiting virus replication and pathogenesis in the liver of vaccine recipients. The contribution of individual mutations identified in the HuH-7 cell-specific ts viruses to the observed phenotypes is envisioned as being assessed by introduction of the individual mutations into recombinant DEN4 viruses.

Recent evidence has indicated that the magnitude of the viremia in DEN-infected patients positively correlates with disease severity, i.e., the higher the titer of viremia the more severe the disease (Murgue, B. et al. 2000 *J Med Virol* 60:432-8; Vaughn, D. W. et al. 2000 *J Infect Dis* 181:2-9). This indicates that mutations that significantly restrict replication of vaccine candidates in vivo are the foundation of a safe and attenuated vaccine. Evaluation of DEN virus vaccine candidates for in vivo attenuation is complicated by the lack of a suitable animal model which accurately mimics the disease caused by dengue viruses in humans. In the absence of such a model, the replication of the panel of 5-FU mutant viruses in the brains of Swiss Webster suckling mice was assessed as a means to identify an in vivo attenuation phenotype since this animal model is well-suited for the evaluation of a large set of mutant viruses. Each of the 20 ts mutant viruses exhibited an att phenotype manifesting a 10- to 6,000-fold reduction in replication in the brain of mice as compared to wt DEN4 virus (Table 2). This indicates that there is a correlation between the presence of the ts phenotype in tissue culture and attenuation of the mutant in vivo confirming the utility of selecting viruses with this marker as vaccine candidates. However, there was no correlation between the level of temperature sensitivity and the level of restriction in vivo. Furthermore, Sabin observed a dissociation between mouse neurovirulence and attenuation in humans by generating an effective live attenuated virus vaccine against DEN by passage of virus in mouse brain. This research actually resulted in a highly mouse-neurotropic DEN virus which, paradoxically, was significantly attenuated in humans (Sabin, A. B. 1952 *Am J Trop Med Hyg* 1:30-50). Despite this, attenuation for the suckling mouse brain has been reported for other live-attenuated DEN virus vaccine candidates including the DEN2 PDK-53 vaccine strain which is non-lethal in mice and DEN-2 PR-159/S-1 vaccine strain which was significantly attenuated compared to its parental wild-type virus (Bhamarapravati, N. & Yoksan, S. 1997 in: *Dengue and Dengue Hemorrhagic Fever* D. J. Gubler & G. Kuno eds. pp. 367-377 CAB International, New York; Butrapet, S. et al. 2000 *J Virol* 74:3011-9; Eckels, K. H. et al. 1980 *Infect Immun* 27:175-80; Innis, B. L. et al.

1988 *J Infect Dis* 158:876-80). Replication in rhesus monkeys has been reported to be predictive of attenuation for humans (Innis, B. L. et al. 1988 *J infect Dis* 158:876-80). Recently, murine models of DEN virus infection have been developed using SCID mice transplanted with human macrophage (Lin, Y. L. et al. 1998 *J Virol* 72:9729-37) or liver cell lines (An, J. et al. 1999 *Virology* 263:70-7), but these mice have not as yet been used to assess att phenotypes of candidate vaccine viruses. Mutant viruses or recombinant viruses bearing one or more of these mutations described herein are envisioned as being tested for replication in rhesus monkeys (or other suitable animal model) as predictive for attenuation in humans.

The chemical mutagenesis of DEN4 virus and sequence analysis of resulting viruses described here has resulted in the identification of a large number of point mutations resulting in amino acid substitutions in all genes except C and NS4A as well as point mutations in the 5' and 3' UTR (Tables 3 and 4). This approach of whole-genome mutagenesis has the benefit of identifying mutations dispersed throughout the entire genome which are pre-selected for viability in the Vero cell substrate. Ten 5-FU mutant viruses which were ts in Vero and HuH-7 cells and three viruses which were selectively ts in HuH-7 cells contained only mutations outside of the genes encoding the structural proteins, i.e., in the 5' and 3' UTR or NS genes. These mutations along with the Δ30 deletion in the 3' UTR are particularly suited for inclusion in antigenic, chimeric vaccines which consist of an attenuated DEN4 vector bearing the wild-type structural genes (C, prM, E) of the other DEN virus serotypes. Use of this strategy has several advantages. Each antigenic chimeric virus that possesses structural proteins from a wild-type virus along with attenuating mutations in their UTRs or NS genes should maintain its infectivity for humans, which is mediated largely by the E protein, and, therefore, each vaccine component should be immunogenic (Huang, C. Y. et al. 2000 *J Virol* 74:3020-8). The replicative machinery of the tetravalent vaccine strains would share the same attenuating mutations in the NS genes or in the UTR which should attenuate each vaccine component to a similar degree and thereby minimize interference or complementation among the four vaccine viruses. In addition, wild-type E protein would be expected to most efficiently induce neutralizing antibodies against each individual DEN virus.

Sequence analysis of dengue viruses (Blok, J. et al. 1992 *Virology* 187:573-90; Lee, E. et al. 1997 *Virology* 232:281-90; Puri, B. et al. 1997 *J Gen Virol* 78:2287-91) and yellow fever viruses (Dunster, L. M. et al. 1999 *Virology* 261:309-18; Holbrook, M. R. et al. 2000 *Virus Res* 69:31-9) previously generated by serial passage in tissue culture have mutations throughout much of the genome, a pattern we have observed in the present study. Recent analysis of the DEN2 PDK-53 vaccine strain has identified the important mutations involved in attenuation which were located in non-structural regions including the 5' UTR, NS1 and NS3 (Butrapet, S. et al. 2000 *J Virol* 74:3011-9). This DEN2 vaccine strain has been used to generate a chimeric virus with DEN1 C-prM-E genes (Huang, C. Y. et al. 2000 *J Virol* 74:3020-8). In separate studies, the sequence of the DEN1 vaccine strain 45AZ5 PDK-27 was determined and compared to parental viruses, but the mutations responsible for attenuation have not yet been identified (Puri, B. et al, 1997 *J Gen Virol* 78:2287-91).

Several amino acid substitutions were identified in more than one ts 5-FU mutant virus (Table 5). Lee et al. have previously reported finding repeated mutations in separate DEN3 virus clones after serial passage in Vero cells (Lee, E. et al. 1997 *Virology* 232:281-90). A mutation (K>N) identified in E at a.a. position 202 in a single DEN3 passage series was also found in our 5-FU mutant virus #1012 (K>E). Mutations observed in the 5-FU sister mutant viruses are envisioned as representing adaptive changes that confer an increased efficiency of DEN4 replication in Vero cells. Such mutations are envisioned as being beneficial for inclusion in a live-attenuated DEN virus vaccine by increasing the yield of vaccine virus during manufacture. Interestingly, three distinct amino acid substitutions were found in NS4B of the 5-FU sister mutant viruses. The exact function of this gene is unknown, but previous studies of live-attenuated yellow fever vaccines (Jennings, A. D. et al. 1994 *J Infect Dis* 169:512-8; Wang, E. et al. 1995 *J Gen Virol* 76:2749-55) and Japanese encephalitis vaccines (Ni, H. et al. 1995 *J Gen Virol* 76:409-13) have identified mutations in NS4B associated with attenuation phenotypes.

The mutation at nt position 4995 of NS3 (S1632P) was present as the only significant mutation identified in three 5-FU mutant viruses (#239, #489, and #773). This mutation was introduced into a recombinant DEN4 virus and found to confer a ts and att phenotype (Table 6). These observations clearly identify the 4995 mutation as an attenuating mutation. Analysis of a sequence alignment (Chang, G.-J. 1997 in: *Dengue and Dengue Hemorrhagic Fever* D. J. Gubler & G. Kuno, eds. pp. 175-198 CAB International, New York) of the four dengue viruses indicated that the Ser at a.a. position 1632 is conserved in DEN1 and DEN2, while DEN3 contains an Asn at this position indicating that the mutation is predicted to be useful in modifying the phenotypes of the other DEN virus serotypes. The NS3 protein is 618 a.a. in length and contains both serine protease and helicase activities (Bazan, J. F. & Fletterick, R. J. 1989 *Virology* 171:637-9; Brinkworth, R. I. et al. 1999 *J Gen Virol* 80:1167-77; Valle, R. P. & Falgout, B. 1998 *J Virol* 72:624-32). The 4995 mutation results in a change at a.a. position 158 in NS3 which is located in the N-terminal region containing the protease domain. Amino acid position 158 is located two a.a. residues away from an NS3 conserved region designated homology box four. This domain has been identified in members of the flavivirus family and is believed to be a critical determinant of the NS3 protease substrate specificity (Bazan, J. F. & Fletterick, R. J. 1989 *Virology* 171:637-9; Brinkworth, R. I. et al. 1999 *J Gen Virol* 80:1167-77). However, the exact mechanism which results in the phenotype associated with the 4995 mutation has not yet been identified. The identification of the 4995 mutation as an attenuating mutation permits a prediction of its usefulness for the further attenuation of rDEN4Δ30.

We have determined the contribution of individual 5-FU mutations to the observed phenotypes by introduction of the mutations into recombinant DEN4 viruses as was demonstrated herein for the 4995 mutation (see Example 3). In addition, combination of individual mutations with each other or with the Δ30 mutation is useful to further modify the attenuation phenotype of DEN4 virus candidate vaccines. The introduction of the 4995 mutation into rDEN4Δ30 described herein rendered the rDEN4Δ30-4995 double mutant ts and 1000-fold more attenuated for the mouse brain than rDEN4Δ30. This observation has demonstrated the feasibility of modifying both tissue culture and in vivo phenotypes of this and other dengue virus vaccine candidates. Once the mutations responsible for the HuH-7 cell-specific ts phenotype are identified as described above and introduced into the rDEN4Δ30 vaccine candidate, we envision confirming that these mutations attenuate rDEN4Δ30 vaccine virus for the liver of humans. A menu of attenuating mutations is envisioned as being assembled that is predicted to be useful in generating satisfactorily attenuated recombinant dengue vaccine viruses and in increasing our understanding of the pathogenesis of dengue virus (see Example 7).

Example 2

Chemical Mutagenesis of DEN4 Virus Results in Small-Plaque Mutant Viruses With Temperature-Sensitive and Attenuation Phenotypes Mutations that restrict replication of dengue virus have been sought for the generation of recombinant live-attenuated dengue virus vaccines. Dengue virus type 4 (DEN4) was previously grown in Vero cells in the presence of 5-fluorouracil, and the characterization of 1,248 mutagenized, Vero cell-passaged clones identified 20 temperature-sensitive (ts) mutant viruses that were attenuated (att) in suckling mouse brain (Example 1). The present investigation has extended these studies by identifying an additional 22 DEN4 mutant viruses which have a small-plaque size (sp) phenotype in Vero cells and/or the liver cell line, HuH-7. Five mutant viruses have a sp phenotype in both Vero and HuH-7 cells, three of which are also ts. Seventeen mutant viruses have a sp phenotype in only HuH-7 cells, thirteen of which are also ts. Each of the sp viruses was growth restricted in the suckling mouse brain, exhibiting a wide range of reduction in replication (9- to 100,000-fold). Complete nucleotide sequence was determined for the 22 DEN4 sp mutant viruses, and nucleotide substitutions were found in the 3' untranslated region (UTR) as well as in all coding regions except NS4A. Identical mutations have been identified in multiple virus clones indicating that they are involved in the adaptation of DEN4 virus to efficient growth in Vero cells.

The DEN viruses cause more disease and death of humans than any other arbovirus, and more than 2.5 billion people live in regions with endemic dengue infection (Gubler, D. J. 1998 Clin Microbiol Rev 11:480-96). Annually, there are an estimated 50-100 million cases of dengue fever (DF) and 500,000 cases of the more severe and potentially lethal dengue hemorrhagic fever/dengue shock syndrome (DHF/DSS) (Gubler, D. J. & Meltzer, M. 1999 Adv Virus Res 53:35-70). Dengue fever is an acute infection characterized by fever, retro-orbital headache, myalgia, and rash. At the time of defervescence during DF, a more severe complication of DEN virus infection, DHF/DSS, may occur which is characterized by a second febrile period, hemorrhagic manifestations, hepatomegaly, thrombocytopenia, and hemoconcentration, which may lead to potentially life-threatening shock (Gubler, D. J. 1998 *Clin Microbiol Rev* 11:480-96).

The sites of DEN virus replication in humans and their importance and relationship to the pathogenesis of DF and DHF/DSS are still incompletely understood (Innis, B. L. 1995 in: *Exotic Viral Infections* J. S. Porterfield, ed. pp. 103-146 Chapman and Hall, London). In addition to replication in lymphoid cells, it has become evident that the liver is involved in DEN infection of humans. Transient elevations in serum alanine aminotransferase (ALT) and aspartate aminotransferase (AST) levels are observed in the majority of DEN virus-infected patients and hepatomegaly is observed in some patients (Kalayanarooj, S. et al. 1997 *J Infect Dis* 176:313-21; Kuo, C. H. et al. 1992 *Am J Trop Med Hyg* 47:265-70; Mohan, B. et al. 2000 *J Trop Pediatr* 46:40-3; Wahid, S. F. et al. 2000 *Southeast Asian J Trop Med Public Health* 31:259-63). DEN virus antigen-positive hepatocytes are seen surrounding areas of necrosis in the liver of fatal cases (Couvelard, A. et al. 1999 *Hum Pathol* 30:1106-10; Huerre, M. R. et al. 2001 *Virchows Arch* 438:107-15), from which dengue virus sequences were identified using RT-PCR. (Rosen, L. et al. 1999 *Am J Trop Med Hyg* 61:720-4). Of potential importance to the etiology of severe dengue virus infection, three studies have demonstrated that the mean levels of serum ALT and AST were significantly increased in patients with DHF/DSS compared to those with DF (Kalayanarooj, S. et al. 1997 *J Infect Dis* 176:313-21; Mohan, B. et al. 2000 *J Trop Pediatr* 46:40-3; Wahid, S. F. et al. 2000 *Southeast Asian J Trop Med Public Health* 31:259-63). As expected, elevation of serum liver enzymes has previously been observed in clinical trials of DEN virus vaccine candidates (Example 8; Eckels, K. H. et al. 1984 *Am J Trop Med Hyg* 33:684-9; Edelman, R. et al. 1994 *J Inject Dis* 170:1448-55; Kanesa-thasan, N. et al. 2001 *Vaccine* 19:3179-3188; Vaughn, D. W. et al. 1996 *Vaccine* 14:329-36).

Based on the increasing disease burden associated with DEN virus infection over the past several decades, a vaccine which confers protection against the four dengue virus serotypes is needed, but none is presently licensed. Because of the increased risk for severe DHF/DSS associated with secondary infection with a heterologous DEN virus serotype (Burke, D. S. et al. 1988 *Am J Trop Med Hyg* 38:172-80; Halstead, S. B. et al. 1977 *J Exp Med* 146:218-29; Thein, S. et al. 1997 *Am J Trop Med Hyg* 56:566-72), an effective vaccine must confer simultaneous protection against each of the four DEN virus serotypes. Several approaches are presently being pursued to develop a tetravalent vaccine against the dengue viruses (Bancroft, W. H. et al. 1984 *J Infect Dis* 149:1005-10; Bhamarapravati, N. & Sutee, Y. 2000 *Vaccine* 18:44-7; Butrapet, S. et al. 2000 *J Viral* 74:3011-9; Guirakhoo, F. et al. 2000 *J Viral* 74:5477-85; Huang, C. Y. et al. 2000 *J Viral* 74:3020-8; Kanesa-thasan, N. et al. 2001 *Vaccine* 19:3179-3188). One such approach, a live-attenuated DEN4 vaccine candidate, termed 2AΔ30, was both attenuated and immunogenic in a cohort of 20 volunteers (Example 8). The recombinant 2AΔ30 virus contains a 30 nt deletion in the 3' UTR which removes nucleotides 10,478-10,507 and was found to produce a low or undetectable level of viremia in vaccinees at a dose of $10^5$ PFU/vaccinee. An asymptomatic rash was reported in 50% of volunteers, and the only laboratory abnormality observed was an asymptomatic, transient rise in the serum ALT level in 5 of the 20 vaccinees. All 2AΔ30 vaccinees developed serum neutralizing antibodies against DEN4 virus (mean titer: 1:580), and 2AΔ30 was not transmitted to mosquitoes that fed experimentally on vaccinees (Troyer, J. M. et al. 2001 *Am J Trop Med Hyg* 65:414-9). Because of the desirable properties conferred by the Δ30 mutation, chimeric vaccine candidates are being constructed which contain the structural genes of DEN virus type 1, 2, and 3, in the attenuated DEN4 background bearing the genetically stable Δ30 mutation. Attenuating mutations outside of the structural genes are particularly attractive for inclusion in antigenic chimeric vaccine candidates because they will not affect the infectivity or immunogenicity conferred by the major mediator of humoral immunity to DEN viruses, the envelope (E) protein.

The presence of rash and elevated ALT levels suggests that the 2AΔ30 vaccine candidate may be slightly under-attenuated in humans. Similarly, many previous attempts to develop live attenuated dengue virus vaccines have yielded vaccine candidates that were either over- or under-attenuated in humans, some of which also induced elevation of serum ALT and AST levels. (Bhamarapravati, N. & Yoksan, S. 1997 in; *Dengue and Dengue Hemorrhagic Fever* D. J. Gubler & G. Kuno eds. pp. 367-377 CAB International, New York; Eckels, K. H. et al. 1984 *Am J Trop Med Hyg* 33:684-9; Innis, B. L. et al. 1988 *J Infect Dis* 158:876-80; Kanesa-thasan, N. et al. 2001 *Vaccine* 19:3179-3188; McKee, K. T., Jr. et al. 1987 *Am J Trop Med Hyg* 36:435-42). Therefore; we have developed a menu of point mutations conferring temperature-sensitive (ts), small-plaque (sp), and attenuation (att) phenotypes capable of attenuating DEN4 viruses to a varying degree (Example 1). We have previously described 20 mutant viruses that exhibit a ts, but not sp, phenotype in Vero cells or HuH-7 liver cells and that show attenuated replication in mouse brain (Example 1). Addition of such mutations to 2AΔ30 or to other dengue virus vaccine candidates is envisioned as yielding vaccine candidates that exhibit a more satisfactory balance between attenuation and immunogenicity.

In the present Example, we have extended our analysis of the panel of 1,248 DEN4 virus clones previously generated by mutagenesis with 5-fluorouracil (5-FU) (Example 1), by identifying a set of 22 sp mutant viruses, some of which also have a ts phenotype. Small plaque mutant viruses were sought since such viruses are often attenuated in humans (Bhamarapravati, N. & Yoksan, S. 1997 in: *Dengue and Dengue Hemorrhagic Fever* D. J. Gubler & G. Kuno eds. pp. 367-377 CAB International, New York; Butrapet, S. et al. 2000 *J Virol* 74:3011-9; Crowe, J. E. Jr. et al. 1994 *Vaccine* 12:783-790; Crowe, J. E. Jr. et al. 1994 *Vaccine* 12:691-699; Eckels, K. H. et al. 1980 *Infect Immun* 27:175-80; Innis, B. L. et al. 1988 *J Infect Dis* 158:876-80; Murphy, B. R. & Chanock, R. M. 2001 in: *Fields Virology* D. M. Knipe, et al. Eds, Vol. 1, pp. 435-468 Lippincott Williams & Wilkins, Philadelphia; Takemoto, K. K. 1966 *Prog Med Virol* 8:314-48). Because natural infection with dengue viruses and vaccination with 2AΔ30 may be associated with liver toxicity in humans, we identified mutant viruses with restricted replication in human liver cells. Accordingly, viruses were screened for plaque size and temperature-sensitivity in the human hepatoma cell line, HuH-7, as well as in Vero cells. Here we describe the ts phenotype, nucleotide sequence, and growth properties in suckling mice of 22 sp DEN4 mutant virus clones.

Cells and Viruses.

WHO Vero cells (African green monkey kidney cells) and HuH-7 cells (human hepatoma cells) (Nakabayashi, H. et al. 1982 *Cancer Res* 42:3858-63) were maintained as described in Example 1. DEN4 2A virus is a wild type virus derived from a cDNA clone of DEN4 strain 814669 (Dominica, 1981) (Lai, C. J. et al. 1991 *PNAS USA* 88:5139-43; Mackow, E. et al. 1987 *Virology* 159:217-28). The nucleotide sequence of DEN4 2A, the parent of the 5-FU mutant viruses, was previously assigned GenBank accession number AF375822 (Example 1). The DEN4 vaccine candidate, 2AΔ30, (Example 8) contains a 30 nt deletion in the 3' untranslated region (UTR) which removes nucleotides 10,478-10,507 (Men, R. et al. 1996 *J Virol* 70:3930-7). The cDNA clones p4, a modified derivative of the DEN4 2A cDNA clone, and p4Δ30 were used to generate recombinant wild type and attenuated viruses, rDEN4 and rDEN4Δ30, respectively (Example 8). GenBank accession numbers were previously assigned as follows (virus: accession number): DEN4 strain 814669: AF326573; 2AΔ30: AF326826; rDEN4: AF326825; rDEN4Δ30: AF326827.

Generation and biological cloning of mutant viruses with a sp phenotype. The generation of 1,248 virus clones from a pool of 5-fluorouracil-mutagenized DEN4 2A has been previously described (Example 1). Briefly, monolayers of Vero cells were infected with DEN4 2A at a multiplicity of infection (MOI) of 0.01 and overlaid with MEM supplemented with 2% FBS and 1 mM 5-fluorouracil (5-FU) (Sigma, St. Louis, Mo.), which reduced replication of DEN4 2A 100-fold. Vero cells in 96-well plates were inoculated with the 5-FU treated virus suspension, and virus clones were harvested from plates receiving terminally-diluted virus. A total of 1,248 virus clones were generated from the cultures treated with 1 mM 5-FU. Two virus clones, 2A-1 and 2A-13, were generated in the same manner from control cultures not treated with 5-FU and served as parallel-passaged control viruses with a wild type phenotype.

Evaluation of in vitro plaque size and temperature sensitivity. The 1,248 5-FU-mutagenized virus clones were screened for temperature sensitivity by assessing virus replication at 35° C. (permissive temperature) and 39° C. (restrictive temperature) in Vero and HuH-7 cells. Cell monolayers in 96-well plates were inoculated with serial ten-fold dilutions of virus and replicate plates were incubated at 35° C. and 39° C. for five days in temperature-controlled water baths. Virus replication was determined by immunoperoxidase staining as previously described (Example 1). A collection of 193 5-FU virus clones demonstrated a 100-fold or greater reduction in titer at 39° C. in either cell line, and these presumptive is viruses were further characterized. The efficiency of plaque formation (EOP) at permissive and restrictive temperatures and the plaque size of each of the 193 virus clones were determined as follows. Serial ten-fold dilutions of virus suspension were inoculated onto confluent Vero cell and HuH-7 cell monolayers in replicate 24-well plates. After incubation at 35° C. for two hours, monolayers were overlaid with 0.8% methylcellulose (EM Science, Gibbstown, N.J.) in L-15 medium (Quality Biologicals, Gaithersburg, Md.) supplemented with 2% FBS, gentamicin, and L-glutamine. After incubation of replicate plates for five days at 35, 37, 38, or 39° C. in temperature-controlled water baths, plaques were visualized by immunoperoxidase staining and counted as previously described. Plaque size of each of the 193 viruses was evaluated at the permissive temperature (35° C.) and compared to that of DEN4 2A-13 parallel-passaged control virus with a wild type plaque size. Mutant viruses incubated at the permissive temperature of 35° C. which had a plaque size ≤1 mm or ≤0.4 mm (approximately ≤50% the size of wild type DEN4 2A-13) in Vero or HuH-7 cells, respectively, were designated as having a sp phenotype. The level of temperature sensitivity and plaque size of each virus was confirmed in at least two separate experiments. Seventy-five viruses which were confirmed to have a putative ts and/or sp phenotype were biologically cloned an additional two times and phenotypes were re-assessed. Twenty-two of the 75 terminally diluted viruses were found to have a sp phenotype. Sixteen of the 22 sp mutant viruses were also found to have a ts phenotype as defined by a 2.5 or 3.5 $\log_{10}$PFU/ml reduction in virus titer in Vero or HuH-7 cells, respectively, at restrictive temperature compared to the permissive temperature of 35° C. as previously described (Example 1). Twenty of the 75 terminally-diluted viruses were found to have a ts phenotype without a sp phenotype and were previously described (Example 1). The remainder of the 75 viruses did not meet either criteria for a ts or sp mutant virus.

Evaluation of sp mutant viruses for restricted replication in suckling mice. Animal experiments were carried out in accordance with the regulations and guidelines of the National Institutes of Health, Bethesda, Md. Growth of DEN4 5-FU mutant viruses was determined in Swiss Webster suckling mice (Taconic Farms, Germantown, N.Y.). Groups of six seven-day-old mice were inoculated intracerebrally with $10^4$ PFU of virus in 30 μl Opti-MEM I (Invitrogen) and the brain of each mouse was removed five days later and individually analyzed as previously described (Example 1). Clarified supernatants of 10% suspensions of mouse brain were frozen at −70° C., and the virus titer was determined by plaque assay in Vero cells.

Determination of the complete genomic sequence of the sp mutant viruses. The nucleotide sequence of the 5-FU-mutagenized DEN4 viruses was determined as described in Example 8. Briefly, genomic RNA was isolated from virus clones and cDNA was prepared by reverse transcription and served as template for the generation of overlapping PCR fragments. A panel of primers was designed to sequence both strands of the PCR product from which consensus sequences were assembled and analyzed. The nucleotide sequence of the 5' and 3' regions of the virus genome was determined after circularization of the RNA genome as described in Example 8.

Figures 3A, 3B, 3C:
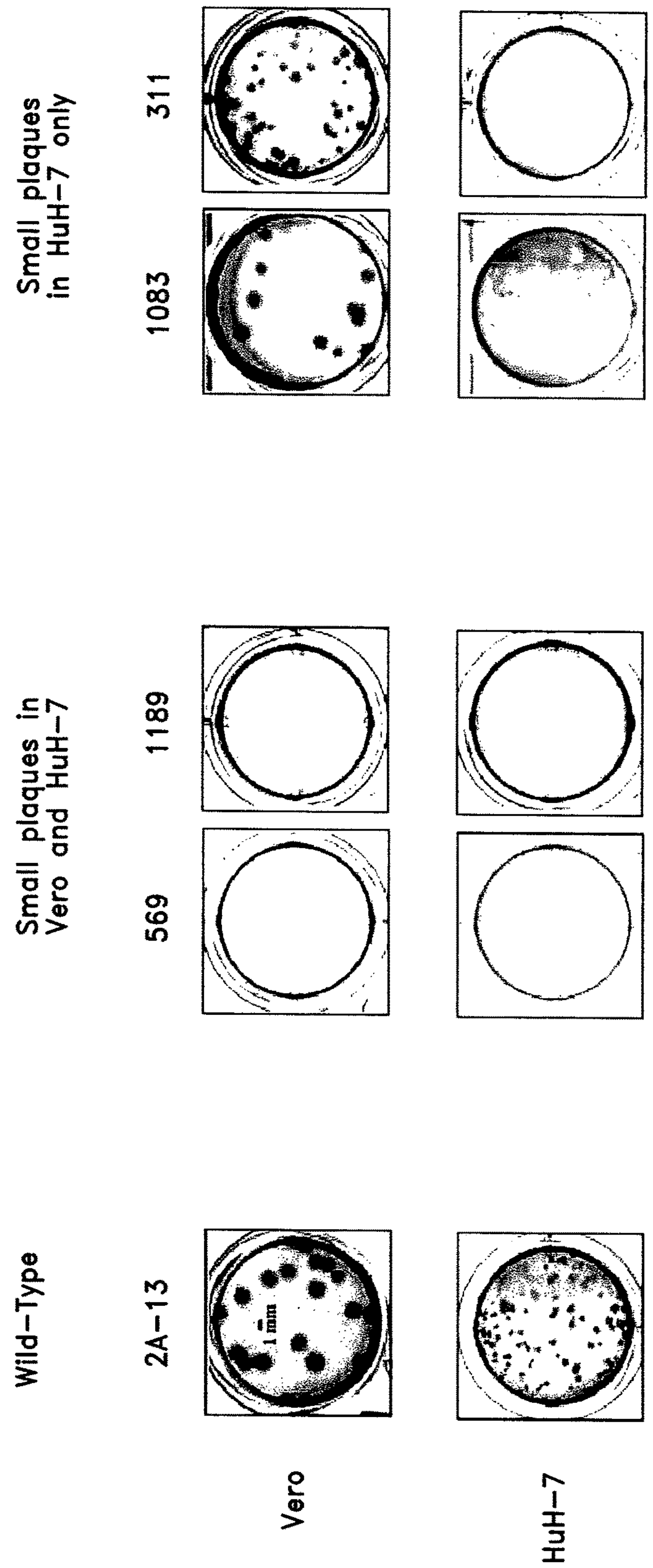
FIGS. 3A-3C show plaque size phenotypes of representative 5-FU mutant DEN4 viruses. Serial ten-fold dilutions of wild-type DEN4 2A-13 (FIG. 3A), 5-FU mutant viruses #569 and #1189 (FIG. 3B), and 5-FU mutant viruses #1083 and #311 (FIG. 3C) were inoculated onto confluent Vero and HuH-7 cell monolayers in 24-well plates. After incubation at 35° C. for two hours, monolayers were overlaid with 0.8% methylcellulose culture media. Following incubation at 35° C. for five days, plaques were visualized by immunoperoxidase staining. Viruses which had a plaque size that was ≤1 mm (approximately ≤50% the size of wt DEN4 2A-13) at the permissive temperature of 35° C. were designated as having the small-plaque (sp) phenotype. Mutant viruses #569 and #1189 (FIG. 3B) were sp in both Vero and HuH-7 cells, and #311 and #1083 (FIG. 3C) were sp in only HuH-7 cells.

Identification of DEN4 5-fluorouracil mutant viruses with a sp phenotype. The generation of a panel of 1,248 virus clones from a wild type DEN4 2A virus suspension mutagenized by 5-FU has been described previously (Example 1). In the present study twenty-two mutant viruses with a sp phenotype were identified. The plaque size of representative mutant viruses is illustrated in FIG. 3. The plaque size of DEN4 2A-13 virus (a parallel-passaged virus with a wild type phenotype derived from control cultures not treated with 5-FU) was consistently smaller in HuH-7 cells than that observed in Vero cells (FIG. 3A). Mutant viruses #569 and #1189 (FIG. 3B) were sp in both Vero and HuH-7 cells. In contrast, 5-FU mutant virus clones #311 and #1083 (FIG. 3C) were sp in only HuH-7 cells, suggesting a liver cell-specific defect in replication within this phenotypic group. As indicated in Table 7, five mutant viruses were found to have a sp phenotype in both Vero and HuH-7 cells while 17 viruses had a sp phenotype in only HuH-7 cells. Each 5-FU mutant virus clone was compared for a sp or ts phenotype with three control viruses, 2A-13, wild type rDEN4, and rDEN4Δ30. The recombinant viruses, rDEN4 and rDEN4Δ30, each had a plaque size in Vero and HuH-7 cells similar to that of DEN4 2A-13 indicating that the Δ30 mutation does not confer a sp phenotype (Table 7).

Most of the sp 5-FU mutant viruses also had a ts phenotype in Vero and/or HuH-7 cells (Table 7) since mutant viruses were initially screened for temperature sensitivity. Temperature-sensitivity was defined as a 2.5 or 3.5 $\log_{10}$PFU/ml reduction in virus titer in Vero or HuH-7 cells, respectively, at restrictive temperature compared to the permissive temperature of 35° C. as previously defined (Example 1). Three mutant viruses (#574, #1269 and #1189) were sp and ts in both Vero and HuH-7 cells, while nine mutant viruses (#506-326 in Table 7) were found to be ts in both cell types but sp only in HuH-7 cells. Four viruses (#1104, 952, 738, and 1083) were found to have a wild type phenotype in Vero cells but were both sp and ts in HuH-7 cells. These four mutant viruses each had a 6,000- to 600,000-fold reduction in virus titer at 39° C. in HuH-7 cells with only a 6- to 40-fold reduction at 39° C. in Vero cells. Finally, sp mutant viruses were identified which did not have a ts phenotype in either cell line; two of these viruses (#569 and #761) were sp in both Vero and HuH-7 cells and four viruses (#1096-1012) were sp in only HuH-7 cells (Table 7). As described previously, the Δ30 mutation did not confer temperature-sensitivity in either cell line (Example 1).

The sp 5-FU mutant viruses have restricted replication in suckling mouse brain. The 22 sp DEN4 5-FU mutant viruses were evaluated for their ability to replicate in the brain of one-week-old suckling mice. As a marker for in vivo attenuation, their level of replication was compared with that of the parallel-passaged control virus with a wild type phenotype, 2A-13 (Table 7). Nineteen of 22 sp mutant viruses had a greater than 100-fold reduction in virus replication in the brain of suckling mice compared to 2A-13 and nine viruses had a reduction of greater than 10,000-fold.

The five mutant viruses which were sp in both Vero and HuH-7 cells were 5,000-fold to 100,000-fold restricted in replication compared to 2A-13. Two of these mutant viruses, #569 and #761, were not ts in either cell line but had a reduction in virus titer of greater than 10,000-fold in mouse brain, indicating that the sp phenotype in both Vero and HuH-7 cells is an important surrogate marker for attenuated replication in suckling mouse brain. 5-FU mutant viruses which were sp in only HuH-7 cells had a more variable range of replication in mouse brain. Three viruses had a mean reduction in virus titer of less than 10-fold when compared to 2A-13 virus. However, 8 of 13 viruses which were ts in Vero and/or HuH-7 cells but sp in only HuH-7 cells had a greater than 5,000-fold reduction in virus replication. The results of the in vivo replication analysis of the previously described 20 ts 5-FU mutant viruses (Example 1) and the 22 sp mutant viruses are summarized in Table 8. Mutant viruses with both a sp and ts phenotype were found to have a significantly greater level of attenuation in the brain of suckling mice when compared to viruses with only a ts phenotype.

Sequence analysis of the sp 5-FU mutant viruses. To initiate an analysis of the genetic basis of the ts, sp, or att phenotype of the 22 sp mutant viruses, the complete nucleotide sequence of each virus genome was determined and is summarized in Table 9 (sp in Vero and HuH-7 cells) and Table 10 (sp in only HuH-7 cells). All identified mutations were nucleotide substitutions, as deletions or insertions were not observed. Point mutations were distributed throughout the genome, including the 3' UTR as well as in all coding regions. Because all 5-FU mutant viruses were found to have at least two mutations (two to six), the observed phenotypes cannot be directly attributed to a specific mutation. The majority of sp viruses also contained translationally silent point mutations (none to four) in the structural or non-structural coding regions. However, these silent mutations are not expected to contribute to the observed phenotypes. Six of the 22 sp mutant viruses (Tables 9 and 10) were found to have mutations in only the NS genes and/or the 3' UTR, indicating that the sp phenotype can be conferred by mutations outside of the structural genes.

Presence of identical mutations in multiple 5-FU mutant viruses. Analysis of the complete nucleotide sequence data for the 5-FU mutant viruses identified several repeated mutations which were present in two or more viruses. Such mutations were also identified previously during our analysis of twenty 5-FU mutant viruses with a ts but not sp phenotype (Example 1). Because these mutations occurred in viruses together with additional mutations, the contribution of the repeated mutations to the observed sp, ts, and att phenotypes remains empirical. Table 11 lists the repeated mutations found among the 20 ts (not sp) mutant viruses described previously (Example 1) and the 22 sp mutant viruses described here. Repeated mutations were identified in the following genes: two in E, two in NS3, five in NS4B, one in NS5, and two in the 3' UTR. Interestingly, within a thirty nucleotide region of NS4B (nt 7153-7182), there were five different nucleotide substitutions which were found in sixteen viruses. Also at nt 7,546 in NS4B, an amino acid substitution (Ala→Val) was found in 10 different 5-FU mutant viruses. The significance of these repeated mutations in NS4B as well as in other DEN4 genomic regions remains empirical, but a reasonable explanation for this phenomenon is that these mutations are involved in adaptation of DEN4 virus for efficient growth in Vero cells, as further discussed in Example 6.

Discussion. As part of a molecular genetic vaccine strategy, we have developed attenuating mutations that are envisioned as being useful in the development of a live attenuated tetravalent dengue virus vaccine. Specifically, mutations which restrict replication of the vaccine virus in human liver cells were generated since there was some residual virulence of the rDEN4Δ30 vaccine candidate for the liver of humans. Mutant viruses with a sp phenotype were sought in both Vero cells and HuH-7 human liver cells, in order to identify host-range mutant viruses that were specifically restricted in replication in HuH-7 cells (sp in HuH-7 but not in Vero). Such mutations are envisioned as being useful in limiting replication of a candidate vaccine in the liver of vaccinees while preserving both efficient replication in Vero cells and immunogenicity in vivo.

Several observations from the present study indicate that sp mutations confer an att phenotype in vivo. This is not surprising since attenuation in suckling mouse brain has been reported for live DEN virus vaccine candidates possessing sp phenotypes, including the DEN2 PDK-53 and DEN2 PR-159/S-1 vaccine strains (Bhamarapravati, N. & Yoksan, S. 1997 in: *Dengue and Dengue Hemorrhagic Fever* D. J. Gubler & G. Kuno eds. pp. 367-377 CAB International, New York; Butrapet, S. et al. 2000 *J Viral* 74:3011-9; Eckels, K. H. et al. 1980 *Infect Immun* 27:175-80; Innis, B. L. et al. 1988 *J Infect Dis* 158:876-80). Each of 22 DEN4 5-FU mutant viruses with a sp phenotype (some of which were also ts) in either Vero or HuH-7 cells manifested restricted replication in the brains of mice. Six 5-FU mutant viruses with a sp phenotype in the absence of a ts phenotype were more attenuated in the brains of suckling mice than mutant viruses with solely a ts phenotype (Example 1), indicating that the sp phenotype specifies a greater level of attenuation for mouse brain than does the ts phenotype. Mutant viruses with both a ts and sp phenotype had an even greater reduction in replication, further indicating that the attenuation conferred by the ts and sp phenotypes can be additive. Importantly, seventeen of the 22 sp mutant viruses were host-range sp mutant viruses, being sp only in HuH-7 cells. Since such mutations are envisioned as being useful in restricting the replication of a DEN4 virus in human liver cells, we used nucleotide sequence analysis to determine the genetic basis of the sp phenotype.

Analysis of the complete genomic sequence of the 22 sp DEN4 viruses revealed substitutions in the 3' UTR as well as coding mutations in all genes except NS4A. It was first noted that several specific mutations were present in two or more of the 22 sp DEN4 mutant viruses and that many of these same mutations were also previously identified among the set of 20 ts DEN4 Mutant viruses (Example 1). Since flaviviruses can rapidly accumulate mutations during passage in tissue culture (Dunster, L. M. et al. 1999 *Virology* 261:309-18; Mandl, C. W. et al. 2001 *J Virol* 75:5627-37), many of these over-represented mutations, previously referred to as putative Vero cell adaptation mutations (Example 1), likely promote efficient replication in Vero cells and were selected unintentionally during the biological cloning of the mutant viruses. The effect of these mutations on DEN virus replication in Vero cells, the proposed substrate for vaccine manufacture, is discussed in Example 6.

The sp mutations identified among the 5-FU mutant viruses are envisioned as being useful in several different approaches for the development of DEN virus vaccine strains. As described above for the generation of antigenic chimeric viruses, one or more sp attenuating mutations are envisioned as being added to the attenuated DEN4Δ30 genetic background to supplement the att phenotype of the Δ30 mutation. A second approach is to introduce a sp attenuating mutation, with or without Δ30, into infectious cDNA clones of the other three DEN serotypes. The ability to transfer mutations among genetically-related viruses and maintain similar att phenotypes has been previously demonstrated (Skiadopoulos, M. H. et al. 1999 *Virology* 260:125-35). These distinct strategies are envisioned as being useful as separate or complementary approaches to the construction of a tetravalent DEN virus vaccine, underlining the importance of the identification of a large panel of att mutations within the DEN viruses.

Example 3

Recombinant DEN4 Viruses Containing Mutations Identified in 5-FU Mutant Viruses Show Restricted Replication in Suckling Mouse Brain and in SCID Mice Transplanted With Human Liver Cells Data was presented in Examples 1 and 2 that summarizes the generation, characterization and sequence analysis of 42 attenuated mutant DEN4 viruses. For three of the mutant viruses (#239, 489, and 773) with a single missense mutation at nt position 4995 in NS3, it was clear that the identified mutation specified the ts and att phenotypes. This conclusion was confirmed in Example 1 by tissue culture and in vivo characterization of rDEN4-4995, a recombinant virus into which the 4995 mutation had been introduced by site-directed mutagenesis. In this analysis, rDEN4-4995 exhibited the same level of temperature sensitivity and attenuation as 5-FU mutant viruses #239, 489, and 773. The individual mutation(s) in the remaining 5-FU mutant viruses that specify the observed phenotypes remains to be identified, since most of these viruses possess more than one nucleotide substitution. We have conducted an analysis to identify the mutations in a subset of the other 39 mutant viruses that specify the ts, sp, and att phenotypes by introduction of each mutation into the wt DEN4 cDNA (p4) and evaluation of the phenotypes of the resulting recombinant DEN4 viruses bearing the individual mutations. Previous studies of a DEN2 virus vaccine candidate (Butrapet, S. et al. 2000 *J Virol* 74:3011-9) as well as other virus vaccines (Whitehead, S. S. et al. 1999 *J Virol* 73:871-7) have demonstrated the utility of this approach for the identification of the genetic basis of attenuation.

As described in Examples 1 and 2, 19 5-FU mutant viruses were identified which were found to contain coding mutations in only the NS genes and/or nucleotide substitutions in the 5' or 3' UTR which would facilitate the generation of antigenic chimeric viruses. In the present example, the genetic basis of the observed sp, ts, and mouse brain att phenotypes was identified for these 19 viruses using reverse genetics to generate recombinant DEN4 (rDEN4) viruses containing individual mutations identified in the panel of DEN4 mutant viruses. In addition, the 19 5-FU mutant viruses were evaluated for replication in a novel small animal model for DEN4 virus replication, SCID mice transplanted with HuH-7 cells (SCID-HuH-7), and the genetic basis of the att viruses was identified using mutant rDEN4 viruses. Also presented are findings describing the generation and characterization of a recombinant virus containing two of the identified attenuating mutations as well as combination of select 5-FU mutations with the Δ30 mutation.

Generation of rDEN4 viruses containing 5-FU mutations. The methods used for the generation of rDEN4 viruses are outlined in FIG. 4 and are similar to those described in Example 1. Briefly, the p4 cDNA was digested with the appropriate restriction enzymes and the resulting fragments were subcloned into a modified pUC119 vector. For Kunkel mutagenesis, single-stranded DNA preparations of the pUC-NS vectors were made, and primers were designed to individually introduce mutations that were present in the 5-FU mutant viruses. The sequences of the 41 mutagenic oligonucleotides used to generate the single-mutation recombinant viruses are presented in Table 12. Primers were designed to co-introduce or co-ablate a translationally-silent restriction enzyme site in the cDNA, which greatly facilitates the screening and identification of cDNA clones possessing the mutant sequence. Fragments containing the introduced mutations were cloned back into p4, and nucleotide sequence analysis confirmed the presence of the nucleotide changes. A total of 33 rDEN4 viruses was generated which contained each of the individual mutations present in the 19 5-FU mutant viruses containing only coding mutations in the NS genes and/or nucleotide substitutions in the 5' or 3' UTR. An additional 8 rDEN4 viruses were generated from mutations identified in the remaining panel of 42 5-FU mutant viruses.

A cDNA clone was also generated which combined the mutations identified at nt position 4995 in NS3 and 7849 in NS5. The 7849 mutation was introduced into the p4-4995 cDNA clone by replacing the XmaI-PstI fragment with that derived from the p4-7849 cDNA clone. The presence of both mutations was confirmed by sequence analysis. The Δ30 mutation was introduced into the 3' UTR of the individual mutant cDNA clones by replacing the MluI-KpnI fragment with that derived from the p4Δ30 cDNA clone, and the presence of the deletion was confirmed by sequence analysis.

Recombinant viruses were recovered by transfection of Vero or C6/36 cells with RNA transcripts derived from the mutant cDNA clones as described in Example 1. Recovered viruses were terminally diluted twice and working stocks of viruses were prepared in Vero cells. Each of the mutant cDNA clones was recovered after transfection as expected since the 5-FU mutant viruses containing these mutations were viable.

Characterization of ts and att phenotypes of the rDEN4 viruses containing introduced mutations. Of the 19 5-FU mutant viruses with mutations in only NS genes and/or the 5' or 3' UTR, six had an sp phenotype (Table 13), ten had a is phenotype in Vero and HuH-7 cells (Table 14), and three had a ts phenotype in only HuH-7 cells (Table 15). For the six sp 5-FU mutant viruses, #738, 922, 1081, 1083, 1136, and 1189, seventeen mutations identified by sequence analysis resulted in a coding change or a nucleotide change in the UTR and each was engineered into an individual DEN4 cDNA clone. Virus containing each defined mutation was successfully recovered and propagated and was tested for efficiency of plaque formation in Vero and HuH-7 cells at various temperatures, plaque size phenotype, and growth properties in suckling mice using methods previously described in Examples 1 and 2.

Table 13 lists the phenotypes of the six sp 5-FU mutant parent viruses and those of the 17 rDEN4 viruses encoding single mutations present in the parent virus. For example, 5-FU mutant #1189 (parent), which was ts and sp in both cell lines and had an almost 10,000-fold reduction in replication in suckling mouse brain, contained 4 coding mutations at nt position 3303 in NS1, 4812 and 5097 in NS3, and 7182 in NS4B. Analysis of the four rDEN4 viruses containing each of these mutations indicated that rDEN4-5097 had a ts, sp, and att phenotype while rDEN4-3303, rDEN4-4812, and rDEN4-7182 had no discernible phenotypes, indicating that the mutation at nt 5097 was responsible for the phenotype observed in the 5-FU parent, #1189. Thus, analysis of the relative contributions of the four mutations present in the 5-FU mutant #1189 to its attenuation phenotype provides the framework for a similar analysis of the remaining 5-FU mutant viruses. This analysis specifically demonstrates the methods used to identify mutations contributing to the observed phenotype. The ts, sp, and att phenotypes of 5-FU parent viruses #738, 922, 1081, and 1083, were similarly attributed to single mutations 3540, 4306, 2650, and 10634, respectively. However, two separate mutations (3771 and 4891) contributed to the phenotypes of 5-FU mutant virus #1136.

Table 14 lists the genetic basis of the ts and mouse brain attenuation for the ten 5-FU mutant viruses with ts phenotypes in both Vero and HuH-7 cells. As described in Example 1, the 4995 mutation which is the only mutation present in three 5-FU mutant viruses, #239, #489, and #773, was found to confer a ts and att phenotype, confirming the genetic basis for the phenotypes exhibited by these viruses. In three separate experiments, the rDEN4-4995 virus was found to have an approximately 1,000-fold decrease in replication in the brains of suckling mice when compared to that of wild-type virus (Table 6 and 14). The 4995 mutation is also present in 5-FU mutant viruses #473, #759, and #816, each of which has additional mutations. The ts and att phenotypes observed in these viruses can be attributed to the 4995 mutation since the additional mutations did not show discernible phenotypes. Interestingly, 5-FU mutant virus #938 has the 4995 mutation and an additional mutation at nt 3442 in NS1 with both mutations independently conferring restricted replication in mouse brain. The remaining three 5-FU parent viruses in Table 14, #173, #509, and #1033, were found to each contain a single mutation responsible for the att phenotype: 7849, 8092, and 4907, respectively.

Three 5-FU mutant viruses, #686, #992, and #1175 with HuH-7 cell-specific is phenotypes are listed in Table 15. Mutations in NS3 (5695) and NS5 (10186) were found to confer the phenotypes observed for parent virus #992 and #1175. Interestingly, two mutations in NS2A, 3575 and 4062, were found to result in a synergistic increase in the level of attenuation. Both individual mutations had an approximately 100-fold decrease in virus replication in the brain while the parent virus with both mutations had an almost 10,000-fold reduction. Table 16 lists two additional mutations with an att phenotype, 4896 and 6259 in NS3.

Replication of DEN4 viruses in SCID mice transplanted with HuH-7 cells. Since DEN viruses replicate poorly in the liver of mice and corresponding studies are impractical to conduct in non-human primates, an animal model that evaluates the in vivo level of replication of DEN virus in liver cells was developed based on a recent report examining the replication of DEN virus in SCID mice transplanted with a continuous cell line of human liver tumor cells (An, J. et al. 1999 *Virology* 263:70-7). SCID mice transplanted with human continuous cell lines, primary cells, or organized tissues have similarly been used to study the replication of other viruses which lack a suitable small animal model (Mosier, D. E. 2000 *Virology* 271:215-9). In our study, SCID mice were transplanted with HuH-7 cells since DEN4 virus replicated efficiently in these cells in tissue culture and since these were the cells used to define the host-range phenotype. These studies are envisioned as addressing the utility of examining DEN virus infection in SCID mouse-xenograft models for vaccine development (An, J. et al. 1999 *Virology* 263:70-7; Lin, Y. L. et al. 1998 *J Virol* 72:9729-37).

To further examine the in vivo growth properties of the 19 5-FU mutant DEN4 viruses with mutations in only the NS genes and/or the 3' UTR and selected corresponding rDEN4 mutant viruses, replication was assessed in SCID mice transplanted with HuH-7 cells (SCID-HuH-7). For analysis of DEN4 virus replication in SCID-HuH-7 mice, four to six week-old SCID mice (Tac:Icr:Ha(ICR)-Prkdc$^{scid}$) (Taconic Farms) were injected intraperitoneally with $10^7$ HuH-7 cells suspended in 200 μl phosphate-buffered saline (PBS). In preparation for transplantation, HuH-7 cells were propagated in cell culture as described above and harvested by trypsinization at approximately 80% confluence. Cells were washed twice in PBS, counted, resuspended in an appropriate volume of PBS, and injected into the peritoneum of mice. Tumors were detected in the peritoneum five to six weeks after transplantation, and only mice with apparent tumors were used for inoculation. Mice were infected by direct inoculation into the tumor with $10^4$ PFU of virus in 50 μl Opti-MEM I. Mice were monitored daily for seven days and serum for virus titration was obtained by tail-nicking on day 6 and 7. Approximately 400 μl blood was collected in a serum separator tube (Sarstedt, Germany), centrifuged, and serum was aliquoted and stored at −70° C. The virus titer was determined by plaque assay in Vero cells. Seven days after infection, most mice developed morbidity and all mice were sacrificed. Tumors were excised and weighed to confirm uniformity of the experimental groups.

Preliminary experiments indicated that SCID-HuH-7 mice inoculated with DEN4 2A-13 directly into the tumor developed viremia with maximum levels (up to 8.0 $log_{10}$PFU/ml serum) achieved on day 5 (Table 17). Virus could also be detected in brain, liver, and tumor homogenates.

The level of viremia in SCID-HuH-7 mice infected with parental 5-FU or rDEN4 mutant viruses was compared with that of the parallel-passaged control virus, 2A-13, or rDEN4, respectively. Results of 4 separate experiments indicated that the vaccine candidate, rDEN4Δ30, had an almost 10-fold reduction in virus replication compared to wild type rDEN4 (Table 13) which reflects the apparent attenuation of the rDEN4Δ30 vaccine candidate in humans (Example 8). Results in Tables 13 to 15 indicate that three 5-FU mutant viruses had a greater than 100-fold reduction in viremia in the SCID-HuH-7 mice compared to wild type 2A-13 virus: #1081, #1.083, and #1189. The common phenotype among these viruses was a sp phenotype in HuH-7 cells. Analysis of the genetic basis of the att phenotype in these parent 5-FU mutant viruses identified three individual mutations in NS1, NS3, and the 3' UTR which conferred at least a 100-fold reduction in viremia. Specifically, rDEN4-2650 (NS1), rDEN4-5097 (NS3), and rDEN4-10634 (3' UTR) manifested a 2.2, 3.6, and 4.3 $log_{10}$PFU/ml reduction in peak titer of viremia compared to rDEN4, respectively. These mutations also conferred the att phenotype in suckling mouse brain. 5-FU mutant virus #738 and #509 had a reduction in viremia in the SCID-HuH-7 mice compared to wild type 2A-13 of 1.9 and 1.5 $log_{10}$PFU/ml, respectively, and the genetic basis for these phenotypes is envisioned as being assessed on an empirical basis.

This analysis of the genetic basis of the phenotypes specified by the mutations in the 5-FU mutant viruses that manifested restricted replication in SCID-HuH-7 mice indicated that (1) three separate mutations conferred the att phenotype; (2) these mutations were located in two proteins, NS1 and NS3, and in the 3' UTR; (3) these three mutations were fully responsible for each of the cell culture (ts or sp) and in vivo (attenuation in mouse brain and SCID-HuH-7 mice) phenotypes of the parent viruses; and (4) two of the three mutations specify the host-range sp phenotype (sp on HuH-7 only) and therefore are envisioned as being useful in a vaccine virus. Although the relevance of such SCID-transplant models to virus replication and disease in humans is unknown, the identification of three novel mutations which restrict DEN4 virus replication in SCID-HuH-7 mice is envisioned as facilitating an examination of the correlation between the att phenotype in SCID-HuH-7 mice with that in rhesus monkeys or humans. Such mutations, specifically the host-range sp mutations, are envisioned as being useful in conjunction with the Δ30 or other mutation to decrease the residual virulence of rDEN4Δ30 or other dengue virus for the human liver, and studies are envisioned as being conducted to construct such rDEN4 viruses and evaluate them in monkeys and humans (Example 8).

Combination of two 5-FU mutations results in an additive ts phenotype. The ability to combine individual mutations in rDEN4 virus as a means to modulate the phenotype of the resulting double mutant virus is a major advantage of using recombinant cDNA technology to generate or modify dengue virus vaccine candidates. Addition of multiple ts and att mutations to recombinant vaccine viruses is envisioned as improving the phenotypic stability of the double recombinant due to the decreased possibility of co-reversion of the two mutations to wild-type virulence (Crowe, J. E. Jr. et al. 1994a *Vaccine* 12:783-790; Skiadopoulos, M. H. et al. 1998 *J Virol* 72:1762-8; Subbarao, E. K. et al. 1995 *J Virol* 69:5969-5977; Whitehead, S. S. et al. 1999 *J Virol* 73:871-7). The mutations identified at nt position 4995 in NS3 and 7849 in NS5 were combined in a single p4 cDNA clone and a recombinant virus, designated rDEN4-4995-7849, was recovered and evaluated for its ts and att phenotypes (Table 18). rDEN4-4995-7849 was more ts than either recombinant virus containing the individual mutations (Table 18), indicating the additive effect of the two ts mutations. The rDEN4-4995-7849 virus had a greater than 10,000-fold reduction in replication in the brains of suckling mice. The reduction in replication of the double mutant virus was only slightly increased over that of rDEN4-7849, however, a difference in the level of replication between rDEN4-4995-7849 and rDEN4-7849 would be difficult to detect since the level of replication of both viruses was close to the lower limit of detection (2.0 $log_{10}$PFU/g brain).

Combination of selected 5-FU mutations with the Δ30 mutation confers increased attenuation of rDEN4Δ30 for the brains of suckling mice. To define the effect of adding individual mutations to the attenuated rDEN4Δ30 background, five combinations have been constructed: rDEN4Δ30-2650, rDEN4Δ30-4995, rDEN4Δ30-5097, rDEN4Δ30-8092, and rDEN4Δ30-10634. Addition of such missense mutations with various ts, sp, and att phenotypes is envisioned as serving to decrease the reactogenicity of rDEN4Δ30 while maintaining sufficient immunogenicity.

The Δ30 mutation was introduced into the 3' UTR of the individual mutant cDNA clones by replacing the MluI-KpnI fragment with that derived from the p4Δ30 cDNA clone, and the presence of the deletion was confirmed by sequence analysis. Recombinant viruses were recovered by transfection in C6/36 cells for each rDEN4 virus. However, upon terminal dilution and passage, the rDEN4Δ30-5097 virus was found to not grow to a sufficient titer in Vero cells and was not pursued further. This is an example of a cDNA in which the 5-FU mutation and the Δ30 mutation are not compatible for efficient replication in cell culture. To begin the process of evaluating the in vivo phenotypes of the other four viruses which replicated efficiently in cell culture, rDEN4 viruses containing the individual mutations and the corresponding rDEN4Δ30 combinations were tested together for levels of replication in suckling mouse brain. The results in Table 19 indicate that addition of each of the mutations confers an increased level of attenuation in growth upon the rDEN4Δ30 virus, similar to the level conferred by the individual 5-FU mutation. No synergistic effect in attenuation was observed between the missense mutations and Δ30. These results indicate that the missense mutations at nucleotides 2650, 4995, 8092, and 10634 are compatible with Δ30 for growth in cell culture and in vivo and can further attenuate the rDEN4Δ30 virus in mouse brain. Further studies in SCID-HuH-7 mice, rhesus monkeys, and humans are envisioned as establishing the effect of the combination of individual mutations and Δ30 upon attenuation and immunogenicity (Example 8).

By identifying the specific mutations in the 5-FU mutant viruses which confer the observed phenotypes, a menu of defined ts, sp, and att mutations is envisioned as being assembled (see Example 7). Numerous combinations of two or more of these mutations are envisioned as being selected with or without the Δ30 mutation. Such mutations and their combinations are envisioned as being useful for the construction of recombinant viruses with various levels of in vivo attenuation, thus facilitating the generation of candidate vaccines with acceptable levels of attenuation, immunogenicity, and genetic stability.

Example 4

Generation of DEN4 Mutant Viruses With Temperature-Sensitive and Mouse Attenuation Phenotypes Through Charge-Cluster-to-Alanine Mutagenesis The previous Examples described the creation of a panel of DEN4 mutant viruses with ts, sp, and att phenotypes obtained through 5-FU mutagenesis. As indicated in these Examples, the attenuating mutations identified in the 5-FU Mutant viruses are envisioned as having several uses including (1) fine tuning the level of attenuation of existing dengue virus vaccine candidates and (2) generation of new vaccine candidates by combination of two or more of these attenuating mutations. In the current example, we created a second panel of mutant viruses through charge-cluster-to-alanine mutagenesis of the NS5 gene of DEN4 and examined the resulting mutant viruses for the ts, sp, and att phenotypes as described in Examples 1 and 2. The charge-cluster-to-alanine mutant viruses recovered demonstrated a range of phenotypes including ts in Vero cells alone, ts in HuH-7 cells alone, ts in both cell types, att in suckling mouse brains, and att in SCID-HuH-7 mice.

The usefulness of mutant viruses expressing these phenotypes has already been described, however charge-cluster-to-alanine mutant viruses possess some additional desirable characteristics. First, the relevant mutations are envisioned as being designed for use in the genes encoding the non-structural proteins of DEN4, and therefore are envisioned as being useful to attenuate DEN1, DEN2, and DEN3 antigenic chimeric recombinants possessing a DEN4 vector background. Second, the phenotype is usually specified by three or more nucleotide changes, rendering the likelihood of reversion of the mutant sequence to that of the wild type sequence less than for a single point mutation, such as mutations identified in the panel of 5-FU mutant viruses. Finally, charge-cluster-to-alanine attenuating mutations are envisioned as being easily combinable among themselves or with other attenuating mutations to modify the attenuation phenotype of DEN4 vaccine candidates or of DEN1, DEN2, and DEN3 antigenic chimeric recombinant viruses possessing a DEN4 vector background.

Charge-Cluster-to-Alanine-Mutagenesis. The cDNA p4, from which recombinant wild type and mutant viruses were generated, has been described in Examples 1, 2, and 3 and in FIG. 4. Charge-cluster-to-alanine mutagenesis (Muylaert, I. R. et al. 1997 *J Viral* 71:291-8), in which pairs of charged amino acids are replaced with alanine residues, was used to individually mutagenize the coding sequence for 80 pairs of contiguous charged amino acids in the DEN4 NS5 gene. Subclones suitable for mutagenesis were derived from the full length DEN4 plasmid (p4) by digestion with XmaI/PstI (pNS5A), PstI/SacII (pNS5B) or SacII/MluI (pNS5C) at the nucleotide positions indicated in FIG. 4. These fragments were then subcloned and Kunkel mutagenesis was conducted as described in Examples 1 and 3. To create each mutation, oligonucleotides were designed to change the sequence of individual pairs of codons to GCAGCX (SEQ ID NO: 69), thereby replacing them with two alanine codons (GCX) and also creating a BbvI restriction site (GCAGC) (SEQ ID NO: 70). The BbvI site was added to facilitate screening of cDNAs and recombinant viruses for the presence of the mutant sequence. Restriction enzyme fragments bearing the alanine mutations were cloned back into the full-length p4 plasmid as described in Examples 1 and 3.

Initial evaluation of the phenotype of the 32 charge-cluster-to-alanine mutant viruses revealed a range in restriction of replication in suckling mouse brain and SCID-HuH-7 mice. To determine whether attenuation could be enhanced by combining mutations, double mutant viruses carrying two pairs of charge-cluster-to-alanine mutations were created by swapping appropriate fragments carrying one pair of mutations into a previously-mutagenized p4 cDNA carrying a second pair of mutations in a different fragment using conventional cloning techniques.

Transcription and Transfection. 5'-capped transcripts were synthesized in vitro from mutagenized cDNA templates using AmpliCap SP6 RNA polymerase (Epicentre, Madison, Wis.). Transfection mixtures, consisting of 1 μg of transcript in 60 μl of HEPES/saline plus 12 μl of dioleoyl trimethylammonium propane (DOTAP) (Roche Diagnostics Corp., Indianapolis, Ind.), were added, along with 1 ml Virus production-serum free medium (VP-SFM) to subconfluent monolayers of Vero cells in 6-well plates. Transfected monolayers were incubated at 35° C. for approximately 18 hr, cell culture medium was removed and replaced with 2 ml VP-SFM, and cell monolayers were incubated at 35° C. After 5 to 6 days, cell culture medium was collected, and the presence of virus was determined by titration in Vero cells followed by immunoperoxidase staining as previously described. Recovered virus was amplified by an additional passage in Vero cells, and virus suspensions were combined with SPG (sucrose-phosphate-glutamate) stabilizer (final concentration: 218 mM sucrose, 6 mM L-glutamic acid, 3.8 mM potassium phosphate, monobasic, and 7.2 mM potassium phosphate, dibasic, pH 7.2), aliquoted, frozen on dry ice, and stored at −70° C.

cDNA constructs not yielding virus after transfection of Vero cells were used to transfect C6/36 cells as follows. Transfection mixtures, as described above, were added, along with 1 ml of MEM containing 10% fetal bovine serum (FBS), 2 mM L-glutamine, 2 mM non-essential amino acids, and 0.05 mg/ml gentamicin, to monolayers of C6/36 cells. Transfected cell monolayers were incubated at 32° C. for 18 hr, cell culture medium was removed and replaced with 2 ml fresh medium, and cell monolayers were incubated at 32° C. After 5 to 6 days, cell culture media were then used to infect Vero cells and incubated for 5-6 days, at which time cell culture media were collected, frozen and titered as described above.

Recovered viruses were biologically cloned by two rounds of terminal dilution in Vero cells followed by an additional amplification in Vero cells. Briefly, virus was initially diluted to a concentration of approximately 20 PFU/ml in VP-SFM and then subjected to a series of two-fold dilutions across a 96-well plate. Virus dilutions were used to infect Vero cell monolayers in a 96-well plate and incubated for 5 to 6 days at 35° C. Following incubation, cell culture media were removed and temporarily stored at 4° C., and the virus-positive cell monolayers were identified by immunoperoxidase staining. Terminal dilution was achieved when ≤25% of cell monolayers were positive for virus. Cell culture medium from a positive monolayer at the terminal dilution was subjected to an additional round of terminal dilution. Following the second terminal dilution, virus was amplified in Vero cells (75 $cm^2$ flask), collected and frozen as previously described.

Assays for temperature-sensitivity and mouse attenuation. Assay of the level of temperature sensitivity of the charge-cluster-to-alanine mutant viruses in Vero and HuH-7 cells and their level of replication in the brain of suckling mice were conducted as described in Example 1 and assay of the level of replication in SCID-HuH-7 mice was conducted as described in Example 3.

Charge-cluster-to-alanine mutant viruses are viable and show temperature-sensitive and mouse attenuation phenotypes. Of 80 full-length DEN4 cDNA constructs containing a single pair of charge-to-alanine mutations, virus was recovered from 32 in either Vero or C6/36 cells (FIG. 5). The level of temperature sensitivity of wt rDEN4, rDEN4Δ30, and the 32 mutant viruses is summarized in Table 20. One mutant virus (645-646) was ts in Vero but not HuH-7 cells and 7 mutant viruses were ts in HuH-7 but not Vero cells. Such mutants whose temperature sensitivity is host-cell dependent are referred to as temperature-sensitive, host-range (tshr) mutants. Thirteen mutant viruses were ts in both cell types, and 11 mutant viruses were not ts on either cell type. Thus a total of 21 mutant viruses were ts with 8 mutant viruses exhibiting an tshr specificity. None of the mutant viruses showed a small plaque phenotype at permissive temperature. Mutant viruses showed a wide range (0 to 10,000-fold) of restricted replication in suckling mouse brain (Table 20). Fourteen mutant viruses were attenuated in suckling mouse brain, arbitrarily defined as a ≥1.5 $log_{10}$-unit reduction in virus titer. There was no correlation between attenuation in mouse brain and temperature sensitivity in either Vero cells (Kendall Rank correlation: P=0.77) or HuH-7 cells (Kendall Rank correlation; P=0.06).

Thirteen mutant viruses that either showed an att phenotype in suckling mouse brain or whose unmutated charged amino acid pair was highly conserved among the four DEN serotypes (see Example 7) were assayed for att in SCID-HuH-7 mice (Table 21). Three of these mutant viruses showed >100-fold decrease in replication relative to wild type DEN4. Overall, mean log reduction from wild type in suckling mice did not show significant correlation with mean log reduction in SCID-HuH-7 mice (Spearman rank correlation, N=13, P=0.06). However, mutant virus 200-201 was unusual in that it showed a high level of restriction in SCID-HuH-7 mice but little restriction in suckling mouse brain. When virus 200-201 was removed from the analysis, restriction of replication in suckling and SCID-HuH-7 mice showed a significant correlation (Spearman rank correlation, N=12, P=0.02).

Combining charge-cluster-to-alanine mutations present in two viruses into one virus can enhance its ts and att phenotypes. Six paired mutations were combined into fourteen double-pair mutant viruses, of which six could be recovered in Vero or C6/36 cells (Table 22). All of the individual paired mutations used in double-pair mutant viruses were ts on HuH-7 cells, none was ts in Vero cells, and for all combinations at least one mutation pair conferred an att phenotype in suckling mouse brain. Evaluation of four of the double-pair mutant viruses (Table 23) revealed that combining charge-cluster-to-alanine mutation pairs invariably resulted in the acquisition of a ts phenotype in Vero cells (4 out of 4 viruses) and often resulted in a lowered shutoff temperature in HuH-7 cells (3 out of 4 viruses). In half of the viruses assayed, combination of charge-cluster-to-alanine mutation pairs resulted in enhanced restriction of replication (10-fold greater than either component mutation) in suckling mouse brain (Table 23) and in. SCID-HuH-7 mice (Table 24).

Summary. The major usefulness of the charge-cluster-to-alanine mutations stems from their design: they are located in the DEN4 non-structural gene region and therefore are envisioned as being useful to attenuate DEN4 itself as well as antigenic chimeric viruses possessing the DEN4 NS gene region. Furthermore, they are predicted to be phenotypically more stable than the single-nucleotide substitution mutant viruses such as the 5-FU mutant viruses. Finally, combinations of mutations are envisioned as being created in order to fine-tune attenuation and to further stabilize attenuation phenotypes.

Example 5

Identification and Characterization of DEN4 Mutant Viruses Restricted in Replication in Mosquitoes Section 1. Identification of Viruses Showing Restriction of Replication in Mosquitoes.

In Examples 1 and 4, DEN4 mutant viruses were generated through 5-FU mutagenesis and charge-cluster-to-alanine mutagenesis, respectively, in order to identify mutations that confer ts, sp and att phenotypes. Another highly desirable phenotype of a dengue virus vaccine is restricted growth in the mosquito host. A dengue virus vaccine candidate should not be transmissible from humans to mosquitoes in order to prevent both the introduction of a dengue virus into an environment in which it is currently not endemic and to prevent the possible loss of the attenuation phenotype during prolonged replication in an individual mosquito host. Loss of the attenuation phenotype could also occur following sustained transmission between humans and mosquitoes. Recently, loss of attenuation of a live attenuated poliovirus vaccine was seen following sustained transmission among humans (CDC 2000 *MMWR* 49:1094).

In the present example, a panel of 1248 DEN4 mutant viruses generated through 5-FU mutagenesis and 32 DEN4 mutant viruses generated through charge-cluster-to-alanine mutagenesis were assayed for restricted growth in mosquito cells. This is a useful preliminary assay for restriction in vivo, since restriction in cultured mosquito cells is often, though not always, associated with poor infectivity for mosquitoes (Huang, C. Y. et al. 2000 *J Viral.* 74:3020-8). Mutant viruses that showed restriction in mosquito cells and robust growth in Vero cells (the substrate for vaccine development, as discussed in Example 6) were targeted for further characterization.

Generation and characterization of the 5-1A1 mutant. The generation and isolation of the panel of 1248 5-FU mutant viruses and the panel of 32 charge-cluster-to-alanine mutant viruses have been described in Examples 1, 2, and 4. Vero and C6/36 cells were maintained as described in Example 1.

Figure 10:
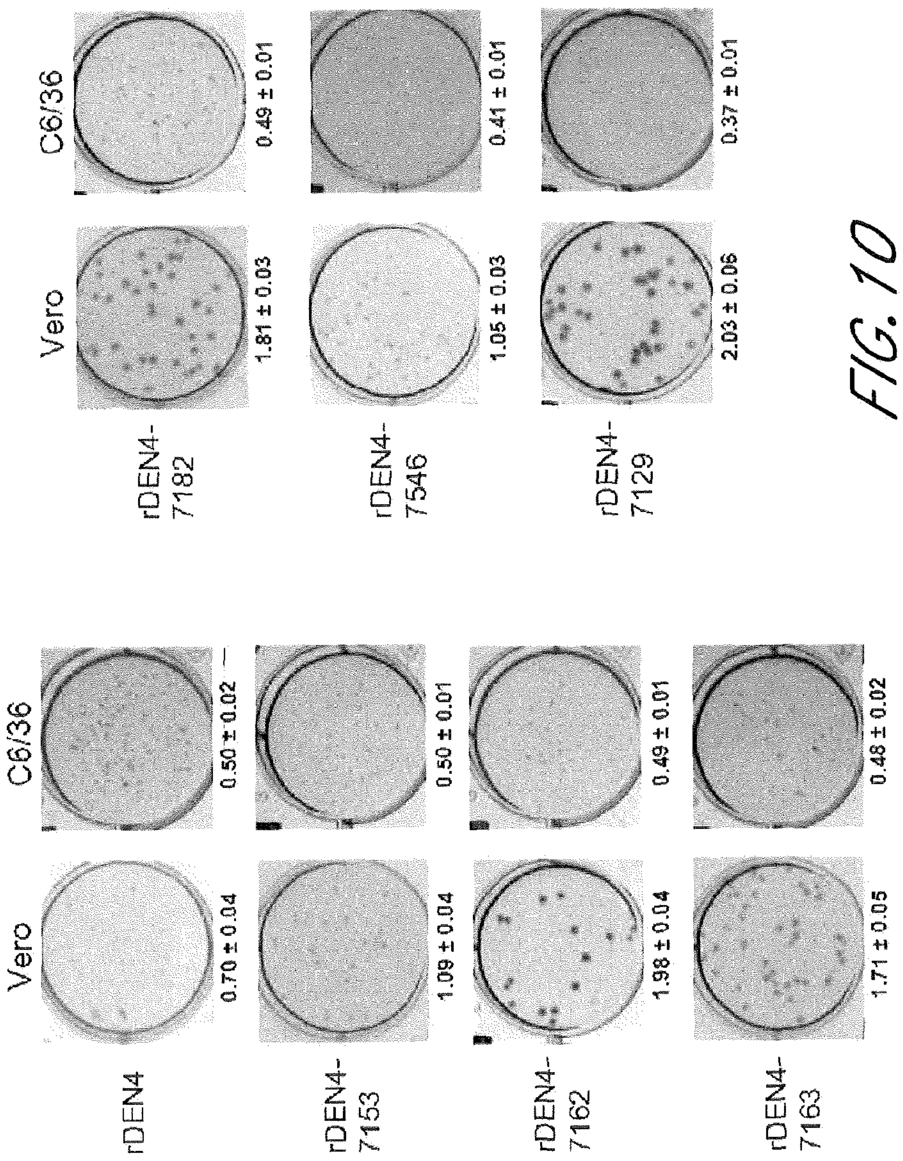
FIG. 10 shows plaque size phenotypes of rDEN4 viruses encoding Vero adaptation mutations. Serial three-fold dilutions of the indicated viruses were inoculated onto confluent Vero and C6/36 cell monolayers in 6-well plates. After incubation at 37° C. (Vero) or 32° C. (C6/36) for two hours, monolayers were overlaid with 0.8% methylcellulose culture media. Following incubation for five days, plaques were visualized by immunoperoxidase staining. Values below each well are the average plaque size in mm standard error. For each of the virus-infected wells, 36 plaques were measured on the digital image of the 6-well plate on Adobe Photoshop at 300% view.

Each of the 1248 5-FU mutant viruses and 32 charge-cluster-to-alanine mutant viruses was titered in C6/36 cell monolayers in 24-well plates at 32° C. and 5% $CO_2$. After 5 days, plaques were immunostained with anti-DEN4 rabbit polyclonal antibody and counted as described in the preceding Examples. Mutant viruses were assayed for one of two phenotypes indicating restricted growth in mosquito cells: either sp in C6/36 cells relative to Vero cells or a ≥3.5 $\log_{10}$PFU/ml decrease in titer between Vero and C6/36 cells at the permissive temperature for each cell type. Two mutant viruses, one generated by 5-FU mutagenesis (#5) and one generated by charge-cluster-to-alanine mutagenesis (rDEN4-356,357), showed reduced plaque size in C6/36 cells. After three terminal dilutions, the 5-FU mutant #5, designated 5-1A1, maintained the reduced plaque size phenotype. Additionally, recombinant virus rDEN4-7546, tested for Vero cell adaptation (discussed in detail in Example 6) also showed reduced plaque size in C6/36 (FIG. 10).

The multicycle growth kinetics of both 5-1A1 and the recombinant wild type rDEN4 in C6/36 cells were determined as described in Example 1. Briefly, cells were infected in triplicate at a multiplicity of infection of 0.01 and samples were harvested at 24-hr intervals. Samples were flash frozen and titered in a single assay in Vero cell monolayers.

Oral infection of mosquitoes. *Aedes aegypti* is one of the primary vectors of dengue virus (Gubler, D. J. 1998 *Clin Microbiol Rev* 11:480-96). This species was reared at 26° C. and 80% relative humidity (RH) with a 16 hr daylight cycle. Adults were allowed continuous access to a cotton pad soaked in a 10% sucrose solution. Five to ten day old female *Ae. aegypti* which had been deprived of a sugar source for 48 hr were fed a bloodmeal consisting of equal volumes of washed human red blood cells, 10% sucrose solution, and dengue virus suspension. The infected blood meal was prepared immediately prior to feeding and offered to mosquitoes in a water-jacketed feeder covered in stretched parafilm and preheated to 38° C. (Rutledge, L. C. et al. 1964 *Mosquito News* 24:407-419). Mosquitoes that took a full bloodmeal within 45 min were transferred to a new container by aspirator and maintained as described above. After 21 days, mosquitoes were stored at −20° C. until dissection.

Intrathoracic inoculation of mosquitoes. The large, non-haematophagous mosquito *Toxorhynchites splendens* is a sensitive host for determining the infectivity of dengue virus. This species was reared at 24° C. and 75% RH with a 12 hr daylight cycle. Larvae and pupae were fed on appropriately sized *Aedes larvae*; adults were allowed continuous access to a cotton pad soaked in a 10% sucrose solution. Groups of one to ten day old adult *T. splendens* of both sexes were immobilized by immersion of their container in an icewater bath and inoculated intrathoracically with undiluted virus and serial tenfold dilutions of virus in 1×PBS. Virus was inoculated in a 0.22 μl dose using a Harvard Apparatus microinjector (Medical Systems Corp, Greenvale N.Y.) and a calibrated glass needle (technique is a modification of the method described in Rosen and Gubler, 1974).

Detection of viral antigen in body and head tissues by immunofluorescence assay (IFA). Head and midgut preparations of *Aedes aegypti* and head preparations of *Toxorhynchites splendens* were made on glass slides as described in Sumanochitrapon et al. (Sumanochitrapon, W. et al. 1998 *Am J Trop Med Hyg* 58:283-6). Slides were fixed in acetone for 20 min, and placed at 4° C. until processed by IFA. The primary antibody, hyperimmune mouse ascites fluid specific for DEN-4 (HMAF), was diluted 1/100 in PBS-Tween 20 (0.05%). Slides were incubated at 37° C. in a humid chamber for 30 min, and subsequently rinsed in PBS-Tween 20. The secondary antibody, FITC conjugated goat anti-mouse IgG (KPL, Gaithersburg, Md.), was diluted 1/200 in PBS-Tween 20 with 0.002% Evan's Blue. Slides were viewed on an Olympus BX60 microscope. The infectious dose required to infect 50% of mosquitoes ($ID_{50}$) was determined by the method of Reed and Muench (Reed, L. J. & Muench, H. 1938 *Am J Hyg* 27:493-497). For *Aedes aegypti* infections, two $OID_{50}$ (oral infectious dose 50) values were calculated for each virus: the $OID_{50}$ required to produce an infection in the midgut, with or without dissemination to the head, and the $OID_{50}$ required to produce disseminated infection. For *Tx. splendens* one $MID_{50}$ (mosquito infectious dose 50) value was calculated.

Statistical Analysis. The percentage of mosquitoes infected by different viruses were compared using logistic regression analysis (Statview, Abacus Inc.).

Mutations restricting growth of DEN4 in mosquito cells but not Vero cells are rare. Out of 1280 mutant viruses initially assayed, only two, #5 and rDEN4-356,357, showed reduced plaque size in C6/36 cells and normal plaque size in Vero cells. One additional virus, rDEN4-7546 (described in Example 6), with reduced plaque size in C6/36 was detected in subsequent assays, Mutant virus #5 was cloned by three successive terminal dilutions and designated 5-1A1; rDEN4-7546 and rDEN4-356,357 had already been twice-terminally diluted when they were tested in C6/36 cells. Virus 5-1A1 has been extensively characterized and its phenotypes are described in detail in the following section. rDEN4-356,357 and rDEN4-7546 are envisioned as being characterized in a similar fashion.

Figure 6:
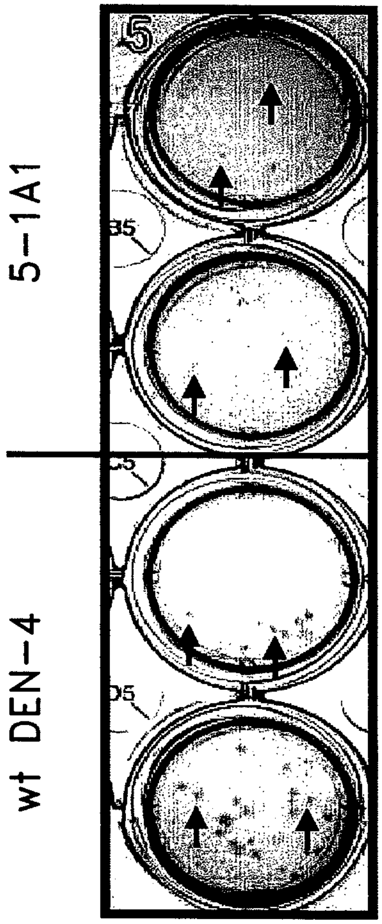
FIG. 6 shows plaque size of mutant 5-1A1 in C6/36 cells. Note that 5-1A1 has a small plaque phenotype in C6/36 cells relative to that of the wild type virus.
Figure 7:
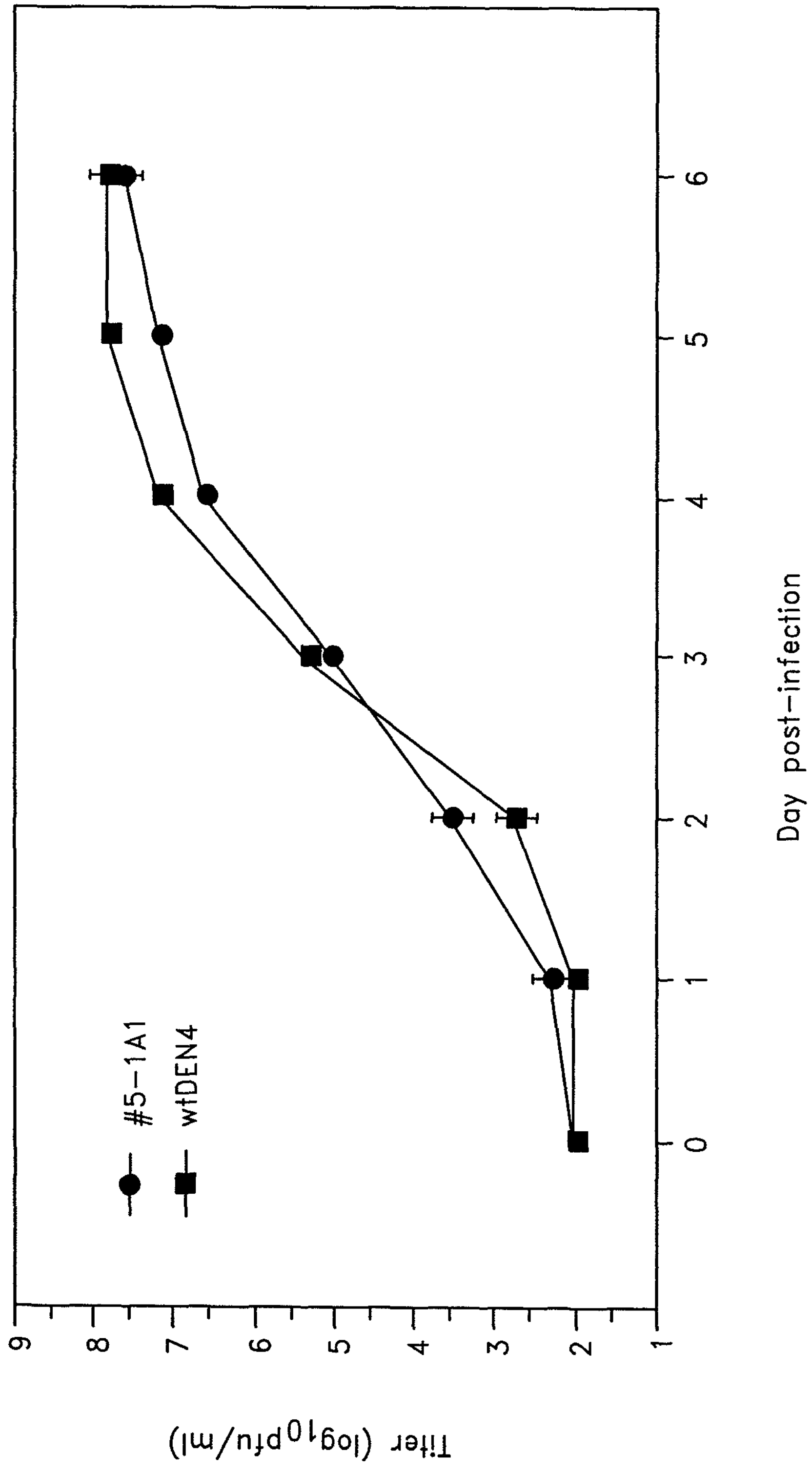
FIG. 7 shows growth of wild type rDEN5 and 5-1A1 in C6/36 cells. Cells were inoculated in triplicate with each virus at an MOI of 0.01, and the amount of virus present in the supernatants that were harvested on the indicated days was determined by plaque enumeration in Vero cells. The titers are expressed as $\log_{10}$PFU/ml±standard error.

Plaque size and growth kinetics of 5-1A1. 5-1A1 replicated to 6.7 $\log_{10}$PFU/ml in Vero cells with normal plaque size and replicated to 7.6 $\log_{10}$PFU/ml in C6/36 cells with small plaque size (FIG. 6, Table 25). In comparison, wild type DEN4 used as a concurrent control replicated to 7.3 $\log_{10}$PFU/ml in Vero cells, 8.3 $\log_{10}$PFU/ml in C6/36 cells, and showed normal plaque size in both cell types (FIG. 6, Table 25). The growth kinetics of 5-1A1 was compared to that of wild type DEN4 by infecting C6/36 cells at an MOI of 0.01 and monitoring the production of infectious virus. The kinetics and magnitude of replication of 5-1A1 in C6/36 cells was comparable to that of wild type DEN4 (FIG. 7).

5-1A1 is restricted in its ability to infect mosquitoes. 5-1A1 was evaluated for its ability to infect *Aedes aegypti* mosquitoes through an artificial bloodmeal (Table 26). In this assay the ability to infect the midgut of the mosquito and the ability for a midgut infection to disseminate to the head are measured separately. The oral infectious dose 50 ($OID_{50}$) of wild type DEN4 for the midgut was 3.3 $\log_{10}$ PFU; the $OID_{50}$ of wild type DEN4 for a disseminated infection was 3.9 $\log_{10}$ PFU. In contrast, 5-1A1 never infected 50% of mosquitoes at the doses used. In order to calculate the $OID_{50}$ for midgut infections by 5-1A1, it was assumed that at a 10-fold higher dose, 100% of 25 mosquitoes would have become infected. Using this assumption, the conservative estimate of the $OID_{50}$ for midgut infections by 5-1A1 was ≥3.9 $log_{10}$PFU. Because 5-1A1 produced only 3 disseminated infections, we did not attempt to calculate an $OID_{50}$ for this category. 5-1A1 was significantly restricted in its ability to infect the midgut relative to wild type DEN4 (logistic regression, N=150, P<0.001). Additionally, 5-1A1 produced very few disseminated infections, but because of low numbers this result was not amenable to statistical analysis.

5-1A1 was also significantly restricted in its ability to infect *Tx. splendens* mosquitoes following intrathoracic inoculation (Table 27). The $MID_{50}$ of wild type DEN4 was 2.3 $log_{10}$PFU whereas the $MID_{50}$ of 5-1A1 was estimated to be >3.0 $log_{10}$ PFU (logistic regression, N=36, P<0.01).

5-1A1 does not show a ts or an att phenotype. 5-1A1 was tested for temperature sensitivity in Vero and HuH-7 cells and for attenuation in suckling mouse brains as described in Example 1. The mutant virus was not temperature sensitive, as defined in Example 1, and was not attenuated in suckling mouse brain (Table 25).

Identification and confirmation of the mutation responsible for the phenotype of 5-1A1. The nucleotide sequence of the entire genome of 5-1A1 was determined as described in Example 1. Sequencing of 5-1A1 revealed three changes from the wild type sequence: two translationally-silent point mutations at positions 7359 and 9047, and one coding point mutation (C to U) at position 7129 in the NS4B gene which resulted in a praline to leucine substitution.

To formally confirm the effect of the C7129U mutation, the mutation was inserted into the cDNA p4, which has been described in Examples 1, 2, and 3 and in FIG. 4, using Kunkel mutagenesis as described in Examples 1 and 3. The mutagenized cDNA was transcribed and transfected as described in Example 3, and the resulting virus, after two terminal dilutions, was designated rDEN4-7129-1A. Like 5-1A1, rDEN4-7129-1A showed normal plaque size and titer in Vero cells and reduced plaque size and normal titer in C6/36 cells (Table 25). rDEN4-7129-1A was not ts on either Vero or HuH-7 cells and was not att in suckling mouse brain. Additionally, rDEN4-7129-1A did not show the SCID-HuH-7 att phenotype described in Example 3 (Table 25). The ability of rDEN4-7129-1A to infect mosquitoes is envisioned as being tested in both *Ae. aegypti* and *Tx. splendens*.

To test the compatibility of the C7129U mutation and the Δ30 deletion, the C7129U mutation was inserted into rDEN4Δ30 using previously described techniques. The resulting virus, designated rDEN4Δ30-7129, is envisioned as being tested for the phenotypes listed in Table 25.

In summary, three mutant viruses, 5-1A1, rDEN4-356, 357 and rDEN4-7546, showed a particular combination of phenotypes characterized by normal plaque size and replication to high titers in Vero cells and small plaque size but unrestricted growth in mosquito cells. 5-1A1 was further characterized and lacked temperature sensitivity in either Vero or HuH-7 cells and showed normal levels of replication in mouse brain and in SCID-HuH-7 mice and restricted infectivity for both *Ae. aegypti* and *Tx. splendens* mosquitoes. In comparison to wild type rDEN4, the 5-1A1 mutant had one coding mutation: a point mutation (C to U) at nucleotide 7129 in NS4B resulting in a replacement of Pro with Leu. Because 5-1A1 contains only a single missense mutation, the phenotype of this mutant virus can be attributed to the effect of the mutation at position 7129. These results indicate that the 7129 mutation is responsible for the phenotype of decreased infectivity for mosquitoes and is predicted to be useful to restrict replication of vaccine candidates in mosquitoes. To formally confirm this, we have inserted the 7129 mutation into a recombinant DEN4 virus. The resulting virus, designated rDEN4-7129-1A, shows an absence of ts and att phenotypes similar to 5-1A1. It is envisioned as being tested for mosquito infectivity.

The 7129 mutation is a valuable point mutation to include in a DEN4 vaccine candidate and into each of the dengue virus antigenic chimeric vaccine candidates since its biological activity is host specific, i.e., it is restricted in replication in mosquitoes but not in mammals. Moreover, as discussed in Example 6, the 7129 mutation has also been shown to enhance replication in Vero cells. Thus, its insertion into a vaccine candidate is envisioned as enhancing vaccine production in tissue culture without affecting the biological properties specified by other attenuating mutations. It is also envisioned as providing a useful safeguard against mosquito transmission of a dengue virus vaccine.

Section II. Design of Mutations to Restrict Replication in Mosquitoes

In Section 1 of Example 5, we screened a large panel of mutant viruses carrying both random mutations (generated with 5-fluorouracil) and specific mutations (generated through charge-cluster-to-alanine mutagenesis) for restricted growth in C6/36 cells, a proxy measure for restriction in mosquitoes. However, in neither case were mutations designed for the specific purpose of restricting replication in mosquitoes. In this section, we identified nucleotide sequences in the 3' UTR that show conserved differences between the mosquito-transmitted and tick-transmitted flaviviruses. We then altered those sequences in the DEN4 cDNA p4 by either deleting them altogether or exchanging them with the homologous sequence of the tick-transmitted Langat virus. The resulting viruses were assayed for reduced plaque size and titer in both Vero and C6/36 cells and for infectivity for *Ae. aegypti* and *Tx. splendens.*

Identification and modification of particular 3' UTR sequences showing conserved differences between vectors. Several studies (Olsthoorn, R. C. & Bol, J. F. 2001 *RNA* 7:1370-7; Proutski, V. et al. 1997 *Nucleic Acids Res* 25:1194-202) have identified conserved differences in the nucleotide sequences of the 3' UTR of mosquito-transmitted and tick-transmitted flaviviruses. Such differences are concentrated in the 3' terminal core region, the approximately 400 3' terminal nucleotides. It has been suggested that these sequences may have a vector-specific function (Proutski, V. et al. 1997 *Nucleic Acids Res* 25:1194-202). While such a function has not been identified, it may nonetheless be possible to disrupt vector infectivity by deleting or otherwise altering these nucleotides.

Figure 8:
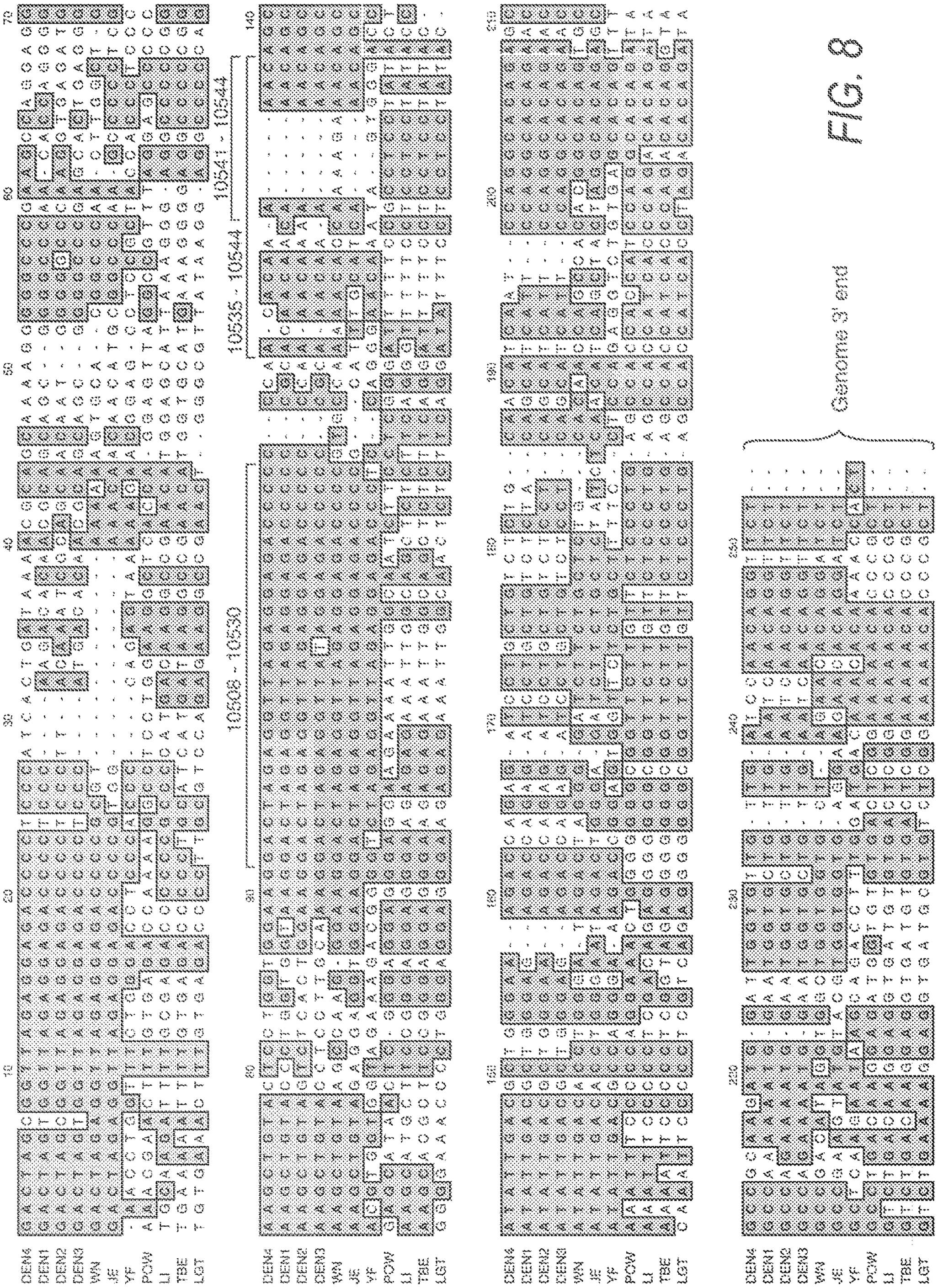
FIG. 8 shows nucleotide alignment of the 3' UTR of mosquito-borne and tick-borne flaviviruses. cDNA sequences are shown 5' to 3' and represent a portion of the UTR corresponding to DEN4 nucleotides 10417 to 10649 (3' genome end). Nucleotide numbering represents the position in the alignment. Regions deleted or swapped are indicated using the nucleotide numbering of DEN4. GenBank accession numbers for mosquito-borne viruses: DEN4 (SEQ ID NO: 2): AF326825, DEN1 (SEQ ID NO: 3): U88535, DEN2 (SEQ ID NO: 4): AF038403, DEN3 (SEQ ID NO: 5): M93130, West Nile virus (WN) (SEQ ID NO: 6): M12294, Japanese encephalitis virus (JE) (SEQ ID NO: 7): AF315119, Yellow fever virus (YF) (SEQ ID NO: 8): U17067; GenBank accession numbers for tick-borne viruses: Powassan virus (POW) (SEQ ID NO: 9): L06436, Louping Ill virus (LI) (SEQ ID NO: 10): Y07863, Tick-borne encephalitis virus (TBE) (SEQ ID NO: 11): U27495, and Langat virus (LGT) (SEQ ID NO: 12): AF253419.
Figure 9:
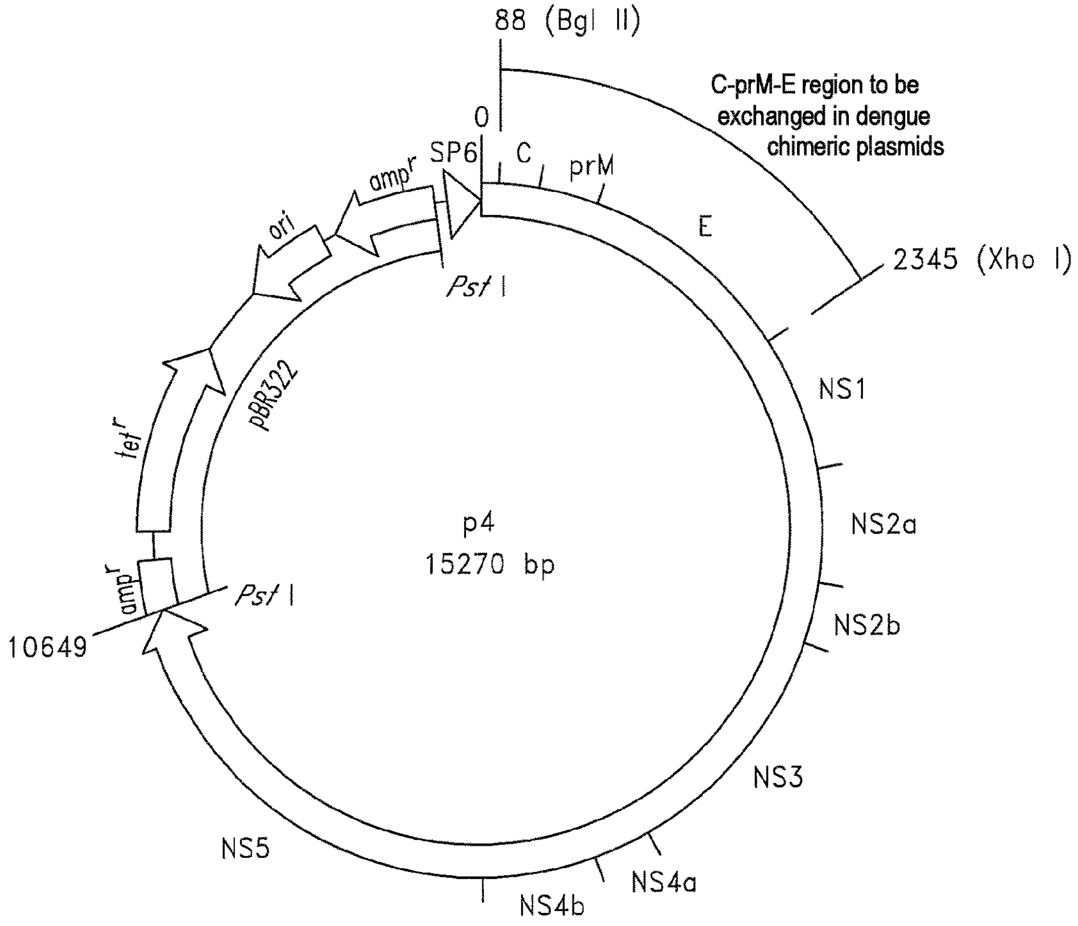
FIG. 9 shows genetic map of plasmid p4. Dengue cDNA is shown as bold line, with the C-prM-E region exchanged during construction of chimeric dengue virus cDNAs indicated.

To identify target sequences for this type of alteration, we constructed an alignment of the 3' UTR nucleotide sequences of seven mosquito-transmitted flaviviruses and four tick-transmitted flaviviruses (FIG. 8). From this alignment, we identified several sequences that showed conserved differences between the mosquito-transmitted flaviviruses and tick-transmitted flaviviruses. We then designed primers to alter these sequences in the wt DEN4 cDNA p4 (FIG. 4) in one of two ways: 1) deletion of the nucleotides (A) or 2) replacement of the nucleotides with the homologous sequence from the tick-transmitted flavivirus Langat (swap). Langat was chosen as the template for swapped nucleotides because it is naturally attenuated (Pletnev, A. G. 2001 *Virology* 282:288-300), and therefore unlikely to enhance the virulence of rDEN4 virus derived from the modified cDNA. The DEN4 sequences altered and the mutagenesis primers used to do so are listed in Table 28. Nucleotides 10508-10530 correspond to the CS2 region identified in previous studies (Proutski, V. et al. 1997 *Nucleic Acids Res* 25:1194-202).

Mutagenesis of p4, transcription and transfection were conducted as previously described in Section I of this Example. All five of the engineered viruses were recovered, and all were subjected to two rounds of terminal dilution as previously described.

Evaluation of phenotypes: cell culture. Viruses were titered in Vero and C6/36 cells as previously described, and the results are listed in Table 29. All of the viruses replicated to >5.0 $log_{10}$ PFU/ml; one of them (rDEN4Δ10508-10530) replicated to >8.0 $log_{10}$ PFU/ml. Only one of the viruses (rDEN4Δ10535-10544) was small plaque in C6/36 cells; this virus showed wild-type plaque size in Vero cells. Interestingly, another virus (rDEN4swap10508-10539) showed wild type plaque size in C6/36 cells but was sp in Vero cells.

Evaluation of phenotypes: mosquito infectivity. To date one of the five viruses has been tested for infectivity via intrathoracic inoculation in *Tx. splendens*, using previously described methods. Virus rDEN4Δ10508-10530 was dramatically restricted in infectivity relative to the wild type (Table 30). So few mosquitoes were infected that it was not possible to calculate an $MID_{50}$ for this virus.

One of the five viruses has been tested for infectivity of *Ae. aegypti* fed on an infectious bloodmeal using previously described methods. rDEN4swap10535-10544 (Table 31) caused significantly fewer midgut infections than wild type rDEN4, but the percentage of disseminated infections did not differ between rDEN4swap10535-10544 and wild type rDEN4. All of the viruses are envisioned as being tested for mosquito infectivity using both methods.

Summary. In this example we have outlined two different strategies for preventing mosquito transmission of a dengue vaccine. First, several small substitution mutations, including two point mutations and one paired charge-to-alanine substitution, have been shown to restrict the replication of DEN4 in mosquito C6/36 cells in cell culture, and one of these mutations (C7129U) has been shown to restrict the ability of DEN4 virus to infect mosquitoes. Second, we have created a variety of deletion and substitution mutations in regions of the DEN4 3' UTR that show conserved differences between mosquito-transmitted and tick-transmitted flaviviruses. One of these viruses is sp in C6/36 cells and at least two of these viruses show some degree of restriction of mosquito infectivity. By design, the nucleotide sequences in which these mutations were made are highly conserved among the four dengue serotypes and among mosquito-transmitted flaviviruses in general, indicating that they are portable to other vaccine candidates for mosquito-borne flaviviruses. All of the mutations discussed in this Example lie outside the structural genes and so are envisioned as being useful in constructing antigenic-chimeric vaccine candidates.

Example 6

Adaptation Mutations Which Enhance the Replication of DEN4 and DEN4 Chimeric Viruses in Vero Cells Vero cells are a highly characterized substrate that should be suitable for the manufacture of live attenuated flavivirus vaccines, such as dengue virus and tick-borne encephalitis virus. In addition, Vero cells can also be used to grow flaviviruses to high titer for the preparation of an inactivated virus vaccine. Optimal sequences for the efficient growth of dengue viruses in Vero cells have not been identified, but it is well known that flaviviruses accumulate mutations during passage in various cell cultures (Dunster, L. M. et al. 1999 *Virology* 261:309-18; Theiler, M. & Smith, H. H. 1937 *J Exp Med* 65:787-800). Inclusion of specific sequences in live attenuated viruses that enhance their replication in Vero cells and increase the number of doses of vaccine produced per unit substrate would greatly facilitate their manufacture. Similarly, inclusion of Vero cell growth-promoting sequences in wild type viruses used for the preparation of an inactivated virus vaccine would also greatly facilitate the manufacture of the vaccine. The present example identifies mutations that occur following passage of DEN4 virus and DEN2/4 chimeric viruses in Vero cells. Data derived from five sources provided information for this analysis making it possible to generate a list of Vero cell growth-promoting sequences.

Presence of identical mutations in multiple 5-FU mutant viruses. First, as described in Examples 1 and 2, the genomes of 42 dengue virus clones isolated from a 5-FU mutagenized stock of virus were completely sequenced. If mutations that enhance replication occurred during the passage of these 42 mutant viruses in Vero cells, then such mutations should reveal themselves by representation in more than one clone. Analysis of the 42 sequences revealed the occurrence of specific missense mutations in coding regions or nucleotide substitutions in UTRs in multiple clones that are not present in the 2A parental virus genome (Tables 11 and 32). These mutations, many of which occur within a 400 nucleotide section of the NS4B coding region, represent Vero cell-adaptation mutations. One mutation, such as the 4995 mutation, present in eight viruses was found to specify both ts and att phenotypes (Examples 1 and 3). In contrast, the 7163 mutation, present in six viruses, does not specify a ts or att phenotype (Table 13) and thus is an example of a specific Vero cell growth-promoting mutation.

Presence of Vero cell adaptation mutations in other DEN4 viruses and DEN2/4 antigenic chimeric viruses. Second, the 2A-13 dengue virus that was used as a parallel passaged wild type control during the 5-FU experiments described in Example 1 was grown and cloned in Vero cells in the absence of 5-FU in a manner identical to that of the 5-FU treated viruses. Sequence analysis of this 5-FU untreated virus, designated 2A-13-1A1, revealed that the virus genome contained a mutation at nucleotide 7163 (Example 1 and Table 32), identical to the missense mutation previously identified in 6 of the 5-FU mutant viruses (Tables 11 and 32). This indicates that growth and passage of DEN4 virus in Vero cells is sufficient to acquire this specific mutation, i.e. mutagenesis with 5-FU is not required. Thus, information from two separate sources indicates that the 7163 mutation appeared in separate Vero cell passaged viruses, thereby strengthening the interpretation that this mutation is growth promoting.

Third, following passage of the 2AΔ30 and rDEN4Δ30 in Vero cells, sequence analysis revealed the presence of a mutation at nucleotides 7153 and 7163, respectively. These two mutations were also previously identified among the 5-FU treated viruses (Table 32). Again, identical mutations appeared following independent passage of virus in Vero cells, corroborating the hypothesis that these mutations confer a growth advantage in Vero cells.

Fourth, an antigenic chimeric dengue virus vaccine candidate was generated that expressed the structural proteins C, prM, and E from DEN2 on a DEN4 wild type genetic background or an attenuated Δ30 genetic background. To construct this virus, the C, prM and E region of wild type cDNA plasmid p4 was replaced with a similar region from DEN2 virus strain NGC (FIG. 10). Specifically, nucleotides between restriction sites BglII (nt 88) and XhoI (nt 2345) of p4 were replaced with those derived from dengue type 2 virus. RNA transcripts synthesized from the resulting p4-D2 plasmid were transfected into Vero cells and rDEN2/4 virus was recovered. A further attenuated version of this chimeric virus containing the Δ30 mutation, rDEN2/4Δ30, was recovered in C6/36 mosquito cells following transfection of cells with RNA transcripts derived p4Δ30-D2. However, rDEN2/4Δ30 could not be recovered directly in Vero cells. The rDEN2/4Δ30 mutant virus recovered in C6/36 cells replicated to very low levels in Vero cells (<1.0 $\log_{10}$PFU/ml) but grew to high titer in C6/36 cells (>6.0 $\log_{10}$PFU/ml). Genomic sequence of the C6/36-derived virus matched the predicted cDNA sequence and is shown in Appendix 3. Nevertheless, when C6/36-derived rDEN2/4Δ30 was serially passaged 3 to 4 times in Vero cells, a virus population adapted for growth in Vero cells emerged. Virus from this Vero cell-adapted preparation was cloned and amplified in Vero cells to a titer >6.0 $\log_{10}$PFU/ml. The genomic sequence was determined for 2 independent virus clones and compared to the predicted cDNA sequence (Table 33 and 34). Each cloned virus contains a mutation in a non-structural gene which coincides closely in location or sequence with a mutation previously identified among the panel of 5-FU mutagenized viruses. The other mutations in these two clones also might confer a growth advantage in Vero cells. Importantly, the mutations identified in Tables 33 and 34 are absolutely required for replication in Vero cells, and it would not be possible to produce the rDEN2/4Δ30 vaccine candidate in Vero cells without the growth-promoting mutations identified in Tables 33 and 34.

Fifth, sequence analysis of the dengue 4 wild-type virus strain 814669 (GenBank accession no. AF326573) following passage in Vero cells identified a mutation in the NS5 region at nucleotide 7630 which had previously been identified among the panel of 5-FU mutagenized viruses (Table 32). This mutation at nucleotide 7630 was introduced into recombinant virus rDEN4 by site-directed mutagenesis as described in Table 16. The resulting virus, rDEN4-7630, was not temperature sensitive when tested at 39° C., indicating that mutation 7630 does not contribute to temperature sensitivity.

Characterization of rDEN2/4Δ30 chimeric viruses containing single and multiple Vero cell adaptation mutations. The generation of chimeric virus rDEN2/4Δ30 provided a unique opportunity for evaluating the capacity of individual mutations to promote increased growth in Vero cells. Because rDEN2/4Δ30 replicates to very low titer in Vero cells, yet can be efficiently generated in C6/36 mosquito cells, recombinant virus bearing putative Vero-cell adapting mutations were first generated in C6/36 cells and then virus titers were determined in both C6/36 and Vero cells. As shown in Table 35, addition of a single mutation to rDEN2/4Δ30 resulted in a greater than 1000-fold increase in titer in Vero cells, confirming the Vero cell adaptation phenotype conferred by these mutations. However, the combination of two separate mutations into a single virus did not increase the titer in Vero cells beyond the level observed for viruses bearing a single adaptation mutation. Inclusion of either the 7182 or 7630 mutation in the cDNA of rDEN2/4Δ30 allowed the virus to be recovered directly in Vero cells, circumventing the need to recover the virus in C6/36 cells.

Characterization of the growth properties of rDEN4 viruses containing single and multiple defined Vero cell adaptation mutations. To confirm the ability of Vero cell adaptation mutations to enhance growth of DEN4 viruses, site-directed mutagenesis was used to generate rDEN4 viruses encoding selected individual mutations as described in Examples 1 and 3. Five mutations in NS4B (7153, 7162, 7163, 7182, and 7546) from the list of repeated mutations in the 5-FU mutant viruses (Table 32) were introduced singly into the p4 cDNA clone. In addition, the mosquito-restricted, rDEN4-7129 virus was evaluated for enhanced growth in Vero cells since the location of this mutation is in the same region of NS4B. Each virus, including wild-type rDEN4, was recovered, terminally diluted, and propagated in C6/36 cells to prevent introduction of additional Vero cell adaptation mutations, however, because of its restricted growth in C6/36 cells, rDEN4-7129 was propagated only in Vero cells.

Plaque size was evaluated for each mutant rDEN4 virus in Vero cells and C6/36 cells and compared to wild-type rDEN4. Six-well plates of each cell were inoculated with dilutions of virus and plaques were visualized five days later. Representative plaques are illustrated in FIG. 10 and demonstrate that the presence of a Vero cell adaptation mutation does indeed confer increased virus cell to cell spread and growth specifically in Vero cells. In C6/36 cells, average plaque size was approximately 0.50 mm for both wild-type rDEN4 and each mutant virus (except for rDEN4-7546 and rDEN4-7129 which were smaller than wild-type; see Example 5). However, rDEN4 viruses expressing mutation 7162, 7163, 7182, and 7129 had a greater than two-fold increase in plaque size in Vero cells compared to wild-type rDEN4 virus. A smaller but consistent increase in plaque size was observed for rDEN4-7153 and rDEN4-7546.

Figure 11:
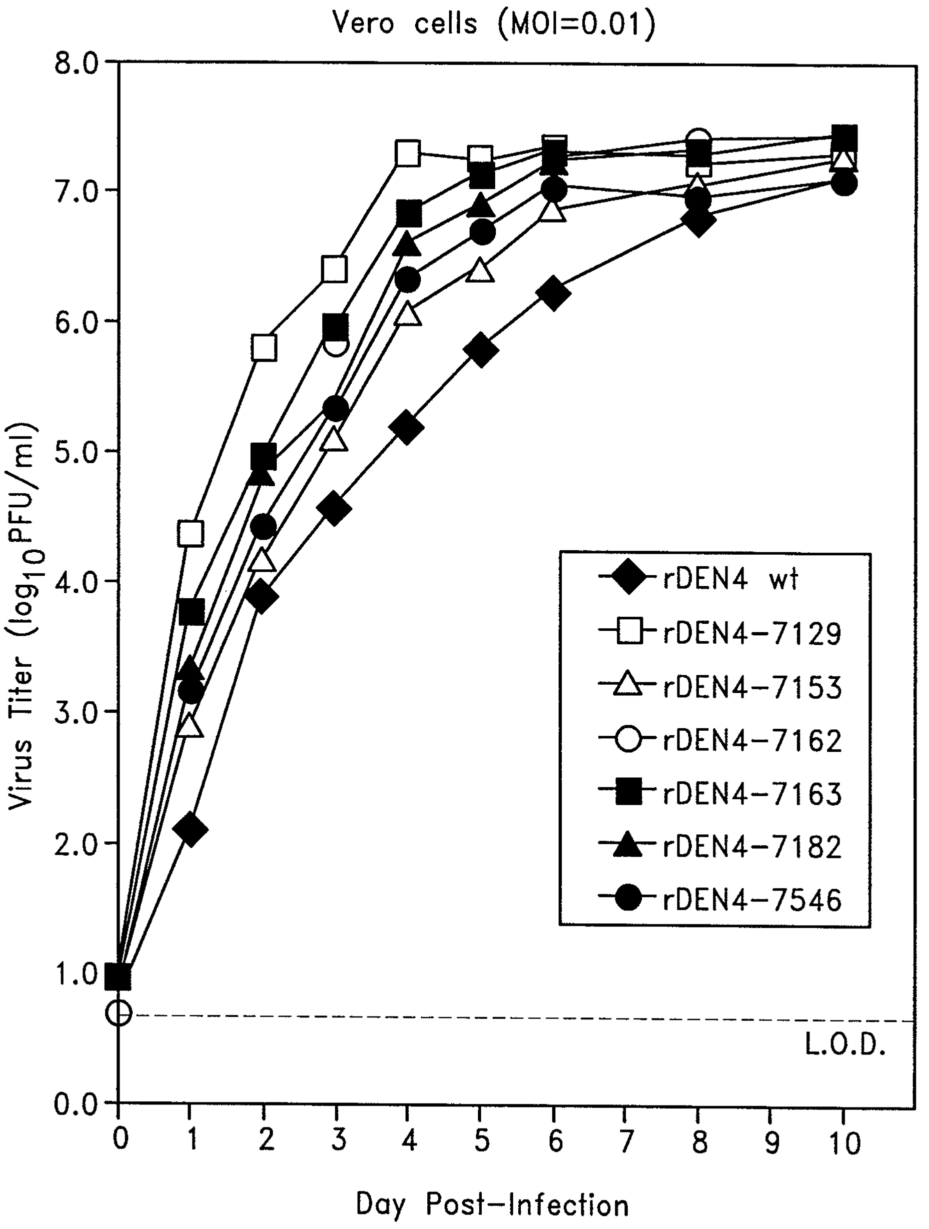
FIG. 11 shows growth curve in Vero cells of rDEN4 viruses encoding single Vero adaptation mutations. Vero cells were infected with the indicated viruses at an MOI of 0.01. Confluent cell monolayers in 25-$cm^2$ tissue culture flasks were washed and overlaid with a 1.5 ml inoculum containing the indicated virus. After a two hour incubation at 37° C., cells were washed three times in PBS and 5 ml of culture medium supplemented with 2% FBS was added. A 1 ml aliquot of tissue culture medium was removed, replaced with fresh medium, and designated the 0 hour time-point. At the indicated time points post-infection, samples of tissue culture medium were removed, clarified, and frozen at −70° C. The level of virus replication was assayed by plaque titration in Vero cells. Briefly, serial ten-fold dilutions of cell culture media samples were inoculated onto confluent Vero cell monolayers in 24-well plates in duplicate and overlaid with Opti-MEM containing 0.8% methylcellulose. After five days, plaques were visualized by immunoperoxidase staining as described in Example 1. Limit of detection (L.O.D.) is ≥0.7 $log_{10}$PFU/ml.

Growth kinetics and virus yield in Vero cells was assessed for the same panel of rDEN4 viruses. Vero cells were infected at an MOI of 0.01 and samples were removed daily for 10 days, titered on Vero cells, and plaques were visualized. The results in FIG. 11 indicate that the presence of a Vero cell adaptation mutation increased the kinetics of virus growth, but had only a marginal effect on the peak virus yield. At day four post-infection, wild-type rDEN4 grew to 5.2 $\log_{10}$PFU/ml while the level of replication in rDEN4-7129-infected cells was 100-fold higher. The rest of the mutant rDEN4 viruses had an increased yield at day four ranging from 0.9 (rDEN4-7153) to 1.6 (rDEN4-7162 and -7163) $\log_{10}$PFU/ml. Interestingly, enhanced kinetics of virus growth correlated with increased plaque size in Vero cells. The peak virus yield was reached by day 6 post-infection for rDEN4-7129, -7162, -7163, and -7182 while wild-type rDEN4 did not reach peak titer until day 10. However, the peak virus yield was only slightly higher in rDEN4 viruses expressing Vero cell adaptation mutations.

Figure 12:
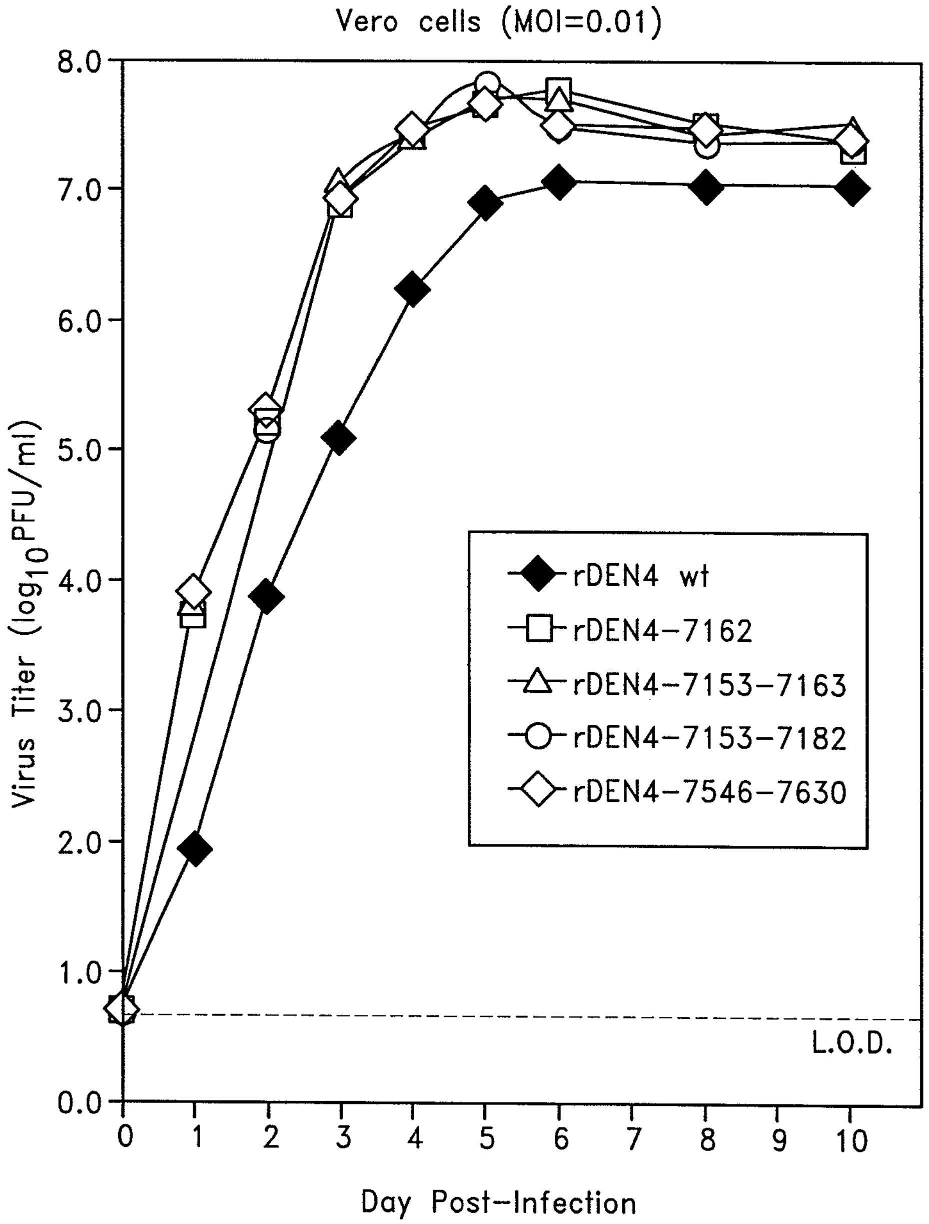
FIG. 12 shows growth curve in Vero cells of rDEN4 viruses encoding combined Vero cell adaptation mutations. Vero cells were infected with the indicated viruses at an MOT of 0.01. Confluent cell monolayers in 25-$cm^2$ tissue culture flasks were washed and overlaid with a 1.5 ml inoculum containing the indicated virus. After a two hour incubation at 37° C., cells were washed three times in PBS and 5 ml of culture medium supplemented with 2% FBS was added. A 1 ml aliquot of tissue culture medium was removed, replaced with fresh medium, and designated the 0 hour time-point. At the indicated time points post-infection, samples of tissue culture medium were removed, clarified, and frozen at −70° C. The level of virus replication was assayed by plaque titration in Vero cells. Limit of detection (L.O.D.) is ≥0.7 $log_{10}$PFU/ml.

In an effort to further enhance rDEN4 replication, especially the peak virus yield, combinations of selected Vero cell adaptation mutations were introduced into the rDEN4 background. Three viruses with dual mutations were generated: rDEN4-7153-7163, rDEN4-7153-7182, and rDEN4-7546-7630 and tested in a Vero cell time course infection as described above along with rDEN4 and rDEN4-7162 as a positive control (FIG. 12). The viruses expressing combined mutations grew in a nearly identical manner to rDEN4-7162 indicating that these selected combinations did not enhance the kinetics or peak virus yield. Additional combinations of these and other Vero cell adaptation mutations are envisioned as increasing peak virus yield.

Discussion. Some of the growth promoting mutations listed in Table 32 are also found in homologous regions of DEN1, DEN2, and DEN3 and are envisioned as serving to promote the replication of these viruses in Vero cells. Specifically, the growth promoting mutations indicated in Table 32 that are present in a DEN4 virus are envisioned as being useful for importation into homologous regions of other flaviviruses, such as DEN1, DEN2 and DEN3. Examples of such conserved regions are shown in Appendix 4 and are listed in Table 36. The nucleotides for both mutation 7129 and 7182 are conserved in all four dengue virus serotypes. It is also interesting to note that mutation 7129 not only increases growth in Vero cells (FIG. 10), but it also forms small plaques in mosquito cells (FIG. 6, Table 25). Lee et al. previously passaged DEN3 virus in Vero cells and performed limited sequence analysis of only the structural gene regions of the resulting viruses (Lee, E. et al. 1997 *Virology* 232:281-90). From this analysis a menu of Vero adaptation mutations was assembled. Although none of these mutations correspond to the Vero adaptation mutations identified in this Example, a single mutation at amino acid position 202 in DEN3 corresponds to mutation 1542 identified in 5-FU mutant virus #1012. The current Example emphasizes the importance in this type of study of determining the sequence of the entire viral genome.

Vero cell growth optimized viruses are envisioned as having usefulness in the following areas. First, the yield of a live attenuated vaccine virus in Vero cells is predicted to be augmented. The live attenuated vaccine candidate is conveniently a DEN4 or other dengue virus or a DEN1/4, DEN2/4, or DEN3/4 antigenic chimeric virus, or a chimeric virus of another flavivirus based on the DEN4 background. The increased yield of vaccine virus is envisioned as decreasing the cost of vaccine manufacture. Second, Vero cell adaptation mutations that are attenuating mutations, such as the 4995 mutation, are envisioned as being stable during the multiple passage and amplification of virus in Vero cell cultures that is required for production of a large number of vaccine doses. Third, Vero cell adaptation mutations are actually required for the growth of the rDEN2/4Δ30 vaccine candidate in Vero cells. Fourth, the increase in yield of a DEN wild type or an attenuated virus is envisioned as making it economically feasible to manufacture an inactivated virus vaccine: Fifth, the presence of the Vero cell growth promoting mutations in the DEN4 vector of the rDEN1/4, rDEN2/4, and rDEN3/4 antigenic chimeric viruses or other flavivirus chimeric viruses based on DEN4 is envisioned as permitting the viruses to grow to a high titer and as thereby being useful in the manufacture of a inactivated virus vaccine. Sixth, the insertion of Vero cell growth promoting mutations into cDNAs such as rDEN2/4Δ30 is envisioned as permitting recovery of virus directly in Vero cells, for which there are qualified master cell banks for manufacture, rather than in C6/36 cells for which qualified cell banks are not available. And seventh, insertion of the 7129 and 7182 mutations into DEN1, DEN2, or DEN3 wt viruses is envisioned as increasing their ability to replicate efficiently and be recovered from cDNA in Vero cells.

Example 7

Assembly of a List of Attenuating Mutations

The data presented in these examples permits the assembly of a list of attenuating mutations that is summarized in Table 37. This list contains individual mutations identified in Tables 13-16, 20, and 21 that are known to independently specify an attenuation phenotype. Mutation 7129 is also included since it is derived from virus 5-1A1 shown to be attenuated in mosquitoes. We envision using various combinations of mutations from this list to generate viruses with sets of desirable properties such as restricted growth in the liver or in the brain as taught in Example 3 (Table 18) and Example 4 (Tables 23 and 24). These mutations are also combinable with other previously described attenuating mutations such as the Δ30 mutation, as taught in Example 1 (Table 6) and Example 3 (Table 19) to produce recombinant viruses that are satisfactorily attenuated and immunogenic. Mutations listed in Table 37 are also envisioned as being combined with other previously described attenuating mutations such as other deletion mutations or other point mutations (Blok, J. et al. 1992 *Virology* 187:573-90; Butrapet, S. et al. 2000 *J Virol* 74:3011-9; Men, R. et al. 1996 *J Virol* 70:3930-7; Puri, B. et al. 1997 *J Gen Virol* 78:2287-91).

The possibility of importing an attenuating mutation present in one paramyxovirus into a homologous region of a second paramyxovirus has recently been described (Durbin, A. P. et al. 1999 *Virology* 261:319-30; Skiadopoulos, M. H. et al. 1999 *Virology* 260:125-35). Such an importation confers an att phenotype to the second virus or, alternatively, further attenuates the virus for growth in vivo. Similarly we envision importing an attenuating mutation present in one flavivirus to a homologous region of a second flavivirus which would confer an att phenotype to the second flavivirus or, alternatively, would further attenuate the virus for growth in vivo. Specifically, the attenuating mutations indicated in Table 37 are envisioned as being useful for importation into homologous regions of other flaviviruses. Examples of such homologous regions are indicated in Appendix 4 for the mutations listed in Table 37.

Example 8

Evaluation of Dengue Virus Vaccine in Humans and Rhesus Monkeys

The present example evaluates the attenuation for humans and rhesus monkeys (as an animal model) of a DEN-4 mutant bearing a 30 nucleotide deletion (Δ30) that was introduced into its 3' untranslated region by site-directed mutagenesis and that was found previously to be attenuated for rhesus monkeys (Men, R. et al. 1996 *J Viral* 70:3930-7), as representative of the evaluation of any dengue virus vaccine for attenuation in humans and rhesus monkeys (as an animal model).

Viruses and cells. The wild type (wt) DEN-4 virus strain 814669 (Dominica, 1981), originally isolated in *Aedes pseudoscutellaris* (AP61) cells, was previously plaque-purified in LLC-MK2 cells and amplified in C6/36 cells as described (Mackow, E. et al. 1987 *Virology* 159:217-28). For further amplification, the C6/36 suspension was passaged 2 times in Vero (WHO) cells maintained in MEM-E (Life Technologies, Grand Island, N.Y.) supplemented with 10% FBS. Viruses derived from RNA transfection or used for clinical lot development were grown in Vero (WHO) cells maintained in serum-free media, VP-SFM (Life Technologies).

Construction of DEN-4 deletion mutants. A 30 nucleotide (nt) deletion was previously introduced into the 3' untranslated region of the 2A cDNA clone of wt DEN-4 strain 814669 as described (Men, R. et al. 1996 *J Virol* 70:3930-7). This deletion removes nucleotides 10478-10507, and was originally designated 3'd 172-143, signifying the location of the deletion relative to the 3' end of the viral genome. In the current example, this deletion is referred to as Δ30. The full-length 2A cDNA clone has undergone several subsequent modifications to improve its ability to be genetically manipulated. As previously described, a translationally-silent XhoI restriction enzyme site was engineered near the end of the E region at nucleotide 2348 to create clone 2A-XhoI (Bray, M. & Lai, C. J. 1991 *PNAS USA* 88:10342-6). In this example, the viral coding sequence of the 2A-XhoI cDNA clone was further modified using site-directed mutagenesis to create clone p4: a unique BbvCI restriction site was introduced near the C-prM junction (nucleotides 447-452); an extra XbaI restriction site was ablated by mutation of nucleotide 7730; and a unique SacII restriction site was created in the NS5 region (nucleotides 9318-9320). Each of these engineered mutations is translationally silent and does not change the amino acid sequence of the viral polypeptide. Also, several mutations were made in the vector region of clone p4 to introduce or ablate additional restriction sites. The cDNA clone p4Δ30 was generated by introducing the Δ30 mutation into clone p4. This was accomplished by replacing the MluI-KpnI fragment of p4 (nucleotides 10403-10654) with that derived from plasmid 2AΔ30 containing the 30 nucleotide deletion. The cDNA clones p4 and p4Δ30 were subsequently used to generate recombinant viruses rDEN4 and rDEN4Δ30, respectively.

Generation of viruses. Full-length RNA transcripts were synthesized from cDNA clones 2A and 2AΔ30 using SP6 RNA polymerase as previously described (Lai, C. J. et al. 1991 *PNAS USA* 88:5139-43; Men, R. et al. 1996 *J Virol* 70:3930-7). The reaction to generate full-length RNA transcripts from cDNA clones p4 and p4Δ30 was modified and consisted of a 50 μl reaction mixture containing 1 μg linearized plasmid, 60 U SP6 polymerase (New England Biolabs (NEB), Beverly, Mass.), 1×RNA polymerase buffer (40 mM Tris-HCl, pH 7.9, 6 mM $MgCl_2$, 2 mM spermidine, 10 mM dithiothreitol), 0.5 mM m7G(5')ppp(5')G cap analog (NEB), 1 mM each nucleotide triphosphate, 1 U pyrophosphatase (NEB), and 80 U RNAse inhibitor (Roche, Indianapolis, Ind.). This reaction mixture was incubated at 40° C. for 90 min and the resulting transcripts were purified using RNeasy mini kit (Qiagen, Valencia, Calif.). For transfection of Vero cells, purified transcripts (1 μg) were mixed with 12 μl DOTAP liposome reagent (Roche) in saline containing 20 mM HEPES buffer (pH 7.6) and added to cell monolayer cultures in a 6-well plate. After 5-17 days, tissue culture medium was harvested, clarified by centrifugation, and virus was amplified in Vero cells. The presence of virus was confirmed by plaque titration. It should be noted that during the course of transfection and amplification of 2AΔ30 to create the vaccine lot, the virus underwent a total of 6 passages entirely in Vero cells. The remaining viruses, rDEN4 and rDEN4Δ30 were passaged 5 times in Vero cells to generate the virus suspension used for sequence analysis and studies in rhesus monkeys.

Vaccine Production. An aliquot of clarified tissue culture fluid containing vaccine candidate 2AΔ30 was submitted to DynCorp (Rockville, Md.) for amplification of virus in Vero cells and production of a vaccine lot. For vaccine production, 2AΔ30 infected tissue culture supernatant was harvested, SPG buffer added (final concentration: 218 mM sucrose, 6 mM L-glutamic acid, 3.8 mM potassium phosphate, monobasic, and 7.2 mM potassium phosphate, dibasic, pH 7.2), and the virus suspension was clarified by low speed centrifugation. To degrade residual Vero cell DNA, the vaccine suspension was treated with Benzonase endonuclease (American International Chemical, Natick, Mass.), 100 U/ml and incubated for 1 hr at 37° C., followed by high-speed centrifugation (17,000×g, 16 hr). The resulting virus pellet was gently rinsed with MEM-E, resuspended in MEM-E containing SPG, sonicated, distributed into heat-sealed ampoules, and stored frozen at −70° C. Final container safety testing confirmed microbial sterility, tissue culture purity, and animal safety. The 2AΔ30 vaccine lot (designated DEN4-9) has a titer of 7.48 log 10PFU/ml, with a single dose of 5.0 log 10 PFU/ml containing <1 pg/ml Vero cell DNA and <0.001 U/ml Benzonase endonuclease.

Sequence of cDNA clones and viral genomes. The nucleotide sequence of the viral genome region of cDNA plasmids 2A and p4 was determined on a 310 genetic analyzer (Applied Biosystems, Foster City, Calif.) using vector-specific and DEN-4-specific primers in BigDye terminator cycle sequencing reactions (Applied Biosystems). The nucleotide sequence of the genomes of the parental wt DEN-4 strain 814669 and of recombinant viruses 2A wt, 2AΔ30 (vaccine lot), rDEN4, and rDEN4Δ30 was also determined. Viral RNA was extracted from virus preparations and serum samples using the QIAamp Viral RNA mini kit (Qiagen). Reverse transcription (RT) was performed using random hexamers and the SuperScript First-Strand Synthesis System for RT-PCR (Life Technologies). Overlapping PCR fragments of approximately 2000 base pairs were generated using optimized DEN-4 specific primers and Advantage cDNA polymerase (ClonTech, Palo Alto, Calif.). Both strands of purified PCR fragments were sequenced directly using dye-terminator reactions as described above and results were assembled into a consensus sequence. To determine the nucleotide sequence of the viral RNA 5' and 3' regions, the 5' cap nucleoside of the viral RNA was removed with tobacco acid pyrophosphatase (Epicentre, Madison, Wis.) followed by circularization of the RNA using RNA ligase (Epicentre). RT-PCR was performed as described and a cDNA fragment spanning the ligation junction was sequenced using DEN-4 specific primers. GenBank accession numbers have been assigned as follows (virus: accession number): 814669: AF326573, 2AΔ30: AF326826, rDEN4: AF326825, and rDEN4Δ30: AF326827.

Human Vaccine Recipients. 20 normal healthy adult volunteers were recruited by the Johns Hopkins School of Hygiene and Public Health Center for Immunization Research (CIR) located in Baltimore, Md. The clinical protocol was reviewed and approved by the Joint Committee for Clinical Investigation of the Johns Hopkins University School of Medicine and informed consent was obtained from each volunteer. Volunteers were enrolled in the study if they met the following inclusion criteria: 18-45 years of age; no history of chronic illness; a normal physical examination; human immunodeficiency virus antibody negative, hepatitis B surface antigen negative, and hepatitis C antibody negative; no stool occult blood; and normal values for complete blood cell count (CBC) with differential, hematocrit, platelet count, serum creatinine, serum aspartate amino transferase (AST), alanine amino transferase (ALT), alkaline phosphatase, bilirubin, prothrombin time (PT), partial thromboplastin time (PTT), and urinalysis. Female volunteers were required to have a negative urine pregnancy test prior to vaccination and on the day of vaccination and to agree to use contraception or abstain from sexual intercourse for the duration of the study. Volunteers also lacked serological evidence of prior flavivirus infection as defined by hemagglutination-inhibition antibody titer <1:10 to DEN-1, DEN-2, DEN-3, DEN-4, St. Louis encephalitis virus, Japanese encephalitis virus, or yellow fever virus and a plaque-reduction neutralization titer <1:10 to DEN-4 and yellow fever virus.

Studies in Humans. Volunteers were immunized in three successive cohorts of four, six, and ten volunteers to assess the safety of the vaccine. In this study, an illness was defined as the following: dengue virus infection associated with a platelet count of <90,000/$mm^3$; serum ALT >4 times normal; oral temperature >38° C. for >2 successive days; or headache and/or myalgia lasting >2 successive days. Systemic illness was defined as the occurrence of fever >38° C. for >2 consecutive days, or any 2 of the following for at least two consecutive study days: headache, malaise, anorexia, and myalgia/arthralgia. The trials were conducted between October and April, a time of low mosquito prevalence, to reduce the risk of transmission of vaccine virus from the volunteers to the community.

On the day of vaccination, vaccine candidate 2AΔ30 was diluted to 5.3 $log_{10}$PFU/ml in sterile saline for injection, USP, and each volunteer was injected subcutaneously with a 0.5 ml containing 5.0 $log_{10}$PFU of vaccine into the left deltoid region. Volunteers were given a home diary card on which they were to record their temperature twice daily for days 0-5 post-vaccination. The volunteers returned to the clinic each day for examination by a physician and their diary cards were reviewed. The injection site was evaluated for erythema, induration, and tenderness. Clinical signs and symptoms such as headache, rash, petechiae, lymphadenopathy, hepatomegaly, abdominal tenderness, anorexia, nausea, fatigue, myalgia, arthralgia, eye pain, and photophobia were assessed daily. Symptoms were graded as mild (no need for treatment or a change in activity), moderate (treatment needed or change in activity noted, yet still able to continue daily activity) or severe (confined to bed). Blood was drawn for CBC with differential and for virus quantitation on days 0, 2 and 4. Volunteers were admitted to the inpatient unit at the CIR on the sixth day after immunization. The study physician evaluated all volunteers each day by physical examination and interview. The volunteers had their blood pressure, pulse, and temperature recorded four times a day. Blood was drawn each day for CBC with differential and for virus quantitation and every other day for ALT measurement. Volunteers were confined to the inpatient unit until discharge on study day 15. On study days 28 and 42, volunteers returned for physical examination and blood was drawn for virus quantitation (day 28) and for serum antibody measurement (day 28 and 42).

Virus quantitation and amplification. Serum was obtained for detection of viremia and titration of virus in positive specimens. For these purposes 8.5 ml of blood was collected in a serum separator tube and incubated at room temperature for less than 30 min. Serum was decanted into 0.5 ml aliquots, rapidly frozen in a dry ice/ethanol bath and stored at −70° C. Serum aliquots were thawed and serial 10-fold dilutions were inoculated onto Vero cell monolayer cultures in 24-well plates. After one hour incubation at room temperature, the monolayers were overlaid with 0.8% methylcellulose in OptiMEM (Life Technologies) supplemented with 5% fetal bovine serum (FBS). Following incubation at 37° C. for four days, virus plaques were visualized by immunoperoxidase staining. Briefly, cell monolayers were fixed in 80% methanol for 30 min and rinsed with antibody buffer (5% nonfat milk in phosphate buffered saline). Rabbit polyclonal DEN-4 antibodies were diluted 1:1000 in antibody buffer and added to each well followed by a one hr incubation at 37° C. Primary antibody was removed and the cell monolayers were washed twice with antibody buffer. Peroxidase-labelled goat-anti-rabbit IgG (KPL, Gaithersburg, Md.) was diluted 1:500 in antibody buffer and added to each well followed by a one hr incubation at 37° C. Secondary antibody was removed and the wells were washed twice with phosphate buffered saline. Peroxidase substrate (4 chloro-1-napthol in $H_2O_2$) was added to each well and visible plaques were counted.

For amplification of virus in serum samples, a 0.3 ml aliquot of serum was inoculated directly onto a single well of a 6-well plate of Vero cell monolayers and incubated at 37° C. for 7 days. Cell culture fluid was then assayed for virus by plaque assay as described above.

Serology. Hemagglutination-inhibition (HAI) assays were performed as previously described (Clarke, D. H. & Casals, J. 1958 *Am J Trop Med Hyg* 7:561-73). Plaque-reduction neutralization titers (PRNT) were determined by a modification of the technique described by Russell (Russell, P. K. et al. 1967 *J Immunol* 99:285-90). Briefly, test sera were heat inactivated (56° C. for 30 min) and serial 2-fold dilutions beginning at 1:10 were made in OptiMEM supplemented with 0.25% human serum albumin. rDEN4Δ30 virus, diluted to a final concentration of 1000 PFU/ml in the same diluent, was added to equal volumes of the diluted serum and mixed well. The virus/serum mixture was incubated at 37° C. for 30 min. Cell culture medium was removed from 90% confluent monolayer cultures of Vero cells on 24-well plates and 50 μl of virus/serum mixture was transferred onto duplicate cell monolayers. Cell monolayers were incubated for 60 min at 37° C. and overlaid with 0.8% methylcellulose in OptiMEM supplemented with 2% FBS. Samples were incubated at 37° C. for 4 days after which plaques were visualized by immunoperoxidase staining as described above, and a 60% plaque-reduction neutralization titer was calculated.

Studies in rhesus monkeys. Evaluation of the replication and immunogenicity of wt virus 814669, and recombinant viruses 2A wt, 2AΔ30 (vaccine lot), rDEN4, and rDEN4Δ30 in juvenile rhesus monkeys was performed as previously described (Men R. et al. 1996 *J Virol* 70:3930-7). Briefly, dengue virus seronegative monkeys were injected subcutaneously with 5.0 $log_{10}$ PFU of virus diluted in L-15 medium (Quality Biological, Gaithersburg, Md.) containing SPG buffer. A dose of 1 ml was divided between two injections in each side of the upper shoulder area. Monkeys were observed daily and blood was collected on days 0-10 and 28, and processed for serum, which was stored frozen at −70° C. Titer of virus in serum samples was determined by plaque assay on Vero cells as described above. Neutralizing antibody titers were determined for the day 28 serum samples as described above. A group of monkeys inoculated with either 2AΔ30 (n=4) or wt virus 814669 (n=8) were challenged on day 42 with a single dose of 5.0 $log_{10}$ PFU/ml wt virus 814669 and blood was collected for 10 days. Husbandry and care of rhesus monkeys was in accordance with the National Institutes of Health guidelines for the humane use of laboratory animals.

Construction and characterization of DEN-4 wild type and deletion mutant viruses. The nucleotide and deduced amino acid sequences of the previously described wt 814669 virus, the DEN-4 2A wt virus derived from it (designated 2A wt), and the 2AΔ30 vaccine candidate derived from 2A wt virus were first determined. Sequence analysis showed that the wt 814669 virus used in this study had apparently accumulated 2 missense mutations (nucleotides 5826 and 7630) and 3 silent mutations during its passage and amplification since these mutations were not described in previously published reports of the viral sequence (GenBank accession number M14931) and were not present in the 2A cDNA derived from the virus. Sequence comparison between viruses 2A wt and vaccine lot 2AΔ30 revealed that 2AΔ30 accumulated 2 missense mutations (nucleotides 7153 and 8308) and also confirmed the presence of the Δ30 mutation (nucleotides 10478-10507) as well as an additional deletion of nucleotide 10475, which occurred during the original construction of the Δ30 mutation (Men, R. et al. 1996 *J Virol* 70:3930-7). This sequence analysis revealed significant sequence divergence between the biologically-derived wt 814669 virus and its recombinant 2A wt derivative and between the 2A wt and 2AΔ30 virus. Since the 2A wt and 2AΔ30 viruses differed at nucleotides other than the deletion mutation, the attenuation phenotype previously reported for 2AΔ30 (Men, R. et al. 1996 *J Virol* 70:3930-7) could not be formally ascribed solely to the Δ30 mutation and may have been specified by the mutations at nucleotides 7153, 8308, 10475, or the Δ30 deletion.

To determine whether the Δ30 mutation was responsible for the observed attenuation of 2AΔ30, a second pair of viruses, one with and one without the Δ30 mutation, were produced for evaluation in monkeys. A new DEN-4 cDNA vector construct, designated p4, was derived from the 2A-XhoI cDNA clone and translationally-silent mutations were introduced to add or ablate several restriction enzyme sites. These sites were added to facilitate the future genetic manipulation of this DEN-4 wt cDNA by the introduction of other attenuating mutations if needed. The sequence of the genomic region of the p4 cDNA plasmid was identical to that of the 2A wt virus except for the engineered restriction site changes and a point mutation at nucleotide 2440 which was introduced during the original mutagenesis of the 2A cDNA plasmid to create the XhoI site (Bray, M. & Lai, C. J. 1991 *PNAS USA* 88:10342-6). The Δ30 mutation and the neighboring deletion at nucleotide 10475 were co-introduced into the p4 plasmid by replacing a short restriction fragment with one derived from the cDNA clone of 2AΔ30. RNA transcripts derived from the p4 cDNA clone and from its Δ30 derivative each yielded virus (designated rDEN4 wt and rDEN4Δ30, respectively) following transfection of Vero cells. Sequence analysis of the rDEN4 virus revealed that during its passage and amplification in Vero cells it accumulated 2 missense mutations (nucleotides 4353 and 6195), a silent mutation (nucleotide 10157), and a point mutation in the 3' untranslated region (nucleotide 10452). In addition to containing the Δ30 and the accompanying deletion at nucleotide 10475, rDEN4Δ30 had also accumulated a missense mutation (nucleotide 7163) and a silent mutation (nucleotide 7295).

Parental wt 814669 virus and recombinant viruses 2A wt, 2AΔ30, rDEN4, and rDEN4Δ30 each replicate in Vero cells to a titer exceeding 7.0 $\log_{10}$PFU/ml, and their replication is not temperature sensitive at 39° C.

Virus replication, immunogenicity, and efficacy in monkeys. Groups of rhesus monkeys were inoculated with wt DEN-4 814669, 2A wt, rDEN4, 2AΔ30 and rDEN4Δ30 to assess the level of restriction of replication specified by the Δ30 mutation. Serum samples were collected daily and titer of virus present in the serum was determined by plaque enumeration on Vero cell monolayer cultures. Monkeys inoculated with wt 814669 virus or its recombinant counterparts, 2A wt or rDEN4, were viremic for 3 to 4 days with a mean peak virus titer of nearly 2 $\log_{10}$PFU/ml. Monkeys inoculated with virus 2AΔ30 or rDEN4Δ30 had a lower frequency of viremia (83% and 50%, respectively), were viremic for only about 1 day, and the mean peak titer was 10-fold lower. Monkeys inoculated with DEN-4 814669, 2A wt, or rDEN4 viruses developed high levels of neutralizing antibody, with mean titers between 442 and 532, consistent with their presumed wild type phenotype. Monkeys inoculated with 2AΔ30 or rDEN4Δ30 developed a lower level of neutralizing antibody, with mean titers of 198 and 223, respectively. The decrease in neutralizing antibody titer in response to 2AΔ30 and rDEN4Δ30 is consistent with the attenuation phenotype of these viruses. Monkeys inoculated with either 2AΔ30 (n=4) or wt 814669 virus (n=8) were challenged after 42 days with wt virus 814669. Dengue virus was not detected in any serum sample collected for up to 10 days following virus challenge, indicating that these monkeys were completely protected following immunization with either wt virus or vaccine candidate 2AΔ30.

Since DEN-4 814669, 2A wt, and rDEN4 each manifest the same level of replication and immunogenicity in rhesus monkeys, it is reasonable to conclude that the identified sequence differences between these presumptive wild type viruses that arose during passage in tissue culture or during plasmid construction do not significantly affect their level of replication in vivo. Similarly, the comparable level of attenuation of 2AΔ30 and rDEN4Δ30 indicates that the mutations shared by these viruses, namely, the Δ30 mutation and its accompanying 10475 deletion mutation, are probably responsible for the attenuation of these viruses rather than their incidental sequence differences.

Clinical Response to immunization with 2AΔ30. The 2AΔ30 vaccine candidate was administered subcutaneously at a dose of $10^5$ PFU to 20 seronegative volunteers. Each of the vaccinees was infected and the virus was well tolerated by all vaccinees. Viremia was detected in 70% of the vaccinees, was present only at low titer, and did not extend beyond day 11.

None of the 20 vaccinees reported soreness or swelling at the injection site. Mild erythema (1-3 mm) around the injection site was noted on examination of 8 volunteers 30 minutes post-vaccination which resolved by the next day in 7 of those volunteers and by the third day in the remaining volunteer. Mild tenderness to pressure at the vaccination site was noted in 2 volunteers and lasted a maximum of 48 hours. During physical examination, ten volunteers (50%) were noted to a have a very mild dengue-like erythematous macular rash (truncal distribution) which occurred with greatest frequency on day 10. None of the volunteers noted the rash themselves, and it was asymptomatic in each instance. Rash was seen only in vaccinees with detectable viremia. Volunteers did not develop systemic illness. Seven volunteers noted an occasional headache that was described as mild, lasting less than 2 hours, and was not present in any volunteer on two consecutive days. One volunteer reported fever of 38.6° C. and 38.2° C. without accompanying headache, chills, eye pain, photophobia, anorexia, myalgia, or arthralgia as an outpatient the evening of day 3 and day 5, respectively. However, this volunteer was afebrile when evaluated by the study staff on the morning of days 3, 4, 5 and 6. All other temperature measurements recorded by the volunteer or study staff were normal. Although tourniquet tests were not performed, two volunteers were noted to have petechiae at the site of the blood pressure cuff after a blood pressure measurement was performed (one on day 6, the other on days 7 and 10). Both of these volunteers had normal platelet counts at that time and throughout the study.

Significant hematological abnormalities were not seen in any vaccinee. Three vaccinees with presumed benign ethnic neutropenia manifested an absolute neutrophil count (ANC) below 1500/$mm^3$. These three volunteers had baseline ANCs which were significantly lower than the remaining 17 volunteers and which did not decrease disproportionately to the other volunteers. Two of the three volunteers who became neutropenic never had detectable viremia. A mild increase in ALT levels was noted in 4 volunteers, and a more significant increase in ALT level (up to 238 IU/L) was noted in one volunteer. These ALT elevations were transient, were not associated with hepatomegaly, and were completely asymptomatic in each of the 5 volunteers. Elevated ALT values returned to normal by day 26 post-vaccination. The volunteer with the high ALT value was also noted to have an accompanying mild elevation in AST on day 14 ($10^4$ IU/L) which also returned to baseline by day 26 post-vaccination. This volunteer did not have an associated increase in LDH, bilirubin, or alkaline phosphatase levels.

Serologic response of humans to immunization with 2AΔ30. Each of the twenty vaccinees developed a significant rise in serum neutralizing antibody titer against DEN-4 by day 28. The level of serum neutralizing antibody was similar in viremic (1:662) and non-viremic vaccinees (1:426). The DEN-4 neutralizing antibody titers of both groups had not changed significantly by day 42.

Genetic stability of the Δ30 mutation. RT-PCR and sequence analysis of viral RNA isolated from serum samples (n=6) collected from volunteers 6 to 10 days post-vaccination confirmed the presence of the Δ30 mutation and neighboring deletion at nucleotide 10475.

Example 9

Pharmaceutical Compositions

Live attenuated dengue virus vaccines, using replicated virus of the invention, are used for preventing or treating dengue virus infection. Additionally, inactivated dengue virus vaccines are provided by inactivating virus of the invention using known methods, such as, but not limited to, formalin or p-propiolactone treatment. Live attenuated or inactivated viruses containing the mutations described above form the basis of an improved vaccine for the prevention or treatment of dengue infection in humans.

Pharmaceutical compositions of the present invention comprise live attenuated or inactivated dengue viruses, optionally further comprising sterile aqueous or non-aqueous solutions, suspensions, and emulsions. The composition can further comprise auxiliary agents or excipients, as known in the art. See, e.g., Berkow et al. eds. 1987 *The Merck Manual,* 15th edition, Merck and Co., Rahway, N.J.; Goodman et al. eds. 1990 Goodman and Gilman's *The Pharmacological Basis of Therapeutics,* 8th edition, Pergamon Press, Inc., Elmsford, N.Y.; *Avery's Drug Treatment: Principles and Practice of Clinical Pharmacology and Therapeutics,* 3rd edition, ADIS Press, LTD., Williams and Wilkins, Baltimore, Md. 1987; Osol, A. ed. 1980 *Remington's Pharmaceutical Sciences* Mack Publishing Co, Easton, Pa. pp. 1324-1341; Katzung, ed. 1992 *Basic and Clinical Pharmacology* Fifth Edition, Appleton and Lange, Norwalk, Conn.

A virus vaccine composition of the present invention can comprise from about $10^2$-$10^9$ plaque forming units (PFU)/ml, or any range or value therein, where the virus is attenuated. A vaccine composition comprising an inactivated virus can comprise an amount of virus corresponding to about 0.1 to 50 μg of E protein/ml, or any range or value therein.

The agents may be administered using techniques well known to those in the art. Preferably, agents are formulated and administered systemically. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intradermal, intranasal, or intraocular injections, just to name a few. For injection, the agents of the invention may be formulated in aqueous solutions, preferably in physiologically compatible buffers such as saline, phosphate buffered saline, Tris buffered saline, Hank's buffered saline, growth media such as Eagle's Minimum Essential Medium (MEM), and the like.

When a vaccine composition of the present invention is used for administration to an individual, it can further comprise salts, buffers, adjuvants, or other substances which are desirable for improving the efficacy of the composition. Adjuvants useful with the invention include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides or bacterial cell wall components), such as for example (a) MF59 (International Publication No. WO 90/14837), containing 5% Squalene, 0.5% Tween 80, and 0.5% Span 85 (optionally containing various amounts of MTP-PE, although not required) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) mucosal adjuvants such as those derived from cholera toxin (CT), pertussis toxin (PT), *E. coli* heat labile toxin (LT), and mutants thereof (see, e.g., International Publication Nos. WO 95/17211, WO 93/13202, and WO 97/02348); and (7) other substances that act as immunostimulating agents to enhance the effectiveness of the composition.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application, which do not deleteriously react with the active compounds. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, drops, suppositories, or capsules. A syrup, elixir, or the like can be used wherein a sweetened vehicle is employed.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a Freon.

The vaccine can also contain variable but small quantities of endotoxin, free formaldehyde, and preservative, which have been found safe and not contributing to the reactogenicity of the vaccines for humans.

Example 10

Pharmaceutical Purposes

The administration of the vaccine composition may be for either a "prophylactic" or "therapeutic" purpose. When provided prophylactically, the compositions are provided before any symptom of dengue viral infection becomes manifest. The prophylactic administration of the composition serves to prevent or attenuate any subsequent infection. When provided therapeutically, the live attenuated or inactivated viral vaccine is provided upon the detection of a symptom of actual infection. The therapeutic administration of the compound(s) serves to attenuate any actual infection. See, e.g., Berkow et al. eds. 1987 *The Merck Manual,* 15th edition, Merck and Co., Rahway, N.J.; Goodman et al. eds. 1990 *Goodman and Gilman's The Pharmacological Basis of Therapeutics,* 8th edition, Pergamon Press, Inc., Elmsford, N.Y.; *Avery's Drug Treatment: Principles and Practice of Clinical Pharmacology and Therapeutics,* 3rd edition, ADIS Press, LTD., Williams and Wilkins, Baltimore, Md. 1987; Katzung, ed. 1992 *Basic and Clinical Pharmacology*, Fifth Edition, Appleton and Lange, Norwalk, Conn.

A live attenuated or inactivated vaccine composition of the present invention may thus be provided either before the onset of infection (so as to prevent or attenuate an anticipated infection) or after the initiation of an actual infection.

The vaccines of the invention can be formulated according to known methods to prepare pharmaceutically useful compositions, whereby live attenuated or inactivated viruses are combined in a mixture with a pharmaceutically acceptable vehicle. A composition is said to be a "pharmacologically acceptable vehicle" if its administration can be tolerated by a recipient patient. Suitable vehicles are well known to those in the art, e.g., in Osol, A. ed. 1980 *Remington's Pharmaceutical Sciences* Mack Publishing Co, Easton, Pa. pp. 1324-1341.

For purposes of administration, a vaccine composition of the present invention is administered to a human recipient in a therapeutically effective amount. Such an agent is said to be administered in a "therapeutically effective amount" if the amount administered is physiologically significant. A vaccine composition of the present invention is physiologically significant if its presence results in a detectable change in the physiology of a recipient patient that generates a host immune response against at least one dengue serotype, stimulates the production of neutralizing antibodies, or leads to protection against challenge.

The "protection" provided need not be absolute, i.e., the dengue infection need not be totally prevented or eradicated, if there is a statistically significant improvement compared with a control population or set of patients. Protection may be limited to mitigating the severity or rapidity of onset of symptoms of the dengue virus infection.

Example 11

Pharmaceutical Administration

A vaccine of the present invention may confer resistance to one or more dengue serotypes by immunization. In immunization, an live attenuated or inactivated vaccine composition is administered prophylactically, according to a method of the present invention. In another embodiment a live attenuated or inactivated vaccine composition is administered therapeutically, according to a different method of the present invention.

The present invention thus includes methods for preventing or attenuating infection by at least one dengue serotype. As used herein, a vaccine is said to prevent or attenuate a disease if its administration results either in the total or partial attenuation (i.e., suppression) of a symptom or condition of the disease, or in the total or partial immunity of the individual to the disease.

At least one live attenuated or inactivated dengue virus, or composition thereof, of the present invention may be administered by any means that achieve the intended purpose, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular, intradermal or subcutaneous application. See, e.g., Berkow et al. eds. 1987 *The Merck Manual* 15th edition, Merck and Co., Rahway, N.J.; Goodman et al. eds. 1990 *Goodman and Gilman's The Pharmacological Basis of Therapeutics,* 8th edition, Pergamon Press, Inc., Elmsford, N.Y.; *Avery's Drug Treatment: Principles and Practice of Clinical Pharmacology and Therapeutics,* 3rd edition, ADIS Press, LTD., Williams and Wilkins, Baltimore, Md. 1987; Osol, A. ed. 1980 *Remington's Pharmaceutical Sciences*, Mack Publishing Co, Easton, Pa. pp. 1324-1341; Katzung, ed. 192 *Basic and Clinical Pharmacology*, Fifth Edition, Appleton and Lange, Norwalk, Conn.

A typical regimen for preventing, suppressing, or treating a dengue virus related pathology, comprises administration of an effective amount of a vaccine composition as described herein, administered as a single treatment, or repeated as enhancing or booster dosages, over a period up to and including between one week and about 24 months, or any range or value therein.

It will be appreciated that the actual preferred amounts of active compound in a specific case will vary according to the specific compound being utilized, the compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

The dosage of a live attenuated virus vaccine for a mammalian (e.g., human) subject can be from about $10^3$-$10^7$ plaque forming units (PFU)/kg, or any range or value therein. The dose of inactivated vaccine can range from about 0.1 to 50 μg of E protein. However, the dosage should be a safe and effective amount as determined by conventional methods, using existing vaccines as a starting point.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

TABLE 1

Susceptibility of mice to intracerebral DEN4 infection is age-dependent[a]

| Virus | Mean virus titer ($log_{10}$ PFU/g brain) ± SE following inoculation at indicated age (days): 7 | 14 | 21 |
|---|---|---|---|
| 2A-13 | >6.0 | 4.0 ± 0.2 | 3.1 ± 0.2 |
| rDEN4 | >6.0 | 3.3 ± 0.4 | 3.3 ± 0.2 |
| rDEN4Δ30 | >6.0 | 3.6 ± 0.2 | 2.8 ± 0.3 |

[a]Groups of 4 or 5 Swiss Webster mice were inoculated intracerebrally with $10^5$ PFU virus in a 30 μl inoculum. After 5 days, brains were removed, homogenized and titered in Vero cells.
SE = Standard error.

TABLE 2

Temperature-sensitive (ts) and mouse brain attenuation (att) phenotypes of 5-FU mutant DEN4 viruses.

| | | Mean virus titer ($log_{10}$ PFU/ml) at indicated temp. (° C.) | | | | | | | | | | Virus replication in suckling mice[b] | | |
|---|---|---|---|---|---|---|---|---|---|---|---|---|---|---|
| | | Vero cells | | | | | HuH-7 cells | | | | | | Mean titer ± SE | Mean $log_{10}$ |
| Phenotype | Virus | 35 | 37 | 38 | 39 | Δ[a] | 35 | 37 | 38 | 39 | Δ | n | ($log_{10}$ PFU/g brain) | reduction from wt[d] |
| wt (not ts) | 2A-13 | 7.8 | 7.7 | 7.6 | 7.3 | 0.5 | 7.8 | 7.7 | 7.4 | 6.4 | 1.4 | 66 | 6.6 ± 0.1[c] | — |
| | rDEN4 | 6.5 | 6.4 | 6.4 | 6.0 | 0.5 | 7.1 | 6.7 | 6.0 | 5.5 | 1.6 | 66 | 6.1 ± 0.1[c] | — |
| | rDEN4Δ30 | 6.3 | 6.1 | 6.1 | 5.7 | 0.6 | 6.9 | 6.3 | 5.9 | 4.7 | 2.2 | 64 | 5.6 ± 0.1[c] | 0.5 |
| ts in Vero and HuH-7 cells | 695 | 6.2 | 6.0 | 5.2 | 2.6[e] | 3.6 | 6.5 | 5.5 | 3.8 | <1.6 | >4.9 | 6 | 3.0 ± 0.2 | **3.2** |
| | 816 | 6.8 | 6.4 | 5.8 | 3.9 | 2.9 | 7.5 | 6.2 | 5.5 | 3.1 | 4.4 | 6 | 3.3 ± 0.4 | **2.9** |
| | 773 | 7.4 | 6.6 | 6.0 | 3.1 | 4.3 | 7.7 | 6.1 | 5.2 | 3.1 | 4.6 | 12 | 3.7 ± 0.1 | **2.6** |
| | 489 | 7.3 | 6.6 | 6.1 | 3.3 | 4.0 | 7.3 | 6.7 | 5.4 | 3.0 | 4.3 | 6 | 4.5 ± 0.5 | **2.3** |
| | 173 | 7.0 | 6.1 | 3.2 | 2.9 | 4.1 | 7.0 | 3.2 | 3.0 | 2.1 | 4.9 | 18 | 4.7 ± 0.4 | **2.2** |
| | 509 | 6.2 | 5.8 | 5.5 | 3.4 | 2.8 | 6.5 | 6.1 | 4.5 | <1.6 | >4.9 | 6 | 4.9 ± 0.3 | **1.9** |
| | 938 | 7.1 | 6.5 | 5.6 | 3.1 | 4.0 | 7.2 | 6.4 | 5.6 | 3.1 | 4.1 | 6 | 5.1 ± 0.2 | **1.7** |
| | 1033 | 6.7 | 6.0 | 5.9 | 4.1 | 2.6 | 6.9 | 5.6 | 4.7 | <1.6 | >5.3 | 12 | 4.7 ± 0.2 | **1.7** |
| | 239 | 7.6 | 6.8 | 5.6 | 3.3 | 4.3 | 7.6 | 6.7 | 4.7 | 2.5 | 5.1 | 12 | 4.7 ± 0.3 | **1.5** |
| | 793 | 6.5 | 5.8 | 5.3 | 4.0 | 2.5 | 7.2 | 6.8 | 5.6 | <1.6 | >5.6 | 6 | 5.4 ± 0.3 | 1.4 |
| | 759 | 7.2 | 6.9 | 6.4 | 4.7 | 2.5 | 7.5 | 6.8 | 6.3 | 3.1 | 4.4 | 12 | 5.1 ± 0.1 | 1.4 |
| | 718 | 6.1 | 5.9 | 5.3 | 3.5 | 2.6 | 7.0 | 6.5 | 5.7 | 1.7 | 5.3 | 12 | 5.0 ± 0.3 | 1.4 |
| | 473 | 6.7 | 6.3 | 5.4 | 2.0 | 4.7 | 7.2 | 6.7 | 3.7 | 1.9 | 5.3 | 12 | 5.1 ± 0.3 | 1.2 |
| ts in only HuH-7 cells | 686 | 7.0 | 6.7 | 6.7 | 6.4 | 0.6 | 7.3 | 6.8 | 6.4 | 2.2 | 5.1 | 12 | 2.7 ± 0.2 | **3.8** |
| | 967 | 6.8 | 6.4 | 6.4 | 5.1 | 1.7 | 6.8 | 6.4 | 5.4 | <1.6 | >5.2 | 6 | 3.6 ± 0.2 | **2.9** |
| | 992 | 7.3 | 7.1 | 6.8 | 5.9 | 1.4 | 7.4 | 6.9 | 5.0 | <1.6 | >5.8 | 6 | 3.8 ± 0.1 | **2.7** |
| | 571 | 6.9 | 7.0 | 6.4 | 4.6 | 2.3 | 7.0 | 6.3 | 5.2 | <1.6 | >5.4 | 6 | 4.4 ± 0.4 | **2.4** |
| | 605 | 7.6 | 7.5 | 7.1 | 6.9 | 0.7 | 7.8 | 7.2 | 6.8 | <1.6 | >6.2 | 12 | 4.5 ± 0.4 | **2.1** |
| | 631 | 7.1 | 6.9 | 6.8 | 5.0 | 2.1 | 7.3 | 7.1 | 6.5 | <1.6 | >5.7 | 12 | 4.8 ± 0.3 | **1.9** |
| | 1175 | 7.4 | 7.1 | 6.9 | 5.3 | 2.1 | 7.6 | 6.5 | 4.7 | 3.3 | 4.3 | 12 | 4.7 ± 0.2 | **1.7** |

[a]Reduction in titer ($log_{10}$ PFU/ml) at 39° C. compared to titer at permissive temperature (35° C.).
[b]Groups of 6 suckling mice were inoculated i.c. with $10^4$ PFU virus in a 30 μl inoculum. Brains were removed 5 days later, homogenized, and titered in Vero cells.
[c]Average of 11 experiments with a total of 64 to 66 mice per group.
[d]Determined by comparing mean viral titers of mice inoculated with mutant virus and the 2A-13 wt control in the same experiment (n = 6 or 12).
[e]Underlined values indicate a 2.5 or 3.5 $log_{10}$ PFU/ml reduction in titer in Vero cells or HuH-7 cells, respectively, at indicated temp when compared to titer at permissive temp (35° C.).

TABLE 3

Nucleotide and amino acid differences of the 5-FU mutant viruses which are ts in both Vero and HuH-7 cells.

| | Mutations in UTR or coding region that result in an amino acid substitution | | | | Mutations in coding region that do not result in an amino acid substitution | | |
|---|---|---|---|---|---|---|---|
| Virus | Nucleotide position | Gene/ region | Nucleotide change | Amino Acid change[b] | Nucleotide position | Gene | Nucleotide change |
| 173[a] | 7163 | NS4B | A > C | L2354F | 10217 | NS5 | A > U |
| | 7849 | NS5 | A > U | N2583I | | | |
| | 8872 | NS5 | A > G | K2924R | | | |

TABLE 3-continued

Nucleotide and amino acid differences of the 5-FU mutant viruses which are ts in both Vero and HuH-7 cells.

| | Mutations in UTR or coding region that result in an amino acid substitution | | | | Mutations in coding region that do not result in an amino acid substitution | | |
|---|---|---|---|---|---|---|---|
| Virus | Nucleotide position | Gene/ region | Nucleotide change | Amino Acid change[b] | Nucleotide position | Gene | Nucleotide change |
| 239[a] | 4995 | NS3 | U > C | S1632P | 7511 | NS4B | G > A |
| | | | | | 10070 | NS5 | U > C |
| 473[a] | 4480 | NS2B | U > C | V1460A | 7589 | NS5 | G > A |
| | 4995 | NS3 | U > C | S1632P | 10070 | NS5 | U > C |
| 489[a] | 4995 | NS3 | U > C | S1632P | 2232 | E | U > C |
| | | | | | 3737 | NS2A | C > U |
| 509[a] | 4266 | NS2B | A > G | S1389G | none | | |
| | 8092 | NS5 | A > G | E2664G | | | |
| 695 | 40 | 5' UTR | U > C | n/a | 1391 | E | A > G |
| | 1455 | E | G > U | V452F | | | |
| | 6106 | NS3 | A > G | E2002G | | | |
| | 7546 | NS4B | C > U | A2482V | | | |
| 718 | 2280 | E | U > C | F727L | none | | |
| | 4059 | NS2A | A > G | I1320V | | | |
| | 4995 | NS3 | U > C | S1632P | | | |
| | 7630 | NS5 | A > G | K2510R | | | |
| | 8281 | NS5 | U > C | L2727S | | | |
| 759[a] | 4995 | NS3 | U > C | S1632P | none | | |
| | 8020 | NS5 | A > U | N2640I | | | |
| 773[a] | 4995 | NS3 | U > C | S1632P | none | | |
| 793 | 1776 | E | G > A | A559T | 5771 | NS3 | U > C |
| | 2596 | NS1 | G > A | R832K | 7793 | NS5 | U > A |
| | 2677 | NS1 | A > G | D859G | | | |
| | 4387 | NS2B | C > U | S1429F | | | |
| 816[a] | 4995 | NS3 | U > C | S1632P | 6632 | NS4A | G > A |
| | 7174 | NS4B | C > U | A2358V | 6695 | NS4A | G > A |
| 938[a] | 3442 | NS1 | A > G | E1114G | 747 | prM | U > C |
| | 4995 | NS3 | U > C | S1632P | 4196 | NS2b | U > C |
| | 10275 | 3' UTR | A > U | n/a | 6155 | NS3 | G > A |
| 1033[a] | 4907 | NS3 | A > U | L1602F | 548 | prM | C > U |
| | 8730 | NS5 | A > C | N2877H | | | |
| | 9977 | NS5 | G > A | M3292I | | | |

[a]Viruses that contain mutation(s) resulting in an a.a. substitution in only a NS gene(s) and/or nucleotide substitutions in the UTRs are indicated; i.e. no a.a. substitutions are present in the structural proteins (C-prM-E).
[b]Amino acid position in DEN4 polyprotein beginning with the methionine residue of the C protein (nt 102-104) as residue #1. Wild-type amino acid on left of amino acid position; mutant amino acid on right.

TABLE 4

Nucleotide and amino acid differences of the 5-FU mutant viruses which are ts in only HuH-7 cells.

| | Mutations in UTR or coding region that result in an amino acid substitution | | | | Mutations in coding region that do not result in an amino acid substitution | | |
|---|---|---|---|---|---|---|---|
| Virus | Nucleotide position | Gene/ region | Nucleotide change | Amino acid change[b] | Nucleotide position | Gene | Nucleotide change |
| 571 | 586 | prM | U > C | V162A | 6413 | NS4A | U > C |
| | 7163 | NS4B | A > U | L2354F | | | |
| | 7947 | NS5 | G > A | G2616R | | | |
| 605 | 1455 | E | G > U | V452F | none | | |
| | 7546 | NS4B | C > U | A2482V | | | |
| 631 | 595 | prM | A > G | K165R | 1175 | E | G > A |
| | 6259 | NS3 | U > C | V2053A | 5174 | NS3 | A > G |
| | 7546 | NS4B | C > U | A2482V | | | |
| 686[a] | 3575 | NS2A | G > A | M1158I | 4604 | NS3 | A > G |
| | 4062 | NS2A | A > G | T1321A | 7937 | NS5 | A > G |
| | 7163 | NS4B | A > U | L2354F | | | |
| 967 | 2094 | E | G > C | A665P | 4616 | NS3 | C > U |
| | 2416 | E | U > C | V772A | | | |
| | 7162 | NS4B | U > C | L2354S | | | |
| | 7881 | NS5 | G > A | G2594S | | | |
| 992[a] | 5695 | NS3 | A > G | D1865G | 3542 | NS2A | A > G |
| | 7162 | NS4B | U > C | L2354S | | | |

TABLE 4-continued

Nucleotide and amino acid differences of the 5-FU mutant viruses which are ts in only HuH-7 cells.

| | Mutations in UTR or coding region that result in an amino acid substitution | | | | Mutations in coding region that do not result in an amino acid substitution | | |
|---|---|---|---|---|---|---|---|
| Virus | Nucleotide position | Gene/ region | Nucleotide change | Amino acid change[b] | Nucleotide position | Gene | Nucleotide change |
| 1175[a] | 7153 | NS4B | U > C | V2351A | 6167 | NS3 | U > C |
| | 10186 | NS5 | U > C | I3362T | 10184 | NS5 | G > A |
| | 10275 | 3' UTR | A > U | n/a | | | |

[a]Viruses that contain mutation(s) resulting in an a.a. substitution in only a NS gene(s) and/or nucleotide substitutions in the UTRs are indicated; i.e. no a.a. substitutions are present in the structural proteins.
[b]Amino acid position in DEN4 polyprotein beginning with the methionine residue of the C protein (nt 102-104) as residue #1. Wild-type amino acid on left of amino acid position; mutant amino acid on right.

TABLE 5

Mutations which are represented in multiple 5-FU mutant DEN4 viruses.

| Nucleotide position | Gene/ region | Nucleotide change | Amino acid change | Number of viruses with "sister" mutations |
|---|---|---|---|---|
| 1455 | E | G > U | val > phe | 2 |
| 4995 | NS3 | U > C | ser > pro | 8 |
| 7162 | NS4B | U > C | leu > ser | 2 |
| 7163 | NS4B | A > U or C | leu > phe | 3 |

TABLE 5-continued

Mutations which are represented in multiple 5-FU mutant DEN4 viruses.

| Nucleotide position | Gene/ region | Nucleotide change | Amino acid change | Number of viruses with "sister" mutations |
|---|---|---|---|---|
| 7546 | NS4B | C > U | ala > val | 3 |
| 10275 | 3' UTR | A > U | n/a[a] | 2 |

[a]not applicable

TABLE 6

Addition of ts mutation 4995 to rDEN4Δ30 confers a ts phenotype and further attenuates its replication in suckling mouse brain.

| | Mean virus titer ($log_{10}$ PFU/ml) at indicated temp (° C.) | | | | | | | | | | Replication in suckling mice[b] | |
|---|---|---|---|---|---|---|---|---|---|---|---|---|
| | Vero cells | | | | | HuH-7 cells | | | | | Mean virus titer ± SE | Mean $log_{10}$ |
| Virus | 35 | 37 | 38 | 39 | Δ[a] | 35 | 37 | 38 | 39 | Δ | ($log_{10}$ PFU/g brain) | reduction from wt[c] |
| 2A-13 | 7.1 | 7.1 | 6.9 | 6.8 | 0.3 | 7.4 | 7.3 | 6.7 | 6.4 | 1.0 | 6.5 ± 0.1 | — |
| rDEN4 | 7.0 | 6.8 | 6.6 | 6.4 | 0.6 | 7.5 | 7.3 | 6.7 | 6.4 | 1.1 | 6.1 ± 0.2 | — |
| rDEN4Δ30 | 7.0 | 6.7 | 6.2 | 6.2 | 0.8 | 7.5 | 7.0 | 6.5 | 5.1 | 2.4 | 5.9 ± 0.1 | 0.2 |
| rDEN4-4995 | 5.7 | 4.9 | 3.6 | <1.6 | >4.1 | 6.4 | 5.7 | 4.0 | <1.6 | >4.8 | 3.2 ± 0.2 | **2.9** |
| rDEN4Δ30-4995 | 5.9 | 4.9 | 3.9 | <1.6[d] | >4.3 | 6.4 | 5.6 | 4.4 | <1.6 | >4.8 | 3.0 ± 0.3 | **3.1** |

[a]Reduction in titer ($log_{10}$ PFU/ml) at 39° C. compared to titer at permissive temperature (35 C.).
[b]Groups of 6 suckling mice were inoculated i.c. with $10^4$ PFU virus in a 30 μl inoculum. Brains were removed 5 days later, homogenized, and titered in Vero cells. The limit of detection is 2.0 $log_{10}$ PFU/g brain.
[c]Determined by comparing mean viral titers of mice inoculated with sample virus and rDEN4 control.
[d]Underlined values indicate a 2.5 or 3.5 $log_{10}$ PFU/ml reduction in titer in Vero cells or HuH-7 cells, respectively, at indicated temperature when compared to permissive temperature.

TABLE 7

Temperature-sensitive (ts) and mouse brain attenuation (att) phenotypes of 5-FU DEN4 mutant viruses which exhibit a small plaque (sp) phenotype.

| Phenotype | | | | | Mean virus titer ($log_{10}$ PFU/ml) at indicated temp (° C.) | | | | | | | | | | Replication in suckling mice[b] | | |
|---|---|---|---|---|---|---|---|---|---|---|---|---|---|---|---|---|---|
| sp | | ts | | | Vero cells | | | | | HuH-7 cells | | | | | | Mean virus titer ± SE | Mean $log_{10}$ |
| Vero | HuH-7 | Vero | HuH-7 | Virus | 35 | 37 | 38 | 39 | Δ[a] | 35 | 37 | 38 | 39 | Δ | n | ($log_{10}$ PFU/g brain) | reduction from wt[d] |
| — | — | — | — | 2A-13 | 7.9 | 7.5 | 7.7 | 7.2 | 0.7 | 7.9 | 7.7 | 7.3 | 6.9 | 1.0 | 66 | 6.6 ± 0.1[c] | — |
| — | — | — | — | rDEN4 | 7.9 | 7.6 | 7.7 | 7.3 | 0.6 | 8.1 | 7.6 | 7.5 | 6.7 | 1.4 | 66 | 6.1 ± 0.1[c] | — |
| — | — | — | — | rDEN4Δ30 | 7.3 | 6.6 | 6.6 | 6.1 | 1.2 | 7.3 | 7.2 | 6.9 | 5.9 | 1.4 | 64 | 5.6 ± 0.1[c] | 0.5 |

TABLE 7-continued

Temperature-sensitive (ts) and mouse brain attenuation (att) phenotypes of 5-FU DEN4 mutant viruses which exhibit a small plaque (sp) phenotype.

| Phenotype sp Vero | Phenotype sp HuH-7 | Phenotype ts Vero | Phenotype ts HuH-7 | Virus | Mean virus titer ($log_{10}$ PFU/ml) at indicated temp (° C.) Vero cells 35 | Vero 37 | Vero 38 | Vero 39 | Vero Δ[a] | HuH-7 cells 35 | HuH-7 37 | HuH-7 38 | HuH-7 39 | HuH-7 Δ | Replication in suckling mice[b] n | Mean virus titer ± SE ($log_{10}$ PFU/g brain) | Mean $log_{10}$ reduction from wt[d] |
|---|---|---|---|---|---|---|---|---|---|---|---|---|---|---|---|---|---|
| + | + | + | + | 574 | 6.6[x] | 5.5 | 3.8 | <1.6[e] | ≥5.0 | 6.6[x] | 4.9 | 5.0 | <1.6 | ≥5.0 | 6 | 2.1 ± 0.1 | **5.1** |
| + | + | + | + | 1,269 | 5.3[x] | 4.8 | 3.9 | <1.6 | ≥3.7 | 4.0[x] | 2.4 | 2.0 | <1.6 | ≥2.4 | 6 | 2.7 ± 0.2 | **4.1** |
| + | + | + | + | 1,189 | 6.3[x] | 5.2 | 4.5 | 3.8 | 2.5 | 5.5[x] | 3.7 | 2.3 | <1.6 | ≥3.9 | 12 | 3.2 ± 0.4 | **3.7** |
| + | + | — | — | 569 | 5.8[x] | 5.6 | 5.6 | 3.7 | 2.1 | 6.2[x] | 6.0 | 5.7 | 5.0 | 1.2 | 12 | 1.9 ± 0.1 | **4.6** |
| + | + | — | — | 761 | 5.0[x] | 4.7 | 4.2 | 2.7 | 2.3 | 5.6[x] | 5.3 | 4.5 | 2.6 | 3.0 | 12 | 2.0 ± 0.1 | **4.2** |
| — | + | + | + | 506 | 7.0 | 6.8 | 5.6 | 2.6 | 4.4 | 6.7[x] | 4.3 | <1.6 | 2.0 | 4.7 | 6 | 2.2 ± 0.1 | **4.7** |
| — | + | + | + | 1,136 | 5.1 | 4.2 | 2.6 | <1.6 | ≥3.5 | 5.7[x] | 3.0 | 3.0 | <1.6 | ≥4.1 | 6 | 2.9 ± 0.3 | **4.5** |
| — | + | + | + | 1,029 | 6.9 | 5.8 | 5.8 | 2.9 | 4.0 | 7.0[x] | 5.8 | 5.2 | 2.5 | 4.5 | 6 | 2.2 ± 0.1 | **4.2** |
| — | + | + | + | 1,081 | 6.9 | 5.8 | 4.7 | 3.9 | 3.0 | 5.8[x] | 4.1 | 3.3 | 1.9 | 3.9 | 12 | 2.6 ± 0.2 | **3.9** |
| — | + | + | + | 529 | 6.9 | 6.5 | 5.9 | 4.0 | 2.9 | 7.1[x] | 5.3 | 4.4 | <1.6 | ≥5.5 | 6 | 3.1 ± 0.7 | **3.8** |
| — | + | + | + | 1,114 | 6.7 | 6.4 | 6.2 | 2.5 | 4.2 | 5.7[x] | 3.0 | 2.9 | 1.9 | 3.8 | 6 | 2.7 ± 0.3 | **3.7** |
| — | + | + | + | 922 | 7.3 | 7.2 | 6.8 | 3.8 | 3.5 | 7.4[x] | 5.3 | 4.1 | 3.0 | 4.4 | 12 | 3.5 ± 0.1 | **2.9** |
| — | + | + | + | 311 | 6.9 | 5.9 | 4.3 | 1.5 | 5.4 | 7.1[x] | 5.4 | 3.6 | <1.6 | ≥5.5 | 12 | 6.1 ± 0.3 | 0.9 |
| — | + | + | + | 326 | 6.6 | 5.7 | 4.5 | 3.1 | 3.5 | 7.0[x] | 5.5 | 4.1 | 2.0 | 5.0 | 6 | 6.0 ± 0.1 | 0.9 |
| — | + | — | + | 1,104 | 7.1 | 6.8 | 6.8 | 6.1 | 1.0 | 7.2[x] | 6.4 | 5.8 | 2.8 | 4.4 | 6 | 2.2 ± 0.1 | **4.7** |
| — | + | — | + | 952 | 7.1 | 7.0 | 6.7 | 5.6 | 1.5 | 7.3[x] | 6.3 | 5.6 | 3.0 | 4.3 | 6 | 2.4 ± 0.3 | **4.5** |
| — | + | — | + | 738 | 6.5 | 6.0 | 5.9 | 5.7 | 0.8 | 6.9[x] | 6.1 | 5.0 | 3.1 | 3.8 | 12 | 4.4 ± 0.4 | **2.3** |
| — | + | — | + | 1,083 | 7.4 | 7.3 | 7.4 | 5.8 | 1.6 | 7.4[x] | 6.6 | 4.5 | <1.6 | ≥5.8 | 12 | 4.5 ± 0.4 | **2.0** |
| — | + | — | — | 1,096 | 7.5 | 7.1 | 6.9 | 5.5 | 2.0 | 7.5[x] | 6.6 | 5.6 | 4.8 | 2.7 | 6 | 2.9 ± 0.2 | **3.5** |
| — | + | — | — | 1,021 | 7.0 | 6.9 | 6.6 | 6.3 | 0.7 | 6.9[x] | 5.7 | 4.4 | 4.0 | 2.9 | 6 | 3.9 ± 0.6 | **2.6** |
| — | + | — | — | 1,023 | 6.6 | 6.4 | 6.0 | 5.8 | 0.8 | 6.1[x] | 5.6 | 4.7 | 3.3 | 2.8 | 12 | 4.2 ± 0.3 | **2.3** |
| — | + | — | — | 1,012 | 7.5 | 7.1 | 7.0 | 5.7 | 1.8 | 7.4[x] | 6.8 | 6.8 | 5.6 | 1.8 | 6 | 6.1 ± 0.1 | 0.8 |

[a]Reduction in mean virus titer ($log_{10}$ PFU/ml) at 39° C. compared to permissive temperature (35° C.).

[b]Groups of 6 suckling mice were inoculated i.c. with $10^4$ PFU virus. Brains were removed 5 days later, homogenized, and titered in Vero cells.

[c]Average of 11 experiments with a total of 64 to 66 mice per group.

[d]Determined by comparing mean viral titers of mice inoculated with mutant virus and concurrent 2A-13 wild type (wt) virus control (n = 6 or 12).

[e]Underlined values indicate a 2.5 or 3.5 $log_{10}$ PFU/ml reduction in titer in Vero cells or HuH-7 cells, respectively, at indicated temperature when compared to permissive temperature (35° C.).

[x]Small plaque size at 35° C.; small plaques have a diameter of <1.0 mm compared to wild type plaque diameter of 1.5-2.0 mm in Vero cells, or a diameter of <0.4 mm compared to wild type plaque diameter of 0.75 to 1.0 mm in HuH-7 cells.

TABLE 8

Viruses with both ts and sp phenotypes are more restricted in replication in mouse brain than those with only a ts phenotype.

| Cell culture phenotype | Number of viruses | Mean $log_{10}$ reduction in virus titer from control[b, c] |
|---|---|---|
| ts[a] | 20 | 2.1 ± 0.2 |
| sp | 6 | 3.0 ± 0.6 |
| ts/sp | 16 | 3.5 ± 0.3 |

[a]20 ts mutant viruses without an sp phenotype were previously described (Example 1).

[b]Determined by comparing mean viral titers of groups of mice inoculated with mutant virus and concurrent 2A-13 parallel-passaged control virus.

[c]Significant difference between ts group and ts/sp group, Tukey-Kramer test ($P < 0.05$)

TABLE 9

Nucleotide and amino acid differences of the 5-FU mutant DEN4 viruses which produce small plaques in both Vero and HuH-7 cells.

| Virus | Mutations in UTR or in coding regions that result in an amino acid substitution: Nucleotide position | Gene/ region | Nucleotide change | Amino acid change[b] | Mutations in coding regions that do not result in an amino acid substitution: Nucleotide position | Gene | Nucleotide change |
|---|---|---|---|---|---|---|---|
| 569 | 826 | prM | G > A | R242K | 1946 | E | C > U |
| | 832 | prM | C > U | P244L | | | |
| | 7546 | NS4B | C > U | A2482V | | | |
| | 10275 | 3' UTR | A > U | n/a | | | |
| | 10279 | 3' UTR | A > U | n/a | | | |
| 574 | 1455 | E | G > U | V452F | 1349 | E | C > U |
| | 1963 | E | U > C | V621A | | | |

TABLE 9-continued

Nucleotide and amino acid differences of the 5-FU mutant DEN4 viruses which produce small plaques in both Vero and HuH-7 cells.

| | Mutations in UTR or in coding regions that result in an amino acid substitution | | | | Mutations in coding regions that do not result in an amino acid substitution | | |
|---|---|---|---|---|---|---|---|
| Virus | Nucleotide position | Gene/ region | Nucleotide change | Amino acid change[b] | Nucleotide position | Gene | Nucleotide change |
| | 3880 | NS2A | A > G | K1260R | | | |
| | 7546 | NS4B | C > U | A2482V | | | |
| | 7615 | NS5 | A > G | N2505S | | | |
| | 10413 | 3' UTR | A > G | n/a | | | |
| 761 | 424 | C | U > C | I108T | none | | |
| | 2280 | E | U > C | F727L | | | |
| | 7131 | NS4B | A > G | T2344A | | | |
| | 7486 | NS4B | A > G | N2462S | | | |
| 1189a | 3303 | NS1 | A > G | R1068G | 6719 | NS4A | U > C |
| | 4812 | NS3 | G > A | V1571I | | | |
| | 5097 | NS3 | G > A | D1666N | | | |
| | 7182 | NS4B | G > A | G2361S | | | |
| 1269 | 2112 | E | U > C | F671L | 542 | prM | C > U |
| | 3256 | NS1 | G > A | G1052E | | | |
| | 3993 | NS2A | U > C | F1298L | | | |
| | 7183 | NS4B | G > U | G2361V | | | |

aVirus contains missense mutations in only the non-structural genes.
[b]Amino acid position in DEN4 polyprotein beginning with the methionine residue of the C protein (nt 102-104). Wild type amino acid on left of amino acid position; mutant amino acid on right.

TABLE 10

Nucleotide and amino acid differences of the 5-FU mutant DEN4 viruses which produce small plaques in only HuH-7 cells.

| | Mutations in UTR or in coding regions that result in an amino acid substitution | | | | Mutations in coding regions that do not result in an amino acid substitution | | |
|---|---|---|---|---|---|---|---|
| Virus | Nucleotide position | Gene/ region | Nucleotide change | Amino acid change[b] | Nucleotide position | Gene | Nucleotide change |
| 311 | 1519 | E | A > G | N473S | 6761 | NS4A | C > U |
| | 2305 | E | G > A | R735K | 10070 | NS5 | U > C |
| | 4896 | NS3 | G > U | A1599S | | | |
| 326 | 1587 | E | C > U | P496S | 1523 | E | G > A |
| | 7546 | NS4B | C > U | A2482V | 6080 | NS3 | U > C |
| | | | | | 10070 | NS5 | U > C |
| 506 | 1455 | E | G > U | V452F | 3887 | NS2A | A > G |
| | 1902 | E | G > A | V601M | 5789 | NS3 | G > C |
| | 7546 | NS4B | C > U | A2482V | | | |
| | 10275 | 3' UTR | A > U | n/a | | | |
| 529 | 777 | prM | U > C | S226P | none | | |
| | 4641 | NS3 | A > G | I1514V | | | |
| | 7153 | NS4B | U > C | V2351A | | | |
| | 8245 | NS5 | U > C | I2715T | | | |
| | 10279 | 3' UTR | A > C | n/a | | | |
| 738[a] | 3540 | NS2A | G > A | E1147K | none | | |
| | 7162 | NS4B | U > C | L2354S | | | |
| 922[a] | 4306 | NS2B | A > G | N1402S | 7736 | NS5 | G > A |
| | 5872 | NS3 | C > U | T1924I | | | |
| | 7163 | NS4B | A > U | L2354F | | | |
| | 10279 | 3' UTR | A > C | n/a | | | |
| 952 | 1449 | E | G > U | V450L | none | | |
| | 1455 | E | G > U | V452F | | | |
| | 7546 | NS4B | C > U | A2482V | | | |
| | 7957 | NS5 | U > C | V2619A | | | |
| | 9543 | NS5 | A > G | I3148V | | | |
| 1012 | 1542 | E | A > G | K481E | 953 | E | A > G |
| | 7162 | NS4B | U > C | L2354S | 1205 | E | G > A |
| | 10542 | 3' UTR | A > G | n/a | 4425 | NS2B | U > C |
| 1021 | 2314 | E | U > C | I738T | 665 | prM | C > A |
| | 3205 | NS1 | C > U | A1035V | 5750 | NS3 | C > U |
| | 4029 | NS2A | U > C | C1310R | 9959 | NS5 | C > U |
| | 7163 | NS4B | A > C | L2354F | | | |
| | 10275 | 3' UTR | A > U | n/a | | | |
| | 10279 | 3' UTR | A > U | n/a | | | |
| 1023 | 2283 | E | G > A | G728R | 1001 | E | C > U |
| | 7182 | NS4B | G > A | G2361S | 1958 | E | A > G |

TABLE 10-continued

Nucleotide and amino acid differences of the 5-FU mutant DEN4 viruses which produce small plaques in only HuH-7 cells.

| | Mutations in UTR or in coding regions that result in an amino acid substitution | | | | Mutations in coding regions that do not result in an amino acid substitution | | |
|---|---|---|---|---|---|---|---|
| Virus | Nucleotide position | Gene/region | Nucleotide change | Amino acid change[b] | Nucleotide position | Gene | Nucleotide change |
| | | | | | 3873 | NS2a | U > C |
| | | | | | 8486 | NS5 | C > U |
| 1029 | 850 | prM | C > U | A250V | 3867 | NS2a | C > U |
| | 3087 | NS1 | A > G | T996A | | | |
| | 4891 | NS3 | U > C | I1597T | | | |
| 1081[a] | 2650 | NS1 | A > G | N850S | 6326 | NS3 | C > U |
| | 7163 | NS4B | A > U | L2354F | 9146 | NS5 | C > U |
| 1083[a] | 3702 | NS2A | G > A | A1201T | 3353 | NS1 | A > G |
| | 7153 | NS4B | U > C | V2351A | 6155 | NS3 | G > A |
| | 10634 | 3' UTR | U > C | n/a | | | |
| 1096 | 892 | prM | G > A | R264Q | 665 | prM | C > A |
| | 7163 | NS4B | A > C | L2354F | 4427 | NS2b | G > A |
| | 8659 | NS5 | C > U | P2853L | | | |
| 1104 | 1692 | E | G > A | V531M | none | | |
| | 5779 | NS3 | C > U | A1893V | | | |
| | 7546 | NS4B | C > U | A2482V | | | |
| 1114 | 709 | prM | A > G | K203R | 1076 | E | U > C |
| | 3693 | NS2A | A > G | I1198V | 1182 | E | C > U |
| | 4614 | NS3 | U > C | F1505L | 5690 | NS3 | C > U |
| | 7546 | NS4B | C > U | A2482V | | | |
| | 9942 | NS5 | A > G | T3281A | | | |
| 1136[a] | 3771 | NS2A | A > G | R1224G | 5621 | NS3 | A > G |
| | 4891 | NS3 | U > C | I1597T | | | |
| | 10275 | 3' UTR | A > U | n/a | | | |

[a]Viruses that contain missense mutations in only the non-structural genes and/or mutations in the UTRs.
[b]Amino acid position in DEN4 polyprotein beginning with the methionine residue of the C protein (nt 102-104). Wild type amino acid on left of amino acid position; mutant amino acid on right.

TABLE 11

Putative Vero cell adaptation mutations derived from the full set of 5-FU mutant viruses.

| | | 5-FU mutant viruses | | |
|---|---|---|---|---|
| Nucleotide position | Gene/region (a.a. #)[b] | Nucleotide change | Amino acid change | No. of viruses with the mutation |
| 1455 | E (452) | G > U | Val > Phe | 5 |
| 2280 | E (727) | U > C | Phe > Leu | 2 |
| 4891 | NS3 (1597) | U > C | Ile > Thr | 2 |
| 4995 | NS3 (1599) | U > C | Ser > Pro | 8 |
| 7153 | NS4B (2351) | U > C | Val > Ala | 3 |
| 7162 | NS4B (2354) | U > C | Leu > Ser | 4 |
| 7163 | NS4B (2354) | A > U or C | Leu > Phe | 7 |
| 7182 | NS4B (2361) | G > A | Gly > Ser | 2 |

TABLE 11-continued

Putative Vero cell adaptation mutations derived from the full set of 5-FU mutant viruses.

| | | 5-FU mutant viruses | | |
|---|---|---|---|---|
| Nucleotide position | Gene/region (a.a. #)[b] | Nucleotide change | Amino acid change | No. of viruses with the mutation |
| 7546 | NS4B (2482) | C > U | Ala > Val | 10 |
| 7630 | NS5 (2510) | A > G | Lys > Arg | 1 |
| 10275 | 3' UTR | A > U | n/a[a] | 6 |
| 10279 | 3' UTR | A > C | n/a | 4 |

[a]not applicable
[b]Amino acid position in DEN4 polyprotein beginning with the methionine residue of the C protein (nt 102-104) as residue #1.

TABLE 12

Mutagenic oligonucleotides used to generate recombinant DEN4 viruses containing single 5-FU mutations.

| SEQ ID NO. | Recombinant virus (rDEN4-) | Nucleotide change | Amino acid change | Gene | pUC clone | RE site[a] | Oligonucleotide[b] |
|---|---|---|---|---|---|---|---|
| 23 | 40 | U > C | n/a | 5' UTR | pUC/NheI | BsaWI | CAGTTCCAAAcCGGAAGCTTG |
| 24 | 2650 | A > G | Asn > Ser | NS1 | pUC-NS1 | BsiWI | CCAACGAGCTAtcgTAcGTTCTCTGGG |
| 25 | 3303 | A > G | Arg > Gly | NS1 | pUC-NS1 | StyI | GATTGTGACCATgGcGGCCCATCTTTG |
| 26 | 3442 | A > G | Glu > Gly | NS1 | pUC-NS1 | BlpI | GGAGATTAGGCCgcTGAGcGgtAAAGAAGAG |
| 27 | 3540 | G > A | Glu > Lys | NS2A | pUC-NS1 | BsmI | GTTTGTGGAAaAATGtcTGAGGAGAA |
| 28 | 3575 | G > A | Met > Ile | NS2A | pUC-NS1 | SspI | CTAGGAAACACATaATATTAGTTGTGG |

TABLE 12-continued

Mutagenic oligonucleotides used to generate recombinant DEN4 viruses containing single 5-FU mutations.

| SEQ ID NO. | Recombinant virus (rDEN4-) | Nucleotide change | Amino acid change | Gene | pUC clone | RE site[a] | Oligonucleotide[b] |
|---|---|---|---|---|---|---|---|
| 29 | 3702 | G > A | Ala > Thr | NS2A | pUC-NS2A | BglI | CAGATCCACCTA**a**CCATaATGGCAGTG |
| 30 | 3771 | A > G | Arg > Gly | NS2A | pUC-NS2A | AvaI | GGAAACTCACcTCg**g**GAGAGACAGC |
| 31 | 4059 | A > G | Ile > Val | NS2A | pUC-NS2A | BstEII | TTGGGTAGAg**g**TcACcGCACTCATCC |
| 32 | 4062 | A > G | Thr > Ala | NS2A | pUC-NS2A | BsrBI | GTAGAAATA**g**CcGCtCTCATCCTAG |
| 33 | 4266 | A > G | Ser > Gly | NS2B | pUC-NS2A | SnaBI | GGCGGCTTACGTaATG**g**GaGGTAGCTCAGC |
| 34 | 4306 | A > G | Asn > Ser | NS2B | pUC-NS2A | AlwNI | CTAGAGAAGGCaGCtt**c**tGTGCAGTGG |
| 35 | 4480 | U > C | Val > Ala | NS2B | pUC-NS2A | MscI | CCTTGGCcATTCCAG**c**aACAATGAC |
| 36 | 4812 | G > A | Val > Ile | NS3 | pUC-NS2A | ApoI | GACGTTCAa**a**TttTaGCCATAGAACC |
| 37 | 4891 | U > C | Ile > Thr | NS3 | pUC-NS2A | KasI | CTGGAGAAA**c**gGGcGCcGTAACATTAG |
| 38 | 4896 | G > U | Ala > Ser | NS3 | pUC-NS2A | BstEII | GAAATTGGA**t**CgGTAACcTTAGATTTC |
| 39 | 4907 | A > U | Leu > Phe | NS3 | pUC-NS2A | AclI | GGAGCAGTAACgTT**t**GATTTCAAACCC |
| 40 | 4995 | U > C | Ser > Pro | NS3 | pUC-NS2A | BsaJI | GTTACCAAA**c**CtGGgGATTACGTC |
| 41 | 5097 | G > A | Asp > Asn | NS3 | pUC-NS3 | BspHI | GATTAACTATcATG**a**ACTTACACCC |
| 42 | 5695 | A > G | Asp > Gly | NS3 | pUC-NS3 | BanI | GGAAAACCTTTG**g**cACcGAGTATCC |
| 43 | 5872 | C > U | Thr > Ile | NS3 | pUC-NS3 | BsrFI | TCCAGTGA**t**aCCgGCtAGCGCTGCTC |
| 44 | 6106 | A > G | Glu > Gly | NS3 | pUC-NS3 | MscI | GCCTCAGAGGtG**g**cCAAAGGAAG |
| 45 | 6259 | U > C | Val > Ala | NS3 | pUC-NS3 | BglII | ACATGGAGG**c**aGAgATcTGGACTAGA |
| 46 | 7153 | U > C | Val > Ala | NS4B | pUC-NS4A | MscI | AAAGCATG**g**CcAAGGATGCTGTC |
| 47 | 7162 | U > C | Leu > Ser | NS4B | pUC-NS4A | BlpI | GCATAATGGACg**c**tAAGCATGACTAAGG |
| 48 | 7163 | A > C | Leu > Phe | NS4B | pUC-NS4A | ApaLI | TTATTGCATAgTGcAC**g**AAAAGCATG |
| 49 | 7174 | C > U | Ala > Vla | NS4B | pUC-NS4A | BsaAI | GGGCCTATTATT**a**CgTAATGGAC |
| 50 | 7182 | G > A | Gly > Ser | NS4B | pUC-NS4A | n/a | CTGCAATCCTGGtg**a**TATTATTGC |
| 51 | 7546 | C > U | Ala > Val | NS4B | pUC-NS4A | AclI | CTCATAAAGAAcG**t**tCAAACCCT |
| 52 | 7630 | A > G | Lys > Arg | NS5 | pUC-NS5A | HgaI | CATTAGACAGAc**g**cGAGTTTGAAG |
| 53 | 7849 | A > U | Asn > Ile | NS5 | pUC-NS5A | HgaI | TGGCGACgCTCAAGA**t**aGTGACTGAAG |
| 54 | 8020 | A > U | Asn > Ile | NS5 | pUC-NS5A | ClaI | GAGTCATCaTCgA**t**aCCAACAATAG |
| 55 | 8092 | A > G | Glu > Gly | NS5 | pUC-NS5A | EcoRI | CTTCAAAACCTG**g**cTTCTGCATCAAAG |
| 56 | 8281 | U > C | Leu > Ser | NS5 | pUC-NS5B | XmnI | CAAAGATGTTGa**g**cAACAGGTTCACAAC |
| 57 | 8730 | A > C | Asn > His | NS5 | pUC-NS5B | AvaI | GGAAAGAAGAAA**c**AcCCgAGACTGTGC |
| 58 | 8872 | A > G | Lys > Arg | NS5 | pUC-NS5B | PvuI | GGGAACTGGTcGAtc**g**AGAAAGGGC |
| 59 | 9977 | G > A | Met > Ile | NS5 | pUC-NS5C | SfcI | CCAGTGGAT**t**ACtACaGAAGATATGCTC |
| 60 | 10186 | U > C | Ile > Thr | NS5 | pUC-NS5C | AgeI | CAGGAACCTGA**c**CGGtAAAGAGGAATACG |
| 61 | 10275 | A > U | n/a | 3' UTR | pUC-NS5C | n/a | CTGTAATTACCAACA**t**CAAACACCAAAG |

TABLE 12-continued

Mutagenic oligonucleotides used to generate recombinant DEN4 viruses containing single 5-FU mutations.

| SEQ ID NO. | Recombinant virus (rDEN4-) | Nucleotide change | Amino acid change | Gene | pUC clone | RE site[a] | Oligonucleotide[b] |
|---|---|---|---|---|---|---|---|
| 62 | 10279 | A > C | n/a | 3' UTR | pUC-NS5C | n/a | CCAACAACAA**c**CACCAAAGGCTATTG |
| 63 | 10634 | U > C | n/a | 3' UTR | pUC-3'UTR | n/a | GGATTGGTGTTGT**c**GATCCAACAGG |

[a]Primers were engineered which introduced (underline) or ablated (hatched line) translationally-silent restriction enzyme sites.

[b]Lowercase letters indicate nt changes and bold letters indicate the site of the 5-FU mutation, which in some oligonucleotides differs from the original nucleotide substitution change in order to create a unique restriction enzyme site. The change preserves the codon for the amino acid substitution.

TABLE 13 sp, ts and mouse attenuation phenotypes of rDEN4 mutant viruses encoding single mutations identified in six sp 5-FU mutant viruses.

| 5-FU mutant virus | Virus | Gene/region containing mutation | Mean virus titer ($log_{10}$ PFU/ml) at indicated temp (° C.): Vero cells 35 | Vero cells 39 | Vero cells Δ[a] | HuH-7 cells 35 | HuH-7 cells 39 | HuH-7 cells Δ | Replication in suckling mice[b]: n | Mean virus titer ± SE ($log_{10}$ PFU/g brain) | Mean $log_{10}$-unit reduction from value for wt[c] | Replication in HuH-7-SCID mice[d]: n | Mean peak virus titer ± SE ($log_{10}$ PFU/ml serum) | Mean $log_{10}$-unit reduction from value for wt[c] |
|---|---|---|---|---|---|---|---|---|---|---|---|---|---|---|
| | 2A-13 | | 7.6 | 7.1 | 0.5 | 7.8 | 6.6 | 1.2 | 30 | 6.5 ± 0.1 | — | 29 | 6.8 ± 0.2 | — |
| | rDEN4 | | 7.6 | 6.8 | 0.8 | 8.0 | 6.7 | 1.3 | 54 | 5.8 ± 0.1 | — | 32 | 6.3 ± 0.2 | — |
| | rDEN4Δ30 | | 7.6 | 6.9 | 0.7 | 7.7 | 5.6 | 2.1 | 30 | 5.6 ± 0.1 | 0.2 | 18 | 5.4 ± 0.2 | 0.9 |
| 738 | parent | | 6.5 | 5.7 | 0.8 | [x]6.9 | 3.1[e] | 3.8 | 12 | 4.4 ± 0.4 | **2.3** | 9 | 5.4 ± 0.7 | 1.9 |
| | rDEN4-3540 | NS2A | 6.9 | 5.1 | 1.8 | 7.4 | 3.7 | 3.7 | 12 | 4.1 ± 0.3 | **1.7** | 5 | 6.1 ± 0.3 | (+)0.1 |
| | rDEN4-7162 | NS4B | 7.2 | 6.8 | 0.4 | 7.4 | 6.6 | 0.8 | 8 | 5.6 ± 0.3 | 0.3 | 5 | 6.8 ± 0.6 | 0.3 |
| 922 | parent | | 7.3 | 3.8 | 3.5 | [x]7.4 | 3.0 | 4.4 | 12 | 3.5 ± 0.1 | **2.9** | 6 | 6.2 ± 0.2 | 0.4 |
| | rDEN4-4306 | NS2B | [x]5.0 | 2.2 | 2.8 | [x]5.6 | ≤1.6 | >4.0 | 12 | 1.7 ± 0.1 | **4.1** | 5 | 5.2 ± 0.6 | 1.1 |
| | rDEN4-5872 | NS3 | 5.7 | 2.5 | 3.2 | [x]6.5 | ≤1.6 | >4.9 | 12 | 4.5 ± 0.3 | 1.3 | 5 | 6.2 ± 0.5 | 0.1 |
| | rDEN4-7163 | NS4B | 7.8 | 7.2 | 0.6 | 8.0 | 7.4 | 0.6 | 6 | 6.2 ± 0.2 | (+)0.1 | 6 | 5.8 ± 0.6 | (+)0.2 |
| | rDEN4-10279 | 3' UTR | 6.9 | 5.7 | 1.2 | 7.7 | 5.7 | 2.0 | 6 | 4.8 ± 0.2 | 0.7 | 4 | 6.7 ± 0.2 | 0.4 |
| 1081 | parent | | 6.9 | 3.9 | 3.0 | [x]5.8 | 1.9 | 3.9 | 12 | 2.6 ± 0.2 | **3.9** | 4 | 4.2 ± 0.5 | **2.4** |
| | rDEN4-2650 | NS1 | 5.1 | 3.0 | 2.1 | [x]5.5 | 2.8 | 2.7 | 12 | 3.0 ± 0.3 | **2.8** | 4 | 4.7 ± 0.5 | **2.2** |
| | rDEN4-7163 | NS4B | 7.8 | 7.2 | 0.6 | 8.0 | 7.4 | 0.6 | 6 | 6.2 ± 0.2 | (+)0.1 | 6 | 5.8 ± 0.6 | (+)0.2 |
| 1083 | parent | | 7.4 | 5.8 | 1.6 | [x]7.4 | ≤1.6 | ≥5.8 | 12 | 4.5 ± 0.4 | **2.0** | 9 | 4.4 ± 0.3 | **2.9** |
| | rDEN4-3702 | NS2A | 6.8 | 5.6 | 1.2 | 7.6 | 4.7 | 2.9 | 18 | 4.9 ± 0.3 | 0.9 | 7 | 6.3 ± 0.3 | 0.2 |
| | rDEN4-7153 | NS4B | 7.7 | 7.2 | 0.5 | 8.0 | 6.9 | 1.1 | 6 | 5.7 ± 0.1 | 0.2 | 4 | 5.9 ± 0.7 | 0.1 |
| | rDEN4-10634 | 3' UTR | 4.9 | 1.6 | 3.3 | [x]5.7 | ≤1.6 | ≥4.1 | 12 | 2.4 ± 0.3 | **3.4** | 7 | 3.3 ± 0.4 | **3.6** |
| 1136 | parent | | 5.1 | ≤1.6 | ≥3.5 | [x]5.7 | ≤1.6 | ≥4.1 | 6 | 2.9 ± 0.3 | **4.5** | 7 | 4.5 ± 0.4 | 1.2 |
| | rDEN4-3771 | NS2A | 7.0 | 4.6 | 2.4 | [x]7.6 | 3.7 | 3.9 | 12 | 2.6 ± 0.4 | **3.2** | 4 | 6.4 ± 0.2 | (+)0.1 |
| | rDEN4-4891 | NS3 | 7.1 | ≤1.6 | >5.5 | [x]7.4 | ≤1.6 | >5.8 | 12 | 2.5 ± 0.3 | **3.5** | 6 | 6.0 ± 0.5 | 0.3 |
| | rDEN4-10275 | 3' UTR | 6.9 | 5.8 | 1.1 | 7.1 | 5.2 | 1.9 | 6 | 5.0 ± 0.3 | 0.5 | 4 | 6.7 ± 0.3 | 0.4 |
| 1189 | parent | | [x]6.3 | 3.8 | 2.5 | [x]5.5 | ≤1.6 | ≥3.9 | 12 | 3.2 ± 0.4 | **3.7** | 13 | 2.3 ± 0.3 | **3.8** |
| | rDEN4-3303 | NS1 | 6.1 | 4.8 | 1.3 | 6.6 | 3.9 | 2.7 | 8 | 5.7 ± 0.4 | 0.2 | 4 | 6.3 ± 0.3 | 0.8 |
| | rDEN4-4812 | NS3 | 7.0 | 6.3 | 0.7 | 7.1 | 6.3 | 0.8 | 12 | 4.8 ± 0.2 | 1.0 | 5 | 6.1 ± 0.5 | (+)0.5 |
| | rDEN4-5097 | NS3 | [x]5.0 | ≤1.6 | >3.4 | [x]4.6 | ≤1.6 | >3.0 | 12 | 1.8 ± 0.1 | **4.0** | 8 | 1.9 ± 0.1 | **4.3** |
| | rDEN4-7182 | NS4B | 7.7 | 6.9 | 0.8 | 7.8 | 6.8 | 1.0 | 6 | 6.2 ± 0.1 | (+)0.1 | 6 | 6.3 ± 0.3 | (+)0.7 |

[a]Reduction in mean virus titer ($log_{10}$ PFU/ml) at 39° C. compared to permissive temperature (35° C.).

[b]Groups of 6 suckling mice were inoculated i.c. with $10^4$ PFU of virus. Brains were removed 5 days later, homogenized, and titered in Vero cells.

[c]Comparison of mean virus titers of mice inoculated with mutant virus and concurrent DEN4 control. Bold denotes ≥50- or ≥100-fold decrease in replication in suckling or SCID-HuH-7 mice, respectively.

[d]Groups of HuH-7-SCID mice were inoculated directly into the tumor with $10^4$ PFU virus. Serum was collected on day 6 and 7 and titered in Vero cells.

[e]Underlined values indicate a 2.5 or 3.5 $log_{10}$ PFU/ml reduction in titer in Vero cells or HuH-7 cells, respectively, at indicated temp when compared to permissive temp (35° C.).

[x]Small plaque size at 35° C.; small plaques have a diameter of <1.0 mm compared to wild type plaque diameter of 1.5-2.0 mm in Vero cells, or a diameter of <0.4 mm compared to wild type plaque diameter of 0.75 to 1.0 mm in HuH-7 cells.

TABLE 14

Phenotypes of rDEN4 mutant viruses encoding single mutations identified in 10 5-FU mutant viruses that are ts in both Vero and HuH-7 cells.

| 5-FU mutant viruses | rDEN4-Mutation (nt position) | Gene/ region | Mean virus titer ($log_{10}$ PFU/ml) at indicated temp (° C.) Vero cells 35 | 37 | 39 | 39 | Δ[a] | HuH-7 cells 35 | 37 | 38 | 39 | Δ | Replication in 7-day mice[b] n | Mean $log_{10}$ reduction from wt[c] ($log_{10}$ PFU/g brain) | Replication in HuH-7-SCID mice[d] n | Mean $log_{10}$ reduction from wt[c] ($log_{10}$ PFU/ml serum) |
|---|---|---|---|---|---|---|---|---|---|---|---|---|---|---|---|---|
| 239, 489 | parent | | 7.6 | 6.8 | 5.6 | 3.3[e] | 4.3 | 7.6 | 6.7 | 4.7 | 2.5 | 5.1 | 30 | **2.1** | 6 | 0.3 |
| 773 | 4995[f] | NS3 | 5.7 | 4.9 | 3.6 | <1.6 | >4.1 | 6.4 | 5.7 | 4.0 | <1.6 | >4.8 | 6 | **2.9** | | |
| 473 | parent | | 6.7 | 6.3 | 5.4 | 2.0 | 4.7 | 7.2 | 6.7 | 3.7 | 1.9 | 5.3 | 12 | **1.2** | 8 | (+)0.3 |
| | 4480 | NS2B | 6.7 | 6.3 | 6.0 | 5.7 | 1.0 | 7.6 | 7.2 | 6.0 | 5.2 | 2.4 | 6 | 0.7 | | |
| | 4995[f] | NS3 | 5.7 | 4.9 | 3.6 | <1.6 | >4.1 | 6.4 | 5.7 | 4.0 | <1.6 | >4.8 | 6 | **2.9** | | |
| 759 | parent | | 7.2 | 6.9 | 6.4 | 4.7 | 2.5 | 7.5 | 6.8 | 6.3 | 3.1 | 4.4 | 12 | **1.4** | 5 | (+)0.4 |
| | 4995[f] | NS3 | 5.7 | 4.9 | 3.6 | <1.6 | >4.1 | 6.4 | 5.7 | 4.0 | <1.6 | >4.8 | 6 | **2.9** | | |
| | 8020 | NS5 | 7.1 | 6.6 | 6.7 | 5.9 | 1.2 | 7.4 | 7.1 | 6.1 | 5.4 | 2.0 | 6 | 0.5 | | |
| 816 | parent | | 6.8 | 6.4 | 5.8 | 3.9 | 2.9 | 7.5 | 6.2 | 5.5 | 3.1 | 4.4 | 6 | **2.9** | 6 | 0.4 |
| | 4995[f] | NS3 | 5.7 | 4.9 | 3.6 | <1.6 | >4.1 | 6.4 | 5.7 | 4.0 | <1.6 | >4.8 | 6 | **2.9** | | |
| | 7174 | NS4B | 6.9 | 7.1 | 6.9 | 6.1 | 0.8 | 7.5 | 7.2 | 7.1 | 5.6 | 1.9 | 6 | 0.6 | | |
| 938 | parent | | 7.1 | 6.5 | 5.6 | 3.1 | 4.0 | 7.2 | 6.4 | 5.6 | 3.1 | 4.1 | 6 | **1.7** | 6 | 0.5 |
| | 3442 | NS1 | 5.1 | 3.6 | 4.3 | 2.1 | 3.0 | 5.9 | 4.9 | 3.9 | <1.6 | 4.3 | 6 | **4.1** | | |
| | 4995[f] | NS3 | 5.7 | 4.9 | 3.6 | <1.6 | >4.1 | 6.4 | 5.7 | 4.0 | <1.6 | >4.8 | 6 | **2.9** | | |
| | 10275 | 3' UTR | 6.9 | 6.4 | 6.4 | 5.8 | 1.1 | 7.1 | 6.8 | 7.1 | 5.2 | 1.9 | 6 | 0.5 | | |
| 173 | parent | | 7.0 | 6.1 | 3.2 | 2.9 | 4.1 | 7.0 | 3.2 | 3.0 | 2.1 | 4.9 | 18 | **2.2** | 6 | 1.1 |
| | 7163 | NS4B | 7.8 | 7.7 | 7.6 | 7.2 | 0.6 | 8.0 | 7.7 | 7.5 | 7.4 | 0.6 | 6 | (+)0.1 | | |
| | 7849 | NS5 | 7.0 | 6.7 | 3.7 | 2.1 | 4.9 | 7.7 | 5.5 | 3.6 | 2.4 | 5.3 | 6 | **3.1** | | |
| | 8872 | NS5 | 7.0 | 6.3 | 6.4 | 4.4 | 2.6 | 7.4 | 6.4 | 5.1 | 2.9 | 4.5 | 6 | 0.1 | | |
| 509 | parent | | 6.2 | 5.8 | 5.5 | 3.4 | 2.8 | 6.5 | 6.1 | 4.5 | <1.6 | >4.9 | 6 | **1.9** | 6 | **1.5** |
| | 4266 | NS2B | 5.9 | 6.1 | 6.1 | 5.2 | 0.7 | 6.7 | 6.1 | 5.7 | 5.3 | 1.4 | 6 | 1.0 | | |
| | 8092 | NS5 | $5.0^x$ | 4.6 | 4.6 | <1.6 | >3.4 | $5.6^x$ | 4.8 | 4.4 | <1.6 | >4.0 | 12 | **4.0** | | |
| 1033 | parent | | 6.7 | 6.0 | 5.9 | 4.1 | 2.6 | 6.9 | 5.6 | 4.7 | <1.6 | >5.3 | 12 | **1.7** | 5 | 0.7 |
| | 4907 | NS3 | 6.7 | 6.0 | 5.8 | 4.0 | 2.7 | 7.1 | 6.1 | 6.8 | 2.3 | 4.8 | 12 | **1.8** | | |
| | 8730 | NS5 | 7.0 | 6.7 | 6.6 | 6.7 | 0.3 | 7.6 | 7.0 | 7.2 | 6.6 | 1.0 | 12 | 0.6 | | |
| | 9977 | NS5 | 5.6 | 5.5 | 4.6 | 4.1 | 1.5 | 6.4 | 6.1 | 6.2 | 4.6 | 1.8 | 6 | 0.7 | | |

[a]Reduction in mean virus titer ($log_{10}$ PFU/ml) at 39° C. compared to permissive temperature (35° C.).

[b]Groups of 6 suckling mice were inoculated i.c. with $10^4$ PFU of virus. Brains were removed 5 days later, homogenized, and titered in Vero cells.

[c]Comparison of mean virus titers of mice inoculated with mutant virus and concurrent DEN4 control. Bold denotes ≥50- or ≥100-fold decrease in replication in suckling or SCID-HuH-7 mice, respectively.

[d]Groups of HuH-7-SCID mice were inoculated directly into the tumor with $10^4$ PFU virus. Serum was collected on day 6 and 7 and titered in Vero cells.

[e]Underlined values indicate a 2.5 or 3.5 $log_{10}$ PFU/ml reduction in titer in Vero cells or HuH-7 cells, respectively, at indicated temp when compared to permissive temp (35° C.).

[f]Data represents the results from a single rDEN4-4995 virus.

[x]Small plaque size at 35° C.; small plaques have a diameter of <1.0 mm compared to wild type plaque diameter of 1.5-2.0 mm in Vero cells, or a diameter of <0.4 mm compared to wild type plaque diameter of 0.75 to 1.0 mm in HuH-7 cells.

TABLE 15 sp, ts and mouse attenuation phenotypes of rDEN4 mutant viruses encoding single mutations identified in 3 HuH-7 cell-specific ts 5-FU mutant viruses.

| 5-FU mutant viruses | rDEN4-Mutation (nt position) | Gene/ region | Mean virus titer ($log_{10}$ PFU/ml) at indicated temp (° C.) Vero cells 35 | 37 | 39 | 39 | Δ[a] | HuH-7 cells 35 | 37 | 38 | 39 | Δ | Replication in 7-day mice[b] n | Mean $log_{10}$ reduction from wt[c] ($log_{10}$ PFU/g brain)$_{10}$ | Replication in HuH-7-SCID mice[b] n | Mean $log_{10}$ reduction from wt[c] ($log_{10}$ PFU/ml serum) |
|---|---|---|---|---|---|---|---|---|---|---|---|---|---|---|---|---|
| 686 | parent | | 7.0 | 6.7 | 6.7 | 6.4 | 0.6 | 7.3 | 6.8 | 6.4 | 2.2 | 5.1 | 12 | **3.8** | 6 | 1.2 |
| | 3575 | NS2A | 6.9 | 6.9 | 7.1 | 7.0 | 0.1 | 7.9 | 6.8 | 6.9 | 4.9 | 3.0 | 12 | **2.3** | | nd[e] |
| | 4062 | NS2A | 6.8 | 6.6 | 6.3 | 4.7 | 2.1 | 6.9 | 6.8 | 7.0 | <1.6 | >5.3 | 12 | **2.2** | | nd |
| | 7163 | NS4B | 7.8 | 7.7 | 7.6 | 7.2 | 0.6 | 8.0 | 7.7 | 7.5 | 7.4 | 0.6 | 6 | (+)0.1 | | nd |
| 992 | parent | | 7.3 | 7.1 | 6.8 | 5.9 | 1.4 | 7.4 | 6.9 | 5.0 | <1.6 | >5.8 | 6 | **2.7** | 7 | 1.3 |
| | 5695 | NS3 | 5.6 | 4.7 | 4.7 | 3.8 | 1.8 | 6.3 | 5.1 | 3.7 | <1.6 | >4.7 | 6 | **2.8** | | nd |
| | 7162 | NS4B | 7.2 | 7.3 | 6.6 | 6.8 | 0.4 | 7.4 | 7.3 | 7.3 | 6.6 | 0.8 | 8 | 0.3 | | nd |
| 1175 | parent | | 7.4 | 7.1 | 6.9 | 5.3 | 2.1 | 7.6 | 6.5 | 4.7 | 3.3 | 4.3 | 12 | **1.7** | 5 | 1.0 |
| | 7153 | NS4B | 7.7 | 7.7 | 7.6 | 7.2 | 0.5 | 8.0 | 7.8 | 7.5 | 6.9 | 1.1 | 6 | 0.2 | | nd |

TABLE 15-continued sp, ts and mouse attenuation phenotypes of rDEN4 mutant viruses encoding single mutations identified in 3 HuH-7 cell-specific ts 5-FU mutant viruses.

| 5-FU mutant viruses | rDEN4-Mutation (nt position) | Gene/ region | Mean virus titer ($log_{10}$ PFU/ml) at indicated temp (° C.): Vero cells 35 | 37 | 39 | 39 | Δ[a] | HuH-7 cells 35 | 37 | 38 | 39 | Δ | Replication in 7-day mice[b]: n | Mean $log_{10}$ reduction from wt[c] ($log_{10}$ PFU/g brain)$_{10}$ | Replication in HuH-7-SCID mice[b]: n | Mean $log_{10}$ reduction from wt[c] ($log_{10}$ PFU/ml serum) |
|---|---|---|---|---|---|---|---|---|---|---|---|---|---|---|---|---|
| | 10186 | NS5 | 4.3 | 3.7 | 2.4 | <1.6 | >2.7 | 5.1 | <1.6 | <1.6 | <1.6 | >3.5 | 6 | **3.4** | | nd |
| | 10275 | 3' UTR | 6.9 | 6.4 | 6.4 | 5.8 | 1.1 | 7.1 | 6.8 | 7.1 | 5.2 | 1.9 | 6 | 0.5 | | nd |

[a]Reduction in titer ($log_{10}$ PFU/ml) at 39° C. compared to permissive temperature (35° C.).

[b]Groups of 6 suckling mice were inoculated i.c. with $10^4$ PFU virus. Brains were removed 5 days later, homogenized, and titered in Vero cells.

[c]Determined by comparing mean viral titers of mice inoculated with mutant virus and concurrent 2A-13 or rDEN4 wt control.

[d] Underlined values indicate a 2.5 or 3.5 $log_{10}$ PFU/ml reduction in titer in Vero cells or HuH-7 cells, respectively, at indicated temp when compared to permissive temp (35° C.).

TABLE 16

Temperature-sensitive (ts) and mouse brain attenuation (att) phenotypes of additional rDEN4 viruses encoding single 5-FU mutations.

| 5-FU mutant virus | Virus | Gene/ region containing mutation | Mean virus titer ($log_{10}$ PFU/ml) at indicated temp (° C.): Vero cells 35 | 37 | 38 | 39 | Δ[a] | HuH-7 cells 35 | 37 | 38 | 39 | Δ | Replication in suckling mice[b]: n | Mean virus titer ± SE ($log_{10}$ PFU/g brain) | Mean $log_{10}$-unit reduction from value for wt[c] |
|---|---|---|---|---|---|---|---|---|---|---|---|---|---|---|---|
| 695 | rDEN4-40 | 5' UTR | 7.4 | 7.2 | 6.7 | 6.2 | 1.2 | 7.6 | 7.5 | 7.1 | 5.8 | 1.8 | | nd[f] | nd |
| 718 | rDEN4-4059 | NS2A | 7.0 | 6.7 | 6.4 | 6.2 | 0.8 | 7.7 | 7.1 | 7.0 | 6.6 | 1.1 | | nd | nd |
| 311 | rDEN4-4896 | NS3 | 7.0 | 6.1 | 5.9 | 4.2 | 2.8 | 6.9[x] | 6.0 | 5.6 | 3.3 | 3.6 | 6 | 4.1 ± 0.4 | **2.0**** |
| 695 | rDEN4-6106 | NS3 | 6.8 | 6.3 | 5.9 | 3.9 | 2.9 | 7.1 | 6.0 | 5.2 | 3.4 | 3.7 | | nd | nd |
| 631 | rDEN4-6259 | NS3 | 7.0 | 6.1 | 5.8 | 5.0 | 2.0 | 7.5 | 6.6 | 5.7 | 4.2 | 3.3 | 6 | 2.2 ± 0.2 | **3.9**** |
| 695[e] | rDEN4-7546 | NS4B | 7.5 | 7.6 | 7.4 | 6.6 | 0.9 | 7.7 | 7.6 | 7.3 | 5.7 | 2.0 | | nd | nd |
| 718 | rDEN4-7630 | NS5 | 7.0 | 6.9 | 6.9 | 6.4 | 0.6 | 7.4 | 7.4 | 7.2 | 6.8 | 0.6 | 6 | 5.0 ± 0.3 | 0.5 |
| 718 | rDEN4-8281 | NS5 | 6.4 | 6.6 | 6.7 | 5.4 | 1.0 | 7.6 | 7.6 | 7.0 | 5.1 | 2.5 | 6 | 5.0 ± 0.5 | 1.1 |

[a]Reduction in titer ($log_{10}$ PFU/ml) at 39° C. compared to titer at permissive temperature (35° C.).

[b]6 mice were inoculated i.c. with $10^4$ PFU virus in 30 μl inoculum. Brains were removed 5 days later, homogenized, and titered on Vero cells. Limit of detection is 2.0 $log_{10}$ PFU/g.

[c]Determined by comparing mean viral titers of mice inoculated with sample virus and wt rDEN4 control.

[d] Underlined values indicate a 2.5 or 3.5 $log_{10}$ PFU/ml reduction in titer in Vero cells or HuH-7 cells, respectively, at indicated temperature when compared to permissive temperature (35° C.).

[e]The 7546 mutation is also present in nine other 5-FU mutant viruses.

[x]Small plaque size at 35° C.; small plaques have a diameter of <0.4 mm compared to wt plaque diameter of 0.75 to 1.0 mm in HuH-7 cells.

[f]not determined

**The att phenotype is defined as a reduction of >1.5 $log_{10}$ PFU/g compared to wt virus.

TABLE 17

Growth of wt DEN-4 2A-13 in SCID mice transplanted with HuH-7 cells.[a]

| Dose ($log_{10}$ PFU/ml) | Mouse # | Virus titer: $log_{10}$ PFU/ml serum day 3 | day 5 | $log_{10}$ PFU/g tissue Brain | Liver | Tumor |
|---|---|---|---|---|---|---|
| 4 | 87 | 2.7 | 5.9 | 2.0 | 6.9 | 8.0 |
| | 88 | 2.0 | 5.9 | 3.8 | 3.3 | 8.0 |
| | 89 | <1.7 | 6.2 | 2.7 | 3.6 | 8.0 |
| | 90 | 1.7 | 3.5 | 3.2 | 3.0 | 7.0 |
| 5 | 84 | <1.7 | 7.2 | 3.2 | 4.0 | 7.0 |
| | 85 | 1.7 | 6.6 | 3.6 | 6.3 | 5.8 |
| 6 | 91 | 4.4 | 8.3 | 6.0 | 7.3 | 8.0 |
| | 92 | 4.2 | 7.7 | 3.3 | 6.9 | 7.3 |

TABLE 17-continued

Growth of wt DEN-4 2A-13 in SCID mice transplanted with HuH-7 cells.[a]

| Dose ($log_{10}$ PFU/ml) | Mouse # | Virus titer: $log_{10}$ PFU/ml serum day 3 | day 5 | $log_{10}$ PFU/g tissue Brain | Liver | Tumor |
|---|---|---|---|---|---|---|
| | 93 | 4.0 | 6.6 | 3.3 | 5.7 | 8.4 |
| | 94 | 4.3 | 8.1 | 5.8 | 7.8 | 7.5 |

[a]SCID mice were injected i.p. with $10^7$ HuH-7 human hepatoma cells. Approximately 8 weeks later, groups of tumor-bearing SCID-HuH-7 mice were inoculated with virus directly into the tumor. Serum and tissues were collected on day 5, processed, and titered in Vero cells.

TABLE 18

Combination of ts mutations, NS3 4995 and NS5 7849, in rDEN4 results in an additive ts phenotype.

| Virus | Mean virus titer ($log_{10}$ PFU/ml) at indicated temp (° C.) | | | | | | | | | | Replication in suckling mice[b] | |
|---|---|---|---|---|---|---|---|---|---|---|---|---|
| | Vero cells | | | | | HuH-7 cells | | | | | Mean virus titer ± SE ($log_{10}$ PFU/g brain) | Mean $log_{10}$ reduction from wt[c] |
| | 35 | 37 | 38 | 39 | Δ[a] | 35 | 37 | 38 | 39 | Δ | | |
| 2A-13 wt | 7.1 | 7.1 | 6.9 | 6.8 | 0.3 | 7.4 | 7.3 | 6.7 | 6.4 | 1.0 | 6.9 ± 0.09 | — |
| rDEN4 wt | 7.0 | 6.8 | 6.6 | 6.4 | 0.6 | 7.5 | 7.3 | 6.7 | 6.4 | 1.1 | 6.5 ± 0.11 | — |
| rDEN4Δ30 | 7.0 | 6.7 | 6.2 | 6.2 | 0.8 | 7.5 | 7.0 | 6.5 | 5.1 | 2.4 | 5.9 ± 0.21 | 0.6 |
| rDEN4-4995 | 5.7 | 4.9 | 3.6 | <1.6[d] | >4.1 | 6.4 | 5.7 | 4.0 | <1.6 | >4.8 | 3.4 ± 0.10 | **3.1** |
| rDEN4-7849 | 7.0 | 6.7 | 3.7 | 2.1 | 4.9 | 7.7 | 5.5 | 3.6 | 2.4 | 5.3 | 2.6 ± 0.29 | **3.9** |
| rDEN4-4995-7849 | 5.9 | 2.8 | <1.6 | <1.6 | >4.3 | 5.6 | 2.4 | <1.6 | <1.6 | >4.0 | 2.3 ± 0.20 | **4.2** |

[a]Reduction in titer ($log_{10}$ PFU/ml) at 39° C. compared to titer at permissive temperature (35° C.).
[b]Groups of 6 suckling mice were inoculated i.c. with $10^4$ PFU virus. Brains were removed 5 days later, homogenized, and titered in Vero cells. The limit of detection is 2.0 $log_{10}$ PFU/g.
[c]Determined by comparing mean viral titers of mice inoculated with sample virus and rDEN4 wt control.
[d]Underlined values indicate a 2.5 or 3.5 $log_{10}$ PFU/ml reduction in titer in Vero cells or HuH-7 cells, respectively, at indicated temperature when compared to permissive temperature.

TABLE 19

The 5-FU mutations are compatible with the Δ30 mutation for replication in the brain of suckling mice.

| Virus | No. of mice/ group | Mean virus titer ± SE ($log_{10}$ PFU/g brain)[a] | Mean $log_{10}$-unit reduction from wt[b] |
|---|---|---|---|
| rDEN4 | 12 | 6.0 ± 0.1 | — |
| rDEN4Δ30 | 12 | 5.3 ± 0.1 | 0.7 |
| rDEN4-2650[c] | 12 | 3.7 ± 0.2 | **2.3** |
| rDEN4Δ30-2650 | 12 | 3.9 ± 0.1 | **2.1** |
| rDEN4-4995[d] | 6 | 3.5 ± 0.2 | **2.5** |
| rDEN4Δ30-4995 | 6 | 2.7 ± 0.4 | **3.3** |
| rDEN4-8092[d] | 12 | 2.0 ± 0.1 | **4.0** |
| rDEN4Δ30-8092 | 6 | 3.2 ± 0.2 | **2.8** |

TABLE 19-continued

The 5-FU mutations are compatible with the Δ30 mutation for replication in the brain of suckling mice.

| Virus | No. of mice/ group | Mean virus titer ± SE ($log_{10}$ PFU/g brain)[a] | Mean $log_{10}$-unit reduction from wt[b] |
|---|---|---|---|
| rDEN4-10634[c] | 12 | 3.8 ± 0.1 | **2.2** |
| rDEN4Δ30-10634 | 12 | 3.6 ± 0.1 | **2.4** |

[a]Groups of 6 suckling mice were inoculated i.c. with $10^4$ PFU of virus. Brains were removed 5 days later, homogenized, and titered in Vero cells.
[b]Comparison of mean virus titers of mice inoculated with mutant virus and rDEN4 control.
[c]Mutation restricts growth in both mouse brain and HuH-7-SCID mice.
[d]Mutation restricts growth in mouse brain only. The 8092 mutation has not been tested in SCID-HuH7 mice.

TABLE 20

Temperature-sensitive and mouse brain attenuation phenotypes of viruses bearing charge-cluster-to-alanine mutations in the NS5 gene of DEN4.

| Mutation[a] | Changed AA Pair | # nt changed | Mean virus titer ($log_{10}$ PFU/ml at indicated temperature (° C.)[b] | | | | | | | | | | Replication in suckling mice[d] | | |
|---|---|---|---|---|---|---|---|---|---|---|---|---|---|---|---|
| | | | Vero Cells | | | | | HuH-7 Cells | | | | | | Mean titer ± SE ($log_{10}$ PFU/g brain) | Mean log reduction from wt[e] |
| | | | 35 | 37 | 38 | 39 | Δ[c] | 35 | 37 | 38 | 39 | Δ | n | | |
| wt (rDEN4) | n/a | 0 | 8.1 | 8.1 | 7.9 | 7.6 | 0.5 | 8.3 | 8.0 | 7.5 | 7.5 | 0.8 | 48 | 6.0 ± 0.16 | — |
| deletion (rDEN4Δ30) | n/a | 30 | 6.3 | 6.1 | 6.1 | 5.7 | 0.6 | 6.9 | 6.3 | 5.9 | 4.7 | 2.2 | 42 | 5.4 ± 0.22 | 0.6 |
| 21-22 | D R | 4 | 7.2 | 6.8 | 6.7 | 6.1 | 1.1 | 7.6 | 7.1 | 7.0 | 4.7 | 2.9 | 6 | 5.0 ± 0.50 | 0.6 |
| 22-23 | R K | 4 | 7.0 | 7.8 | 6.9 | 3.7 | 3.3 | 7.6 | 7.6 | 6.5 | <1.7 | >5.9 | 6 | 2.6 ± 0.19 | **2.9** |
| 23-24 | K E | 3 | 6.7 | 6.6 | 6.0 | 6.5 | 0.2 | 7.1 | 7.3 | 5.6 | <1.7 | >5.4 | 18 | 4.7 ± 0.09 | **1.5** |
| 26-27 | E E | 3 | 7.8 | 7.6 | 6.8 | 4.0 | 3.8 | 8.4 | 8.2 | 7.3 | 4.9 | 3.5 | 6 | 5.7 ± 0.30 | +0.1 |
| 46-47 | K D | 3 | 7.4 | 7.4 | 7.3 | 7.0 | 0.4 | 7.8 | 7.8 | 7.3 | 6.8 | 1.0 | 6 | 5.4 ± 0.42 | 0.5 |
| 157-158 | E E | 3 | 6.5 | 7.2 | 5.1 | 5.1 | 1.4 | 7.6 | 7.4 | 5.9 | <1.7 | >5.9 | 6 | 2.8 ± 0.31 | **2.7** |
| 200-201 | K H | 4 | 5.3 | 4.6 | 5.3 | 4.1 | 1.2 | 5.6 | 4.9 | 3.7 | <1.7 | >3.9 | 12 | 5.5 ± 0.45 | 0.8 |
| 246-247 | R H | 5 | 6.9 | 5.8 | 5.7 | 5.4 | 1.5 | 6.4 | 6.1 | 6.1 | 5.5 | 0.9 | 6 | 6.1 ± 0.17 | +0.5 |
| 253-254 | E K | 4 | 7.1 | 6.9 | 6.8 | 7.0 | 0.1 | 7.9 | 7.5 | 7.6 | 6.8 | 1.1 | 6 | 6.2 ± 0.13 | +0.6 |
| 356-357 | K E | 3 | 7.7 | 7.6 | 7.0 | 7.0 | 0.7 | 8.0 | 7.3 | 6.4 | <1.7 | >6.3 | 6 | 3.5 ± 0.58 | **2.0** |
| 387-388 | K K | 5 | 7.7 | 6.1 | 7.0 | <1.7 | >6.0 | 7.0 | 6.3 | 7.0 | <1.7 | >5.3 | 6 | 3.1 ± 0.33 | **2.4** |
| 388-389 | K K | 5 | 5.1 | 4.5 | <1.7 | <1.7 | >3.4 | 6.1 | 5.0 | <1.7 | <1.7 | >4.4 | 6 | 5.0 ± 0.23 | 1.4 |
| 396-397 | R E | 4 | 7.0 | 7.3 | 6.5 | 5.5 | 1.5 | 7.5 | 7.6 | 7.5 | <1.7 | >5.8 | 18 | 5.4 ± 0.35 | 1.1 |
| 397-398 | E E | 2 | 7.0 | 7.1 | 7.0 | 3.0 | 4.0 | 8.0 | 7.6 | 7.0 | <1.7 | >6.3 | 6 | 6.0 ± 0.22 | 0.8 |
| 436-437 | D K | 4 | 4.5 | 3.3 | 3.0 | 2.0 | 2.5 | 5.7 | 4.5 | <1.7 | <1.7 | >4.0 | 12 | 2.3 ± 0.14 | **3.9** |
| 500-501 | R E | 3 | 6.6 | 6.3 | 5.7 | 2.3 | 4.3 | 7.1 | 6.5 | <1.7 | <1.7 | >5.4 | 6 | 6.9 ± 0.49 | +0.7 |

TABLE 20-continued

Temperature-sensitive and mouse brain attenuation phenotypes of viruses bearing charge-cluster-to-alanine mutations in the NS5 gene of DEN4.

| | | | Mean virus titer ($log_{10}$ PFU/ml at indicated temperature (° C.)[b] | | | | | | | | | | Replication in suckling mice[d] | | |
|---|---|---|---|---|---|---|---|---|---|---|---|---|---|---|---|
| | Changed | # nt | Vero Cells | | | | | HuH-7 Cells | | | | | | Mean titer ± SE ($log_{10}$ PFU/g | Mean log reduction |
| Mutation[a] | AA Pair | changed | 35 | 37 | 38 | 39 | Δ[c] | 35 | 37 | 38 | 39 | Δ | n | brain) | from wt[e] |
| 520-521 | E E | 3 | 5.6 | 4.7 | 4.3 | ≤1.7 | >3.9 | 6.7 | 5.7 | ≤1.7 | ≤1.7 | >5.0 | 6 | 5.2 ± 0.48 | 0.2 |
| 523-524 | D K | 4 | 6.6 | 6.3 | 6.3 | 5.8 | 0.8 | 7.1 | 6.6 | ≤1.7 | ≤1.7 | >5.4 | 6 | 4.2 ± 0.47 | 1.3 |
| 524-525 | K K | 5 | 7.1 | 6.9 | 6.9 | 6.6 | 0.5 | 7.8 | 7.4 | 7.0 | 5.3 | 2.5 | 6 | 3.4 ± 0.54 | **2.1** |
| 525-526 | K D | 4 | 7.8 | 7.1 | 7.6 | 6.8 | 1.0 | 7.9 | 7.7 | 8.0 | 6.9 | 1.0 | 6 | 3.7 ± 0.64 | **1.8** |
| 596-597 | K D | 3 | 4.6 | 4.0 | 2.6 | ≤1.7 | >2.9 | 5.7 | 4.9 | 4.0 | ≤1.7 | >4.0 | 6 | 5.9 ± 0.14 | 0.5 |
| 641-642 | K E | 4 | 7.3 | 6.9 | 6.9 | 5.2 | 2.1 | 7.8 | 7.5 | 7.2 | 6.9 | 0.9 | 6 | 4.7 ± 0.45 | 1.2 |
| 642-643 | E R | 3 | 6.8 | 6.1 | 4.0 | 3.3 | 3.5 | 7.5 | 7.1 | 6.6 | 3.0 | 4.5 | 12 | 2.6 ± 0.15 | **3.6** |
| 645-646 | E K | 4 | 6.3 | 5.3 | 5.9 | 3.1 | 3.2 | 6.4 | 5.8 | 5.5 | 4.5 | 1.9 | 6 | 5.4 ± 0.51 | 0.2 |
| 649-650 | K E | 3 | 6.9 | 6.8 | 6.9 | 6.3 | 0.6 | 7.1 | 7.3 | 7.5 | 7.0 | 0.1 | 12 | 6.4 ± 0.20 | +0.2 |
| 654-655 | D R | 4 | 6.3 | 5.7 | ≤1.7 | ≤1.7 | >4.6 | 7.0 | 7.1 | 4.6 | ≤1.7 | >5.3 | 12 | 1.8 ± 0.10 | **4.0** |
| 750-751 | R E | 3 | 7.1 | 7.1 | 6.9 | 5.7 | 1.4 | 7.8 | 6.9 | 6.5 | 5.6 | 2.2 | 6 | 6.0 ± 0.18 | 0.7 |
| 808-809 | E D | 3 | 4.6 | 4.1 | ≤1.7 | ≤1.7 | >2.9 | 5.2 | ≤1.7 | ≤1.7 | ≤1.7 | >3.5 | 6 | 1.8 ± 0.05 | **3.1** |
| 820-821 | E D | 2 | 6.3 | 6.3 | 5.6 | ≤1.7 | >4.6 | 6.9 | 6.0 | 5.7 | ≤1.7 | >5.2 | 6 | 5n5 ± 0.33 | 1.2 |
| 827-828 | D K | 4 | 6.9 | 6.3 | 6.3 | 5.9 | 1.0 | 7.5 | 6.9 | 5.0 | ≤1.7 | >5.8 | 6 | 3.6 ± 0.76 | **2.3** |
| 877-878 | K E | 3 | 7.6 | 7.3 | 7.0 | 7.0 | 0.6 | 7.9 | 7.9 | 7.3 | 5.8 | 2.1 | 12 | 4.4 ± 0.65 | **1.8** |
| 878-879 | E E | 3 | 7.6 | 7.3 | 7.3 | 7.1 | 0.5 | 8.1 | 8.1 | 7.9 | 6.6 | 1.5 | 12 | 2.4 ± 0.10 | **3.8** |

[a]Positions of the amino acid pair mutated to an alanine pair; numbering starts at the amino terminus of the NS5 protein.

[b]Underlined values indicate a 2.5 or 3.5 log10 PFU/ml reduction in titer in Vero or HuH-7 cells, respectively, at the indicated temperatures when compared to permissive temperature (35° C.).

[c]Reduction in titer (log10 PFU/ml) at 39° C. compared to permissive temperature (35° C.).

[d]Groups of six mice were inoculated i.c. with 4.0 log10 PFU virus in a 30 μl inoculum. The brain was removed 5 days later, homogenized, and titered in Vero cells.

[e]Determined by comparing mean viral titers in mice inoculated with sample virus and concurrent wt controls (n = 6). The attenuation phenotype is defined as a reduction of ≥1.5 log10 PFU/g compared to wt virus; reductions of ≥1.5 are listed in boldface.

TABLE 21

SCID-HuH-7 attenuation phenotypes of viruses bearing charge-cluster-to-alanine mutations in the NS5 gene of DEN4.

| | | Replication in SCID-HuH-7 mice[b] | | |
|---|---|---|---|---|
| Mutation[a] | AA changed | n | Mean peak virus titer ± SE ($log_{10}$ PFU/ml serum) | Mean log reduction from wt[c] |
| wt | na | 21 | 5.4 ± 0.4 | — |
| Δ30 | na | 4 | 3.7 ± 0.6 | **2.5** |
| 23-24 | KE | 19 | 4.7 ± 0.5 | 1.3 |
| 157-158 | EE | 6 | 4.6 ± 0.6 | 1.3 |
| 200-201 | KH | 12 | 3.7 ± 0.2 | **2.6** |
| 356-357 | KE | 10 | 6.3 ± 0.7 | (−) 1.1 |
| 396-397 | RE | 12 | 4.4 ± 1.3 | 1.2 |
| 397-398 | EE | 6 | 6.0 ± 0.5 | (−) 0.1 |
| 436-437 | DK | 6 | 3.6 ± 0.2 | **2.6** |
| 500-501 | RE | 8 | 5.1 ± 0.4 | 1.1 |
| 523-524 | DK | 5 | 5.3 ± 0.7 | 0.6 |
| 750-751 | RE | 8 | 5.1 ± 0.4 | 1.1 |
| 808-809 | ED | 8 | 3.2 ± 0.4 | **3.0** |
| 827-828 | DK | 5 | 2.9 ± 0.2 | 1.6 |
| 878-879 | EE | 5 | 4.4 ± 0.7 | 1.5 |

[a]Positions of the amino acid pair changed to a pair of alanines; numbering starts at the amino terminus of the NS5 protein.
[b]Groups of SCID-HuH-7 mice were inoculated directly into the tumor with $10^4$ PFU virus. Serum was collected on days 6 and 7 and titered in Vero cells.
[c]Comparison of mean virus titers of mice inoculated with mutant virus and concurrent DEN4 control. Bold denotes a ≥100-fold decrease in replication. A (−) sign indicates an increase in replication relative to wt.

TABLE 22

Combination of paired charge-cluster-to-alanine mutations into double-pair mutant viruses.

| Mutation Pair 1 | Mutation Pair 2 | Recovered |
|---|---|---|
| 23-24 | 200-201 | Yes |
| 23-24 | 356-357 | Yes |
| 23-24 | 396-397 | Yes |
| 23-24 | 523-524 | Yes |
| 23-24 | 827-828 | No |
| 157-158 | 200-201 | No |
| 157-158 | 356-357 | No |
| 157-158 | 396-397 | No |
| 157-158 | 523-524 | Yes |
| 157-158 | 827-828 | No |
| 827-828 | 200-201 | No |
| 827-828 | 356-357 | No |
| 827-828 | 396-397 | Yes |
| 827-828 | 523-524 | No |

TABLE 23

Temperature-sensitive and mouse brain attenuation phenotypes of double charge-cluster-to-alanine mutants of the NS5 gene of rDEN4.

| | | | Mean virus titer (log10 PFU/ml) at indicated temperature (° C.)[b] | | | | | | | | | | | Replication in suckling mice[d] | |
|---|---|---|---|---|---|---|---|---|---|---|---|---|---|---|---|
| | | | Vero Cells | | | | | HuH-7 cells | | | | | | Mean virus titer ± SE | Mean log reduction |
| Mutation[a] | Charged AA Pair | #nt changed | 35 | 37 | 38 | 39 | Δ[c] | 35 | 37 | 38 | 39 | Δ | n | ($log_{10}$ PFU/g brain) | from wt[e] |
| wt | n/a | 0 | 8.1 | 8.1 | 7.9 | 7.6 | 0.5 | 8.3 | 8.0 | 7.5 | 7.5 | 0.8 | 48 | 6.0 ± 0.16 | — |
| Δ30 | n/a | 30 | 6.3 | 6.1 | 6.1 | 5.7 | 0.6 | 6.9 | 6.3 | 5.9 | 4.7 | 2.2 | 42 | 5.4 ± 0.22 | 0.6 |
| 23-24 | K E | 3 | 6.7 | 6.6 | 6.0 | 6.5 | 0.2 | 7.1 | 7.3 | 5.6 | <1.7 | >5.4 | 18 | 4.7 ± 0.09 | **1.5** |
| 200-201 | K H | 4 | 5.3 | 4.6 | 5.3 | 4.1 | 1.2 | 5.6 | 4.9 | 3.7 | <1.7 | >3.9 | 12 | 5.5 ± 0.45 | 0.8 |
| 23-24; 200-201 | K E, K H | 7 | 7.1 | 6.5 | 6.6 | <1.7 | >5.4 | 7.8 | 7.3 | <1.7 | <1.7 | >6.1 | 6 | 5.8 ± 0.16 | 0.6 |
| 23-24 | K E | 3 | 6.7 | 6.6 | 6.0 | 6.5 | 0.2 | 7.1 | 7.3 | 5.6 | <1.7 | >5.4 | 18 | 4.7 ± 0.09 | **1.5** |
| 356-357 | K E | 3 | 7.7 | 7.6 | 7.0 | 7.0 | 0.7 | 8.0 | 7.3 | 6.4 | <1.7 | >6.3 | 6 | 3.5 ± 0.58 | **2.0** |
| 23-24; 356-357 | K E, K E | 6 | | | | | | | | | | | | | |
| 23-24 | K E | 3 | 6.7 | 6.6 | 6.0 | 6.5 | 0.2 | 7.1 | 7.3 | 5.6 | <1.7 | >5.4 | 18 | 4.7 ± 0.09 | **1.5** |
| 396-397 | R E | 4 | 7.0 | 7.3 | 6.5 | 5.5 | 1.5 | 7.5 | 7.6 | 7.5 | <1.7 | >5.8 | 18 | 5.4 ± 0.35 | 1.1 |
| 23-24; 396-397 | K E, R E | 7 | 6.3 | 4.9 | <1.7 | <1.7 | >4.6 | 7.1 | 6.0 | 5.6 | <1.7 | >5.4 | 6 | 3.7 ± 0.44 | **2.7** |
| 157-158 | E E | 3 | 6.5 | 7.2 | 5.1 | 5.1 | 1.4 | 7.6 | 7.4 | 5.9 | <1.7 | >5.9 | 6 | 2.8 ± 0.31 | **2.7** |
| 396-397 | R E | 4 | 7.0 | 7.3 | 6.5 | 5.5 | 1.5 | 7.5 | 7.6 | 7.5 | <1.7 | >5.8 | 18 | 5.4 ± 0.35 | 1.1 |
| 157-158; 396-397 | E E, R E | 7 | | | | | | | | | | | 6 | 2.0 ± 0.12 | **4.8** |
| 157-158 | E E | 3 | 6.5 | 7.2 | 5.1 | 5.1 | 1.4 | 7.6 | 7.4 | 5.9 | <1.7 | >5.9 | 6 | 2.8 ± 0.31 | **2.7** |
| 523-524 | D K | 4 | 6.6 | 6.3 | 6.3 | 5.8 | 0.8 | 7.1 | 6.6 | <1.7 | <1.7 | >5.4 | 6 | 4.2 ± 0.47 | 1.3 |
| 157-158; 523-524 | E E, D K | 7 | 5.6 | 3.9 | <1.7 | <1.7 | >3.9 | 6.3 | 4.1 | <1.7 | <1.7 | >4.6 | | | |
| 396-397 | R E | 4 | 7.0 | 7.3 | 6.5 | 5.5 | 1.5 | 7.5 | 7.6 | 7.5 | <1.7 | >5.8 | 6 | 4.8 ± 0.54 | **1.6** |
| 827-828 | D K | 4 | 6.9 | 6.3 | 6.3 | 5.9 | 1.0 | 7.5 | 6.9 | 5.0 | <1.7 | >5.8 | 6 | 3.6 ± 0.76 | **2.3** |
| 396-397; 827-828 | R E, D K | 8 | 7.0 | 6.5 | 6.0 | <1.7 | 5.3 | >6.7 | 5.7 | <1.7 | <1.7 | >5.0 | 6 | 4.7 ± 0.10 | 1.2 |

[a]Positions of the amino acid pair mutated to an alanine pair; numbering starts at the amino terminus of the NS5 protein.

[b]Underlined values indicate a 2.5 or 3.5 $log_{10}$ PFU/ml reduction in titer in Vero or HuH-7 cells respectively, at the indicated temperatures when compared to permissive temperature (35° C.).

[c]Reduction in titer ($log_{10}$ PFU/ml) at 39° C. compared to permissive temperature (35° C.).

[d]Groups of six suckling mice were inoculated i.c. with 4.0 $log_{10}$PFU virus in a 30 μl inoculum. Brains were removed 5 days later, homogenized, and titered in Vero cells.

[e]Determined by comparing mean viral titers in mice inoculated with sample virus and concurrent wt controls (n = 6); reductions ≥1.5 are listed in boldface.

TABLE 24

SCID-HuH-7 attenuation phenotypes of double charge-cluster-to-alanine mutants of the NS5 gene of rDEN4.

| | | Replication in SCID-HuH-7 mice[b] | | |
|---|---|---|---|---|
| Mutation[a] | Charged AA Pair | n | Mean peak virus titer ± SE ($log_{10}$ PFU/ml serum) | Mean log reduction from wt[c] |
| wt | n/a | 21 | 5.4 ± 0.4 | — |
| Δ30 | n/a | 4 | 3.7 ± 0.6 | **2.5** |
| 23-24 | K E | 19 | 4.7 ± 0.5 | 1.3 |
| 200-201 | K H | 12 | 3.7 ± 0.2 | **2.6** |
| 23-24; 200-201 | K E, K H | 13 | 3.4 ± 0.1 | **2.9** |
| 23-24 | K E | 19 | 4.7 ± 0.5 | 1.3 |
| 356-357 | K E | 10 | 6.3 ± 0.7 | (+) 1.1 |
| 23-24; 356-357 | K E, K E | 4 | 3.6 ± 0.3 | **2.3** |
| 23-24 | K E | 19 | 4.7 ± 0.5 | 1.3 |
| 396-397 | R E | 12 | 4.4 ± 1.3 | 1.2 |
| 23-24; 396-397 | K E, R E | 10 | 3.4 ± 0.5 | **3.3** |
| 157-158 | E E | 6 | 4.6 ± 0.6 | 1.3 |
| 396-397 | R E | 12 | 4.4 ± 1.3 | 1.2 |
| 157-158; 396-397 | E E, R E | 6 | 2.2 ± 0.2 | **3.6** |
| 157-158 | E E | 6 | 4.6 ± 0.6 | 1.3 |
| 523-524 | D K | 5 | 5.3 ± 0.7 | 0.6 |
| 157-158; 523-524 | E E, D K | 3 | 5.1 ± 0.6 | 0.8 |
| 396-397 | R E | 12 | 4.4 ± 1.3 | 1.2 |
| 827-828 | D K | 5 | 2.9 ± 0.2 | 1.6 |
| 396-397; 827-828 | R E, D K | 4 | 4.1 ± 0.7 | 0.4 |

[a]Positions of the amino acid pair mutated to an alanine pair; numbering starts at the amino terminus of the NS5 protein.

[b]Groups of SCID-HuH-7 mice were inoculated directly into the tumor with $10^4$ PFU of virus. Serum was collected on days 6 and 7 and titered in Vero cells.

[c]Comparison of mean virus titers of mice inoculated with mutant virus and concurrent DEN4 control. Bold denotes a ≥100-fold decrease in replication. A (+) sign indicates an increase in replication relative to wt.

TABLE 25

Phenotypes (temperature sensitivity, plaque size and replication in mouse brain and SCID-HuH-7 mice) of wt DEN4 and viruses containing the Δ30 and 7129 mutations.

| | | Mean virus titer ($log_{10}$ PFU/ml) at indicated temperature (° C.) | | | | | | | Replication in suckling mouse brain[c] | | | Replication in SCID-HuH-7 mice[e] | | |
|---|---|---|---|---|---|---|---|---|---|---|---|---|---|---|
| | | VERO | | | HUH7 | | | C6/36 | | Mean virus titer ± SE ($log_{10}$ PFU/g brain) | Mean log reduction from wt[d] | | Mean peak virus titer ± SE ($log_{10}$ PFU/ml serum)[f] | Mean log reduction from wt[d] |
| Virus ID | Mutation[a] | 35 | 39 | Δ[b] | 35 | 39 | Δ | 32 | n | | | n | | |
| 1-TD-1A | wt | 7.3 | 6.8 | 0.5 | 8 | 6.8 | 1.2 | 8.3 | 36 | 6.1 ± 0.21 | — | 21 | 5.4 ± 0.4 | — |
| p4Δ30 | Δ30 | 6.6 | 6.5 | 0.1 | 7.4 | 6.4 | 1.0 | | 42 | 5.4 ± 0.22 | 0.6 | 4 | 3.7 ± 0.6 | 2.5 |
| 5-1A1 | C7129U | 6.7 | 6.5 | 0.2 | 7.5 | 6 | 1.5 | 7.6* | 6 | 6.2 ± 0.30 | 0.0 | | | |
| rDEN4-7129-1A | C7129U | 7.3 | 7.0 | 0.3 | 7.6 | 6.3 | 1.3 | 7.5* | 6 | 7.2 ± 0.12 | (−) 0.4 | 4 | 5.4 ± 0.8 | (−) 0.8 |
| rDEN4Δ30-7129 | C7129U + Δ30 | 7.0 | | | | | | 7.1* | | | | | | |

[a]Position and identity of the mutated nucleotides.

[b]Reduction in titer ($log_{10}$ PFU/ml) at 39° C. compared to permissive temperature (35° C.).

[c]Groups of six suckling mice were inoculated i.c. with 4.0 $log_{10}$ PFU virus in a 30 μl inoculum. The brain was removed 5 days later, homogenized, and titered in Vero cells.

[d]Determined by comparing mean viral titers in mice inoculated with sample virus and concurrent wt controls (n = 6). The attenuation phenotype is defined as a ≥50- or ≥100-fold decrease in replication in suckling or SCID-HuH-7 mice, respectively. A (−) sign indicates an increase in replication relative to the wt control.

[e]Groups of SCID-HuH-7 mice were inoculated directly into the tumor with $10^4$ PFU virus. Serum was collected on days 6 and 7 and titered in Vero cells.

*Small plaque size.

TABLE 26

The 5-fluorouracil 5-1A1 small plaque mutant demonstrates a restriction of midgut infection following oral infection of *Aedes aegytpi* mosquitoes.

| Virus tested | Dose ingested ($log_{10}$ PFU) [a] | No. mosquitoes tested | Midgut-only infection [b] | Disseminated infection [c] | Total no. infected [d, e] |
|---|---|---|---|---|---|
| wtDEN4 | 4.5 | 19 | 1 (5%) | 17 (89%) | 18 (95%) |
| (2A-13) | 3.5 | 26 | 9 (35%) | 7 (27%) | 16 (62%) |
| | 2.5 | 28 | 1 (4%) | 0 | 1 (4%) |
| | | | | **$OID_{50}$ = 3.9** | **$OID_{50}$ = 3.3** |
| 5-1A1 | 3.5 | 34 | 4 (12%) | 2 (6%) | 6 (18%) |
| | 2.5 | 9 | 0 | 1 (11%) | 1 (11%) |
| | 1.5 | 23 | 0 | 0 | 0 |
| | | | | | **$OID_{50}$ ≥ 3.9** |

[a] Amount of virus ingested, assuming a 2 μl bloodmeal.

[b] Number (percentage) of mosquitoes with detectable dengue virus antigen in midgut tissue, but no detectable dengue virus antigen in head; mosquitoes were assayed 21 days post-feed, and dengue virus antigen was identified by IFA.

[c] Number (percentage) of mosquitoes with detectable dengue virus antigen in both midgut and head tissue.

[d] Total number (percentage) of mosquitoes with detectable dengue virus antigen.

[e] The proportion of total infections caused by wild type DEN4 was significantly higher than the proportion caused by 5-1A1 (logistic regression, N = 426, P < 0.0001). There were too few disseminated infection caused by 5-1A1 to permit statistical analysis.

TABLE 27

The 5-fluorouracil 5-1A1 small plaque mutant demonstrates a restriction of infection following intrathoracic inoculation of *Toxorhynchites spiendens* mosquitoes.

| Virus tested | Dose ingested ($log_{10}$ PFU) [a] | No. mosquitoes tested | No (%) infected [c] |
|---|---|---|---|
| wtDEN4 | 4.0 | 5 | 5 (100) |
| (2A-13) | 3.0 | 4 | 4 (100) |
| | 2.0 | 4 | 1 (25) |
| | | | **$MID_{50}$ = 2.3 $log_{10}$ PFU** |
| 5-1A1 | 3.0 | 9 | 0 |
| | 2.0 | 7 | 1 (14) |
| | 1.0 | 7 | 0 |
| | | | **$MID_{50}$ > 3.0 $log_{10}$ PFU** |

[a] Amount of virus inoculated in a 0.22 μl inoculum.

[b] Number (percentage) of mosquitoes with detectable dengue virus antigen in head tissue; mosquitoes were assayed 14 days post-inoculation, and dengue virus antigen was identified by IFA.

[c] The proportion of infections caused by wild type DEN4 was significantly higher than the proportion caused by 5-1A1 (logistic regression, N = 36, P < 0.01).

TABLE 28

Mutagenesis primers for the deletion or swap of sequences in DEN4 showing conserved differences from tick-borne flaviviruses.

| DEN4 nucleotides[1] | Type of mutation[2] | Mutagenesis Primer[3] | SEQ ID NO |
|---|---|---|---|
| 10508-10530 | Δ | CTGGTGGAAGCCCAACACAAAAAC | 64 |
| 10508-10530 | swap | CTGGTGGAAGGAAGAGAGAAATTGGCAACTCCCCAACACAAAAAC | 65 |
| 10535-10544 | Δ | AGACCCCCCCAAGCATATTGAC | 66 |
| 10535-10544 | swap | AGACCCCCCCAATATTTCCTCCTCCTATAGCATATTGAC | 67 |
| 10541-10544 | Δ | CCCAACACAAAGCATATTGAC | 68 |

[1]Nucleotides numbered 5' to 3', in the opposite direction from FIG. 5.3

[2]Δ: deletion of specified DEN4 nucleotides; swap: exchange of specified DEN4 nucleotides with homologous sequence from Langat

[3]no swap mutation was made for nucleotides 10541-10544

TABLE 29

Virus titer and plaque size of 3' UTR mutant viruses in Vero and C6/36 cells.

| | Vero | | C6/36 | |
|---|---|---|---|---|
| Virus | Titer ($log_{10}$ PFU/ml) | Plaque size[1] | Titer ($log_{10}$ PFU/ml) | Plaque size |
| rDEN4Δ10508-10530 | 8.1 | wt | 7.5 | wt |
| rDEN4swap10508-10530 | 5.4 | sp | 6.6 | wt |
| rDEN4Δ10535-10544 | 5.8 | wt | 7.0 | sp |
| rDEN4swap10535-10544 | 7.0 | wt | 7.3 | wt |
| rDEN4Δ10541-10544 | 6.4 | wt | >7.0 | wt |

[1]Plaque size is designated as equivalent to wild type (wt) or ≤50% of wild type (sp) on the designated cell type.

TABLE 30

Infectivity of wt DEN4 and 3' UTR mutants for *Toxorhynchites splendens* via intrathoracic inoculation.

| Virus | Dose ($log_{10}$ PFU)[a] | No. mosquitoes tested | % Infected[b] | $MID_{50}$ ($log_{10}$ PFU) |
|---|---|---|---|---|
| rDEN4 wt | 3.3 | 6 | 83 | 2.3 |
| | 2.3 | 7 | 57 | |
| | 1.3 | 6 | 0 | |
| | 0.3 | 6 | 0 | |

TABLE 30-continued

Infectivity of wt DEN4 and 3' UTR mutants for *Toxorhynchites splendens* via intrathoracic inoculation.

| Virus | Dose ($log_{10}$ PFU)[a] | No. mosquitoes tested | % Infected[b] | $MID_{50}$ ($log_{10}$ PFU) |
|---|---|---|---|---|
| rDEN4Δ10508-10530 | 4.4 | 8 | 0 | |
| | 3.4 | 9 | 11 | |
| | 2.4 | 4 | 0 | |

[a]Amount of virus inoculated in a 0.22 μl inoculum.
[b]Percentage of mosquitoes with detectable dengue virus antigen in head tissue; mosquitoes were assayed 14 days post-inoculation, and dengue virus antigen was identified by IFA

TABLE 31

Infectivity of 3' UTR swap mutant viruses for *Aedes aegypti* fed on an infectious bloodmeal.

| Virus Tested | Dose ingested ($log_{10}$ PFU)[a] | No. Mosquitoes Tested | Total No. Infected[b,c] | Disseminated Infections[c,d] |
|---|---|---|---|---|
| rDEN4 | 3.8 | 18 | 11 (61%) | 4 (22%) |
| | 2.8 | 15 | 5 (33%) | 1 (6%) |
| | 1.8 | 15 | 0 | 0 |
| | | | **$OID_{50}$ = 3.4** | **$OID_{50}$ = ≥4.2** |
| rDEN4swap 10535-10544 | 3.8 | 25 | 5 (20%) | 2 (8%) |
| | 2.8 | 25 | 0 | 0 |
| | 1.8 | 20 | 0 | 0 |
| | | | **$OID_{50}$ = ≥4.2** | |

[a] Amount of virus ingested, assuming a 2 μl bloodmeal.
[b]Number (%) of mosquitoes with detectable dengue virus antigen in the midgut tissue; mosquitoes were assayed either 14 d post-feed and dengue virus antigen was identified by IFA.
[c]At a dose of 3.8 $log_{10}$ PFU, rDEN4swap10535-10544 infected significantly fewer mosquitoes at the midgut than wt rDEN4 (Fisher's exact test, N = 43, P < 0.01), although disseminated infections were not significantly different (Fisher's exact test, N = 43, P = 0.38).
[d]Number (%) of mosquitoes with detectable dengue virus antigen in the head tissue.

TABLE 32

Putative Vero cell adaptation mutations derived from the set of 5-FU mutant viruses and other DEN4 viruses passaged in Vero cells.

| | | 5-FU mutant viruses | | | Other DEN viruses passaged in Vero cells | | |
|---|---|---|---|---|---|---|---|
| Nucleotide position | Gene/region (a.a. #)[b] | Nucleotide change | Amino acid change | No. of viruses with the mutation | Virus | Nucleotide change | Amino acid change |
| 1455 | E (452) | G > U | val > phe | 5 | | | |
| 2280[1,2,3] | E (727) | U > C | phe > leu | 2 | | | |
| 4891[2,3] | NS3 (1597) | U > C | ile > thr | 2 | | | |
| 4995[1,2] | NS3 (1599) | U > C | ser > pro | 8 | | | |
| 7153 | NS4B (2351) | U > C | val > ala | 3 | 2AΔ30 | U > C | val > ala |
| 7162 | NS4B (2354) | U > C | leu > ser | 4 | 2A-1 | U > C | leu > ser |
| 7163 | NS4B (2354) | A > U or C | leu > phe | 7 | rDEN4Δ30 | A > U | leu > phe |
| | | | | | 2A-13-1A1 | A > U | leu > phe |
| 7182[1,2,3] | NS4B (2361) | G > A | gly > ser | 2 | | | |
| 7546 | NS4B (2482) | C > U | ala > val | 10 | | | |
| 7630[3] | NS5 (2510) | A > G | lys > arg | 1 | 814669 | A > G | lys > arg |
| 10275 | 3' UTR | A > U | n/a[c] | 6 | | | |
| 10279 | 3' UTR | A > C | n/a | 4 | | | |

[a] Conservation with DEN1, DEN2, or DEN3 is designated by superscript. Lack of conservation is designated by no superscript.
[b]Amino acid position in DEN4 polyprotein beginning with the methionine residue of the C protein (nt 102-104) as residue #1.
[c]not applicable

TABLE 33

Sequence analysis of rDEN2/4Δ30 clone 27(p4)-2-2A2.

| Nucleotide | Gene | Mutation Nucleotide | Mutation Amino acid |
|---|---|---|---|
| 743 | M anchor | G > A | Gly > Glu |
| 1493 | E | C > U | Ser > Phe |
| 7544* | NS4B | C > U | Ala > Val |

*Same as DEN4 nucleotide position 7546

TABLE 34

Sequence analysis of rDEN2/4Δ30 clone 27(p3)-2-1A1.

| Nucleotide | Gene | Mutation Nucleotide | Mutation Amino acid |
|---|---|---|---|
| 1345 | E | U > C | Tyr > His |
| 4885* | NS3 | G > A | Glu > Lys |
| 8297 | NS5 | G > A | Arg > Lys |

*Codon adjacent to 5-FU mutation 4891

TABLE 35

Recombinant virus rDEN2/4Δ30 bearing Vero adaptation mutations can be recovery and titered on Vero cells.

| Virus | Virus titer in indicated cell line[1] ($log_{10}$ PFU/ml) C6/36 | Vero | Virus titer following recovery in Vero cells ($log_{10}$ PFU/ml) |
|---|---|---|---|
| rDEN2/4Δ30 wt | 5.2 | 1.1 | <0.7 |
| rDEN2/4Δ30-7153 | 5.4 | 5.2 | <0.7 |
| rDEN2/4Δ30-7162 | 5.4 | 5.3 | nd[2] |
| rDEN2/4Δ30-7182 | 4.7 | 4.9 | 2.3 |
| rDEN2/4Δ30-7630 | 5.3 | 4.8 | 1.3 |
| rDEN2/4Δ30-7153-7163 | 5.1 | 4.7 | nd |

TABLE 35-continued

Recombinant virus rDEN2/4Δ30 bearing Vero adaptation mutations can be recovery and titered on Vero cells.

| Virus | Virus titer in indicated cell line[1] ($log_{10}$ PFU/ml) C6/36 | Vero | Virus titer following recovery in Vero cells ($log_{10}$ PFU/ml) |
|---|---|---|---|
| rDEN2/4Δ30-7153-7182 | 4.1 | 3.2 | nd |
| rDEN2/4Δ30-7546-7630 | 5.2 | 5.2 | nd |

[1]Virus recovered following transfection of C6/36 mosquito cells was terminally diluted once in C6/36 cells and titered simultaneously in C6/36 cells and Vero cells.
[2]not determined

TABLE 36

Putative Vero cell adaptation mutations of dengue type 4 virus and the corresponding wildtype amino acid residue in other dengue viruses.

| Mutation | Amino acid position[a] | Mutant residue | Amino acid in indicated wt dengue virus[b] DEN4 | DEN1 | DEN2 | DEN3 |
|---|---|---|---|---|---|---|
| 1455 | 452 | F | V | I | A | A |
| 2280 | 727 | L | F[c] | F | F | F |
| 4891 | 1597 | T | I | V | I | I |
| 4995 | 1632 | P | S | S | S | N |
| 7129 | 2343 | L | P | P | P | P |
| 7153 | 2351 | A | V | F | F | L |
| 7162 | 2354 | S | L | V | V | V |
| 7163 | 2354 | F | L | V | V | V |
| 7182 | 2361 | S | G | G | G | G |
| 7546 | 2482 | V | A | L | T | V |
| 7630 | 2510 | R | K | S | S | K |

[a]Amino acid position is given for the polyprotein of DEN4
[b]DEN4 = rDEN4 (GenBank AF326825); DEN1 = Western pacific (GenBank DVU88535); DEN2 = New Guinea C (GenBank AF038403); DEN3 = H87 (GenBank M93130)
[c]Underlined nucleotides are shared between DEN4 and one or more additional DEN types.

TABLE 37

Mutations known to attenuate dengue type 4 virus and the corresponding wildtype amino acid residue in other dengue virus.

| | Mutation | Amino acid position[a] | Mutant residue | Amino acid in indicated wt dengue virus[b] DEN4 | DEN1 | DEN2 | DEN3 |
|---|---|---|---|---|---|---|---|
| 5-FU mutations | 2650 | 850 | S | N[d] | N | N | N |
| | 3442 | 1114 | G | E | E | E | E |
| | 3540 | 1147 | K | E | E | E | E |
| | 3575 | 1158 | I | M | L | A | M |
| | 3771 | 1224 | G | R | R | K | R |
| | 4062 | 1321 | A | T | L | A | T |
| | 4306 | 1402 | S | N | E | D | D |
| | 4891 | 1597 | T | I | V | I | I |
| | 4896 | 1599 | S | A | A | A | A |
| | 4907 | 1602 | F | L | L | L | L |
| | 4995 | 1632 | P | S | S | S | N |
| | 5097 | 1666 | N | D | D | D | D |
| | 5695 | 1865 | G | D | D | D | D |
| | 6259 | 2053 | A | V | V | V | V |
| | 7129[c] | 2343 | L | P | P | P | P |
| | 7849 | 2583 | I | N | K | N | K |
| | 8092 | 2664 | G | E | Q | Q | Q |
| | 10186 | 3362 | T | I | I | I | I |
| | 10634 | 3' UTR | — | — | — | — | — |
| Charge-cluster-to- | 22, 23 | 2509, 2510 | AA | RK | KS | KS | RK |
| | 23, 24 | 2510, 2511 | AA | KE | SE | SE | KE |

TABLE 37-continued

Mutations known to attenuate dengue type 4 virus and the corresponding wildtype amino acid residue in other dengue virus.

| Mutation | | Amino acid position[a] | Mutant residue | Amino acid in indicated wt dengue virus[b] | | | |
|---|---|---|---|---|---|---|---|
| | | | | DEN4 | DEN1 | DEN2 | DEN3 |
| alanine mutations | 157, 158 | 2644, 2645 | AA | <u>EE</u> | <u>EE</u> | EA | <u>EE</u> |
| | 200, 201 | 2687, 2688 | AA | <u>KH</u> | <u>KH</u> | KY | <u>KH</u> |
| | 356, 357 | 2843, 2844 | AA | <u>KE</u> | <u>KE</u> | <u>KE</u> | <u>KE</u> |
| | 387, 388 | 2874, 2875 | AA | <u>KK</u> | RN | <u>KK</u> | RN |
| | 436, 437 | 2923, 2924 | AA | <u>DK</u> | HR | <u>DK</u> | <u>DK</u> |
| | 524, 525 | 3011, 3012 | AA | <u>KK</u> | KI | <u>KK</u> | KI |
| | 525, 526 | 3012, 3013 | AA | KD | IP | KE | IP |
| | 642, 643 | 3129, 3130 | AA | <u>ER</u> | <u>ER</u> | IA | KK |
| | 654, 655 | 3141, 3142 | AA | DR | ER | ER | ER |
| | 808, 809 | 3295, 3296 | AA | <u>ED</u> | <u>ED</u> | <u>ED</u> | <u>ED</u> |
| | 827, 828 | 3314, 3315 | AA | <u>DK</u> | <u>DK</u> | <u>DK</u> | <u>DK</u> |
| | 877, 878 | 3364, 3365 | AA | KE | NE | NE | NE |
| | 878, 879 | 3365, 3366 | AA | <u>EE</u> | EN | <u>EE</u> | <u>EE</u> |

[a] Amino acid position is given for the polyprotein of DEN4
[b] DEN4 = rDEN4 (GenBank AF326825); DEN1 = Western pacific (GenBank U88535); DEN2 = New Guinea C (GenBank AF038403); DEN3 = H87 (GenBank M93130)
[c] This mutation results in decreased replication of DEN4 in mosquitoes.
[d] Underlined nucleotides are shared between DEN4 and one or more additional DEN types.

APPENDIX 1

Sequence of recombinant dengue type 4 virus strain 2A

```
LOCUS           AF375822               10649 bp ss-RNA     linear VRL19-SEP-2001
DEFINITION      Dengue virus type 4 recombinant clone 2A, complete genome.
ACCESSION       AF375822
VERSION         AF375822.1  GI:14269097
KEYWORDS        .
SOURCE          Dengue virus type 4.
  ORGANISM      Dengue virus type 4
                Viruses; ssRNA positive-strand viruses, no DNA stage;
                Flaviviridae;
                Flavivirus; Dengue virus group.
REFERENCE       1  (bases 1 to 10649)
  AUTHORS       Blaney,J.E. Jr., Johnson,D.H., Firestone,C.Y., Hanson,C.T.,
                Murphy,B.R. and Whitehead,S.S.
  TITLE         Chemical Mutagenesis of Dengue Virus Type 4 Yields Mutant
                Viruses
                Which Are Temperature Sensitive in Vero Cells or Human Liver
                Cells
                and Attenuated in Mice
  JOURNAL       J. Virol. 75 (20), 9731-9740 (2001)
  MEDLINE       21443968
   PUBMED       11559806
REFERENCE       2  (bases 1 to 10649)
  AUTHORS       Blaney,J.E. Jr., Johnson,D.H., Firestone,C.Y., Hanson,C.T.,
                Murphy,B.R. and Whitehead,S.S.
  TITLE         Direct Submission
  JOURNAL       Submitted (02-MAY-2001) LID, NIAID, 7 Center Drive, Bethesda,
                MD
                20892, USA
FEATURES             Location/Qualifiers
     source          1..10649
                     /organism="Dengue virus type 4"
                     /virion
                     /db_xref="taxon:11070"
     mat_peptide     102..440
                     /note="anchC"
                     /product="anchored capsid protein"
     mat_peptide     102..398
                     /note="virC"
                     /product="virion capsid protein"
     CDS             102..10265
                     /codon_start=1
                     /product="polyprotein precursor"
                     /protein_id="AAK58017.1"
                     /db_xref."GI:14269098"

/translation="MNQRKKVVRPPFNMLKRERNRVSTPQGLVKRESTGLFSGKGPLR
```

APPENDIX 1-continued

Sequence of recombinant dengue type 4 virus strain 2A

```
MVLAFITFLRVLSIPPTAGILKRWGQLKKNKAIKILIGFRKEIGRMLNILNGRKRSTI
TLLCLIPTVMAFSLSTRDGEPLMIVAKHERGRPLLFKTTEGINKCTLIAMDLGEMCED
TVTYKCPLLVNTEPEDIDCWCNLTSTWVMYGTCTQSGERRREKRSVALTPHSGMGLET
RAETWMSSEGAWKHAQRVESWILRNPGFALLAGFMAYMIGQTGIQRTVFFVLMMLVAP
SYGMRCVGVGNRDFVEGVSGGAWVDLVLEHGGCVTTMAQGKPTLDFELTKTTAKEVAL
LRTYCIEASISNITTATRCPTQGEPYLKEEQDQQYICRRDVVDRGWGNGCGLFGKGGV
VTCAKFSCSGKITGNLVQIENLEYTVVVTVHNGDTHAVGCDTSNHGVTAMITPRSPSV
EVKLPDYGELTLDCEPRSGIDFNEMILMKMKKKTWLVHKQWFLDLPLPWTAGADTSEV
HWNYKERMVTFKVPHAKRQDVTVLGSQEGAMHSALAGATEVDSGDGNHMFAGHLKCKV
RMEKLRIKGMSYTMCSGKFSIDKEMAETQHGTTVVKVKYEGAGAPCKVPIEIRDVNKE
KVVGRIISSTPLAENTNSVTNIELEPPFGDSYIVIGVGNSALTLHWFRKGSSIGKMFE
STYRGAKRMAILGETAWDFGSVGGLFTSLGKAVHQVFGSVYTTMFGGVSWMIRILIGF
LVLWIGTNSRNTSMAMTCIAVGGITLFLGFTVQADMGCVVSWSGKELKCGSGIFVVDN
VHTWTEQYKFQPESPARLASAILNAHKDGVCGIRSTTRLENVMWKQITNELNYVLWEG
GHDLTVVAGDVKGVLTKGKRALTPPVSDLKYSWKTWGKAKIFTPEARNSTFLIDGPDT
SECPNERRAWNSLEVEDYGFGMFTTNIWMKFREGSSEVCFHRLMSAAIKDQKAVHADM
GYWIESSKNQTWQIEKASLIEVKTCLWPKTHTLWSNGLVESQMLIPKSYAGPFSQHNY
RQGYATQTVGPWHLGKLEIDFGECPGTTVTIQEDCDHRGPSLRTTTASGKLVTQWCCR
SCTMPPLRFLGEDGCWYGMEIRPLSEKEENMVKSQVTAGQGTSETFSMGLLCLTLFVE
ECLRRRVTRKHMILVVVITLCAIILGGLTWMDLLRALIMLGDTMSGRIGGQIHLAIMA
VFKMSPGYVLGVFLRKLTSRETALMVIGMAMTTVLSIPHDLMELIDGISLGLILLKIV
TQFDNTQVGTLALSLTFIRSTMPLVMAWRTIMAVLFVVTLIPLCRTSCLQKQSHWVEI
TALILGAQALPVYLMTLMKGASRRSWPLNEGIMAVGLVSLLGSALLKNDVPLAGPMVA
GGLLLAAYVMSGSSADLSLEKAANVQWDEMADITGSSPIIEVKQDEDGSFSIRDVEET
NMITLLVKLALITVSGLYPLAIPVTMTLWYMWQVKTQRSGALWDVPSPAATKKAALSE
GVYRIMQRGLFGKTQVGVGIHMEGVFHTMWHVTRGSVICHETGRLEPSWADVRNDMIS
YGGGWRLGDKWDKEEDVQVLAIEPGKNPKHVQTKPGLFKTLTGEIGAVTLDFKPGTSG
SPIINRKGKVIGLYGNGVVTKSGDYVSAITQAERIGEPDYEVDEDIFRKKRLTIMDLH
PGAGKTKRILPSIVREALKRRLRTLILAPTRVVAAEMEEALRGLPIRYQTPAVKSEHT
GREIVDLMCHATFTTRLLSSTRVPNYNLIVMDEAHFTDPSSVAARGYISTRVEMGEAA
AIFMTATPPGATDPFPQSNSPIEDIEREIPERSWNTGFDWITDYQGKTVWFVPSIKAG
NDIANCLRKSGKKVIQLSRKTFDTEYPKTKLTDWDFVVTTDISEMGANFRAGRVIDPR
RCLKPVILPDGPERVILAGPIPVTPASAAQRRGRIGRNPAQEDDQYVFSGDPLKNDED
HAHWTEAKMLLDNIYTPEGIIPTLFGPEREKTQAIDGEFRLRGEQRKTFVELMRRGDL
PVWLSYKVASAGISYKDREWCFTGERNNQILEENMEVEIWTREGEKKKLRPRWLDARV
YADPMALKDFKEFASGRKSITLDILTEIASLPTYLSSRAKLALDNIVMLHTTERGGRA
YQHALNELPESLETLMLVALLGAMTAGIFLFFMQGKGIGKLSMGLITIAVASGLLWVA
EIQPQWIAASIILEFFLMVLLIPEPEKQRTPQDNQLIYVILTILTIIGLIAANEMGLI
EKTKTDFGFYQVKTETTILDVDLRPASAWTLYAVATTILTPMLRHTIENTSANLSLAA
IANQAAVLMGLGKGWPLHRMDLGVPLLAMGCYSQVNPTTLTASLVMLLVHYAIIGPGL
QAKATREAQKRTAAGIMKNPTVDGITVIDLEPISYDPKFEKQLGQVMLLVLCAGQLLL
MRTTWAFCEVLTLATGPILTLWEGNPGRFWNTTIAVSTANIFRGSYLAGAGLAFSLIK
NAQTPRRGTGTTGETLGEKWKRQLNSLDRKEFEEYKRSGILEVDRTEAKSALKDGSKI
KHAVSRGSSKIRWIVERGMVKPKGKVVDLGCGRGGWSYYMATLKNVTEVKGYTKGGPG
HEEPIPMATYGWNLVKLHSGVDVFYKPTEQVDTLLCDIGESSSNPTIEEGRTLRVLKM
VEPWLSSKPEFCIKVLNPYMPTVIEELEKLQRKHGGNLVRCPLSRNSTHEMYWVSGAS
GNIVSSVNTTSKMLLNRFTTRHRKPTYEKDVDLGAGTRSVSTETEKPDMTIIGRRLQR
LQEEHKETWHYDQENPYRTWAYHGSYEAPSTGSASSMVNGVVKLLTKPWDVIPMVTQL
AMTDTTPFGQQRVFKEKVDTRTPQPKPGTRMVMTTTANWLWALLGKKKNPRLCTREEF
ISKVRSNAAIGAVFQEEQGWTSASEAVNDSRFWELVDKERALHQEGKCESCVYNMMGK
REKKLGEFGRAKGSRAIWYMWLGARFLEFEALGFLNEDHWFGRENSWSGVEGEGLHRL
GYILEEIDKKDGDLMYADDTAGWDTRITEDDLQNEELITEQMAPHHKILAKAIFKLTY
QNKVVKVLRPTPRGAVMDIISRKDQRGSGQVGTYGLNTFTNMEVQLIRQMEAEGVITQ
DDMQNPKGLKERVEKWLKECGVDRLKRMAISGDDCVVKPLDERFGTSLLFLNDMGKVR
KDIPQEEPSKGWKNWQEVPFCSHHFHKIFMKDGRSLVVPCRNQDELIGRARISQGAGW
SLRETACLGKAYAQMWSLMYFHRRDLRLASMAICSAVPTEWFPTSRTTWSIHAHHQWM
TTEDMLKVWNRVWIEDNPNMTDKTPVHSWEDIPYLGKREDLWCGSLIGLSSRATWAKN
IHTAITQVRNLIGKEEYVDYMPVMKRYSAPSESEGVL”
     mat_peptide          441..938
                          /note=“prM”
                          /product=“membrane precursor protein”
     mat_peptide          714..938
                          /note= “M”
                          /product=“membrane protein”
     mat_peptide          939..2423
                          /note “E”
                          /product=“envelope protein”
     mat_peptide          2424..3479
                          /product=“NS1 protein”
     mat_peptide          3480..4133
                          /product=“NS2A protein”
     mat_peptide          4134..4523
                          /product=“NS2B protein”
     mat_peptide          4524..6377
                          /product=“NS3 protein”
     mat_peptide          6378..6758
                          /product=“NS4A protein”
     mat_peptide          6759..6827
```

APPENDIX 1-continued

Sequence of recombinant dengue type 4 virus strain 2A

```
                        /product="2K protein"
     mat_peptide        6828..7562
                        /product="NS4B protein"
     mat_peptide        7563..10262
                        /product="NS5 protein"
BASE COUNT     3302 a      2212 c   2800 g   2335 t
ORIGIN
    1 agttgttagt ctgtgtggac cgacaaggac agttccaaat cggaagcttg cttaacacag
   61 ttctaacagt ttgtttgaat agagagcaga tctctggaaa aatgaaccaa cgaaaaaagg
  121 tggttagacc acctttcaat atgctgaaac gcgagagaaa ccgcgtatca acccctcaag
  181 ggttggtgaa gagattctca accggacttt tttctaggaa aggaccctta cggatggtgc
  241 tagcattcat cacgtttttg cgagtccttt ccatcccacc aacagcagag attctgaaga
  301 gatggggaca gttgaagaaa aataaggcca tcaagatact gattggattc aggaaggaga
  361 taggccgcat gctgaacatc ttgaacggga gaaaaaggtc aacgataaca ttgctgtgct
  421 tgattcccac cgtaatggcg ttttccttgt caacaagaga tggcgaaccc ctcatgatag
  481 tggcaaaaca tgaaaggggg agacctctct tgtttaagac aacagaggag atcaacaaat
  541 gcactctcat tgccatggac ttgggtgaaa tgtgtgagga cactgtcacg tataaatgcc
  601 ccctactggt caataccgaa cctgaagaca ttgattgctg gtgcaacctc acgtctacct
  661 gggtcatgta taggacatgc acccagagcg gagaacggag acgagagaag cgctcagtag
  721 ctttaacacc acattcagga atgggattgg aaacaagagc tgagacatgg atgtcatcgg
  781 aaggggcttg gaagcatgct cagagagtag agagctggat actcagaaac ccaggattcg
  841 cgctcttggc aggatctatg gcttatatga ttgggcaaac aggaatccag cgaactgtct
  901 tctttgtcct aatgatgctg gtcgccccat cctacggaat gcgatgcgta agagtagaaa
  961 acagagactt tgtggaagga gtctcaggtg gagcatgggt cgacctggtg ctagaacatg
 1021 gaggatgcgt cacaaccatg gcccagggaa aaccaacctt ggattttgaa ctgactaaga
 1081 caacagccaa ggaagtggct ctgttaagaa cctattgcat tgaagcctca atatcaaaca
 1141 taactacggc aacaagatgt ccaacgcaag gagagcctta tctgaaagag aaacaggacc
 1201 aacagtacat ttgccggaga gatgtggtag acagagggtg gggcaatggc tgtggcttgt
 1261 ttggaaaagg aggaattgtg acatgtgcga agttttcatg ttcggggaag ataacaggca
 1321 atttggtcca aattgagaac cttgaataca cagtggttgt aacagtccac aatggagaca
 1381 cccatgcagt aggaaatgac acatccaatc atggagttac agccatgata actcccaggt
 1441 caccatcggt ggaagtcaaa ttgccggact atggagaact aacactcgat tgtgaaccca
 1501 ggtctggaat tgactttaat gagatgattc tgatgaaaat gaaaaagaaa acatggctcg
 1561 tgcataagca atggtttttg gatctgcctc ttccatggac agcaggagca gacacatcag
 1621 aggttcactg gaattacaaa gagagaatgg tgacatttaa ggttcctcat gccaagagac
 1681 aggatgtgac agtgctggga tctcaggaag gagccatgca ttctgccctc gctggagcca
 1741 cagaagtgga ctccggtgat ggaaatcaca tgtttgcagg acatcttaag tgcaaagtcc
 1801 gtatggagaa attgagaatc aagggaatgt catacacgat gtgttcagga aagttttcaa
 1861 ttgacaaaga gatggcagaa acacagcatg ggacaacagt ggtgaaagtc aagtatgaag
 1921 gtgctggagc tccgtgtaaa gtccccatag agataagaga tgtaaacaag gaaaaagtgg
 1981 ttgggcgtat catctcatcc accccttttg ctgagaatac caacagtgta accaacatag
 2041 aattagaacc cccctttggg gacagctaca tagtgatagg tgttggaaac agcgcattaa
 2101 cactccatta gttcaggaaa gggagttcca ttggcaagat gtttgagtcc acatacagag
 2161 gtgcaaaacg aatggccatt ctaagtgaaa cagcttggga ttttggttcc gttggtggac
 2221 tgttcacatc attgggaaag gctgtgcacc aggtttttgg aagtgtgtat acaaccatgt
 2281 ttggaggagt ctcatggatg attagaatcc taattgggtt cttagtgttg tggattggca
 2341 cgaactcaag gaacacttca atggctatga cgtgcatagc tgttggagga atcactctgt
 2401 ttctgggctt cacagttcaa gcagacatgg gttgtgtggt gtcatggagt gggaaagaat
 2461 tgaagtgtgg aaacggaatt tttgtggttg acaacgtgca cacttggaca gaacagtaca
 2521 aatttcaacc agagtcccca gcgagactag cgtctgcaat attaaatgcc cacaaagatg
 2581 gggtctgtgg aattagatca accacgaggc tggaaaatgt catgtggaag caaataacca
 2641 acgagctaaa ctatgttctc tgagaaggag gacatgacct cactgtagtg gctggggatg
 2701 tgaagggggt gttgaccaaa ggcaagagag cactcacacc cccagtgagt gatctgaaat
 2761 attcatggaa gacatgggga aaagcaaaaa tcttcacccc agaagcaaga aatagcacat
 2821 ttttaataga cggaccagac acctctgaat gccccaatga acgaagagca tggaactctc
 2881 ttgaggtgga agactatgga tttggcatgt tcacgaccaa catatggatg aaattccgag
 2941 aaggaagttc agaagtgtgt gaccacaggt taatgtcagc tgcaattaaa gatcagaaag
 3001 ctgtgcatgc tgacatgggt tattggatag agagctcaaa aaaccagacc tggcagatag
 3061 agaaagcatc tcttattgaa gtgaaaacat gtctgtggcc caagacccac acactgtgga
 3121 gcaatggagt gctggaaagc cagatgctca ttccaaaatc atatgcgggc cctttttcac
 3181 agcacaatta ccgccagggc tatgccacgc aaaccatggg cccatggcac ttaggcaaat
 3241 tagagataga ctttggagaa tgccccggaa caacagtcac aattcaggag gattgtgacc
 3301 atagaggccc atctttgagg accaccactg catctggaaa actagtcacg caatggtgct
 3361 gccgctcctg cacgatgcct cccttaaggt tcttgggaga agatgggtgc tggtatggga
 3421 tggagattag gcccttgagt gaaaaagaag agaacatggt caaatcacag gtgacggccg
 3481 gacagggcac atcagaaact ttttctatgg gtctgttgtg cctgaccttg tttgtggaag
 3541 aatgcttgag gagaagagtc actaggaaac acatgatatt agttgtggtg atcactcttt
 3601 gtgctatcat cctgggaggc ctcacatgga tggacttact acgagccctc atcatgttgg
 3661 gggacactat gtctggtaga ataggaggac agatccacct agccatcatg gcagtgttca
 3721 agatgtcacc aggatacgtg ctgggtgtgt ttttaaggaa actcacttca agagagacag
 3781 cactaatggt aatagaaatg gccatgacaa cggtgctttc aattccacat gaccttatgg
 3841 aactcattga tggaatatca ctgggactaa ttttgctaaa aataataaca cagtttgaca
 3901 acacccaagt gggaacctta gctctttcct tgactttcat aagatcaaca atgccattgg
 3961 tcatggcttg gaggaccatt atggctgtgt tgtttgtggt cacactcatt cctttgtgca
 4021 ggacaagctg tcttcaaaaa cagtctcatt gggtagaaat aacagcactt atcctaggag
 4081 cccaagctct gccagtgtac ctaatgactc ttatgaaagg agcctcaaga agatcttggc
 4141 ctcttaacga gggcataatg gctgtgggtt tggttagtct cttaggaagc gctcttttaa
 4201 agaatgatgt ccctttagct ggcccaatgg tggcaggagg cttacttctg gcggcttacg
```

APPENDIX 1-continued

Sequence of recombinant dengue type 4 virus strain 2A

```
4261 tgatgagtgg tagctcagca gatctgtcac tagagaaggc agccaacgtg cagtgggatg
4321 aaatggcaga cataacaggc tcaagcccaa tcatagaaat gaagcaggat gaagatggct
4381 ctttctccat acgggacgtc gaggaaacca atatgataac ccttttggtg aaactggcac
4441 tgataacagt gtcaggtctc taccccttgg caattccagt cacaatgacc ttatggtaca
4501 tatggcaagt gaaaacacaa agatcaggag ccctgtggga cgtcccctca cccgctgcca
4561 ctaaaaaagc cgcactgtct gaaggagtgt acaggatcat gcaaagaggg ttattcggga
4621 aaactcaggt tggagtaggg atacacatgg aaggtgtatt tcacacaatg tggcatgtaa
4681 caagaggatc agtgatctgc cacgagactg ggagattgga gccatcttgg gctgacgtca
4741 ggaatgacat gatatcatac ggtgggggat ggaggcttgg agacaaatgg gacaaagaag
4801 aagacgttca ggtcctcgcc atagaaccag gaaaaaatcc taaacatgtc caaacgaaac
4861 ctggcctttt caagacccta actggagaaa ttggagcagt aacattagat ttcaaacccg
4921 gaacgtctgg ttctcccatc atcaacagga aaggaaaagt catcggactc tatggaaatg
4981 gagtagttac caaatcaggt gattacgtca gtgccataac gcaagccgaa agaattggag
5041 agccagatta tgaagtggat gaggacattt ttcgaaagaa aagattaact ataatggact
5101 tacaccccgg agctggaaag acaaaaagaa ttcttccatc aatagtgaga gaagccttaa
5161 aaaggaggct acgaactttg attttagctc ccacgagagt ggtggcggcc gagatggaag
5221 aggccctacg tggactgcca atccgttatc agaccccagc tgtgaaatca gaacacacag
5281 gaagagagat tatagacctc atgtatcatg caaccttcac aacaagactt ttgtcatcaa
5341 ccagggttcc aaattacaac cttatagtga tggatgaagc acatttcacc gatccttcta
5401 gtgtcgcggc tagaggatac atctcgacca gggtggaaat gggagaggca gcagccatct
5461 tcatgaccgc aacccctccc ggagcgacag atccctttcc ccaaagcaac agcccaatag
5521 aagacatcga gagggaaatt ccggaaaggt catggaacac agggttcgac tggataacag
5581 actaccaagg gaaaactgtg tggtttgttc ccagcataaa agctggaaat gacattgcaa
5641 attgtttgag aaagtcggga aagaaagtta tccagttgag taggaaaacc tttgatacag
5701 agtatccaaa aacgaaactc acggactggg actttgtggt cactacagac atatctgaaa
5761 tgggggccaa ttttagagcc gggagagtga tagaccctag aagatgcctc aagccagtta
5821 tcctaccaga tgggccagag agagtcattt tagcaggtcc tattccagtg actccagcaa
5881 gcgctgctca gagaagaggg cgaataggaa ggaacccagc acaagaagac gaccaatacg
5941 ttttctccgg agacccacta aaaaatgatg aagatcatgc ccactggaca gaagcaaaga
6001 tgctgcttga caatatctac accccagaag ggatcattcc aacattgttt ggtccggaaa
6061 gggaaaaaac ccaaaccatt gatggagagt ttcgcctcag aggggaacaa aggaagactt
6121 ttgtggaatt aatgaggaga ggagaccttc cggtgtggct gagctataag gtagcttctg
6181 ctggcatttc ttacaaagat cgagaatggt gcttcacagg ggaaagaaat aaccaaattt
6241 tagaagaaaa catggaggtt gaaatttgga ctagagaggg agaaaagaaa aagctaaggc
6301 caagatgatt agatgcacgt gtatacgctg accccatggc tttgaaggat ttcaaggagt
6361 ttgccagtgg aaggaagagt ataactctcg acatcctaac agagattgcc agtttgccaa
6421 cttacctttc ctctagggcc aagctcgccc ttgataacat agtcatgctc cacacaacag
6481 aaagaggagg gagggcctat caacacgccc tgaacgaact tccggagtca ctggaaacac
6541 tcatgcttgt agctttacta ggtgctatga cagcaggcat cttcctgttt ttcatgcaag
6601 ggaaaggaat agggaaattg tcaatgggtt tgataaccat tgcggtggct aatggcttgc
6661 tctgggtagc agaaattcaa ccccagtgga tagcggcctc aatcatacta gagtttttc
6721 tcatggtact gttgataccg gaaccagaaa aacaaaggac cccacaagac aatcaattga
6781 tctacgtcat attgaccatt ctcaccatca ttggtctaat agcagccaac gagatggggc
6841 tgattgaaaa aacaaaaacg gattttgggt tttaccaggt aaaaacagaa accaccatcc
6901 tcgatgtgga cttgagacca gcttcagcat ggacgctcta tgcagtagcc accacaattc
6961 tgactcccat gctgagacac accatagaaa acacgtcggc caacctatct ctagcagcca
7021 ttgccaacca ggcagccgtc ctaatggggc ttggaaaagg atggccgctc cacagaatgg
7081 acctcggtgt gccgctgtta gcaatgggat gctattctca agtgaaccca acaaccttaa
7141 cagcatcctt agtcatgctt ttagtccatt atgcaataat aagcccagga ttgcaggcaa
7201 aagccacaag agaggcccag aaaaggacag ctgctgggat catgaaaaat cccacagtgg
7261 acgggataac agtaatagat ctagaaccaa tatcctatga cccaaaattt gaaaagcaat
7321 tagggcaggt catactacta gtcttgtgtg ctggacaact actcttgatg agaacaacat
7381 gggctttctg tgaagtcttg actttggcca caggaccaat cttgaccttg tgggagggca
7441 acccgggaag gttttggaac acgaccatag ccgtatccac cgccaacatt ttcaggggaa
7501 gttacttggc gggagctgga ctggcttttt cactcataaa gaatgcacaa acccctagga
7561 ggggaactgg gaccacagga gagacactgg gagagaagtg gaagagacag ctaaactcat
7621 tagacagaaa agagtttgaa gagtataaaa gaagtggaat actagaagtg gacaggactg
7681 aagccaagtc tgccctgaaa gatgggtcta aaatcaagca tgcagtatct agagggtcca
7741 gtaagatcag atggattgtt gagagaggga tggtaaagcc aaaagggaaa gttgtagatc
7801 ttggctgtgg gagaggagga tggtcttatt acatggcgac actcaagaac gtgactgaag
7861 tgaaagggta tacaaaagga ggtccaggac atgaagaacc gattcccatg gctacttatg
7921 gttggaattt ggtcaaactc cattcagggg ttgacgtgtt ctacaaaccc acagagcaag
7981 tggacaccct gctctgtgat attggggagt catcttctaa tccaacaata gaggaaggaa
8041 gaacattaag agttttgaag atggtggagc catggctctc ttcaaaacct gaattctgca
8101 tcaaagtcct taacccctac atgccaacag tcatagaaga gctggagaaa ctacagagaa
8161 aacatggtgg gaaccttgtc agatgcccgc tgtccaggaa ctccacccat gagatgtatt
8221 gggtgtcagg agcgtcggga aacattgtga gctctgtgaa cacaacatca aagatgttgt
8281 tgaacaggtt cacaacaagg cataggaaac ccacttatga gaaggacgta gatcttgggg
8341 cagaaacgag aagtgtctcc actgaaacag aaaaaccaga catgacaatc attgggagaa
8401 ggcttcagcg attgcaagaa gaacacaaag aaacctggca ttatgatcag gaaaacccat
8461 acagaacctg ggcgtatcat ggaagctatg aagctccttc gacaggctct gcatcctcca
8521 tggtgaacgg ggtggtaaaa ctgctaacaa aaccctggga tgtgattcca atggtgactc
8581 agttagccat gacagataca accccttttg ggcaacaaag agtgttcaaa gagaaggtgg
8641 ataccagaac accacaacca aaacccggta cacgaatggt tatgaccacg acagccaatt
8701 ggctgtgggc cctccttgga aagaagaaaa atcccagact gtgcacaagg gaagagttca
8761 tctcaaaagt taaatcaaac gcagccatag gcgcagtctt tcaggaagaa cagggatgga
8821 catcagccaa tgaagctgtg aatgacagcc ggttttggga actggttgac aaagaaaggg
8881 ccctacacca ggaagggaaa tgtgaatcgt gtgtctataa catgatggga aaacatgaga
```

APPENDIX 1-continued

Sequence of recombinant dengue type 4 virus strain 2A

```
 8941 aaaagttagg agagtttggc agagccaagg gaagccgagc aatctagtac atgtggctgg
 9001 gagcgcggtt tctggaattt gaagccctag gtttttgaa tgaagatcac tggtttggca
 9061 gagaaaattc atggagtgga gtggaagggg aaggtctgca cagattggga tatatcctgg
 9121 aggagataga caagaaggat ggagacctaa tgtatgctga tgacacagca ggctgggaca
 9181 caagaatcac tgaggatgac cttcaaaatg aggaactgat cacggaacag atggctcccc
 9241 accacaagat cctagccaaa gccattttca aactaaccta tcaaaacaaa gtggtgaaag
 9301 tcctcagacc cacaccgaga ggagcggtga tggatatcat atccaggaaa gaccaaagag
 9361 gtagtggaca agttggaaca tatggtttga acacattcac caacatggaa gttcaactca
 9421 tccgccaaat ggaagctgaa ggagtcatca cacaagataa catgcagaac ccaaaagggt
 9481 tgaaagaaag agttgagaaa tggctgaaag agtgtggtgt cgacaggtta aagaggatgg
 9541 caatcagtgg agacgattgc gtggtgaagc ccctagatga gaggtttggc acttccctcc
 9601 tcttcttgaa cgacatggga aaggtgagga aagacattcc gcagtgggaa ccatctaagg
 9661 gatggaaaaa ctggcaagag gttccttttt gctcccacca ctttcacaag atctttatga
 9721 aggatggccg ctcactagtt gttccatgta gaaaccagga tgaactgata aggagagcca
 9781 gaatctcgca gggagctgga tggagcttaa gagaaacagc ctgcctgggc aaagcttacg
 9841 cccagatgtg gtcgcttatg tacttccaca gaagggatct acgtttagcc tccatggcca
 9901 tatgctcagc agttccaacg aaatggtttc caacaagcag aacaacatgg tcaatccacg
 9961 ctcatcacca gtggatgacc actgaagata tgctcaaagt gtggaacaga gtgtggatag
10021 aagacaaccc taatatgact gacaagactc cagtccattc gtgggaagat ataccttacc
10081 tagggaaaag agaggatttg tggtgtggat ccctgattgg actttcttcc agagccacct
10141 gggcgaagaa cattcacacg gccataaccc aggtcaggaa cctgatcgga aaagaggaat
10201 acgtggatta catgccagta atgaaaagat acagtgctcc ttcagagagt gaaggagttc
10261 tgtaattacc aacaacaaac accaaaggct attgaagtca ggccacttgt gccacagttt
10321 aagcaaaccg tgctgcctgt agctccgcca ataatgggaa gcgtaataat ccccagggag
10381 gccatgcgcc acggaagctg tacgcgtggc atattggact agcggttaga ggagacccct
10441 cccatcactg acaaaacgca gcaaaagggg gcccgaagcc aggaggaagc tgtactcctg
10501 gtggaaggac tagaggttag aggagacccc cccaacacaa aaacagcata ttgacgctgg
10561 gaaagaccag agatcctgct gtctctgcaa catcaatcca ggcacagagc gccgcaagat
10621 ggattggtgt tgttgatcca acaggttct
```

APPENDIX 2

Sequence of recombinant dengue typ 4 virus strain rDEN4

```
LOCUS           AF326825     10649 bp   RNA            VRL       03-JAN-2001
DEFINITION      Dengue virus type 4 recombinant clone rDEN4, complete sequence.
ACCESSION       AF326825
VERSION         AF326825.1 GI:12018169
KEYWORDS        .
SOURCE          Dengue virus type 4.
  ORGANISM      Dengue virus type 4
                Viruses; ssRNA positive-strand viruses, no DNA stage;
Flaviviridae;
                Flavivirus; Dengue virus group.
REFERENCE       1 (bases 1 to 10649)
  AUTHORS       Durbin,A.P., Karron,R.A., Sun, W., Vaughn,D.W., Reynolds,M.J.,
                Perreault,J.R., Men,R.H., Lai,C.J., Elkins,W.R., Chanock,R.M.,
                Murphy,B.R. and Whitehead,S.S.
  TITLE         A live attenuated dengue virus type 4 vaccine candidate with a
30
                nucleotide deletion in the 3' untranslated region is highly
                attenuated and immunogenic in humans
  JOURNAL       Unpublished
REFERENCE       2 (bases 1 to 10649)
  AUTHORS       Whitehead,S.S.
  TITLE         Direct Submission
JOURNAL         Submitted (08-DEC-2000) LID, NIAID, 7 Center Drive, Bethesda,
MD
                20892, USA
FEATURES                 Location/Qualifiers
     source              1..10649
                         /organism="Dengue virus type 4"
                         /db_xref="taxon:11070"
                         /clone="rDEN4"
     mat_peptide         102..440
                         /product="anchored capsid (anchC) protein"
     mat_peptide         102..398
                         /product="virion capsid (virC) protein"
     CDS                 102..10265
                         /codon_start=1
                         /product="polyprotein precursor"
                         /protein_id="AAG45435.1"
                         /db_xref="GI:12018170"

/translation="MNQRKKVVRPPFNMLKRERNRVSTGQGLVKRFSTGLFSGKGPLR
```

APPENDIX 2-continued

| Sequence of recombinant dengue typ 4 virus strain rDEN4 |
|---|

```
MVLAFITFLRVLSIPPTAGILKRWGQLKKNKAIKILIGFRKEIGRMLNILNGRKRSTI
TLLCLIPTVMAFSLSTRDGEPLMIVAKHERGRPLLFKTTEGINKCTLIAMDLGEMCED
TVTYKCPLLVNTEPEDIDCWCNLTSTWVMYGTCTQSGERRREKRSVALTPHSGMGLET
RAETWMSSEGAWKHAQRVESWILRNPGFALLAGFMAYMIGQTGIQRTVFFVLMMLVAP
SYGMRCVGVGNRDFVEGVSGGAWVDLVLEHGGCVTTMAQGKPTLDFELTKTTAKEVAL
LRTYCIEASISNITTATRCPTQGEPYLKEEQDQQYICRRDVVDRGWGNGCGLFGKGGV
VTCAKFSCSGKITGNLVQIENLEYTVVVTVHNGDTHAVGNDTSNHGVTAMITPRSPSV
EVKLPDYGELTLDCEPRSGIDFNEMILMKMKKKTWLVHKQWFLDLPLPWTAGADTSEV
HWNYKERMVTFKVPHAKRQDVTVLGSQEGAMHSALAGATEVDSGDGNHMFAGHLKCKV
RMEKLRIKGMSYTMCSGKFSIDKEMAETQHGTTVVKVKYEGAGAPCKVPIEIRDVNKE
KVVGRIISSTPLAENTNSVTNIELEPPFGDSYIVIGVGNSALTLHWFRKGSSIGKMFE
STYRGAKRMAILGETAWDFGSVGGLFTSLGKAVHQVFGSVYTTMFGGVSWMIRILIGF
LVLWIGTNSRNTSMAMTCIAVGGITLFLGFTVQADMGCVASWSGKELKCGSGIFVVDN
VHTWTEQYKFQPESPARLASAILNAHKDGVCGIRSTTRLENVMWKQITNELNYVLWEG
GHDLTVVAGDVKGVLTKGKRALTPPVSDLKYSWKTWGKAKIFTPEARNSTFLIDGPDT
SCEPNERRAWNSLEVEDYGFGMFTTNIWMKFREGSSEVCDHRLMSAAIKDQKAVHADM
GYWIESSKNQTWQIEKASLIEVKTCLWPKTHTLWSNGVLESQMLIPKSYAGPFSQHNY
RQGYATQTVGPWHLGKLEIDFGECPGTTVTIQEDCDHRGPSLRTTTASGKLVTQWCCR
SCTMPPLRFLGEDGCWYGMEIRPLSEKEENMVKSQVTAGQGTSETFSMGLLCLTLFVE
ECLRRRVTRKHMILVVVITLCAIILGGLTWMDLLRALIMLGDTMSGRIGGQIHLAIMA
VFKMSPGYVLGVFLRKLTSRETALMVIGMAMTTVLSIPHDLMELIDGISLGLILLKIV
TQFDNTQVGTLALSLTFIRSTMPLVMAWRTIMAVLFVVTLIPLCRTSCLQKQSHWVEI
TALILGAQALPVYLMTLMKGASRRSWPLNEGIMAVGLVSLLGSALLKNDVPLAGPMVA
GGLLLAAYVMSGSSADLSLEKAANVQWDEMADITGSSPIVEVKQDEDGSFSIRDVEET
NMITLLVKLALITVSGLYPLAIPVTMTLWYMWQVKTQRSGALWDVPSPAATKKAALSE
GVYRIMQRGLFGKTQVGVGIHMEGVFHTMWHVTRGSVICHETGRLEPSWADVRNDMIS
YGGGWRLDGKWDKEEDVQVLAIEPGKNPKHVQTKPGLFKTLTGEIGAVTLDFKPGTSG
SPIINRKGKVIGLYGNGVVTKSGDYVSAITQAERIGEPDYEVDEDIFRKKRLTIMDLH
PGAGKTKRILPSIVREALKRRLRTLILAPTRVVAAEMEEALRGLPIRYQTPAVKSEHT
GREIVDLMCHATFTTRLLSSTRVPNYNLIVMDEAHFTDPSSVAARGYISTRVEMGEAA
AIFMTATPPGATDPFPQSNSPIEDIEREIPERSWNTGFDWITDYQGKTVWFVPSIKAG
NDIANCLRKSGKKVIQLSRKTFDTEYPKTKLTDWDFVVTTDISEMGANFRAGRVIDPR
RCLKPVILPDGPERVILAGPIPVTPASAAQRRGRIGRNPAQEDDQYVFSGDPLKNDED
HAHWTEAKMLLDNIYTPEGIIPTLFGPEREKTQAIDGEFRLRGEQRKTFVELMRRGDL
PVWLSYKVASAGISYEDREWCFTGERNNQILEENMEVEIWTREGEKKKLRPRWLDARV
YADPMALKDFKEFASGRKSITLDILTEIASLPTYLSSRAKLALDNIVMLHTTERGGRA
YQHALNELPESLETLMLVALLGAMTAGIFLFFMQGKGIGKLSMGLITIAVASGLLWVA
EIQPQWIAASIILEFFLMVLLIPEPEKQRTPQDNQLIYVILTILTIIGLIAANEMGLI
EKTKTDFGFYQVKTETTILDVDLRPASAWTLYAVATTILTPMLRHTIENTSANLSLAA
IANQAAVLMGLGKGWPLHRMDLGVPLLAMGCYSQVNPTTLTASLVMLLVHYAIIGPGL
QAKATREAQKRTAAGIMKNPTVDGITVIDLEPISYDPKFEKQLGQVMLLVLCAGQLLL
MRTTWAFCEVLTLATGPILTLWEGNPGRFWNTTIAVSTANIFRGSYLAGAGLAFSLIK
NAQTPRRGTGTTGETLGEKWKRQLNSLDRKEFEEYKRSGILEVDRTEAKSALKDGSKI
KHAVSRGSSKIRWIVERGMVKPKGKVVDLGCGRGGWSYYMATLKNVTEVKGYTKGGPG
HEEPIPMATYGWNLVKLHSGVDVFYKPTEQVDTLLCDIGESSSNPTIEEGRTLRVLKM
VEPWLSSKPEFCIKVLNPYMPTVIEELEKLQRKHGGNLVRCPLSRNSTHEMYWVSGAS
GNIVSSVNTTSKMLLNRFTTRHRKPTYEKDVDLGAGTRSVSTETEKPDMTIIGRRLQR
LQEEHKETWHYDQENPYRTWAYHGSYEAPSTGSASSMVNGVVKLLTKPWDVIPMVTQL
AMTDTTPFGQQRVFKEKVDTRTPQPKPGTRMVMTTTANWLWALLGKKKNPRLCTREEF
ISKVRSNAAIGAVFQEEQGWTSASEAVNDSRFWELVDKERALHQEGKCESCVYNMMGK
REKKLGEFGRAKGSRAIWYMWLGARFLEFEALGFLNEDHWFGRENSWSGVEGEGLHRL
GYILEEIDKKDGDLMYADDTAGWDTRITEDDLQNEELITEQMAPHHKILAKAIFKLTY
QNKVVKVLRPTPRGAVMDIISRKDQRGSGQVGTYGLNTFTNMEVQLIRQMEAEGVITQ
DDMQNPKGLKERVEKWLKECGVDRLKRMAISGDDCVVKPLDERFGTSLLFLNDMGKVR
KDIPQWEPSKGWKNWQEVPFCSHHFHKIFMKDGRSLVVPCRNQDELIGRARISQGAGW
SLRETACLGKAYAQMWSLMYFHRRDLRLASMAICSAVPTEWRPTSRTTWSIHAHHQWM
TTEDMLKVWNRVWIEDNPNMTDKTPVHSWEDIPYLGKREDLWCGSLIGLSSRATWAKN
IHTAITQVRNLIGKEEYVDYMPVMKRYSAPSESEGVL"
     mat_peptide         441..938
                         /product="membrane precursor (prM) protein"
     mat_peptide         714..938
                         /product="membrane (M) protein"
     mat_peptide         939..2423
                         /product="envelope (E) protein"
     mat_peptide         2424..3479
                         /product="NS1 protein"
     mat_peptide         3480..4133
                         /product="NS2A protein"
     mat_peptide         4134..4523
                         /product="NS2B protein"
     mat_peptide         4524..6377
                         /product="NS3 protein"
     mat_peptide         6378..6758
                         /product="NS4A protein"
     mat_peptide         6759..6827
                         /product="2K protein"
     mat_peptide         6828..7562
                         /product="NS4B protein"
```

APPENDIX 2-continued

Sequence of recombinant dengue typ 4 virus strain rDEN4

```
    mat_peptide         7563..10262
                        /product="NS5 protein"

rDEN4 sequence

   1 agttgttagt ctgtgtggac cgacaaggac agttccaaat cggaagcttg cttaacacag
  61 ttctaacagt ttgtttgaat agagagcaga tctctggaaa aatgaaccaa cgaaaaaagg
 121 tggttagacc acctttcaat atactgaaac gcgagagaaa ccgcgtatca acccctcaag
 181 ggttggtgaa gagattctca accggacttt tttctgggaa aggaccctta cggatggtac
 241 tagcattcat cacgtttttg cgagtccttt ccatcccacc aacagcaggg attctgaaga
 301 gatggggaca gttgaagaaa aataaggcca tcaagatact gattggattc aggaaggaga
 361 taggccgcat gctgaacatc ttgaacggga gaaaaaggtc aacgataaca ttgctgtgct
 421 tgattcccac cgtaatggcg ttttccctca gcacaagaga tggcgaaccc ctcatgatag
 481 tggcaaaaca tgaaaggggg agacctctct tgtttaagac aacagagagg atcaacaaat
 541 gcactctcat tgccatggac ttgggtgaaa tgtgtgagga cactgtcacg tataaatgcc
 601 ccctactggt caatagcgaa cctgaagaca ttgattgctg gtgcaacctc acgtctacct
 661 gggtcatgta tgggacatgc acccagagcg gagaacggag acgagagaag cgctcagtag
 721 ctttaacacc acattcagga atgggattgg aaacaagagc taagacatgg atgtcatcgg
 781 aaggggcttg gaagcatgct cagagagtag agagctggat actcagaaac ccaagattcg
 841 cgctcttggc aggatttatg gcttatatga ttgggcaaac aggaatccag cgaactgtct
 901 tctttatcct aatgatgctg gtcgccccat cctacggaat gcgatgcgta ggagtaggaa
 961 acagagactt tgtggaagga gtctcaggtg gagcatgggt cgacctggtg ctagaacatg
1021 gaggatgcgt cacaaccatg gcccagggaa aaccaacctt gaattttgaa ctgactaaga
1081 caacagccaa ggaagtggct ctgttaagaa cctattgcat tgaagcctca atatcaaaca
1141 taactacggc aacaagatgt ccaacgcaag gagagcctta tctgaaagag gaacaggacc
1201 aacagtacat ttgccggaga gatgtggtag acagagggtg gagcaatggc tgtggcttgt
1261 ttggaaaagg aggagttgtg acatgtgcga aattttcatg ttcggggaag ataacaggca
1321 atttggtcca aattgagaac cttgaataca cagtggttgt aacagtccac aatggagaca
1381 cccatacagt aggaaatgac acatccaatc atggagttac agccatgata actcccaggt
1441 caccatcggt ggaagtcaaa ttgccggact atggaaaact aacactcgat tgtgaaccca
1501 gatctggaat tgactttaat gagataattc tgatgaaaat gaaaaagaaa acatggctcg
1561 tgcataagca atggtttttg gatctgcctc ttccatggac agcaggagca gacacatcag
1621 aggttcactg gaattacaaa gagagaatgg tgacatttaa ggttcctcat gccaagagac
1681 aggatgtgac agtgctggaa tctcaggaag gagccatgca ttctgccctc gctggagcca
1741 cagaagtgga ctccggtgat ggaaatcaca tgtttgcagg acatcttaag tgcaaagtcc
1801 gtatggagaa attgagaatc aagggaatgt catacacgat gtgttcagga aagttttcaa
1861 ttgacaaaga gatggcagaa acacagcatg gaacaacagt ggtgaaaatc aagtatgaag
1921 gtgctggagc tccgtgtaaa gtccccatag agataagaga tgtaaacaag gaaaaagtgg
1981 ttgggcgtat catctcatcc accccttttgg ctgagaatac caacagtgta accaacatag
2041 aattagaacc cccctttggg gacagctaca tagtgatagg tgttggaaac agcgcattaa
2101 cactccattg gttcaggaaa gggagttcca ttggcaagat gtttgagtcc acatacagag
2161 gtgcaaaacg aatggccatt ctaggtgaaa cagcttggga ttttggttcc gttggtggac
2221 tgttcacatc attgggaaag gctgtgcacc aggtttttgg aagtgtgtat acaaccatgt
2281 ttggaggagt ctcatggatg attagaatcc taattgggtt cttagtgttg tggattggca
2341 cgaactcgag gaacacttca atggctatga cgtgcatagc tgttggagga atcactctgt
2401 ttctgggctt cacagttcaa gcagacatgg gttgtgtggc gtcatggagt gggaaagaat
2461 tgaagtgtgg aagcagaatt tttgtggttg acaacgtgca cacttggaca gaacagtaca
2521 aatttcaacc agagtcccca gcgagactag cgtctgcaat attaaatgcc cacaaagatg
2581 gggtctgtgg aattagatca accacgaggc tggaaaatgt catgtggaag caaataacca
2641 acgagctaaa ctatgttctc tgggaaggag gacatgacct cactgtagtg gctggggatg
2701 tgaagggggt gttgaccaaa ggcaagagag cactcacacc cccagtgagt gatctgaaat
2761 attcatggaa gacatgggga aaagcaaaaa tcttcacccc agaagcaaga aatagcacat
2821 ttttaataga cggaccagac acctctgaat gccccaatga acgaagagca tggaactctc
2661 ttgaggtgga agactatgga tttggcatgt tcacgaccaa catatggatg aaattccgag
2941 aaggaagttc agaagtgtgt gaccacaggt taatgtcagc tgcaattaaa gatcagaaag
3001 ctgtgcatgc tgacatgggt tattggataa agagctcaaa aaaccagacc tgacagatag
3061 agaaagcatc tcttattgaa gtgaaaacat gtctgtggcc caaaacccac acactgtgga
3121 gcaatggagt gctggaaagc cagatgctca ttccaaaatc atatgcgggc cctttttcac
3181 agcacaatta ccgccagggc tatgccacgc aaaccgtggg cccatggcac ttaggcaaat
3241 tagagataga ctttggagaa tgccccggaa caacagtcac aattcaggag gattgtgacc
3301 ataaaggccc atctttgagg accaccactg catctggaaa actagtcaca caatggtgct
3361 gccgctcctg cacgatgcct cccttaaggt tcttgggaga agatgggtgc tggtatagga
3421 tggagattag gcccttgagt gaaaaagaaa agaacatggt caaatcacag gtgacggccg
3481 gacagggcac atcagaaact tttctatga gtctgttgtg cctgaccttg tttgtggaag
3541 aatgcttgag gagaagagtc actaggaaac acatgatatt agttgtggta atcactcttt
3601 gtgctatcat cctgggaggc ctcacatgga tggacttact acgagccctc atcatattgg
3661 gggacactat gtctggtaga ataggaggac agatccacct agccatcatg gcagtgttca
3721 agatgtcacc aggatacgtg ctgggtgtat ttttaaggaa actcacttca agagagacag
3781 cactaatggt aataggaatg gccatgacaa cggtgctttc aattccacat gaccttatgg
3841 aactcattga tggaatatca ctgggactaa ttttgctaaa aatagtaaca cagtttgaca
3901 acacccaagt gggaacctta gctctttcct tgactttcat aagatcaaca atgccattgg
3961 tcatggcttg gaggaccatt atggctgtat tgtttgtggt cacactcatt cctttgtgca
4021 ggacaagctg tcttcaaaaa cagtctcatt gggtagaaat aacagcactc atcctaggag
4081 cccaagctct gccagtgtac ctaatgactc ttatgaaagg agcctcaaga agatcttggc
4141 ctcttaacga gggcataata gctgtgggtt tggttagtct cttaggaagc gctcttttaa
4201 agaatgatgt ccctttagct ggcccaatgg tggcaggagg cttacttctg gcggcttacg
4261 tgatgagtgg tagctcagca gatctgtcac tagagaaggc cgccaacgtg cagtgggatg
4321 aaatggcaga cataacaggc tcaagcccaa tcgtagaagt gaagcaggat gaagatggct
```

APPENDIX 2-continued

Sequence of recombinant dengue typ 4 virus strain rDEN4

4381 ctttctccat acgggacgtc gaggaaacca atatgataac ccttttggtg aaactggcac
4441 tgataacagt gtcaggtctc tacccccttgg caattccagt cacaatgacc ttatggtaca
4501 tgtggcaagt gaaaacacaa agatcaggag ccctgtggga cgtcccctca cccgctgcca
4561 ctaaaaaagc cgcactgtct gaaggagtgt acaggatcat gcaaagaggg ttattcggga
4621 aaactcaggt tggagtagga atacacatgg aaggtgtatt tcacacaatg tggcatgtaa
4681 caagaggatc agtgatctgc cacgagactg ggagattgga gccatcttgg gctgacgtca
4741 gaaatgacat gatatcatac ggtgggggat ggaggcttgg aaacaaatgg gacaaagaag
4801 aagacgttca ggtcctcgcc atagaaccag gaaaaaatcc taaacatgtc caaacgaaac
4861 ctggcctttt caagacccta actggagaaa ttagagcagt aacattagat ttcaaacccg
4921 gaacgtctgg ttctcccatc atcaacagga aaggaaaagt catcggactc tatggaaatg
4981 gagtagttac caaatcaggt gattacgtca gtgccataac gcaagccgaa agaattggag
5041 agccagatta tgaagtggat gaggacattt ttcgaaagaa aagattaact ataatggact
5101 tacaccccgga agctgaaaag acaaaaagaa ttcttccatc aatagtgaaa gaagccttaa
5161 aaaggaggct acgaactttg attttagctc ccacgagagt ggtggcggcc gagatggaag
5221 aggccctacg tggactgcca atccgttatc agaccccagc tgtgaaatca gaacacacag
5281 gaagagagat tgtagacctc atgtgtcatg caaccttcac aacaagactt ttgtcatcaa
5341 ccagggttcc aaattacaac cttatagtga tggatgaagc acatttcacc gatccttcta
5401 gtgtcgcggc tagaggatac atctcgacca gggtggaaat gggagaggca gcagccatct
5461 tcatgaccgc aacccctccc ggagcgacag atccctttcc ccagagcaac agcccaataa
5521 aagacatcga gagggaaatt ccggaaaggt catggaacac agggttcgac tggataacag
5581 actaccaagg gaaaactgtg tggtttgttc ccagcataaa agctggaaat gacattgcaa
5641 attgtttgag aaagtcggga aagaaagtta tccagttgag taggaaaacc tttgatacag
5701 agtatccaaa aacgaaactc acggactggg actttgtggt cactacagac atatctgaaa
5761 tgggggccaa ttttagagcc gggagagtga tagaccctag aagatgcctc aagccagtta
5821 tcctaccaga tgggccagag agagtcattt tagcaggtcc tattccagtg actccagcaa
5881 gcgctgctca gagaagaggg cgaataggaa ggaacccagc acaagaagac gaccaatacg
5941 ttttctccgg agacccacta aaaaatgatg aagatcatgc ccactggaca gaagcaaaga
6001 tgctgcttga caatatctac accccagaag ggatcattcc aacattgttt ggtccggaaa
6061 gggaaaaaac ccaagccatt gatggagagt ttcgcctcag aggggaacaa aggaagactt
6121 ttgtggaatt aatgaggaga ggagaccttc cggtgtggct gagctataag gtagcttctg
6181 ctggcatttc ttacgaagat cgggaatggt gcttcacagg ggaaagaaat aaccaaattt
6241 tagaagaaaa catggaggtt gaaatttgga ctagagaggg agaaaagaaa aagctaaggc
6301 caagatggtt agatgcacgt gtatacgcta accccatggc tttgaaggat ttcaaggagt
6361 ttgccagtgg aaggaagagt ataactctcg acatcctaac agagattgcc agtttgccaa
6421 cttacctttc ctctagggcc aagctcgccc ttgataacat agtcatgctc cacacaacag
6481 aaagaggagg gagggcctat caacacgccc tgaacgaact tccggagtca ctggaaacac
6541 tcatgcttgt agctttacta ggtgctatga cagcaggcat cttcctgttt ttcatgcaag
6601 ggaaaggaat agggaaattg tcaatgggtt tgataaccat tgcggtggct agtggcttgc
6661 tctgggtagc agaaattcaa ccccagtgga tagcggcctc aatcatacta gagttttttc
6721 tcatggtact gttgataccg gaaccagaaa aacaaaggac cccacaagac-aatcaattga
6781 tctacgtcat attgaccatt ctcaccatca ttggtctaat agcagccaac gagatggggc
6841 tgattgaaaa aacaaaaacg gattttgggt tttaccaggt aaaaacagaa accaccatcc
6901 tcgatgtgga cttgagacca gcttcagcat ggacgctcta tgcagtagcc accacaattc
6961 tgactcccat gctgagacac accatagaaa acacgtcggc caacctatct ctagcagcca
7021 ttgccaacca ggcagccgtc ctaatggggc ttggaaaagg atgaccgctc cacagaatgg
7081 acctcggtgt gccgctgtta gcaatgggat gctattctca agtaaaccca acaaccttga
7141 cagcatcctt agtcatgctt ttagtccatt atgcaataat aggcccagga ttgcaggcaa
7201 aagccacaag agaggcccag aaaaggacaa ctgctgggat catgaaaaat,cccacagtgg
7261 acgggataac agtaatagat ctagaaccaa tatcctatga cccaaaattt gaaaagcaat
7321 taggacaggt catgctacta gtcttgtgtg ctggacaact actcttgatg agaacaacat
7381 gggctttctg tgaagtcttg actttggcca caggaccaat cttgaccttg tgggagggca
7441 acccgggaag gttttggaac acgaccataa ccgtatccac cgccaacatt ttcaggggaa
7501 gttacttggc gggagctgga ctggcttttt cactcataaa gaatgcacaa acccctagga
7561 ggggaactgg gaccacagga gagacactgg gagagaagtg gaaaagacag ctaaactcat
7621 tagacagaaa agagtttgaa gagtataaaa gaagtggaat actagaagtg gacaggactg
7681 aagccaagtc tgccctgaaa gatgggtcta aaatcaagca tgcagtatca agagggtcca
7741 gtaagatcag atggattgtt aagagaggga tggtaaagcc aaaagggaaa gttgtagatc
7801 ttggctgtgg gagaggagga tggtcttatt acatggcgac actcaagaac gtgactgaag
7861 tgaaagggta tacaaaagga ggtccaggac atgaagaacc gattcccatg gctacttatg
7921 gttggaattt ggtcaaactc cattcagggg ttgacgtgtt ctacaaaccc acagagcaag
7981 tggacaccct gctctgtgat attggggagt catcttctaa tccaacaata gaggaaggaa
8041 gaacattaag agttttgaag atggtggagc catggctctc ttcaaaacct gaattctgca
8101 tcaaagtcct taacccctac atgccaacag tcatagaaga gctggagaaa ctgcagagaa
8161 aacatggtgg gaaccttgtc agatgcccgc tgtccaggaa ctccacccat gagatgtatt
8221 gggtgtcagg agcgtcggga aacattgtga gctctgtgaa cacaacatca aagatgttgt
8281 tgaacaggtt cacaacaagg cataggaaac ccacttatga gaaggacgta gatcttgggg
8341 caggaacgag aagtgtctcc actgaaacag aaaaaccaga catgacaatc attgggagaa
8401 ggcttcagcg attgcaagaa gagcacaaag aaacctggca ttatgatcag gaaaacccat
8461 acagaacctg ggcgtatcat ggaagctatg aagctccttc gacaggctct gcatcctcca
8521 tggtgaacgg ggtggtaaaa ctgctaacaa aaccctggga tgtgattcca atggtgactc
8581 agttagccat gacagataca acccctttttg ggcaacaaag agtgttcaaa gagaaggtgg
8641 ataccagaac accacaacca aaacccggta cacgaatggt tatgaccacg acagccaatt
8701 ggctgtgggc cctccttgga aagaagaaaa atcccagact gtgcacaagg gaagagttca
8761 tctcaaaagt tagatcaaac gcagccatag gcgcagtctt tcaggaagaa cagggatgga
8821 catcagccag tgaagctgtg aatgacagcc ggttttggga actggttgac aaagaaaggg
8881 ccctacacca ggaagggaaa tgtgaatcgt gtatctataa catgatggga aaacgtgaga
8941 aaaagttagg agagtttggc agagccaagg gaagccgagc aatctggtac atgtggctgg
9001 gagcgcggtt tctggaattt gaagccctgg gtttttgaa tgaagatcac tggtttggca APPENDIX 2-continued Sequence of recombinant dengue typ 4 virus strain rDEN4

```
 9061 gagaaaattc atggagtgga gtggaagggg aaggtctgca cagattggga tatatcctgg
 9121 aggagataga caagaaggat ggagacctaa tgtatgctga tgacacagca ggctgggaca
 9181 caagaatcac tgaggatgac cttcaaaatg aggaactgat cacggaacag atggctcccc
 9241 accacaagat cctagccaaa gccattttca aactaaccta tcaaaacaaa gtggtgaaag
 9301 tcctcagacc cacaccgcgg ggagcggtga tggatatcat atccaggaaa gaccaaagag
 9361 gtagtggaca agttggaaca tatggtttga acacattcac caacatggaa gttcaactca
 9421 tccgccaaat ggaagctgaa ggagtcatca cacaagatga catgcagaac ccaaaagggt
 9481 tgaaagaaag agttgagaaa tggctgaaag agtgtggtgt cgacaggtta aagaggatgg
 9541 caatcagtgg agacgattgc gtggtgaagc ccctagatga gaggtttagc acttccctcc
 9601 tcttcttgaa cgacatggga aaggtgagga aagacattcc gcagtgggaa ccatctaagg
 9661 gatggaaaaa ctagcaagag gttccttttt gctcccacca ctttcacaag atctttatga
 9721 agaatggccg ctcactagtt gttccatgta gaaaccagga tgaactgata gggagagcca
 9781 gaatctcgca gggagctgga tggagcttaa gagaaacagc ctgcctgagc aaagcttacg
 9841 cccagatgtg gtcgcttatg tacttccaca gaagggatct gcgtttagcc tccatggcca
 9901 tatgctcagc agttccaacg gaatggtttc caacaagcag aacaacatgg tcaatccacg
 9961 ctcatcacca gtggatgacc actgaagata tgctcaaagt gtggaacaga gtgtggatag
10021 aaaacaaccc taatatgact gacaagactc cagtccattc gtgggaagat ataccttacc
10081 tagggaaaag agaggatttg tggtgtggat ccctgattgg actttcttcc agagccacct
10141 gggcgaagaa cattcatacg gccataaccc aggtcaggaa cctgatcgga aaagaggaat
10201 acatggatta catgccagta atgaaaagat acagtgctcc ttcagagagt gaaggagttc
10261 tgtaattacc aacaacaaac accaaaggct attgaagtca ggccacttgt gccacggttt
10321 gagcaaaccg tgctgcctgt agctccgcca ataatgggag gcgtaataat ccccagggag
10381 gccatacgcc acggaagctg tacgcgtggc atattggact agcggttaga ggagacccct
10441 cccatcactg ataaaacgca gcaaaagggg gcccgaagcc aggaggaagc tgtactcctg
10501 gtagaaggac tagaagttag aggagacccc cccaacacaa aaacagcata ttgacgctgg
10561 gaaagaccag agatcctgct gtctctgcaa catcaatcca ggcacagagc gccgcaagat
10621 ggattggtgt tgttgatcca acaggttct
```

APPENDIX 3

Sequence of recombinant dengue type 2 chimeric virus strain rDEN2/4Δ30

```
LOCUS            Submission pending
DEFINITION       Dengue virus type 2 recombinant clone rDEN2/4Δ30, complete
sequence.
ACCESSION        Submission pending
VERSION
KEYWORDS         .
SOURCE           Dengue virus type 2 NGC.
  ORGANISM       Dengue virus type 2
                 Viruses; ssRNA positive-strand viruses, no DNA stage;
Flavivirdiae;
                 Flavivirus; Dengue virus group.
REFERECNE        1 (bases 1 to 10616)
  AUTHORS.
  TITLE
  JOURNAL        Unpublished
FEATURES                  Location/Qualifiers
     source               1..10616
                          /organism="Dengue virus type 2"
                          /clone="rDEN2/4Δ30"
     mat_peptide          97..438
                          /product="anchored capsid (anchC) protein"
     mat_peptide          97..396
                          /product="virion capsid (virC) protein"
     CDS                  97..10263
                          /codon_start=1
                          /product="polyprotein precursor"

/translation=MNNQRKKARNTPFNMLKRERNRVSTVQQLTKRFSLGMLQGRGPLK
LFMALVAFLRFLTIPPTAGILKRWGTIKKSKAINVLRGFRKEIGRMLNILNRRRRTAG
MIIMLIPTVMAFHLTTRNGEPHMIVSRQEKGKSLLFKTEDGVNMCTLMAMDLGELCED
TITYKCPLLRQNEPEDIDCWCNSTSTWVTYGTCTTTGEHRREKRSVALVPHVGMGLET
RTETWMSSEGAWHKAQRIETWILRHPGFTIMAAILAYTIGTTHFQRALIFILLTAVAP
SMTMRCIGISNRDFVEGVSGGSWVDIVLEHGSCVTTMAKNKPTLDFELIKTEAKQPAT
LRKYCIEAKLTNTTTESRCPTQGEPSLNEEQDKRFVCKHSMVDRGWGNGCGLFGKGGI
VTCAMFTCKKNMEGKVVQPENLEYTIVITPHSGEEHAVGNDTGHKGKEIKITPQSSIT
EAELTGYGTVTMECSPRTGLDFNEMVLLQMENKAWLVHRQWFLDLPLPWLPGADTQGS
NWIQKETLVTFKNPHAKKQDVVVLGSQEGAMHTALTGATEIQMSSGNLLFTGHLKCRL
RMDKLQLKGMSYSMCTGKFKVVKEIAETQHGTIVIRVQYEGDGSPCKIPFEIMDLEKR
HVLGRLITVNPIVTEKDSPVNIEAEPPFGDSYIIIGVEPGQLKLNWFKKGSSIGQMFE
TTMRGAKRMAILGDTAWDFGSLGGVFTSIGKALHQVFGAIYGAAFSGVSWTMKILIGV
IITWIGMNSRNTSMAMTCIAVGGITLFLGFTVQADMGCVASWSGKELKCGSGIFVVDN
VHTWTEQYKFQPESPARLASAILNAHKDGVCGIRSTTRLENVMWKQITNELNYVLWEG
GHDLTVVAGDVKGVLTKGKRALTPPVSDLKYSWKTWGKAKIFTPEARNSTFLIDGPDT
```

APPENDIX 3-continued

Sequence of recombinant dengue type 2 chimeric virus strain rDEN2/4Δ30

```
SCEPNERRAWNSLEVEDYGFGMFTTNIWMKFREGSSEVCDHRLMSAAIKDQKAVHADM
GYWIESSKNQTWQIEKASLIEVKTCLWPKTHTLWSNGVLESQMLIPKSYAGPFSQHNY
RQGYATQTVGPWHLGKLEIDFGECPGTTVTIQEDCDHRGPSLRTTTASGKLVTQWCCR
SCTMPPLRFLGEDGCWYGMEIRPLSEKEENMVKSQVTAGQGTSETFSMGLLCLTLFVE
ECLRRRVTRKHMILVVVITLCAIILGGLTWMDLLRALIMLGDTMSGRIGGQIHLAIMA
VFKMSPGYVLGVFLRKLTSRETALMVIGMAMTTVLSIPHDLMELIDGISLGLILLKIV
TQFDNTQVGTLALSLTFIRSTMPLVMAWRTIMAVLFVVTLIPLCRTSCLQKQSHWVEI
TALILGAQALPVYLMTLMKGASRRSWPLNEGIMAVGLVSLLGSALLKNDVPLAGPMVA
GGLLLAAYVMSGSSADLSLEKAANVQWDEMADITGSSPIVEVKQDEDGSFSIRDVEET
NMITLLVKLALITVSGLYPLAIPVTMTLWYMWQVKTQRSGALWDVPSPAATKKAALSE
GVYRIMQRGLFGKTQVGVGIHMEGVFHTMWHVTRGSVICHETGRLEPSWADVRNDMIS
YGGGWRLGDKWDKEEDVQVLAIEPGKNPKHVQTKPGLFKTLTGEIGAVTLDFKPGTSG
SPIINRKGKVIGLYGNGVVTKSGDYVSAITQAERIGEPDYEVDEDIFRKKRLTIMDLH
PGAGKTKRILPSIVREALKRRLRTLILAPTRVVAAEMEEALRGLPIRYQTPAVKSEHT
GREIVDLMCHATFTTRLLSSTRVPNYNLIVMDEAHFTDPSSVAARGYISTRVEMGEAA
AIFMTATPPGATDPFPQSNSPIEDIEREIPERSWNTGFDWITDYQGKTVWFVPSIKAG
NDIANCLRKSGKKVIQLSRKTFDTEYPKTKLTDWDFVVTTDISEMGANFRAGRVIDPR
RCLKPVILPDGPERVILAGPIPVTPASAAQRRGRIGRNPAQEDDQYVFSGDPLKNDED
HAHWTEAKMLLDNIYTPEGIIPTLFGPEREKTQAIDGEFRLRGEQRKTFVELMRRGDL
PVWLSYKVASAGISYEDREWCFTGERNNQILEENMEVEIWTREGEKKKLRPRWLDARV
YADPMALKDFKEFASGRKSITLDILTEIASLPTYLSSRAKLALDNIVMLHTTERGGRA
YQHALNELPESLETLMLVALLGAMTAGIFLFFMQGKGIGKLSMGLITIAVASGLLWVA
EIQPQWIAASIILEFFLMVLLIPEPEKQRTPQDNQLIYVILTILTIIGLIAANEMGLI
EKTKTDFGFYQVKTETTILDVDLRPASAWTLYAVATTILTPMLRHTIENTSANLSLAA
IANQAAVLMGLGKGWPLHRMDLGVPLLAMGCYSQVNPTTLTASLVMLLVHYAIIGPGL
QAKATREAQKRTAAGIMKNPTVDGITVIDLEPISYDPKFEKQLGQVMLLVLCAGQLLL
MRTTWAFCEVLTLATGPILTLWEGNPGRFWNTTIAVSTANIFRGSYLAGAGLAFSLIK
NAQTPRRGTGTTGETLGEKWKRQLNSLDRKEFEEYKRSGILEVDRTEAKSALKDGSKI
KHAVSRGSSKIRWIVERGMVKPKGKVVDLGCGRGGWSYYMATLKNVTEVKGYTKGGPG
HEEPIPMATYGWNLVKLHSGVDVFYKPTEQVDTLLCDIGESSSNPTIEEGRTLRVLKM
VEPWLSSKPEFCIKVLNPYMPTVIEELEKLQRKHGGNLVRCPLSRNSTHEMYWVSGAS
GNIVSSVNTTSKMLLNRFTTRHRKPTYEKDVDLGAGTRSVSTETEKPDMTIIGRRLQR
LQEEKHETWHYDQENPYRTWAYHGSYEAPSTGSASSMVNGVVKLLTKPWDVIPMVTQL
AMTDTTPFGQQRVFKEKVDTRTPQPKPGTRMVMTTTANWLWALLGKKKNPRLCTREEF
ISKVRSNAAIGAVFQEEQGWTSASEAVNDSRFWELVDKERALHQEGKCESCVYNMMGK
REKKLGEFGRAKGSRAIWYMWLGARFLEFEALGFLNEDHWFGRENSWSGVEGEGLHRL
GYILEEIDKKDGDLMYADDTAGWDTRITEDDLQNEELITEQMAPHHKILAKAIFKLTY
QNKVVKVLRPTPRGAVMDIISRKDQRGSGQVGTYGLNTFTNMEVQLIRQMEAEGVITQ
DDMQNPKGLKERVEKWLKECGVDRLKRMAISGDDCVVKPLDERFGTSLLFLNDMGKVR
KDIPQWEPSKGWKNWQEVPFCSHHFHKIFMKDGRSLVVPCRNQDELIGRARISQGAGW
SLRETACLGKAYAQMWSLMYFHRRDLRLASMAICSAVPTEWFPTSRTTWSIHAHHQWM
TTEDMLKVWNRVWIEDNPNMTDKTPVHSWEWIPYLGKREDLWCGSLIGLSSRATWAKN
IHTATIQVRNLIGKEEYVDYMPVMKRYSAPSESEGVL"
     mat_peptide         439..936
                         /product="membrane precursor (prM) protein"
     mat_peptide         712..936
                         /product="membrane (M) protein"
     mat_peptide         937..2421
                         /product="envelope (E) protein"
     mat_peptide         2422..3477
                         /product="NS1 protein"
     mat_peptide         3478..4131
                         /product="NS2A protein"
     mat_peptide         4132..4521
                         /product="NS2B protein"
     mat_peptide         4522..6375
                         /product="NS3 protein"
     mat_peptide         6376..6756
                         /product="NS4A protein"
     mat_peptide         6757..6825
                         /product="2K protein"
     mat_peptide         6826..7560
                         /product="NS4B protein"
     mat_peptide         7561..10260
                         /product="NS5 protein"
```

rDEN2/4Δ30 sequence

```
   1 agttgttagt ctgtgtggac cgacaaggac agttccaaat cagaagcttg
  51 cttaacacag ttctaacagt ttgtttgaat agagagcaga tctctgatga
 101 ataaccaacg aaaaaaggcg agaaatacgc ctttcaatat gctgaaacgc
 151 gagagaaacc gcgtgtcgac tgtacaacag ctgacaaaga gattctcact
 201 tggaatgctg cagggacgag gaccattaaa actgttcatg accctggtgg
 251 cgttccttcg tttcctaaca atcccaccaa cagcagggat actgaagaga
 301 tggggaacaa ttaaaaaatc aaaagccatt aatgttttaa gagagttcag
 351 gaaagagatt ggaaggatgc tgaacatctt gaacaggaga cgcagaactg
 401 caagcatgat cattatgctg attccaacag tgatagcgtt ccatttaacc
 451 acacgtaacg gagaaccaca catgatcgtc agtagacaag agaaagggaa
```

APPENDIX 3-continued

| Sequence of recombinant dengue type 2 chimeric virus strain rDEN2/4Δ30 |
|---|
| 501 aagtcttctg tttaaaacag aggatggtgt gaacatgtat accctcatgg |
| 551 ccatggacct tggtgaattg tgtgaagata caatcacgta caagtgtcct |
| 601 cttctcaggc agaatgaacc agaagacata gattgttggt gcaactctac |
| 651 gtccacatgg gtaacttatg ggacgtgtac caccacagga gaacacagaa |
| 701 gagaaaaaag atcagtggca ctcgttccac atgtaggaat aggactggag |
| 751 acacgaactg aaacatggat gtcatcagaa ggggcctgga aacatgccca |
| 801 gaaaattgaa acttggatct tgagacatcc aggctttacc ataatggcag |
| 851 caatcctagc atacaccata ggaacgacac atttccaaag agccctgatt |
| 901 ttcatcttac tgacagctgt cgctccttca atgacaatgc gttgcatagg |
| 951 aatatcaaat agagactttg tagaaggggt ttcaggagga agctgggttg |
| 1001 acatagtctt agaacatgga agctgtgtga cgacgatagc aaaaaacaaa |
| 1051 ccaacattgg attttgaact gataaaaaca gaagccaaac aacctgccac |
| 1101 tctaaggaag tactgtatag aggcaaagct gaccaacaca acaacagaat |
| 1151 ctcgctgccc aacacaagga gaacctagcc taaatgaaga gcaggacaaa |
| 1201 aggttcgtct gcaaacactc catagtggac agaggatagg gaaatggata |
| 1251 tggattattt ggaaaaggag gcattgtgac ctgtgctatg ttcacatgca |
| 1301 aaaagaacat ggaaggaaaa gtcgtgcaac cagaaaactt ggaatacacc |
| 1351 attgtgataa cacctcactc aggggaagag catgcagtcg gaaatgacac |
| 1401 aggaaaacat ggcaaggaaa tcaaaataac accacagagt tccatcacag |
| 1451 aagcagagtt gacaggctat ggcactgtca cgatggagtg ctctccgaaa |
| 1501 acaggcctcg acttcaatga gatggtgttg ctgcaaatgg aaaataaagc |
| 1551 ttagctggtg cacaggcaat ggttcctaga cctgccgttg ccatggctgc |
| 1601 ccggagcgga cacacaagga tcaaattgga tacagaaaga gacattggtc |
| 1651 actttcaaaa atccccatgc gaagaaacag gatgttgttg ttttgggatc |
| 1701 ccaagaaggg gccatgcaca cagcactcac aggggccaca gaaatccaga |
| 1751 tgtcatcagg aaacttactg ttcacaggac atctcaagtg caggctaagg |
| 1801 atggacaaac tacagctcaa aggaatgtca tactctatgt gcacaggaaa |
| 1851 gtttaaagtt gtgaaggaaa tagcagaaac acaacatgga acaatagtta |
| 1901 tcagagtaca atatgaagga gacggttctc catgtaagat cccttttgag |
| 1951 ataatggatt tggaaaaaag acatgtttta ggtcgcctga ttacagtcaa |
| 2001 cccaatcgta acagaaaaag atagcccagt caacatagaa gcagaacctc |
| 2051 cattcggaga cagctacatc atcataggag tagagccggg acaattgaag |
| 2101 ctcaactggt ttaagaaagg aagttctatc agccaaatgt ttgagacaac |
| 2151 aatgagggga gcgaagagaa tggccatttt aggtgacaca gcttgggatt |
| 2201 ttggatccct gggaggagtg tttacatcta taggaaaggc tctccaccaa |
| 2251 gttttcggag caatctatgg ggctgccttc agtggggtct catggactat |
| 2301 gaaaatcctc ataggagtca ttatcacatg aataggaatg aactcgagga |
| 2351 acacttcaat ggctatgacg tgcatagctg ttggaggaat cactctgttt |
| 2401 ctgggcttca cagttcaagc agacatgggt tgtgtggcgt catggagtgg |
| 2451 gaaagaattg aaatgtggaa acggaatttt tgtggttgac aacgtgcaca |
| 2501 cttggacaga acagtacaaa tttcaaccag agtccccagc gagactagcg |
| 2551 tctgcaatat taaatgccca caaagatggg gtctgtggaa ttagatcaac |
| 2601 cacgaggctg gaaaatgtca tgtggaagca aataaccaac gagctaaact |
| 2651 atgttctctg ggaaggagga catgacctca ctgtagtggc tggggatgtg |
| 2701 aagggggtgt tgaccaaagg caagagagca ctcacacccc cagtgagtga |
| 2751 tctgaaatat tcatggaaga catgggaaaa agcaaaaatc ttcaccccag |
| 2801 aagcaagaaa tagcacattt ttaatagacg gaccagacac ctctgaatgc |
| 2851 cccaatgaac gaagagcatg gaactctctt gaggtggaag actatggatt |
| 2901 tggcatgttc acgaccaaca tatggatgaa attccgagaa ggaagttcag |
| 2951 aagtgtgtga ccacaggtta atgtcagctg caattaaaga tcagaaagct |
| 3001 gtgcatgctg acatgggtta ttggatagag agctcaaaaa accagacctg |
| 3051 gcagatagag aaagcatctc ttattgaagt gaaaacatgt ctgtggccca |
| 3101 agacccacac actgtggagc aatggagtgc tggaaagcca gatgctcatt |
| 3151 ccaaaatcat atgcgggccc tttttcacag cacaattacc gccaaggcta |
| 3201 tgccacgcaa accgtgggcc catggcactt aggcaaatta gagatagact |
| 3251 ttggagaata ccccggaaca acagtcacaa ttcaggagga ttgtgaccat |
| 3301 agaggcccat ctttgaggac caccactgca tctggaaaac tagtcacgca |
| 3351 atggtgctgc cactcctgca cgatgcctcc cttaaggttc ttggaagaag |
| 3401 atgggtgctg gtatgggatg gagattaggc ccttgagtga aaaagaagag |
| 3451 aacatggtca aatcacaggt gacggccgga cagggcacat cagaaacttt |
| 3501 ttctatgggt ctgttatgcc tgaccttgtt tgtggaagaa tgcttgagga |
| 3551 gaagagtcac taggaaacac atgatattag ttgtggtgat cactctttgt |
| 3601 gctatcatcc tgggaggcct cacatggata gacttactac gagccetcat |
| 3651 catgttgggg gacactatgt ctggtagaat aggaggacag atccacctag |
| 3701 ccatcatggc agtgttcaag atgtcaccag gatacgtgct gggtgtgttt |
| 3751 ttaagaaaac tcacttcaag agagacagca ctaatggtaa taggaatggc |
| 3801 catgacaacg gtgctttcaa ttccacatga ccttatggaa ctcattgatg |
| 3851 gaatatcact gggactaatt ttgctaaaaa tagtaacaca gtttgacaac |
| 3901 acccaagtgg gaaccttagc tctttccttg actttcataa gatcaacaat |
| 3951 gccattggtc atggcttgga ggaccattat ggctgtgttg tttgtggtca |
| 4001 cactcattcc tttgtgcagg acaagctgtc ttcaaaaaca gtctcattgg |
| 4051 gtagaaataa cagcactcat cctaggagcc caagctctgc cagtgtacct |
| 4101 aatgactctt atgaaaggag cctcaagaag atcttggcct cttaacgagg |
| 4151 gcataatggc tgtgggtttg gttagtctct taggaagcgc tcttttaaag |
| 4201 aatgatgtcc ctttagctgg cccaatggtg gcaggaggct tacttctggc |
| 4251 ggcttacgtg atgagtggta gctcagcaga tctgtcacta gagaaggccg |
| 4301 ccaacgtgca gtgggatgaa atggcagaca taacaggctc aagcccaatc |
| 4351 atagaagtga agcaggatga agatggctct ttctccatac gggacgtcga |

APPENDIX 3-continued

Sequence of recombinant dengue type 2 chimeric virus strain rDEN2/4Δ30

4401 ggaaaccaat atgataaccc ttttggtgaa actggcactg ataacagtgt
4451 caggtctcta ccccttggca attccagtca caatgacctt atggtacatg
4501 tggcaagtga aaacacaaag atcaggagcc ctgtgggacg tcccctcacc
4551 cgctgccact aaaaaagccg cactgtctga aggagtgtac aggatcatgc
4601 aaagagggtt attcgggaaa actcaggttg gagtagggat acacatggaa
4651 ggtgtatttc acacaatgtg gcatgtaaca agaggatcag tgatctgcca
4701 cgagactggg agattggagc catcttgggc tgacgtcagg aatgacatga
4751 tatcatacgg tgggggatgg aggcttggag acaaatggga caaagaagaa
4801 gacgttcagg tcctcgccat agaaccagga aaaaatccta aacatgtcca
4851 aacgaaacct ggccttttca agaccctaac tggagaaatt ggagcagtaa
4901 cattagattt caaacccgga acgtctggtt ctcccatcat caacaggaaa
4951 ggaaaagtca tcggactcta tggaaatgga gtagttacca aatcaggtga
5001 ttacgtcagt gccataacgc aagccgaaag aattggagag ccagattatg
5051 aagtggatga ggacattttt cgaaagaaaa gattaactat aatggactta
5101 caccccggag ctggaaagac aaaaagaatt cttccatcaa tagtgagaga
5151 agccttaaaa aggaggctac gaactttgat tttagctccc acgagagtgg
5201 tggcggccga gatggaagag accctacgtg gactgccaat ccgttatcag
5251 accccagctg tgaaatcaga acacacagga agagagattg tagacctcat
5301 gtgtcatgca accttcacaa caagactttt gtcatcaacc agagttccaa
5351 attacaacct tatagtgatg gatgaagcac atttcaccga tccttctagt
5401 gtcgcggcta gaggatacat ctcgaccagg gtggaaatag gagagacagc
5451 agccatcttc atgaccgcaa ccectcccag agcgacagat ccctttcccc
5501 agagcaacag cccaatagaa gacatcgaga gggaaattcc ggaaaggtca
5551 tggaacacag ggttcgactg gataacagac taccaaggaa aaactatgtg
5601 gtttgttccc agcataaaag ctggaaatga cattgcaaat tgtttgagaa
5651 aatcgggaaa gaaagttatc cagttgagta ggaaaacctt tgatacagag
5701 tatccaaaaa cgaaactcac ggactgggac tttgtggtca ctacagacat
5751 atctgaaatg ggggccaatt ttagagccgg aagagtgata gaccctagaa
5801 gatgcctcaa gccagttatc ctaccagatg ggccagagag agtcatttta
5851 gcaggtccta ttccagtgac tccagcaagc gctgctcaga gaagagggcg
5901 aataggaaga aacccagcac aagaagacga ccaatacgtt ttctccggag
5951 acccactaaa aaatgatgaa gatcatgccc actggacaga agcaaagatg
6001 ctgcttgaca atatctacac cccagaaggg atcattccaa cattgtttgg
6051 tccggaaaga gaaaaaaccc aagccattga tggagagttt cgcctcagag
6101 aggaacaaag gaagactttt gtggaattaa tgaggagagg agaccttccg
6151 gtgtggctga gctataaggt agcttctgct ggcatttctt acaaagatcg
6201 ggaatggtgc ttcacaggag aaagaaataa ccaaatttta gaaaaaaaca
6251 tggaggttaa aatttggact agagaaagag aaaagaaaaa gctaaggcca
6301 agatggttag atgcacgtgt atacgctgac cccatggctt tgaaggattt
6351 caaggagttt gccagtggaa ggaagagtat aactctcgac atcctaacag
6401 agattgccag tttgccaact tacctttcct ctagggccaa gctcgccctt
6451 gataacatag tcatgctcca cacaacagaa agaggaggga gggcctatca
6501 acacgccctg aacgaacttc cggagtcact ggaaacactc atgcttgtag
6551 ctttactagg tgctatgaca gcaggcatct tcctgttttt catgcaaggg
6601 aaaggaatag ggaaattgtc aatggatttg ataaccattg cggtggctag
6651 tggcttgctc tgggtagcag aaattcaacc ccagtggata gcggcctcaa
6701 tcatactaga gtttttctc atggtactgt tgataccgga accagaaaaa
6751 caaaggaccc cacaagacaa tcaattgatc tacgtcatat tgaccattct
6801 caccatcatt agtctaatag cagccaacga gatggagctg attgaaaaaa
6851 caaaaacgga ttttgggttt taccaggtaa aaacagaaac caccatcctc
6901 gatgtggact tgagaccagc ttcagcatgg acactctatg cagtagccac
6951 cacaattctg actcccatgc tgagacacac catagaaaac acgtcggcca
7001 acctatctct agcagccatt gccaaccagg cagccatcct aatggggctt
7051 ggaaaaggat ggccgctcca cagaatggac ctcggtgtgc cgctgttaac
7101 aatgggatgc tattctcaag tgaacccaac aaccttgaca gcatccttag
7151 tcatgctttt agtccattat gcaataatag gcccaggatt gcaggcaaaa
7201 gccacaagag aggcccagaa aaggacagct gctgggatca tgaaaaatcc
7251 cacagtggac gggataacag taatagatct agaaccaata tcctatgacc
7301 caaaatttga aaagcaatta gggcaggtca tgctactagt cttgtgtgct
7351 ggacaactac tcttgatgag aacaacatgg gctttctgtg aagtettgac
7401 tttggccaca ggaccaatct tgaccttgtg ggagggcaac ccgggaaggt
7451 tttggaacac gaccatagcc gtatccaccg ccaacatttt caggggaagt
7501 tacttggcgg gagctggact ggctttttca ctcataaaga atgcacaaac
7551 ccctaggagg ggaactggga ccacaggaga gacactggga gagaagtgga
7601 agagacagct aaactcatta gacagaaaag agtttgaaga gtataaaaga
7651 agtggaatac tagaagtgga caggactgaa gccaagtctg ccctgaaaga
7701 tgggtctaaa atcaagcatg cagtatcaag agggtccagt aagatcagat
7751 ggattgttga gagagggatg gtaaagccaa aagggaaagt tgtagatctt
7801 ggctgtggga gaggaggatg gtcttattac atggcgacac tcaagaacgt
7851 gactgaagtg aaagggtata caaaaggagg tccaggacat gaagaaccga
7901 ttcccatggc tacttatggt tggaatttgg tcaaactcca ttcaggggtt
7951 gacgtgttct acaaacccac agagcaagtg gacaccctgc tctgtgatat
8001 tggggagtca tcttctaatc caacaataga ggaaggaaga acattaagag
8051 ttttgaagat ggtggagcca tggctctctt caaaacctaa attctgcatc
8101 aaagtcctta acccctacat gccaacagtc atagaagagc tggagaaact
8151 gcagagaaaa catggtggga accttgtcag atgcccgctg tccaggaact
8201 ccacccatga gatgtattgg gtgtcaggag cgtcgggaaa cattatgagc
8251 tctgtgaaca caacatcaaa gatgttgttg aacaggttca caacaaggca

APPENDIX 3-continued

Sequence of recombinant dengue type 2 chimeric virus strain rDEN2/4Δ30

```
 8301 taggaaaccc acttatgaga aggacgtaga tcttggggca agaacgagaa
 8351 gtgtctccac tgaaacagaa aaaccagaca tgacaatcat tgggagaagg
 8401 cttcagcgat tgcaagaaga gcacaaagaa acctggcatt atgatcagga
 8451 aaacccatac agaacctggg cgtatcatgg aagctatgaa gctccttcga
 8501 caggctctgc atcctccatg gtgaacgggg tggtaaaact actaacaaaa
 8551 ccctgggatg tgattccaat ggtgactcag ttagccatga cagatacaac
 8601 ccctttgggg caacaaagag tgttcaaaga gaaggtggat accagaacac
 8651 cacaaccaaa accggtaca cgaatggtta tgaccacgac agccaattgg
 8701 ctgtgggccc tccttggaaa gaagaaaaat cccagactgt gcacaaggga
 8751 agagttcatc tcaaaagtta gatcaaacgc agccataggc acagtctttc
 8801 aggaagaaca gggatggaca tcaaccagtg aagctgtgaa tgacagccgg
 8851 ttttgggaac tggttgacaa agaaagggcc ctacaccagg aagggaaatg
 8901 tgaatcatgt gtctataaca tgatgggaaa acgtgagaaa aagttaggag
 8951 agtttggcag agccaaggga agccgagcaa tctggtacat atggctggga
 9001 gcgcggtttc tggaatttga agccctgggt ttttgaatg aagatcactg
 9051 gtttggcaga gaaaattcat ggagtggagt ggaaggggaa ggtctgcaca
 9101 gattggaata tcctggag gagatagaca agaaggatgg agacctaatg
 9151 tatgctgatg acacagcagg ctgggcacaa agaatcactg aggatgacct
 9201 tcaaaatgag gaactgatca cggaacagat ggctccccac cacaagatcc
 9251 tagccaaagc cattttcaaa ctaacctatc aaaacaaagt ggtgaaagtc
 9301 ctcagaccca caccgcgggg agcggtgatg gatatcatat ccaggaaaga
 9351 ccaaagaggt agtggacaag ttggaacata tggtttgaac acattccaca
 9401 acatgaagt tcaactcatc cgccaaatgg aagctgaagg agtcatccaa
 9451 caagatgaca tgcagaaccc aaaagggttg aagaaaagag ttgagaaatg
 9501 gctgaaagag tgtgtggtcg acaggttaaa gaggatggca atcagtggag
 9551 acgattgcgt ggtgaagccc ctagatgaga ggtttggcac ttccctcctc
 9601 ttcttgaacg acatgggaaa ggtgaggaaa gacattccgc agtgggaacc
 9651 atctaaggga tggaaaaact ggcaagaggt tccttttgc tcccaccact
 9701 ttcacaagat ctttatgaag gatggccgct cactagttgt tccatgtaga
 9751 aaccaggatg aactgatagg gagagccaga atctcgcagg gagctggatg
 9801 gagcttaaga gaaacagcct gcctgggcaa agcttacgcc cagatgtggt
 9851 cgcttatgta cttccacaga agggatctgc gtttagcctc catggccata
 9901 tgctcagcag ttccaacgga atggtttcca acaagcagaa caacatggtc
 9951 aatccacgct catcaccagt ggatgaccac tgaagatatg ctcaaagtgt
10001 ggaacagagt gtggatagaa gacaacccta atatgactga caagactcca
10051 gtccattcgt gggaagatat accttaccta gggaaaagag aggatttgtg
10101 gtgtggatcc ctgattggac tttcttccag agccacctgg gcgaagaaca
10151 ttcacacggc cataacccag atcaggaacc tgatcggaaa agaggaatac
10201 gtggattaca tgccagtaat gaaaagatac agtgctcctt cagagagtga
10251 aggagttctg taattaccaa caacaaacac caaaggctat taagtcagg
10301 ccacttgtgc cacggtttga gcaaaccgtg ctgcctgtag ctccgccaat
10351 aatgggaggc gtaataatcc ccagggaggc catgcgccac ggaagctgta
10401 cgcgtggcat attggactag cggttagagg agacccctcc catcactgac
10451 aaaacgcagc aaaagggggc ccaagactag aggttagagg agaccccccc
10501 aacacaaaaa cagcatattg acgctgggaa agaccagaga tcctgctgtc
10551 tctgcaacat caatccaggc acagagcgcc gcaagatgga ttggtgttgt
10601 tgatccaaca ggttct
```

APPENDIX 4

Alignment of dengue virus polyproteins

```
DEN4       1 MNQRKKVVRPPFNMLKRERNRVSTPQGLVKRFSTGLFSGKGPLRMVLAF       49
DEN1-WP    1 MNNQRKKTGRPSFNMLKRARNRVSTVSQLAKRFSKGLLSGQGPMKLVMAF      50
DEN2-NGC   1 MNNQRKKARNTPFNMLKRERNRVSTVQQLTKRFSLGMLQGRGPLKLFMAL      50
DEN3-H87   1 MNNQRKKTGKPSINMLKRVRNRVSTGSQLAKRFSRGLLNGQGPMKLVMAF      50
             *****     ***** ******  * **** *.  *.**....*

DEN4      50 ITFLRVLSIPPTAGILKRWGQLKKNKAIKILIGFRKEIGRMLNILNGRKR       99
DEN1-WP   51 IAFLRFLAIPPTAGILARWGSFKKNGAIKVLRGFKKEISNMLNIMNRKKR      100
DEN2-NGC  51 VAFLRFLTIPPTAGILKRWGTIKKSKAINVLRGFRKEIGRMLNILNRRRR      100
DEN3-H87  51 IAFLRFLAIPPTAGVLARWGTFKKSGAIKVLKGFKKEISNMLSIINKRKK      100
             ..***  *.******.* ***    **  .*  ** .*** ** *.* *..

DEN4     100 STITLLCLIPTVMAFSLSTRDGEPLMIVAKHERGRPLLFKTTEGINKCTL      149
DEN1-WP  101 SVTMLLMLLPTALAFHLTTRGGEPHMIVSKQERGKSLLFKTSAGVNMCTL      150
DEN2-NGC 101 TAGMIIMLIPTVMAFHLTTRNGEPHMIVSRQEKGKSLLFKTEDGVNMCTL      150
DEN3-H87 101 TSLCLAMMLPATLAFHLTSRDGEPRMIVGKNERGKSLLFKTASGINMCTL      150
             .    ...* .**. ** *** *** ***       * *  * * ***

DEN4     150 IAMDLGEMCEDTVTYKCPLLVNTEPEDIDCWCNLTSTWVMYGTCTQSGER      199
DEN1-WP  151 IAMDLGELCEDTMTYKCPRITETEPDDVDCWCNATETWVTYGTCSQTGEH      200
DEN2-NGC 151 MAMDLGELCEDTITYKCPFLPQNEPEDIDCWCNSTSTWVTYGTCTTTGEH      200
DEN3-H87 151 IAMDLGEMCDDTVTYKCPHITEVEPEDIDCWCNLTSTWVTYGTCNQAGEH      200
             .******.*.**.****** .  **.* ***** .** **** **.  **.
```

APPENDIX 4-continued

Alignment of dengue virus polyproteins

```
DEN4     200 RREKRSVALTPHSGMGLETRAETWMSSEGAWKHAQRVESWILRNPGFALL 249
DEN1-WP  201 RRDKRSVALAPHVGLGLETRTETWMSSEGAWKQIQKVETWALRHPGFTVI 250
DEN2-NGC 201 RREKRSVALVPHVGMGLETRTETWMSSEGAWKHAQRIETWILRHPGFTIM 250
DEN3-H87 201 RRDKRSVALAPHVGMGLDTRTQTWMSAEGAWRQVEKVETWALRHPGFTIL 250
             **.****** ** *.**.**..****.****.. ...*.* **.***...

DEN4     250 AGFMAYMIGQTGIQRTVFFVLMMLVAPSYGMRCVGVGNRDEVEGVSGGAW 299
DEN1-WP  251 ALFLAHAIGTSITQKGIIFILLMLVTPSMAMRCVGIGNRDEVEGLSGATW 300
DEN2-NGC 251 AAILAYTIGTTHFQRALIFILLTAVAPSMTMRCIGISNRDFVEGVSGGSW 300
DEN3-H87 251 ALFLAHYIGTSLTQKVVIFILLMLVTPSMTMRCVGVGNRDFVEGLSGATW 300
              *  .*  **  .*.   *.*.   *.** *** *. ******.** .*

DEN4     300 VDLVLEHGGCVTTMAQGKPTLDFELTKTTAKEVALLRTYCIEASISNITT 349
DEN1-WP  301 VDVVLEHGSCVTTMAKDKPTLDIELLKTEVTNPAVLRKLCIEAKISNTTT 350
DEN2-NGC 301 VDIVLEHGSCVTTMAKNKPTLDFELIKTEAKQPATLRKYCIEAFLTNTTT 350
DEN3-H87 301 VDVVLEHGGCVTTMAKNKPTLDIELQKTEATQLATLRKLCIEGKITN1TT 350
             **.***** ******. ***** ** **      *  ***   ..* **

DEN4     350 ATRCPTQGEPYLKEEQDQQYICRRDVVDRGWGNGCGLFGKGGVVTCAKFS 399
DEN1-WP  351 DSRCPTQGEATLVEEDQTNFVCRRTFVDRGWGNGCGLFGKGSLITCAKFK 400
DEN2-NGC 351 DSRCPTQGEPSLNEEQDKREVCKHSMVDRGWGNGCGLFGKGGIVTCAMFT 400
DEN3-H87 351 DSRCPTQGEAILPEEQDQNYVCKHTYVDRGWGNGCGLFGKGELVTCAKFQ 400
              .******  *  ****   .*...  ***************  .*** *

DEN4     400 CSGKITGNLVQIENLEYTVVVTVHNGDTHAVGNDTSNHGVTAMITPRSPS 449
DEN1-WP  401 CVTKLEGKIVQYENLKYSVIVTVHGDQHQVNGETTEHGTTATITPQAPT 449
DEN2-NGC 401 CKKNMKGKVVQPENLEYTIVITPHSGEEHAVGNDTGKHGKEIKITPQSSI 450
DEN3-H87 401 CLESIEGKVVQHENLKYTVIITVHTGDQHQVGENT--QGVTAEITSQAST 448
              *   .  * .** ***  *. . *  *  . *    * ***.    **

DEN4     450 VEVKLPDYGELTLDCEPRSGIDFNEMILMKMKKKTWLVHKQWFLDLPLPW 499
DEN1-WP  451 SEIQLTDYGALTLDCSPRTGLDFNEMVLLTMEKKSWLVHKQWFLDLPLPW 500
DEN2-NGC 451 TEAELTGYGTVTMECSPRTGLDFNEMVLLQMENKAWINHRQWFLDLPLPW 500
DEN3-H87 449 AEAILPEYGTLGLECSPRTGLDFNEMILLTMKNKAWMVHRQWETDLPLPW 498
              *  *    ..* **.*.******.*.  *   *.**.*** ******

DEN4     500 TAGADTSEVHWNYKERMVTFKVPHAKRQDVTVLGSQEGAMHSALAGATEV 549
DEN1-WP  501 TSGASTSQETWNRQDLINTFICTAHAKKQEVVVLGSQEGAMTALTGATEI 550
DEN2-NGC 501 LPGADTQGSNWIQKETLVTFKNPHAKKQDVVVLGSQEGAMHTALTGATEI 550
DEN3-H87 499 TSGATTKTPTWNRKELLVTFKNAHAKKQEVVVLGSQEGAMHTALTGATEI 548
              . *  *     *   .. .****  ***.*.* **********.**.****.

DEN4     550 DSGDGNHMFAGHLKCKVRMEKLRIKGMSYTMCSGKFSIDKEMAETQHGTT 599
DEN1-WP  551 QTSGTTTIFAGHLKCRLKMDKLTLKGMSYVMCTGSFKLEKEVAETQHGTV 600
DEN2-NGC 551 QMSSGNLLFTGHLKCRLRMDKLQLKGMSYSMCTGKFKVVKEIAETQHGTI 600
DEN3-H87 549 QTSGGTSIFAGHLKCRLKMDKLKLKGMSYAMCLNTFVLKKEVSETQHGTI 598
               .*.*****. .*.**. *****. **  . *  **. *******

DEN4     600 VVKVKYEGAGAPCKVPIEIRDVNKEKVVGRIISSTPLAENTVSVTNIELE 649
DEN1-WP  601 LVQVKYEGTDAPCKIPFSSQDEKGVTQNGRLITANPIVTDKEKPVNIEAE 650
DEN2-NGC 601 VIRVQYEGDGSPCKIPFEIMDLEKRHVLGRLITVNPIVTEKDSPVNIEAE 650
DEN3-H87 599 LIKVEYKGEDAPCKIPFSTEDGQGKAHNGRLITANPVVTKKEEPVNIEAE 648
              ..  * * *    . ***. *    *       **..* .*.   *** *

DEN4     650 PPFGDSYIVIGVGNSALTLHWFRKGSSIGKMFESTYRGAKRMAILGETAW 699
DEN1-WP  651 PPFGESYIVVGAGEKALKLSWFKKGSSIGKMFEATARGARRMAILGDTAW 700
DEN2-NGC 651 PPFGDSYIIIGVEPGQLKLNWFKKGSSIGQMEITTMRGAKRMAILGDTAW 700
DEN3-H87 649 PPFGESNIVIGIGDKALKINWYRKGSSIGKMFEATARGARRMAILGDTAW 698
             ****.*.*..*     *   .*.*******.*  *  ***.******.***

DEN4     700 DFGSVGGLFTSLGKAVHQVFGSVYTTMFGGVSWMIRILIGFLVLWIGTNS 749
DEN1-WP  701 DFGSIGGVFTSVGKLIHQIFGTAYGVLFSGVSWTMKIGIGILLTWLGLNS 750
DEN2-NGC 701 DFGSLGGVFTSIGKALHQVFGAIYGAAFSGVSWTMKILIGVIITWIGMNS 750
DEN3-H87 699 DFGSVGGVLNSLGKMVHQIFGSAYTALFSGVSWIMKIGIGVLLTWIGLNS 748
             ****.**. *.* **.*   .*    .******.   **.   .*. .*.  *

DEN4     750 RNTSMAMTCAIVGGITLFLGFTVQADMGCVASWSGKELKCGSGIFVVDNV 799
DEN1-WP  751 RSTSLSMTCIAVGMVTLYLGVMVQADSGCVINWKGRELKCGSGIFVTNEV 800
DEN2-NGC 751 RSTSLSVSLVLVGVVTLYLGVMVQADSGCVVSWKNKELKCGSGIFITDNV 800
DEN3-H87 749 KNTSMSFSCIAIGIITLYLGVVVQADMGCVINWKGKELKCGSGIFVTNEV 798
              . **..   . ..  **.** ****  ***    .*********.  *

DEN4     800 HTWTEQYKFQPESPARLASAILNAHKDGVCGIRSTTRLENVMWKQITNEL 849
DEN1-WP  801 HTWTEQYKFQADSPKRLSAAIGKAWEEGVCGIRSATRLENIMWKQISNEL 850
DEN2-NGC 801 HTWTEQYKFQPESPSKLASAIQKAHEEGICGIRSVTRLENLMWKQITPEL 850
DEN3-H87 799 HTWTEQYKFQADSPKRVATAIAGAWENGVCGIRSTTRMENLLWKQIANEL 848
             **********.**     .**    .* .***** **.** *.**** **
```

APPENDIX 4-continued

Alignment of dengue virus polyproteins

```
DEN4        850 NYVLWEGGHDLTVVAGDVKGVLTKGKRALTPPVSDLKYSWKTWGKAKIFT   899
DEN1-WP     851 NHILLENDMKFTVVVGDVSGILAQGKKMIRPQPMEHKYSWKSWGKAKIIG   900
DEN2-NGC    851 NHILSENEVKLTIMTGDIKGIMQAGKRSLQPQPTELKYSWKTWGKAKMLS   900
DEN3-H87    849 NYILWENDIKLTVVVGDITGVLEQGKRTLTPQPMELKYSWKTWGLAKIVT   898
                * .* *.    *.. **. *..  **. . *    . *****.** **.

DEN         900 PEARNSTFLIDGPDTSECPNERRAWNSLEVEDYGFGMGTTNIWMKFREGS   949
DEN1-WP     901 ADVQNTTFIIDGPNTPECPDNQRAWNIWEVEDYGFGIFTTNIWLKLRDSY   950
DEN2-NGC    901 TESHNQTFLIDGPETAECPNTNRAWNSLEVEDYGFGVGTTNIWLKLREKQ   950
DEN3-H87    899 AETQNSSFIIDGPSTPECPSASRAWNVWEVEDYGFGVFTTNIWLKLREVY   948
                  . .* .*.**** * ***    ****  ********.******.* *.

DEN4        950 SEVCDHRLMSAAIKDQKAVHADMGYWIESSKNQTWQIEKASLEIVKTCLW   999
DEN141P     951 TQVCDHRLMSAAIKDSKAVHADMGYWIESEKNETWKLARASFIEVKTCIW  1000
DEN2-NGC    951 DVFCDSKLMSAAIKDNRAVHADMGYWIESALNDTWKIEKASFIEVKSCHW  1000
DEN3-H87    949 TQLCDHRLMSAAVKDERAVHADMGYWIESQKNGSWKLEKASLIEVKTCTW   998
                   ** .*****.** .************  * .*.. .** ****.* *

DEN4       1000 PKTHTLWSNGVLESQMLIPKSYAGPFSQHNYRQGYATQTVGPWHLGKLEI  1049
DEN1-WP    1001 PKSHTLWSNGVLESEMIIPKIYGGPISQHNYRPGYFTQTAGPWHLGKLEL  1050
DEN2-NGC   1001 PKSHTLWSNGVLESEMIIPKNFAGPVSQHNYRPGYHTQTAGPWHLGKLEM  1050
DEN3-H87    999 PKSHTLWSNGVLESDMIIPKSLAGPISQHNHRPGYHTQTAGPWHLGKLEL  1048
                **.*********** *.***    ** **** * ** *** *********.

DEN4       1050 DFGECPGTTVTIQEDCDHRGPSLRTTTASGKLVTQWCCRSCTMPPLRFLG  1099
DEN1-WP    1051 DFDLCEGTTVVVDEHCGNRGPSLRTTTVTGKTIHEWCCRSCTLPPLRFKG  1100
DEN2-NGC   1051 DFDFCEGTTVVVTEDCGNRGPSLRTTTASGKLITEWCCRSCTLPPLRYRG  1100
DEN3-H87   1049 DFNYCEGTTVVISENCGTRGPSLRTTTVSGKLIHEWCCRSCTLPPLRYMG  1098
                **   * ****  . * *  ********* .**  . .*******.****. *

DEN4       1100 EDGCWYGMEIRPLSEKEENMVKSQVTAGQGTSETFSMGLLCLTLFVEECL  1149
DEN1-WP    1101 EDGCWYGMEIRPVKEKEENLVKSMVSAGSGEVDSFSLGLLCISISIEEVM  1150
DEN2-NGC   1101 EDGCWYGMEIRPLKEKEENLVNSLVTAGHGQIDNFSLGVLGMALFLEEML  1150
DEN3-H87   1099 EDGCWYGMEIRPINEKEENMVKSLASAGSGKVDNFTMGVLCLAILFEEVM  1148
                ************. *****.* *  .** *   . *..*.*  ...  ** .

DEN4       1150 RRRVTRKHMILVVVITLCAIILGGLTWMDLLRALIMLGDTMSGRIG-GQI  1198
DEN1-WP    1151 RSRWSRKMLMTGTLAVFLLLTMGQLTWNDLIRLCIMVGANASDKMGMGTT  1200
DEN2-NGC   1151 RTRVGTKHAILLVAVSFVTLITGNMSFRDLGRMVMVMGATMTDDIGMGVT  1200
DEN3-H87   1149 RGKFGKKHMIAGVLFTFVLLLSGQITWRGMAHTLIMIGSNASDRMGMGVT  1198
                *  .   *  .           .  * ..   . .   .*.*  .  .   .* *

DEN4       1199 HLAIMAVFKMSPGYVLGVFLRKLTSRETALMVIGMAMTTVLSIPHDLMEL  1248
DEN1-WP    1201 YLALMATFRMRPMFAVGLLFRRLTSREVLLLTVGLSLVASVELPNSLEEL  1250
DEN2-NGC   1201 YLALLAAFKVRPTFAAGLLLRKLTSKELMMTTIGIVLLSQSTIPETILEL  1250
DEN3-H87   1199 YLALIATFKIQPFLALGFFLRKLTSRENLLLGVGLAMAATLRLPEDIEQM  1248
                  **..* *.. *    *    *.***.*   .  .*.  .  .   .*   . ..

DEN4       1249 IDGISLGLILLKIVTQFDNTQVGTLALSLTFIRSTMPLVMAWRTIMAVLF  1298
DEN1-WP    1251 GDGLAMGIMMLKLLTDFQSHQLWATLLSLTFVKTTFSLHYAWKTMAMILS  1300
DEN2-NGC   1251 TDALALGMMVLKMVRKMEKYQLAVTIMAILCVPNAVILQNAWKVSCTILA  1300
DEN3-H87   1249 ANGIALGLMALKLITQFETYQLWTALVSLTCSNTIFTLTVAWRTATLILA  1298
                   ...*.. **..       *.     ...          *  **.     .*

DEN4       1299 VVTLIPLCRTSCLQKQSHWVEITALILGAQALPVYLMTLMKGASRRSWPL  1348
DEN1-WP    1301 IVSLFPLCLSTTSQK-TTWLPVLLGSLGCKPLTMFLITENKIWGRKSWPL  1349
DEN2-NGC   1301 VVSVSPLFLTSSQQK-ADWIPLALTIKGLNPTAIFLTTLSRTNKKRSWPL  1349
DEN3-H87   1299 GISLLPVCQSSSMRK-TDWLPMTVAAMGVPPLPLFIFSLKDTLKRRSWPL  1347
                  ... *.  ... .* . *. .       *        ... .       ..****

DEN4       1349 NEGIMAVGLVSLLGSALLKNDVPLAGPMVAGGLLLAAYVMSGSSADLSLE  1398
DEN1-WP    1350 NEGIMAVGIVSILLSSLLKNDVPLAGPLIAGGMLIACYVISGSSADLSLE  1399
DEN2-NGC   1350 NEAIMAVGMVSILASSLLKNDIPMTGPLVAGGLLTVCYVLTGRSADLELE  1399
DEN3-H87   1348 NEGVMAVGLVSILASSLLRNDVPMAGPLVAGGLLIACYVITGTSADLTVE  1397
                **  .****.**.* *.**.**.*..**..***.*   .**..* ****  .*

DEN4       1399 KAANVWWDEMADITGSSPIIEVKQDEDGSFSIRDVEETNMITLLVKLALI  1448
DEN- -WP   1400 KAAEVSWEEEAEHSGASHNILVEVQDDGTMKIKDEERDDTLTILLKATLL  1449
DEN2-NGC   1400 RAADVKWEDQAEISGSSPILSITISEDGSMSIKNEEEEQTLTILIRTGLL  1449
DEN3-H87   1398 KAADVTWEEEAWQTGVSHNLMITVDDDGTMRIKDDETENILTVLLKTALL  1447
                .** * *.. *. .* *   . .    .**.  *.  *      .*.*..   *.

DEN4       1449 TVSGLYPLAIPVTMTLWYMWQVKTQRSGALWDVPSPAATKKAALSEGVYR  1493
DEN1-WP    1450 AISGNYPMSIPATLFVWYFWQKKKQRSGVLWDTPSPPEVERAVLDDGIYR  1499
DEN2-NGC   1450 VISGLFPVSIPITAAAWYLWEVKKQRAGVLWDVPSPPPVGKAELEDGAYR  1499
DEN3-H87   1448 IVSGIFPYSIPATMLVWHTWQKQTQRSGVLWDVPSPPETQKAELEEGVYR  1497
                  .**..* .** *    *   *. . **.* *** ***      .* *  .* **
```

APPENDIX 4-continued

Alignment of dengue virus polyproteins

```
DEN4      1499 IMQRGLFGKTQVGVGIHMEGVFHTMWHVTRGSVICHETGRLEPSWADVRN  1548
DEN- WP   1500 ILQRGLLGRSQVGVGVFQEGVFHTMWHVTRGAVLMYQGKRLEPSWASVKK  1549
DEN2-NGC  1500 IKQKGILGYSQIGAGVYKEGTFHTMWHVTRGAVLMHKGKRIEPSWADVKK  1549
DEN3-H87  1498 IKQQGIFGKTQVGVGVQKEGVFHTMWHVTRGAVLTHNGKRLEPNWASVKK  1547
               * *.*. * .*.* *.  ** **********.*.     *.** ** *.

DEN4      1549 DMISYGGGWRLGDKWDKEEDVQVLAIEPGKNPKHVQTKPGLFKTLTGEIG  1598
DEN1-WP   1550 DLISYGGGWRFQGSWNAGEEVQVIAVEPGKNPKNVQTAPGTFKTPEGEVG  1599
DEN2-NGC  1550 DLISYGGGWKLEGEWKEGEEVQVLALEPGKNPRAVQTKPGLFKTNAGTIG  1599
DEN3-H87  1548 DLISYGGGWRLSAQWQKGEEVQVIAVEPGKNPKNFQTMPGIFQTTTGEIG  1597
               *.*******.    *   *.***.*.******.  ** ** *.*  * .*

DEN4      1599 AVTLDFKPGTSGSPIINRKGKVIGLYGNGVVTKSGDYVSAITQAERIGEP  1648
DEN1-WP   1600 AIALDFKPGTSGSPIVNREGKIVGLYGNGVVTTSGTYVSAIAQAKASQEQ  1649
DEN2-NGC  1600 AVSLDFSPGTSGSPIIDKKGKVVGLYGNGVVTRSGAYVSAIAQTEKSIED  1649
DEN3-H87  1598 AIALDFKPGTSGSPIINREGKVVGLYGNGVVTKNGGYVSGIAQTNAEPDG  1647
               *..*** ********. . **..*********  * *** *.*.    .

DEN4      1649 -DYEVDEDIFRKKRLTIMDLHPGAGTKTRILPSIVREALKRRLRTLILAP  1697
DEN1-WP   1650 PLPEIEDEVFRKRNLTIMDLHPGSGKTRRYLPAIVREAIRRNVRTLVLAP  1699
DEN2-NGC  1650 -NPEIEDDIFRKRKLTIMDLHPGAGKTKRYLPAIVREAIKRGLRTLILAP  1698
DEN3-H87  1648 PTPELEEEMFKKRNLTIMDLHPGSGKTRKYLPAIVREAIKRRLRTLILAP  1697
                  *.....*.*. *********.***.. **.*****..* .***.***

DEN4      1698 TRVVAAEMEEALRGLPIRYQTPAVKSEHTGREIVDLMCHATFTTRLLSST  1747
DEN1-WP   1700 TRVVASEMAELLKGMPIRYQTTAVKSEHTGKEIVDLMCHATFTMRLLSPV  1749
DEN2-NGC  1699 TRVVAAEMEEALRGLPIRYQTPARIAEHTGREIVDLMCHATFTMRLLSPV  1748
DEN3-H87  1698 TRVVAAMEMMEMKGLPIRYQTTATKSEHTGREIVDLMCHATFTMRLLSPV  1747
               *****.** **..*.****** * ..****.************ ****

DEN4      1748 RVPNYNLIVMDEAHFTDPSSVAARGYISTRVEMGEAAAIFMTATPPGATD  1797
DEN1-WP   1750 RVPNYNMIIMDEAHFTDPASIAARGYISTRVGMGEAAAIFMTATPPGSVE  1799
DEN2-NGC  1749 RNPNYNLIIMDEAHFTDPASIAARGYISTRVEMGEAAGIFMTATPPGSRD  1798
DEN3-H87  1748 RVPNYNLIIMDEAHFTDPASIAARGYISTRVGMGEAAAIFMTATPPGTAD  1797
               ******.*.*********.*.********** ***** *********. .

DEN4      1798 PFPQSNSPIEDIEREIPERSWNTGFDWITDYQGKTVWFVPSIKAGNDIAN  1847
DEN1-WP   1800 AFPQSNAVIQDEERDIPERSWNSGYDWITDFPGKTVWFVPSIKSGNDIAN  1849
DEN2-NGC  1799 PFPQSNAPIMDEEREIPERSWSSGHEWVTDFKGKTVWFVPSIKAGNDIAA  1848
DEN3-H87  1798 AFPQSNAPIQDEERDIPERSWNSGNEWITDFVGKTVWFVPSIKAGNVIAN  1847
                *****. * * **.****** .* .*.**. ***********.** **

DEN4      1848 CLRKSGKKVIQLSRKTFDTEYPKTKLTDWDFVVTTDISEMGANFRAGRVI  1897
DEN1-WP   1850 CLRKNGKRVVQLSRKTFDTEYQKTKNNDWDYVVTTDISEMGANFRADRVI  1899
DEN2-NGC  1849 CLRKNGKKVIQLSRKTFDSEYVKTRTNDWDFVVTTDISEMGANFKAERVI  1898
DEN3-H87  1848 CLRKNGKKVIQLSRKTFDTEYQKTKLNDWDFVVTTDISEMGANFIADRVI  1897
               **** **.*.********.** **. .***.************* * ***

DEN4      1898 DPRRCLKPVILPDGPERVILAGPIPVTPASAAQRRGRIGRNPAQEDDQYV  1947
DEN1-WP   1900 DPRRCLKPVILKDGPERVILAGPMPVTVASAAQRRGRIGRNQNKEGDQYI  1949
DEN2-NGC  1899 DPRRCMKPVILTDGEERVILAGPMPVTHSSAAQRRGRIGRNPKNENDQYI  1948
DEN3-H87  1898 DRPPCLKPVILTDGPERVILAGPMPVTVASAAQRRGRVGRNPQKENDQYI  1947
               *****.***** ** ********.*** .********.***   * ***.

DEN4      1948 FSGDPLKNDEDHAHWTEAKMLLDNIYTPEGIIPTLFGPEREKTQAIDGEF  1997
DEN1-WP   1950 YMGQPLNNDEDHAHWTEAKMLLDNINTPEGIIAPLFEPEREKSAAIDGEY  1999
DEN2-NGC  1949 YMGEPLENDEDCAHWKEAKMLLDNINTPEGIIPSMFEPEREKVDAIDGEY  1998
DEN3-H87  1948 FMGQPLNKDEDHAHWTEAKMLLDNINTPEGIIPALFEPEREKSAAIDGEY  1997
               . * **  *** *** ********* *******..* *****  *****.

DEN4      1998 RLRGEQRKTFVELMRRGDLPVWLSYKVASAGISYKDREWCFTGERNNQIL  2047
DEN1-WP   2000 RLRGEARKTFVELMRRGDLPVWLSYKVASEGFQYSDRRWCFDGERNNQVL  2049
DEN2-NGC  1999 RLRGEARKTFVDLMRRGDLPVWLAYRVAAEGINYADRRWCFDGIKNNQIL  2048
DEN3-H87  1998 RLKGESRKTFVELMRRGDLPVWLAHKVASEGIKYTDRKWCFDGERNNQIL  2047
               **.** *****.***********. .**. *  * ** *** * .***.*

DEN4      2048 EENMEVEIWTREGEKKKLRPRWLDARVYADPMALKDFKEFASGRKSITLD  2097
DEN1-WP   2050 EENMDVEIWTKEGERKKLRPRWLDARTYSDPLALREFKEFAAGRRSVSGD  2099
DEN2-NGC  2049 EENVEVEIWTKEGERKKLKPRWLDARIYSDPLTLKEFKEFAAGRKSLTLN  2098
DEN3-H87  2048 EENMDVEIWTKEGEKKKLRPRWLDARTYSDPLALKEFKDFAAGRKSIALD  2097
               ***..*****.***.***.******* *.**..*..**.**.**.*..

DEN4      2098 ILTEIASLPTYLSSRAKLALDNIVMLHTTERGGRAYQHALNELPESLETL  2147
DEN1-WP   2100 LILEIGKLPQHLTQRAQNALDNLVMLHNSEQGGKAYRHAMEELPDTIETL  2149
DEN2-NGC  2099 LITEMGRLPTFMTQKARDALDNLAVLHTAEAGGRAYNHALSELPETLETL  2148
DEN3-H87  2098 LVTEIGRVPSHLAHRTRNALDNLVMLHTSEHGGRAYRHAVEELPETMETL  2147
               .. *.  .*  .. ... ****. .**..* **.** **. ***...***
```

APPENDIX 4-continued

Alignment of dengue virus polyproteins

```
DEN4      2148 MLVALLGAMTAGIFLFFMQGKGIGKLSMGLITIAVASGLLWVAEIQPQWI  2197
DEN1-WP   2150 MLLALIAVLTGGVTLFFLSGRGLGKTSIGLLCVIASSALLWMASVEPHWI  2199
DEN2-NGC  2149 LLLTLLATVTGGIFLFLMSGRGIGKMTLGMCCIITASILLWYAQIQPHWI  2198
DEN3-H87  2148 LLLGLMILLTGGAMLFLISGKGIGKTSIGLICVIASSGMLWMADVPLQWI  2197
               .*. *.  .* *  ** . *.*.** ..*. ..  .* .** * .  .**

DEN4      2198 AASIILEFFLMVLLIPEPEKQPTPQDNQLIYVILTILTIIGLIAANEMGL  2247
DEN1-WP   2200 AASIILEFFLMVLLIPEPDRQRTPQDNQLAYVVIGLLFMILTAAANEMGL  2249
DEN2-NGC  2199 AASIILEFFLIVLLIPEPEKQRTPQDNQLTYVVIAILTVVAATMANEMGF  2248
DEN3-H87  2198 ASAIVLEFFMMVLLIPEPEKQRTPQDNQLAYVVIGILTLAAIVAANEMGL  2247
               *..*.****..*******..********* **.. .* .     *****

DEN4      2248 IEKTKTDFGFY----QVKTETTILDVDLRPASAWTLYAVATTILTPMLRH  2293
DEN1-WP   2250 LETTKKDLGIGHAAAENHHHAAMLDVDLHPASAWTLYAVATTIITPMMRH  2299
DEN2-NGC  2249 LEKTKKDLGLG-SITTQQPESNILDIDLRPASAWTLYAVATTFVTPMLRH  2297
DEN3-H87  2248 LETTKRDLGMS-KEPGVVSPTSYLDVDLHPASAWTLYAVATTVITPMLRH  2296
               .* ** * *           .  **.**.************* .***.**

DEN4      2294 TIENTSANLSLAAIANQAAVLMGLGKGWPLHRMDLGVPLLAMGCYSQVNP  2343
DENI-WP   2300 TIENTTANISLTAIANQAAILMGLDKGWPISKMDIGVPLLALGCYSQVNP  2349
DEN2-NGC  2298 SIENSSVNVSLTAIANQATVLMGLGKGWPLSKMDIGVPLLAIGCYSQVNP  2347
DEN3-H87  2297 TIENSTANVSLAAIANQAVVLMGLDKGWPISKMDLGVPLLALGCYSQVNP  2346
               .***.. *.**.****** .**** ****. .**.******.********

DEN4      2344 TTLTASLVMLLVHYAIIGPGLQAKATREAQKRTAAGIMKNPTVDGITVID  2393
DEN1-WP   2350 LTLTAAVFMLVAHYAIIGPGLQAKATREAQKRTAAGIMKNPTVDGIVAID  2399
DEN2-NGC  2348 ITLTAALFLLVAHYAIIGPGLQAKATREAQKRAAAGIMKNPTVDGITVID  2397
DEN3-H87  2347 LTLIAAVLLLVTHYAIIGPGLQAKATREAQKRTAAGIMKNPTVDGIMTID  2396
                ** *.. .*. ********************.*************  **

DEN4      2394 LEPISYDPKFEKQLGQVMLLVLCAGQLLLMRTTWAFCEVLTLATGPILTL  2443
DEN1-WP   2400 LDPVVYDAKFEKQLGQIMLLILCTSQILLMRTTWALCESITLATGPLTTL  2449
DEN2-NGC  2398 LDPIPYDPKFEKQLGQVMLLVLCVTQVLMMRTTWALCEALTLATGPISTL  2447
DEN3-H87  2397 LDPVIYDSKFEKQLGQVMLLVLCAVQLLLMRTSWALCEVLTLATGPITTL  2446
               *.*. ** ********.***.**  *.*.***.** ** .******. **

DEN4      2444 WEGNPGRFWNTTIAVSTANIFRGSYLAGAGLAFSLIKNAQTPRRGTGTTG  2493
DEN1-WP   2450 WEGSPGKFWNTTIAVSMANIFRGSYLAGAGLAFSLMKSLGGGRRGTGAQG  2499
DEN2-NGC  2448 WEGNPGRFWNTTIAVSMANIFRGSYLAGAGLLFSIMKNTTNTRRGTGNIG  2497
DEN3-H87  2447 WEGSPGKFWNTTIAVSMANIFRGSYLAGAGLALSIMKSVGTGKRGTGSQG  2496
               *** **.********* **************  *..*     .****  *

DEN4      2494 ETLGEKWKRQLNSLDRKEFEEYKRSGILEVDRTEAKSALKDGSKIKHAVS  2543
DEN1-WP   2500 ETLGEKWKRQLNQLSKSEFNTYKRSGIIEVDRSEAKEGLKRGEPTKAHVS  2549
DEN2-NGC  2498 ETLGEKWKSRLNALGKSEFQIYKKSGIQEVDRTLAKEGIKRGETDHHAVS  2547
DEN3-H87  2497 ETLGEKWKKKLNQLSRKEFDLYKKSGITEVDRTEAKEGLKRGEITHHAVS  2546
               ******** .** * . **  **.*** ****. **  .* *   .****

DEN4      2544 RGSSKIRWIVERGMVKPKGKVVDLGCGRGGWSYYMATLKNVTEVKGYTKG  2593
DEN1-WP   2550 RGTAKLRWFVERNLVKPEGKVIDLGCGRGGWSYYCAGLKKVTEVKGYTKG  2599
DEN2-NGC  2548 RGSAKLRWFVERNMVTPEGKVVDLGCGRGGWSYYCGGLKNVREVKGLTKG  2597
DEN3-H87  2547 RGSAKLWWFVERNMVIPEGRVIDLGCGRGGWSYYCAGLKKVTEVRGYTKG  2596
               **..*..* ***..* * *.*.************   ** * **.* ***

DEN4      2594 GPGHEEPIPMATYGWNLVKLHSGVDVFYKPTEQVDTLLCDIGESSSNPTI  2643
DEN1-WP   2600 GPGHEEPIPMATYGWNLVKLYSGKDVFFTPPEKCDTLLCDIGESSPNPTI  2649
DEN2-NGC  2598 GPGHEEPIPMSTYGWNLVRLQSGVDVFFTPPEKCDTLLCDIGESSPNPTV  2647
DEN3-H87  2597 GPGHEEPVPMSTYGWNIVKLMSGKDVFYLPPEKCDTLLCDIGESSPSPTV  2646
               *******.**.*****.*.*  * ***. * *. ***********  **.

DEN4      2644 EEGRTLRVLKMVEPWLSSKPEFCIKVLNPYMPTVIEELEKLQRKHGGNLV  2693
DEN1-14P  2650 EEGRTLRVLKMVEPWLRGN-QFCIKILNPYMPSVVETLEQMQRKHGGMLV  2698
DEN2-NGC  2648 EAGRTLRVLNLVENWLNNNTQFCIKVLNPYMPSVIEKMEALQRKYGGALV  2697
DEN3-H87  2647 EESRTIRVLKMVEPWLKNN-QFCIKVLNPYMPTVIEHLERLQRKHGGMLV  2695
               *  **.*** .** **    .****.******.*.* .* .*** ** **

DEN4      2694 RCPLSRNSTHEMYWVSGASGNIVSSVNTTSKMLLNRFTTRHRKPTYEKDV  2743
DEN1-WP   2699 RNPLSRNSTHEMYWVSCGTGNIVSAVNMTSRMLLNRFTMAHRKPTYERDV  2748
DEN2-NGC  2698 RNPLSRNSTHEMYWVSNASGNIVSSVNMISRMLINRFTMRHKKATYEPDV  2747
DEN3-H87  2696 RNPLSRNSTHEMYWISNGTGNIVSSVNMVSRLLLNRFTMTHRRPTIEKDV  2745
               * ************.*  .*****.**  *..*.****  *.. * * **

DEN4      2744 DLGAGTRSVSTETEKPDMTIIGRRLQRLQEEHKETWHYDQENPYRTWAYH  2793
DEN1-WP   2749 DLGAGTRHVAVEPEVANLDIIGQRIENIKNGHKSTWHYDEDNPYKTWAYH  2798
DEN2-NGC  2748 DLGSGTRNIGIESEIPNLDIIGKRIEKIKQEHETSWHYDQDHPYKTWAYH  2797
DEN3-H87  2746 DLGAGTRHVNAEPETPNMDVIGERIKRIKEEHSSTWHYDDENPYKTWAYH  2795
               ***.*** .  * *   . .** *.  ..  *  .****  ..**.*****
```

APPENDIX 4-continued

Alignment of dengue virus polyproteins

```
DEN4     2794 GSYEAPSTGSASSMVNGVVKLLTKPWDVIPMVTQLAMTDTTPFGQQRVFK  2843
DEN1-WP  2799 GSYEVKPSGSASSMVNGVVRLLTKPWDVIPMVTQIAMTDTTPFGQQRVFK  2848
DEN2-NGC 2798 GSYETKQTGSASSMVNGVVRLLTKPWDVVPMVTQMAMTDTTPFGQQRVFK  2847
DEN3-H87 2796 GSYEVKATGSASSMINGVVKLLTKPWDVVPMVTQMAMTDTTPFGQQRVFK  2845
              ****   .******.****.********.*****.***************

DEN4     2844 EKVDTRTPQPKPGTRMVMTTTANWLWALLGKKKNPRLCTREEFISKVRSN  2893
DEN1-WP  2849 EKVDTRTPKAKRGTAQIMEVTARWLWGFLSRNKKPRICTREEFTRKVRSN  2898
DEN2-NGC 2848 EKVDTRTQEPKEGTKKLMKITAEWLWKELGKKKTPRMCTREEFTRKVRSN  2897
DEN3-H87 2846 EKVDTRTPRPMPGTRKVMEITAEWLWRTLGRNKRPRLCTREEFTKKVRTN  2895
              *******     **  .*  ** ***  * . * **.******  ***.*

DEN4     2894 AAIGAVFQEEQGWTSASEAVNDSRFWELVDKERALHQEGKCESCVYNMMG  2943
DEN1-WP  2899 AAIGAVFVDENQWNSAKEAVEDERFWDLVHRERELHKQGKCATCVYNMMG  2948
DEN2-NGC 2898 AALGAIFTDENKWKSAREAVEDSRFWELVDKERNLHLEGKCETCVYNMMG  2947
DEN3-H87 2896 AAMGAVFTEENQWDSARAAVEDEEFWKLVDRERELHKLGKCGSCVYNMMG  2945
              **.**.* .*. * **  ** *  ** ** .** **  *** .*******

DEN4     2944 KREKKLGEFGRAKGSRAIWYMWLGARFLEFEALGFLNEDHWFGRENSWSG  2993
DEN1-WP  2949 KREKKLGEFGKAKGSRAIWYMWLGARFLEFEALGFMNEDHWFSRENSLSG  2998
DEN2-NGC 2948 KREKKLGEFGKAKGSRAIWYMWLGARFLEFEALGFLNEDHWFSRENSLSG  2997
DEN3-H87 2946 KREKKLGEFGKAKGSRAIWYMWLGARYLEFEALGFLNEDHWFSRENSYSG  2995
              **********.***************.********.****** **** **

DEN4     2994 VEGEGLHRLGYILEEIDKKDGDLMYADDTAGWDTRITEDDLQNEELITEQ  3043
DEN1-WP  2999 VEGEGLHKLGYILRDISKIPGGNMYADDTAGWDTRITEDDLQNEAKITDI  3048
DEN2-NGC 2998 VEGEGLHKLGYILRDVSKKEGGAMYADDTAGWDTRITLEDLKNEEMVTVN  3047
DEN3-H87 2996 VEGEGLHKLGYILRDISKIPGGAMYADDTAGWDTRITEDDLHNEEKITQQ  3045
              *******.***** .. *  *  ************** .**.**  .*

DEN4     3044 MAPHHKILAKAIFKLTYQNKVVKVLRPTPRGAVMDIISRKDQRGSGQCGT  3093
DEN1-WP  3049 MEPEHALLATSIFKLTYQNKVVRVQRPAKNGTVMDVISRRDQRGSGQVGT  3098
DEN2-NGC 3048 MEGEHKLLAEAIFKLTYQNKVVRVQRPTPRGTVMDIISRRDQRGSGQVGT  3097
DEN3-H87 3046 MDPEHRQLANAIFKLTYQNKVVKVQRPTPKGTVMDIISRKDQRGSGQVGT  3095
              *   *  ** .***********.* **.  *.***.***.**********

DEN4     3094 YGLNTFTNMEVQLIRQMEAEGVITQDDMQNPKGLKERVEKWLEKCGVDRL  3143
DEN1-WP  3099 YGLNTFTNMEAQLIRQMESEGIFSPSELETPN-LAERVLDWLKKHGTERL  3147
DEN2-NGC 3098 YGLNTFTNMEAQLIRQMEGEGVFKSIQHLTVT-EEIAVQNWLARVGRERL  3146
DEN3-H87 3096 YGLNTFTNMEAQLIRQMEGEGVLSKADLENPHPLEKKITQWLETKGVERL  3145
              ********** ******* **.       .       .  **   * .**

DEN4     3144 KRMAISGDDCVVKPLDERFGTSLLFLNDMGKVRKDIPQWEPSKGWKNWQE  3193
DEN1-WP  3148 KRMAISGDDCVVKPIDDRFATALTALNDMGKVRKDIPQWEPSKGWNDWQQ  3197
DEN2-NGC 3147 SRMAISGDDCVVKPLDDRFASALTALNDMGKVRKDIQQWEPSRGWNDWTQ  3196
DEN3-H87 3146 KRMAISGDDCVVKPIDDRFANALLALNDMGKVRKDIPQWQPSKGWHDWQQ  3195
               *************.*.**  .*  *********** **.**.**  * .

DEN4     3194 VPFCSHHFHKIFMKDGRSLVVPCRNQDELIGRARISQGAGWSLRETACLG  3243
DEN1-WP  3198 VPFCSHHFHQLIMKDGERIVVPCRNQDELVGRARVSQGAGWSLRETACLG  3247
DEN2-NGC 3197 VPFCSHHFHELIMKDGRVLVVPCRNQDELIGRARISQGAGWSLRETACLG  3246
DEN3-H87 3196 VPFCSHHFHELIMKDGRKLVVPCRPQDELIGRARISQGAGWSLRETACLG  3245
              ********* . ***** .***** ****.****.***************

DEN4     3244 KAYAQMWSLMYFHRRDLRLASMAICSAVPTEWFPTSRTTWSIHAHHQWMT  3293
DEN1-WP  3248 KSYQAMWQLMYFHRRDLRLAANAICSAVPVDWVPTSRTTWSIHAHHQWMT  3297
DEN2-NGC 3247 KSYAQMWSLMYFHRRDLRLAANAICSAVPSHWVPTSRTTWSIHAKHEWMT  3296
DEN3-H87 3246 KAYAWMWTLMYFHRRDLRLASNAICSAVPVHWVPTSRTTWSIHAHHQWMT  3295
              *.***** ************. *******  * ***********.*.***

DEN4     3294 TEDMLKVWNRVWIEDNPNMTDKTPVHSWEDIPYLGKREDLWCGSLIGLSS  3343
DEN1-WP  3298 TEDMLSVWNRVWIEENPWMEDKTHVSSWEDVPYLGKREDRWCGSLIGLTA  3347
DEN2-NGC 3297 TEDMLTVWNRVWIQENPWMEDKTPVESWEEIPYLGKREDQWCGSLIGLTS  3346
DEN3-H87 3296 TEDMLTVWNRVWIEDNPWMEDKTPVTTWEDVPYLGKREDQWCGSLIGLTS  3345
              ***** *******..** * *** * .**..******** ********..

DEN4     3344 RATWAKNIHTAITQVRNLIGKEEYVDYMPVMKRYSAPSESEGVL        3387
DEN1-WP  3348 RATWATNIQVAINQVRRLIGNENYLDFMTSMKRFKNESDPEGALW       3392
DEN2-NGC 3347 RATWAKNIQTAINQVRSLIGNEEYTDYMPSMKRFRREEEEAGVLW       3391
DEN3-H87 3346 RATWAQNILTAIQQVRSLIGNEEFLDYMPSMKRFRKEEESEGAIW       3390
             ***** **  ** *** *** * . *.*  ***.    .  * .
```

*Residue identity

.Residue similarity

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A dengue virus comprising a U to C mutation at nucleotide 10634 of the 3' untranslated region, wherein the numbering is based upon the prototypic isolate DEN4 Dominica 1981 and wherein the virus has a phenotype comprising temperature sensitivity in Vero cells or human liver cell line HuH-7 and/or attenuation in mice.

2. The dengue virus of claim 1, further comprising the 430 mutation.

3. The dengue virus of claim 1, wherein the dengue virus is a dengue virus type 1, a dengue virus type 2, a dengue virus type 3, or a dengue virus type 4.

4. The dengue virus of claim 1, wherein the dengue virus is a chimeric virus.

5. The chimeric virus of claim 4 having a dengue 1 backbone, a dengue 2 backbone, a dengue 3 backbone, or a dengue 4 backbone.

6. A pharmaceutical composition comprising a pharmacologically acceptable vehicle and a dengue virus according to claim 1.

7. A kit comprising a pharmaceutical composition according to claim 6 in a pack or dispenser device and instructions for administration.

8. A method of producing neutralizing antibodies against dengue virus in a subject comprising administering a therapeutically effective amount of a pharmaceutical composition comprising a pharmacologically acceptable vehicle and the dengue virus according to claim 1 to the subject.

9. The method of claim 8, wherein administration is by subcutaneous, intradermal, or intramuscular injection.

10. An immunogenic composition comprising a pharmacologically acceptable vehicle and a dengue virus according to claim 1.

11. The immunogenic composition of claim 10 in unit dosage form having from about $10^2$-$10^9$ plaque forming units (PFU)/ml.

12. The immunogenic composition of claim 10 in unit dosage form having from about 0.1 to 50 μg of E protein/ml.

13. A method of making a pharmaceutical composition comprising:

isolating the dengue virus according to claim 1; and combining the isolated dengue virus with a pharmacologically acceptable vehicle.

* * * * *